United States Patent
Thompson et al.

(10) Patent No.: US 8,865,741 B2
(45) Date of Patent: Oct. 21, 2014

(54) AMINOINDANE COMPOUNDS AND USE THEREOF IN TREATING PAIN

(75) Inventors: Scott Kevin Thompson, Phoenixville, PA (US); Tony Priestley, West Chester, PA (US); Roger Astbury Smith, Chester Springs, PA (US); Ashis K. Saha, Stow, MA (US); Sonali Rudra, Kolkata (IN); Arun Kuma Hajra, Kolkata (IN); Dipanwita Chatterjee, Kolkata (IN); Carl Henry Behrens, Newark, DE (US); Yigang He, Ewing, NJ (US); Hui-Yin Li, Hockessin, DE (US)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

(21) Appl. No.: 13/400,039

(22) Filed: Feb. 18, 2012

(65) Prior Publication Data

US 2012/0214809 A1    Aug. 23, 2012

Related U.S. Application Data

(60) Provisional application No. 61/444,379, filed on Feb. 18, 2011.

(51) Int. Cl.
*A61K 31/445*    (2006.01)
*C07D 211/26*    (2006.01)

(52) U.S. Cl.
USPC ........ 514/319; 514/235.5; 514/275; 514/278; 514/318; 514/321; 514/408; 544/71; 544/330; 546/16; 546/194; 546/197; 546/205; 548/566

(58) Field of Classification Search
USPC .............. 514/235.5, 275, 278, 318, 319, 321, 514/408; 544/71, 330; 546/16, 194, 197, 546/205; 548/566
See application file for complete search history.

(56) References Cited

U.S. PATENT DOCUMENTS

| | | |
|---|---|---|
| 5,190,956 A | 3/1993 | Afonso |
| 5,344,836 A | 9/1994 | Hamanaka |
| 5,854,268 A | 12/1998 | Baker |
| 5,998,440 A | 12/1999 | Castro |
| 6,127,388 A | 10/2000 | Bourrain |
| 6,413,987 B1 | 7/2002 | Aberg |
| 6,630,451 B1 | 10/2003 | Zhang |
| 6,696,467 B2 | 2/2004 | Mattei |
| 6,858,577 B1 | 2/2005 | Zhang |
| 6,921,759 B2 | 7/2005 | Anthony |
| 6,995,162 B2 | 2/2006 | Chen |
| 7,049,297 B2 | 5/2006 | Zhang |
| 7,101,868 B2 | 9/2006 | Elbaum |
| 7,102,009 B2 | 9/2006 | Patel |
| 7,399,774 B2 | 7/2008 | Siegel |
| 7,511,149 B2 | 3/2009 | Arndt |
| 7,514,564 B2 | 4/2009 | Chen |
| 7,604,815 B2 | 10/2009 | Loso |
| 7,709,649 B2 | 5/2010 | Zhu |
| 7,718,674 B2* | 5/2010 | Aberg ........................... 514/319 |
| 8,110,575 B2 | 2/2012 | Gottschling |
| 2002/0147198 A1 | 10/2002 | Chen |
| 2004/0156869 A1 | 8/2004 | Bakthavatchalam |
| 2005/0222266 A1 | 10/2005 | Pietra |
| 2006/0063789 A1 | 3/2006 | Freyne |
| 2006/0079558 A1 | 4/2006 | Aberg |
| 2009/0069323 A1 | 3/2009 | Coulter |
| 2009/0137628 A1* | 5/2009 | Aberg et al. .................. 514/319 |
| 2010/0324028 A1 | 12/2010 | Gottschling |
| 2011/0195954 A1 | 8/2011 | Gottschling |

FOREIGN PATENT DOCUMENTS

| | | |
|---|---|---|
| GB | 1321424 | 12/1969 |
| WO | WO98/24428 | * 11/1998 |
| WO | WO-00/76510 | 12/2000 |
| WO | WO-01/05767 | 1/2001 |
| WO | WO-01/36381 | 5/2001 |

(Continued)

OTHER PUBLICATIONS

Edgcombe et al. "Local anaesthetic . . . " p. 1-7 (2005).*

(Continued)

*Primary Examiner* — Celia Chang
(74) *Attorney, Agent, or Firm* — RatnerPrestia

(57) ABSTRACT

The present application provides novel aminoindane compounds and methods for preparing and using these compounds. These compounds are useful in treating pain and/or itch in patients by administering one or more of the compounds to a patient. The methods include administering a compound of formula (I) or (II) and a TRPV1 receptor activator. In one embodiment, the TRPV1 receptor activator is lidocaine.

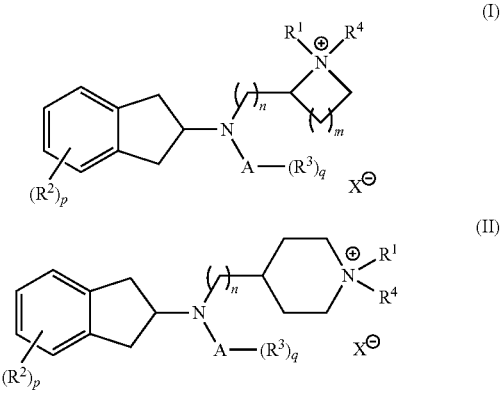

55 Claims, 11 Drawing Sheets

(56) References Cited

FOREIGN PATENT DOCUMENTS

| WO | WO-2006/036936 | 4/2006 |
| WO | WO-2006/037047 | 4/2006 |
| WO | WO-2006/050908 | 5/2006 |
| WO | WO-2007/038325 | 4/2007 |
| WO | WO-2008/063603 | 5/2008 |
| WO | WO-2008/097235 | 8/2008 |
| WO | WO-2008/099022 | 8/2008 |
| WO | WO-2009/065922 | 5/2009 |
| WO | WO-2009/114139 | 9/2009 |
| WO | WO-2010/021864 | 2/2010 |
| WO | WO-2011/006073 | 1/2011 |

OTHER PUBLICATIONS

Narahashi T. "Neurorecetors . . . " J. Pharmcol. Exp. Ther. v. 294(1) p. 1-26 (2000).*

Roberson, "Targeting of sodium channel blockers into nociceptors to produce long-duration analgesia: a systematic study and review", British Journal of Pharmacology, 164(1):48-58 (Sep. 2011; e-publication: Aug. 5, 2011).

Zuliani, "Sodium channel blockers for neuropathic pain", Expert Opinion Therapeutic Patents, 20(6):755-779 (Jun. 2010).

International Search Report dated May 25, 2012 and issued in International Patent Application No. PCT/US2012/025759.

* cited by examiner

AMINOINDANE COMPOUNDS AND USE THEREOF IN TREATING PAIN

CROSS-REFERENCE TO RELATED APPLICATIONS

This application claims the benefit of the priority of U.S. Provisional Patent Application No. 61/444,379, filed Feb. 18, 2011, which is incorporated by reference herein.

BACKGROUND

Local anesthetics such as lidocaine are useful in pain relief in numerous applications, but suffer from the drawback of undesired blockade of motor function. They are non-selective sodium channel blockers that fail to discriminate between sodium channel activity required for normal ongoing sensation and similar activity involved in nociceptor signaling. The cationic sodium channel blocker, QX-314, selectively blocks sodium channel activity in nociceptor neurons when administered in the presence of capsaicin, an agonist for the transient receptor potential cation channel, subfamily V, member 1 (TRPV1). TRPV1 is preferentially expressed peripherally in small-diameter primary afferent nociceptors and is up-regulated in chronic pain states. However, TRPV1 is not present in the large diameter afferent neurons that convey tactile sensations nor is TRPV1 present in motor neuron efferent fibers.

QX-314 is the N-ethylated analog of lidocaine and bears a permanent positive charge. It is unable to cross the neuronal cell membrane when applied externally and has no effect on neuronal sodium-channel activity unless afforded access to the cell cytoplasm through open TRPV1 channels in which case it causes prolonged block of sodium-channel activity. Voltage-clamp single cell electrophysiology experiments illustrated that QX-314 permeates through capsaicin-activated TRPV1 channels and blocks sodium channel activity. In vivo, perisciatic administration of a QX-314/capsaicin combination produced pronounced and long-lasting nociceptor-selective nerve blockade.

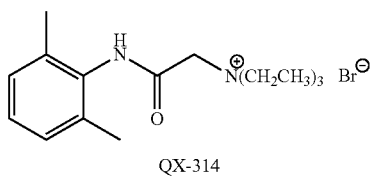

QX-314

The in vitro apparent affinity (IC$_{50}$) of QX-314 for blocking sodium current in DRG neurons (when co-applied with 1 μM capsaicin and measured using the whole-cell voltage clamp approach) is modest at 30 μM.

There remains a need in the art for compounds which are useful in the management of long-term or chronic pain and compounds for pain management which minimize impairment of motor function.

SUMMARY OF THE INVENTION

In one aspect, the present invention provides a compound of formula (I) or (II), wherein $R^1$-$R^4$, X, A, m, n, p, and q are defined herein.

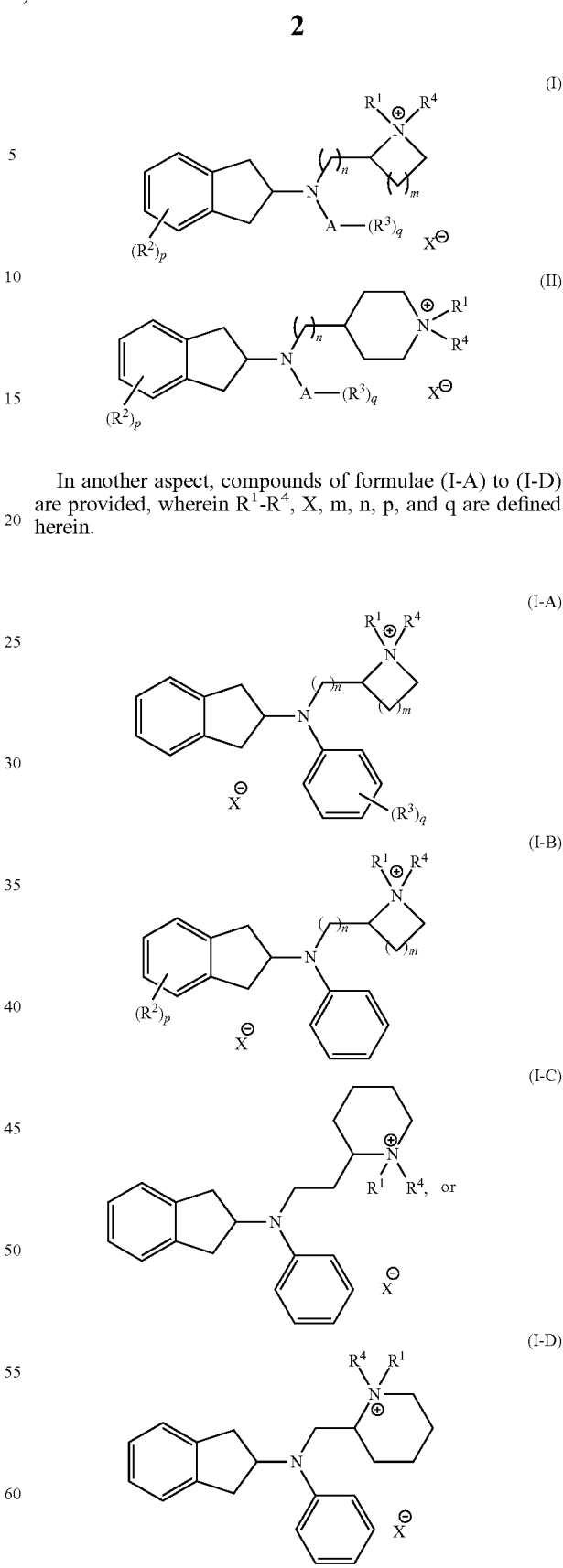

In another aspect, compounds of formulae (I-A) to (I-D) are provided, wherein $R^1$-$R^4$, X, m, n, p, and q are defined herein.

In yet another aspect, the invention provides a pharmaceutical composition containing a compound of any of formulae (I) to (I-NN) and a pharmaceutically acceptable carrier. In one embodiment, the pharmaceutical composition also contains a TRPV1 receptor activator. In another embodiment, the TRPV1 receptor activator is lidocaine.

In a further aspect, a pharmaceutical composition is provided and contains lidocaine and the following compound, wherein X is defined herein.

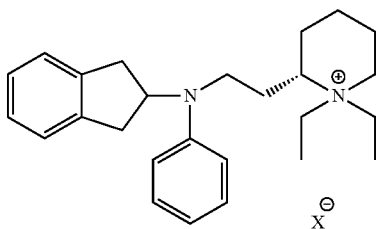

In still a further aspect, the invention provides a pharmaceutical composition containing a combination of, optionally with lidocaine, wherein X is defined herein:

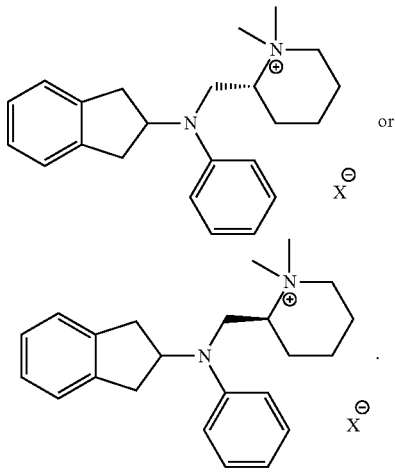

In another aspect, methods for treating pain or itch are provided and include administering a compound of formula (I) and/or (II) to a patient in need thereof. In one embodiment, the methods also include administration of a TRPV1 receptor activator.

In still another aspect, methods for assessing the inhibition of sodium channel response by a compound are provided.

In a further aspect, neuroblastoma cell line N1E115 which stably expresses human TRPV1 is provided.

Other aspects and advantages of the invention will be readily apparent from the following detailed description of the invention.

BRIEF DESCRIPTION OF THE DRAWINGS

FIG. 1 illustrates the anti-nociceptive effect of QX-314 using the rat pinch model. Two doses of a 0.5% QX-314 solution were utilized in the presence and absence of a fixed amount (2%) of lidocaine with the drug combination being injected directly around the sciatic nerve (i.e., perisciatic) of one hind limb. The black diamonds (♦) represent results for a 200 μL injection of a combined QX-314 and lidocaine solution. The black squares (■) represent results for a 100 μL injection of a combined QX-314 and lidocaine solution. The inverted triangles (▼) represent results for a 200 μL injection of a QX-314-only solution. The triangles (▲) represent results for a 100 μL injection of a QX-314-only solution. The black circles (●) represent results for a 200 μL injection of 2% lidocaine only.

FIG. 2 illustrates the anti-nociceptive effect of the compound of example 2, i.e., (S)-1,1-diethyl-2-[2-((indan-2-yl)(phenyl)amino)-ethyl]piperidinium iodide, using the rat pinch model. Two doses of a 0.5% solution of (S)-1,1-diethyl-2-[2-((indan-2-yl)(phenyl)amino)-ethyl]piperidinium iodide were utilized in the presence and absence of a fixed amount (2%) of lidocaine. The black diamonds (♦) represent results for a 200 μL injection of a combined solution of (S)-1,1-diethyl-2-[2-((indan-2-yl)(phenyl)amino)-ethyl]piperidinium iodide (200 μL) and lidocaine. The black circles (●) represent results for a 100 μL injection of a combined solution of (S)-1,1-diethyl-2-[2-((indan-2-yl)(phenyl)amino)-ethyl]piperidinium iodide and lidocaine. The inverted triangles (▼) represent results for a 200 μL injection of a (S)-1,1-diethyl-2-[2-((indan-2-yl)(phenyl)amino)-ethyl]piperidinium iodide-only solution. The triangles (▲) represent results for a 100 μL injection of a (S)-1,1-eiethyl-2-[2-((indan-2-yl)(phenyl)amino)-ethyl]piperidinium iodide-only solution.

FIG. 3 illustrates the anti-nociceptive effect of the compound of example 3, i.e., 1,1-dimethyl-2-[((indan-2-yl)(phenyl)amino)methyl]piperidinium iodide, using the rat pinch model. Two doses of a 0.5% solution of 1,1-dimethyl-2-[((indan-2-yl)(phenyl)amino)methyl]piperidinium iodide were utilized in the presence and absence of a fixed amount (2%) of lidocaine. The black circles (●) represent results for a 200 μL injection of a combined solution of 1,1-dimethyl-2-[((indan-2-yl)(phenyl)amino)methyl]piperidinium iodide and lidocaine. The black squares (■) represent results for a 100 μL injection of a combined solution of 1,1-dimethyl-2-[((indan-2-yl)(phenyl)amino)methyl]piperidinium iodide and lidocaine. The triangles (▲) represent results for a 200 μL of an injection of a 1,1-dimethyl-2-[((indan-2-yl)(phenyl)amino)methyl]piperidinium iodide-only solution. The inverted triangles (▼) represent results for a 100 μL injection of a 1,1-dimethyl-2-[((indan-2-yl)(phenyl)amino)methyl]piperidinium iodide-only solution.

FIG. 4 illustrates the anti-nociceptive effect of 1,1-dimethyl-2-[2-((indan-2-yl)(2-methylphenyl)amino)ethyl]piperidinium iodide (Example 24) using the rat pinch model. Doses of 0.25% and 0.5% solutions of 1,1-dimethyl-2-[2-((indan-2-yl)(2-methylphenyl)amino)ethyl]piperidinium iodide were utilized in the presence and absence of fixed amounts (1 and 2%) of lidocaine. The inverted triangles (▼)

represent results for a 200 μL injection of a combined solution of 1,1-dimethyl-2-[2-((indan-2-yl)(2-methylphenyl)amino) ethyl]piperidinium iodide (0.5%) and lidocaine (2%). The triangles (▲) represent results for a 100 μL injection of a combined solution of 1,1-dimethyl-2-[2-((indan-2-yl)(2-methylphenyl)amino)ethyl]piperidinium iodide (0.5%) and lidocaine (2%). The diamonds (♦) represent results for a 200 μL injection of a combined solution of 1,1-dimethyl-2-[2-((indan-2-yl)(2-methylphenyl)amino)ethyl]piperidinium iodide (0.25%) and lidocaine (1%). The filled circles (●) represent results for a 200 μL of an injection of a 1,1-dimethyl-2-[2-((indan-2-yl)(2-methylphenyl)amino)ethyl]piperidinium iodide-only (0.5%) solution. The filled squares (■) represent results for a 200 μL injection of a 1,1-dimethyl-2-[2-((indan-2-yl)(2-methylphenyl)amino)ethyl]piperidinium iodide-only (0.25%) solution.

Figure 1:
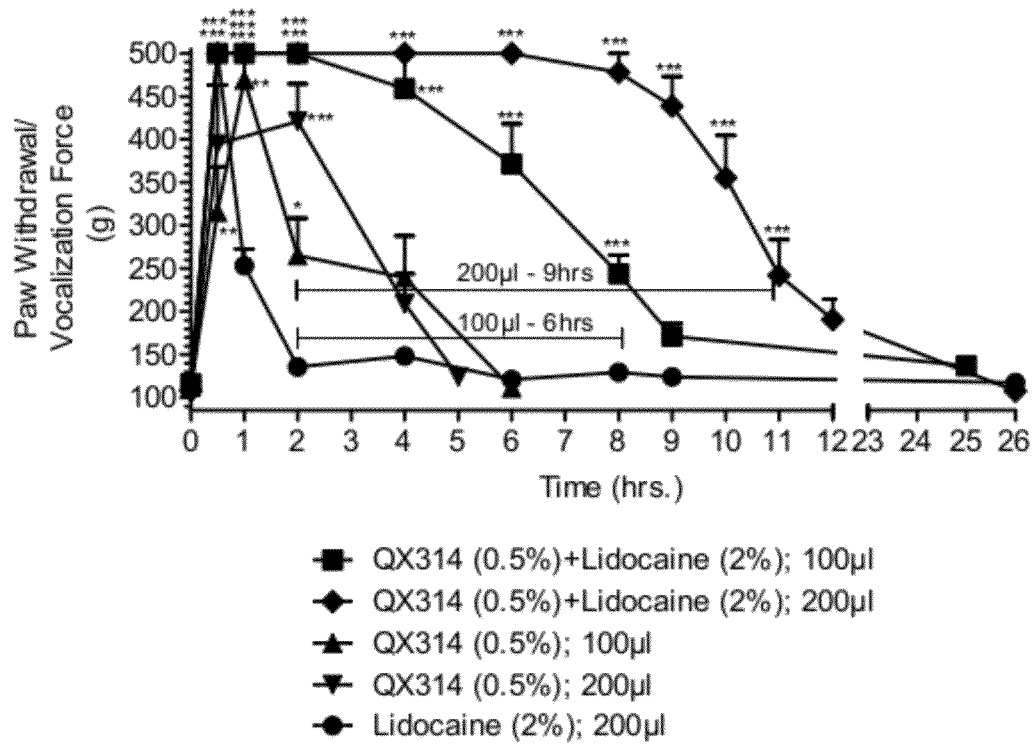
FIGS. 1-11 provide comparative data illustrating the anti-nociceptive effect of QX-314, a known anti-nociceptive agent, and three (3) compounds described herein which are encompassed by the compound of formula (I). Figures are either plots of paw withdrawal vocalization force (g) vs. time (hours) for pinch pain data or % maximal possible effect in the case of cutaneous trunci muscle reflex model data. When shown, three stars (*) designate a probability of less than 0.001. Two stars () designate a probability of less than 0.01. One star (*) designates a probability of less than 0.05. The bars (⊢) contained within the graph, if present, represent the difference between the duration of anti-nociception with and without lidocaine, if any. Finally, the arrow (→) on the y-axes represents the highest force applied. These data and the data in the examples illustrates that tested compounds for new and novel cationic sodium channel blockers with more potent activity than QX-314 in vitro and longer duration of action in vivo when co-administered with appropriate TRPV1 stimuli and in at least one instance, even without co-administration of TRPV1 stimuli (see Table 7 herein).
Figure 2:
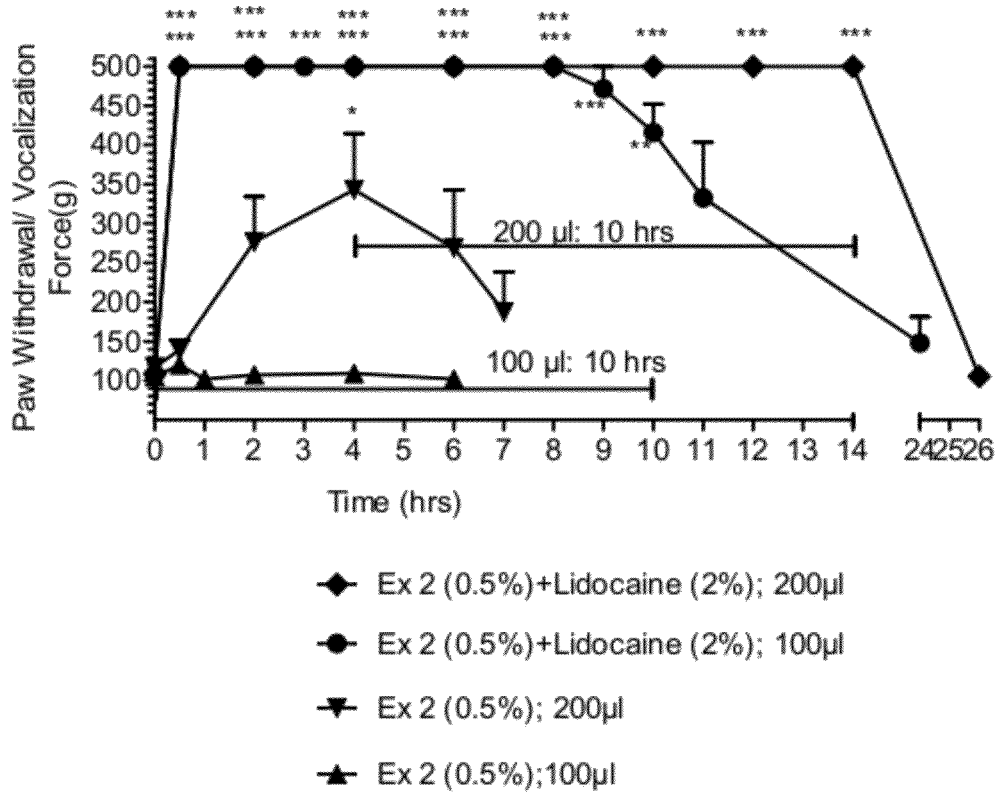
Figure 3:
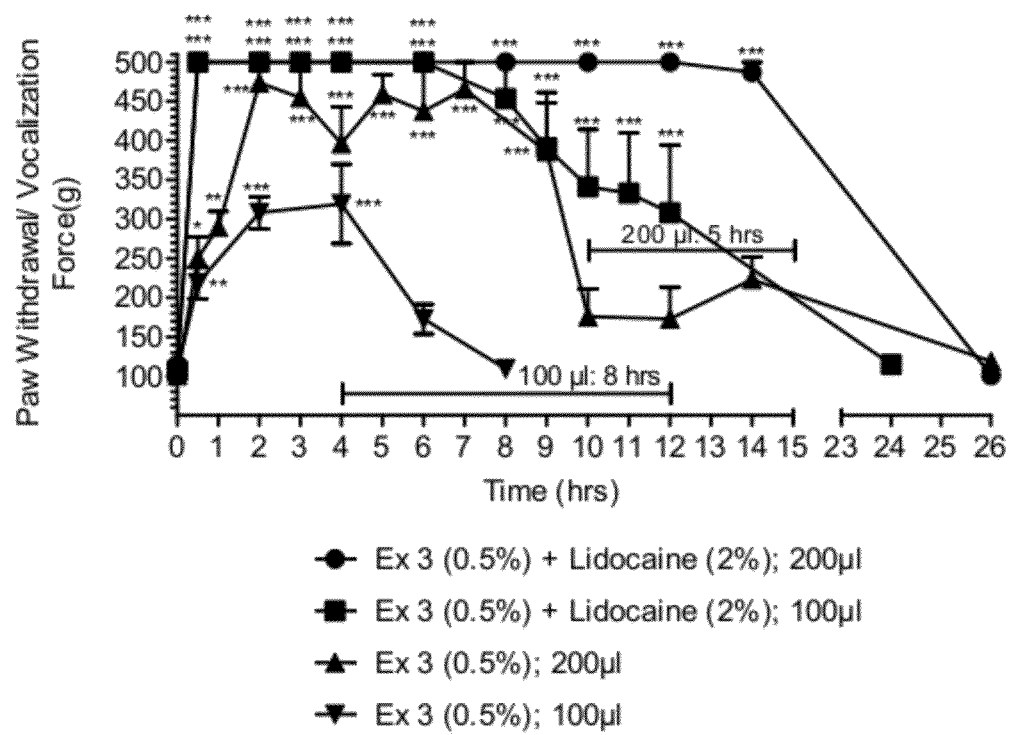
Figure 4:
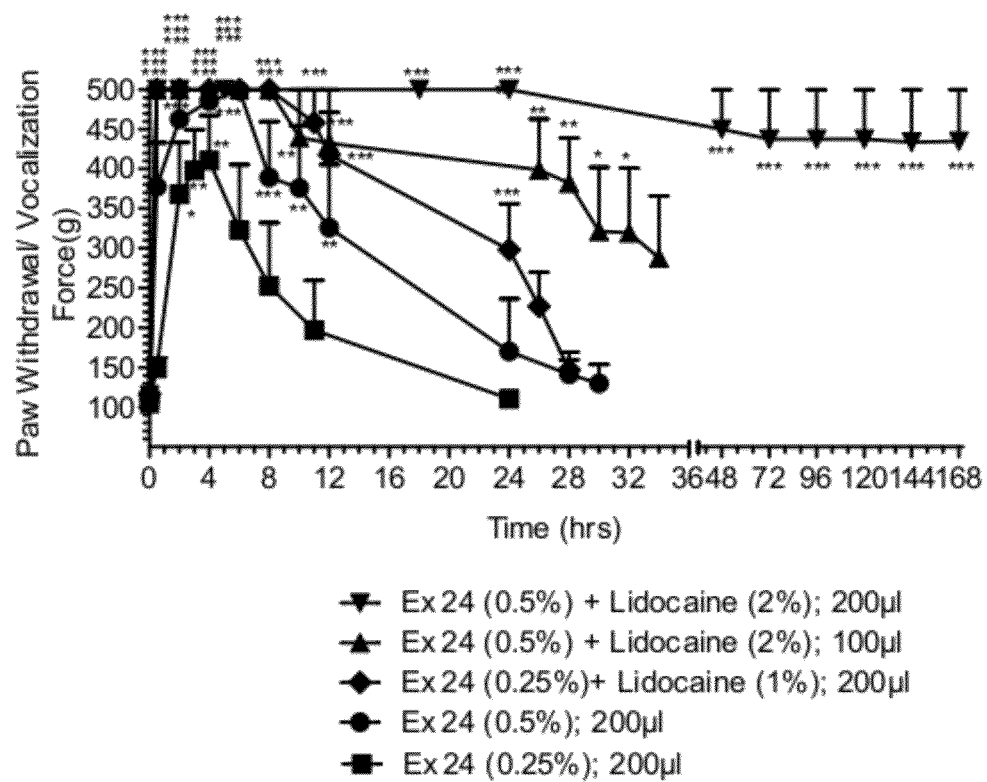
Figure 5:
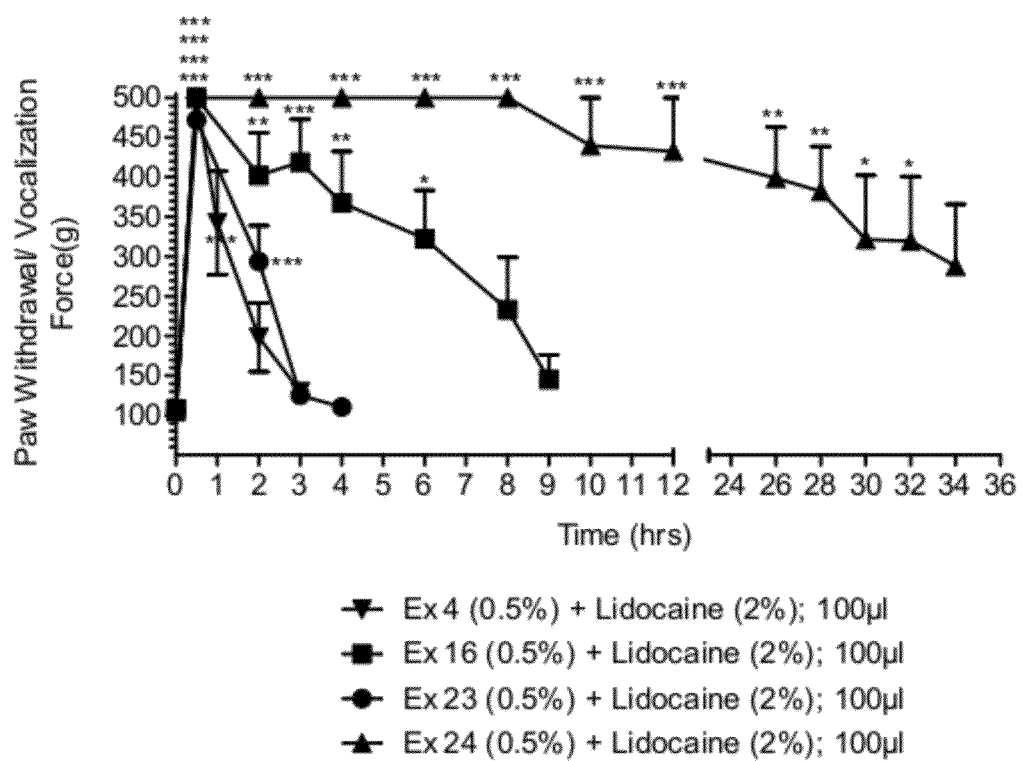

FIG. 5 compares the anti-nociceptive effect of compounds of Examples 4, 16, 23 and 24 using the rat pinch model. One hundred μL, independent, injections of combined solutions of each of the noted compounds (0.5%) in the presence of a fixed amount (2%) of lidocaine were utilized. The inverted triangles (▼) represent results for the compound of Example 4. The squares (■) represent results for the compound of Example 16. The circles (●) represent results for the compound of Example 23. The triangles (▲) represent results for the compound of Example 24.

Figure 6:
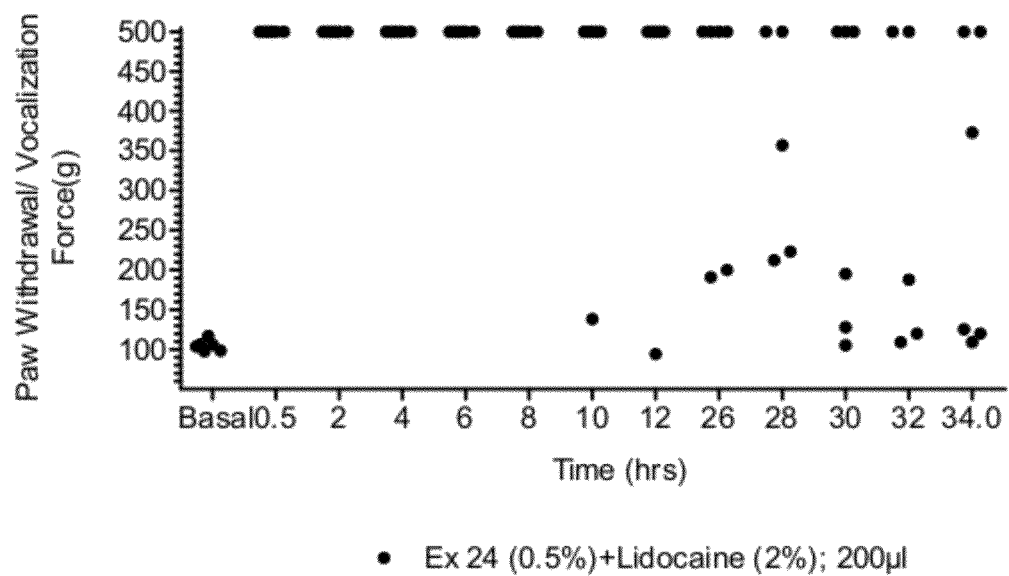
Figure 7:
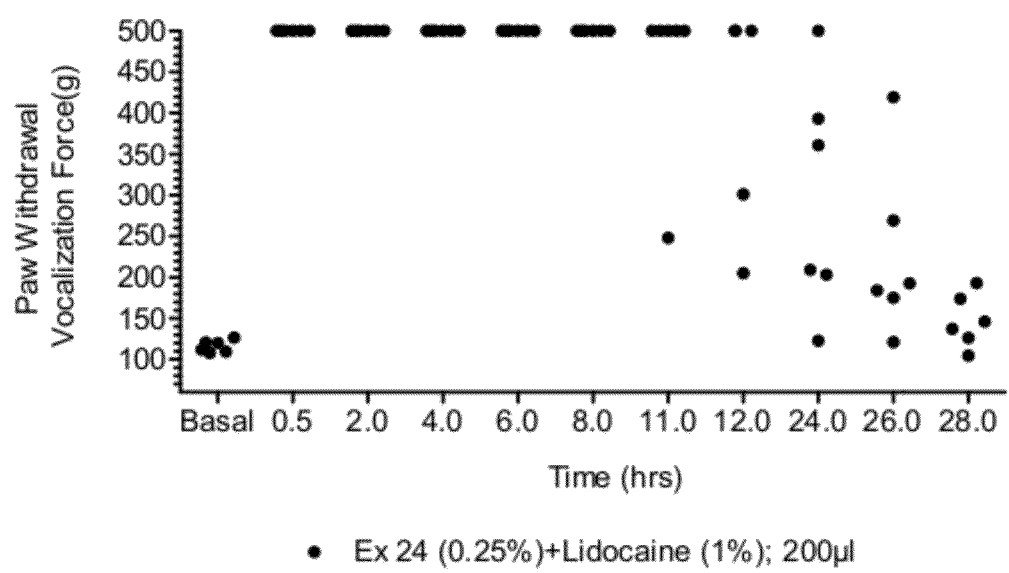

FIGS. 6-7 illustrate the effect of injection volume on the anti-nociceptive effect of solutions containing the compound of Example 24 and lidocaine and is a plot of paw withdrawal vocalization force (g) vs. time (hours). The arrow (→) on the y-axis represents the highest force applied.

FIG. 6 contains data for 100 μL injections of combined 0.5% solutions of the compound of Example 24 in the presence of a fixed amount (2%) of lidocaine. Each circle (●) represents an individual animal's pain response as a function of time, for the total cohort of six rats.

FIG. 7 contains data for 200 μL injections of combined 0.25% solutions of the compound of Example 24 in the presence of a fixed amount (1%) of lidocaine. Each circle (●) represents an individual animal's pain response as a function of time, for the total cohort of six rats.

Figure 8:
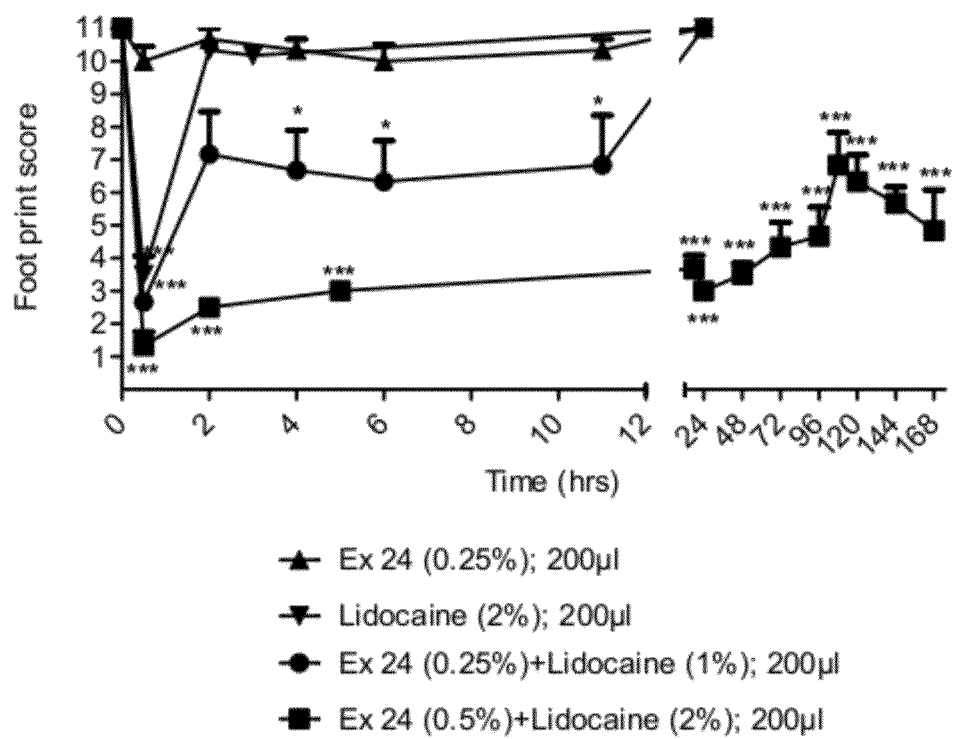

FIG. 8 provides data illustrating the anti-nociceptive effect of the compound of Example 24, i.e., 1,1-dimethyl-2-[2-((indan-2-yl)(2-methylphenyl)amino)ethyl]piperidinium iodide, which is encompassed by the compound of formula (I), using the sciatic function index and the rat footprint model. The figure is a plot of foot print score vs. time (hours). A footprint score of 0 indicates that no weight was borne on the injected paw, the paw was dragged or twisted with the plantar surface facing up. A footprint score of 1-3 reflected that the weight bearing was primarily on the knees, that the ankle and toes were used sparingly, the toes were curled, and or the plantar surface of the paw is uplifted in a concave fashion. A footprint score of 4-6 reflects that the weight bearing is primarily on the knees and angle, with very little weight bearing on the toes. A footprint score of 6-10 reflects that the weight bearing is distributed over the knee, ankle, and toes and that there is an occasional sparing of the knee joints. A footprint score of 11 indicates that the weight distribution is normal and there is perfect placement of the plantar surface of the paw. Doses of 0.25% and 0.5% solutions of 1,1-dimethyl-2-[2-((indan-2-yl) (2-methylphenyl)amino)ethyl]piperidinium iodide were utilized in the presence and absence of fixed amounts (1 and 2%) of lidocaine. The squares (■) represent results for a 200 μL injection of a combined solution of 1,1-dimethyl-2-[2-((indan-2-yl)(2-methylphenyl)amino)ethyl]piperidinium iodide (0.5%) and lidocaine (2%). The circles (●) represent results for a 200 μL injection of a combined solution of 1,1-dimethyl-2-[2-((indan-2-yl)(2-methylphenyl)amino)ethyl]piperidinium iodide (0.25%) and lidocaine (1%). The upright triangles (▲) represent results for a 200 μL injection of a 1,1-dimethyl-2-[2-((indan-2-yl)(2-methylphenyl)amino)ethyl] piperidinium iodide-only (0.25%) solution. The inverted triangles (▼) represent results for a 200 μL of an injection of a lidocaine-only (2%) solution. Three stars (*) designate a probability of less than 0.001; two stars () designate a probability of less than 0.01; and one star (*) designates a probability of less than 0.05.

Figure 9:
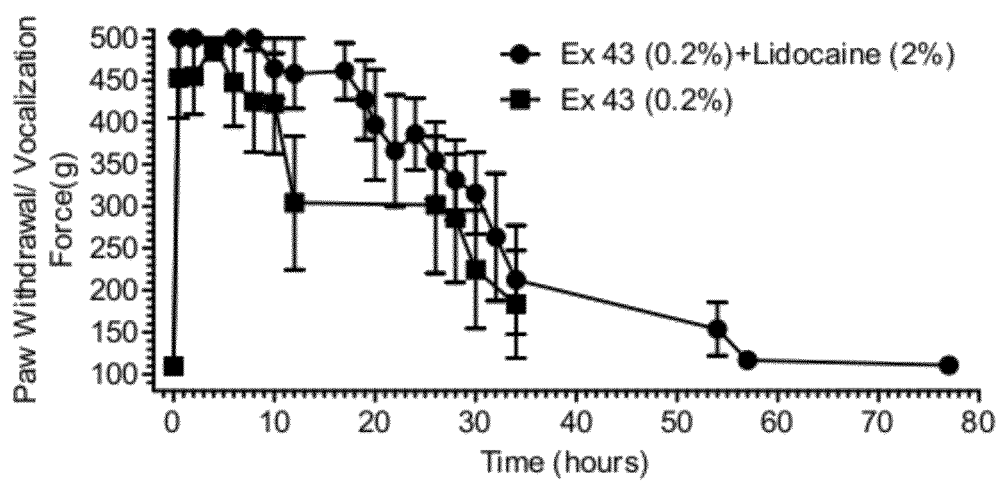

FIG. 9 compares the antinociceptive effect of the compound of example 43, i.e., ((R)-2-[2-(indan-2-yl-o-tolyl-amino)-ethyl]-1,1-dimethyl-piperidinium bromide), when administered directly around the sciatic nerve as a unilateral 200 μL injection of a 0.2% solution alone (■) or in combination with lidocaine (2%, ●).

Figure 10:
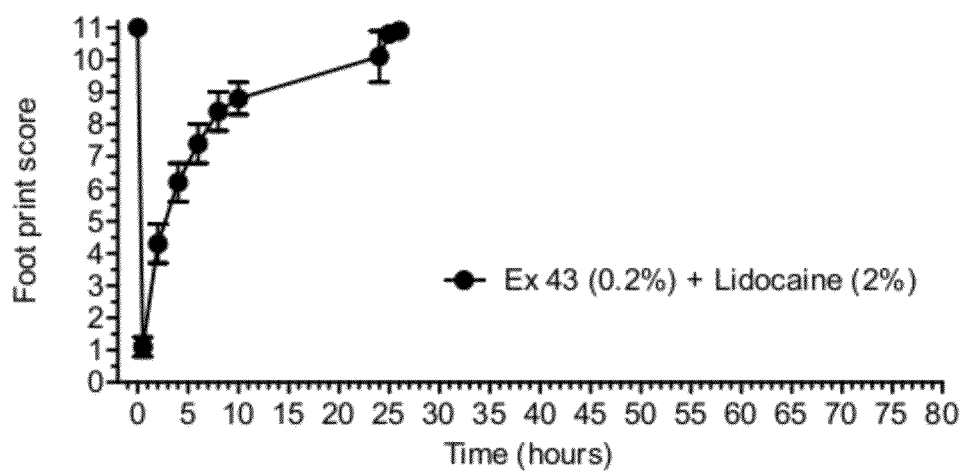

FIG. 10 shows the effects of a 200 μL unilateral injection, around a sciatic nerve, of a combined solution of the compound of example 43, i.e., ((R)-2-[2-(indan-2-yl-o-tolyl-amino)-ethyl]-1,1-dimethyl-piperidinium bromide, 0.2%) and lidocaine (2%) on motor function as assessed using the gait scoring system described herein. The data were plotted on the same scale as used for FIG. 9 to facilitate comparion of the time courses for analgesia and motor impairment induced by the compound of example 43.

Figure 11:
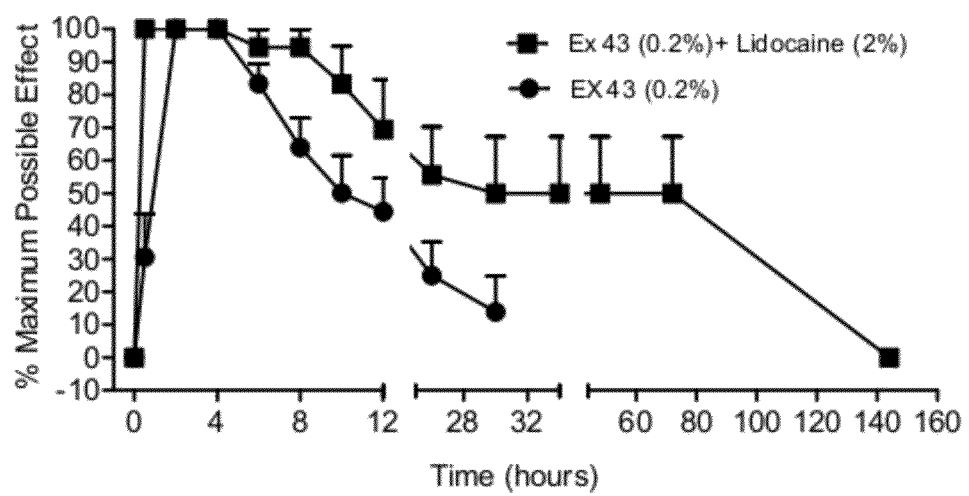

FIG. 11 shows the antinociceptive effects of a 100 μL sub-cutaneous injection of the compound of example 43, i.e., ((R)-2-[2-(indan-2-yl-o-tolyl-amino)-ethyl]-1,1-dimethyl-piperidinium bromide, 0.2%), either alone (●) or in combination with lidocaine (2%, ■), in the cutaneous trunci muscle reflex pain model. The combination solution resulted in an extended duration of analgesia compared to that produced by the compound of example 43 alone. A similar injection of 100 μL lidocaine (2%), without example 43, produced a brief analgesia that reached 100% for around 0.5 hours post injection and had returned to baseline by around 2 hours (data not shown).

DETAILED DESCRIPTION OF THE INVENTION

The present invention provides novel compounds which, when optionally utilized in combination with a TRPV1 agonist, are capable in reducing or eliminating pain or itch caused by tissue insult, injury or pathology. These novel compounds are permanently charged by virtue of the presence of quaternary nitrogen-atom contained within the nitrogen-containing ring rendering them highly soluble. These compounds are quaternary ammonium salts, where the counter-anion is a halogen anion, i.e., chloride, bromide, or iodide ion; or trifluoroacetate, sulfate, phosphate, acetate, fumarate, maleate, citrate, pyruvate, succinate, oxalate, a sulfonate, e.g., methanesulfonate, trifluoromethanesulfonate, toluenesulfonate such as p-toluenesulfonate, benzenesulfonate, ethanesulfonate, camphorsulfonate, 2-mesitylenesulfonate, or naphthalenesulfonate such as 2-naphthalenesulfonate, bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), D-mandelate, L-mandelate, propionate, phthalate, hydrochlorate, hydrobromate or nitrate.

The novel charged compounds disclosed herein are incapable of passing through the cell membrane. However, it is believed that they will penetrate into the cell, in therapeutically effective amounts, when access is afforded via open TRPV1 channels. This is one advantage of the charged compounds of the invention as compared to their corresponding neutral molecules that are believed to freely penetrate all cell membranes.

In one aspect, the present invention provides a compound of formula (I) or (II).

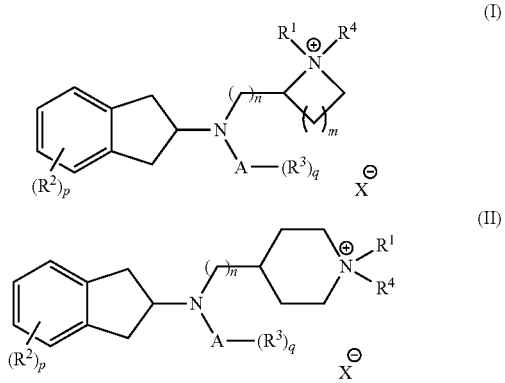

In these compounds, n is 1 to 3; m is 1 to 4; p is 0 to 2; and q is 0 to 4. In one embodiment, n is 1. In another embodiment, n is 2. In yet another embodiment, n is 3. In a further embodiment, p is 0. In yet another embodiment, p is 1. In another embodiment, p is 2. In still another embodiment, q is 0. In yet a further embodiment, q is 1. In still a further embodiment, q is 2. In yet another embodiment, q is 3. In yet a further embodiment, q is 4. In still a further embodiment, m is 2 and n is 1. In another embodiment, m is 2 and n is 2. In a further embodiment, m is 3 and n is 2. In a further embodiment, m is 3 and n is 1. In still a further embodiment, m is 4 and n is 2. In another embodiment, m is 4 and n is 3. In yet another embodiment, m is 2. In a still further embodiment, m is 3.

A is phenyl or heteroaryl.

$R^1$ and $R^4$ are, independently, $C_1$ to $C_6$ alkyl, or $CH_2CH_2OH$. Alternatively, $R^1$ and $R^4$ are joined together to form a 4- to 6-membered carbocyclic or heterocyclic ring. In one embodiment, $R^1$ and $R^4$ are joined to form an optionally substituted carbocyclic ring such as cyclobutane, cyclopentane, cyclohexane, cycloheptane, and cyclooctane. In another embodiment, $R^1$ and $R^4$ are joined to form an optionally substituted heterocyclic ring such as a cyclic ether, amine, or sulfide. In a further embodiment, $R^1$ and $R^4$ are joined to form a cyclic ether.

$R^2$ is H, halogen, $NO_2$, OH, or $C_1$ to $C_6$ alkoxy. In one embodiment, $R^1$ and $R^4$ are the same. In another embodiment, $R^1$ and $R^4$ differ. In a further embodiment, $R^1$ and/or $R^4$ are methyl, ethyl, propyl (n-propyl or i-propyl), butyl, pentyl, hexyl, or the like.

$R^3$ is hydrogen, halogen, CN, $NO_2$, $NH_2$, optionally substituted $C_1$ to $C_6$ alkyl, $C_2$ to $C_6$ alkenyl, $C_2$ to $C_6$ alkynyl, OH, $CF_3$, $OCF_3$, $SCF_3$, optionally substituted $C_1$ to $C_6$ alkoxy, $C_2$ to $C_6$ alkynyloxy, heterocyclyloxy, heteroaryloxy, optionally substituted $C_1$ to $C_6$ alkylthio, heteroarylthio, C(O)O($C_1$ to $C_6$ alkyl), C(O)($C_1$ to $C_6$ alkyl), C(O)(aryl), C(O)(heterocycle), $C(O)NH_2$, C(O)NH($C_1$ to $C_6$ alkyl), C(O)NH(aryl), C(O)NH(heterocycle), C(O)NH(heteroaryl), C(O)N($C_1$ to $C_6$ alkyl)($C_1$ to $C_6$ alkyl), C(O)N(aryl)($C_1$ to $C_6$ alkyl), $C(S)NH_2$, optionally substituted aryl, heteroaryl, heterocycle, NHC(O)($C_1$ to $C_6$ alkyl), NHC(O)(aryl), NHC(O)(heteroaryl), NHC(O)O($C_1$ to $C_6$ alkyl), N($C_1$ to $C_6$ alkyl)C(O)($C_1$ to $C_6$ alkyl), N($C_1$ to $C_6$ alkyl)C(O)O($C_1$ to $C_6$ alkyl), $NHC(O)NH_2$, NHC(O)NH($C_1$ to $C_6$ alkyl), NHC(O)NH(heteroaryl), $NHSO_2$($C_1$ to $C_6$ alkyl), $SO_2$($C_1$ to $C_6$ alkyl), $SO_2NH_2$, $SO_2NH$($C_1$ to $C_6$ alkyl), $SO_2NH$($C_2$ to $C_6$ alkynyl), $SO_2N$($C_1$ to $C_6$ alkyl)($C_1$ to $C_6$ alkyl), $SO_2NH$(heteroaryl), NH($C_1$ to $C_6$ alkyl), N($C_1$ to $C_6$ alkyl)($C_1$ to $C_6$ alkyl), N($C_1$ to $C_6$ alkyl)($C_2$ to $C_6$ alkenyl), or N($C_1$ to $C_6$ alkyl)(heterocycle). Alternatively, two $R^3$ groups are joined to form an optionally substituted 6-membered aryl, optionally substituted 5- or 6-membered carbocyclic ring, or optionally substituted 5- or 6-membered heterocycle or heteroaryl containing 1 to 3 oxygen, nitrogen, or sulfur atoms and 4 or 5 carbon atoms. In one embodiment, $R^3$ is halogen. In another embodiment, $R^3$ is chlorine or fluorine. In a further embodiment, $R^3$ is CN. In yet another embodiment, $R^3$ is $C(O)OCH_3$. In still a further embodiment, $R^3$ is $C(O)NH_2$. In yet a further embodiment, $R^3$ is $SO_2CH_3$. In another embodiment, $R^3$ is $CH_3$.

$X^-$ is halogen anion, trifluoroacetate, sulfate, phosphate, acetate, fumarate, maleate, citrate, pyruvate, succinate, oxalate, a sulfonate, e.g., methanesulfonate, trifluoromethanesulfonate, toluenesulfonate such as p-toluenesulfonate, benzenesulfonate, ethanesulfonate, camphorsulfonate, 2-mesitylenesulfonate, or naphthalenesulfonate such as 2-naphthalenesulfonate, bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), D-mandelate, L-mandelate, propionate, tartarate, phthalate, hydrochlorate, hydrobromate, and nitrate. In one embodiment, X is halogen. In another embodiment, X is chlorine, bromine or iodine. In another embodiment, X is iodine.

Also contemplated by the present invention is the one embodiment that two hydrogen atoms attached to a carbon atom, i.e., $CH_2$, can be replaced with a double bond to an oxygen atom or sulfur atom to form a carbonyl, i.e., C(O), or thiocarbonyl, i.e., C(S), respectively.

In another embodiment, the compound is of formula (I-A), (I-AA), or (II-A), wherein $R^1$, $R^3$, $R^4$, A, X, m, n, and q are defined herein. In one example, m is 2 or 3.

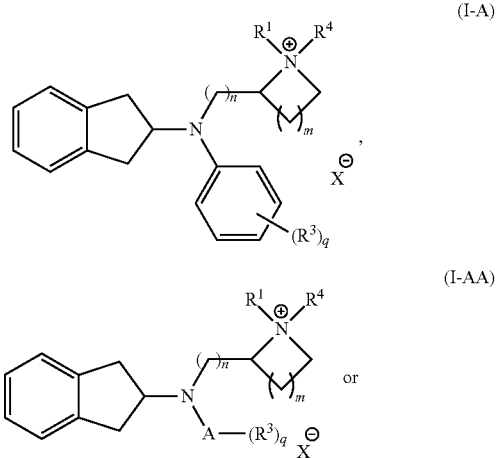

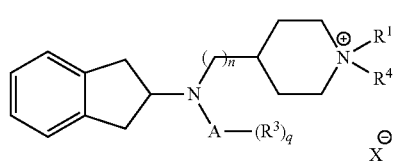
In a further embodiment, the compound is of formula (I-B), (I-BB), or (II-B) wherein R¹, R², R⁴, A, X, m, n, and p are defined herein. In one example, m is 2 or 3.
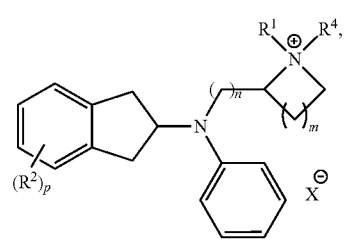
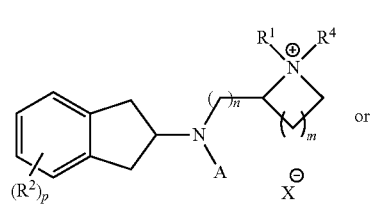
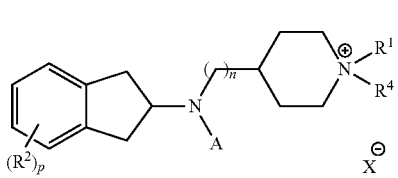
In yet another embodiment, the compound is of formula (I-C), (I-CC), or (II-C) wherein R¹, R⁴, A, and X are defined herein.
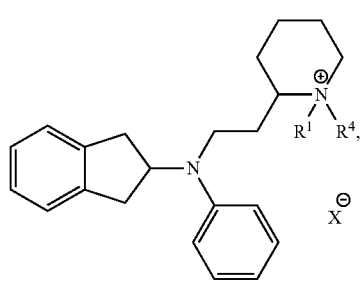
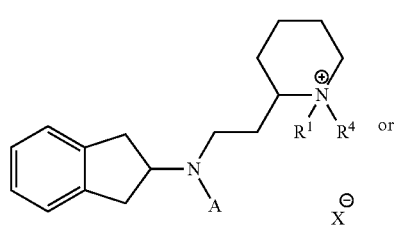
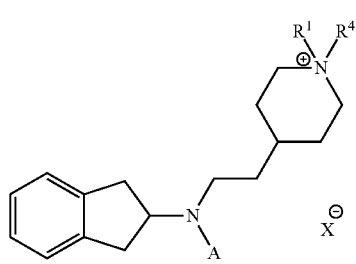
In still a further embodiment, the compound is of formula (I-D) or (I-DD),
wherein R¹, R⁴, and X are defined herein.
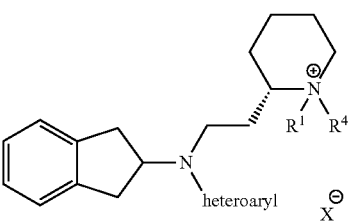
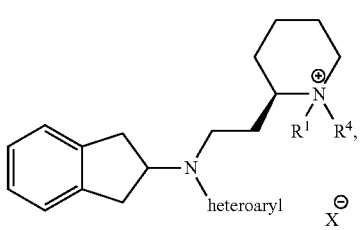

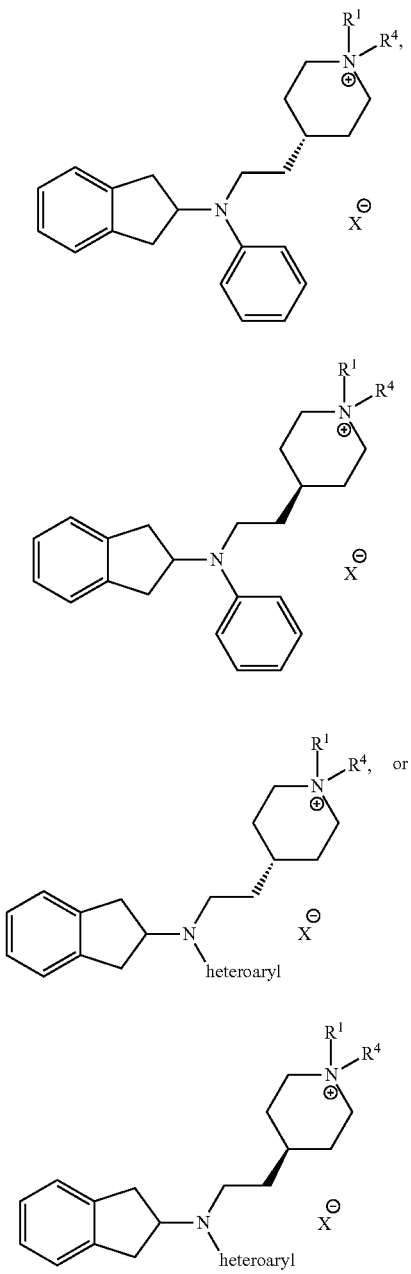
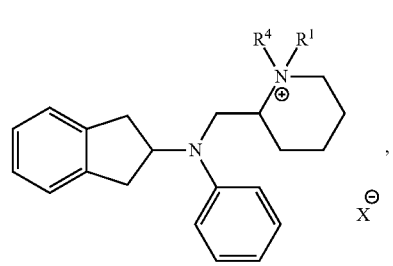
In another embodiment, the compound is of formula (I-E), wherein $R^1$, $R^4$, and X are defined herein.
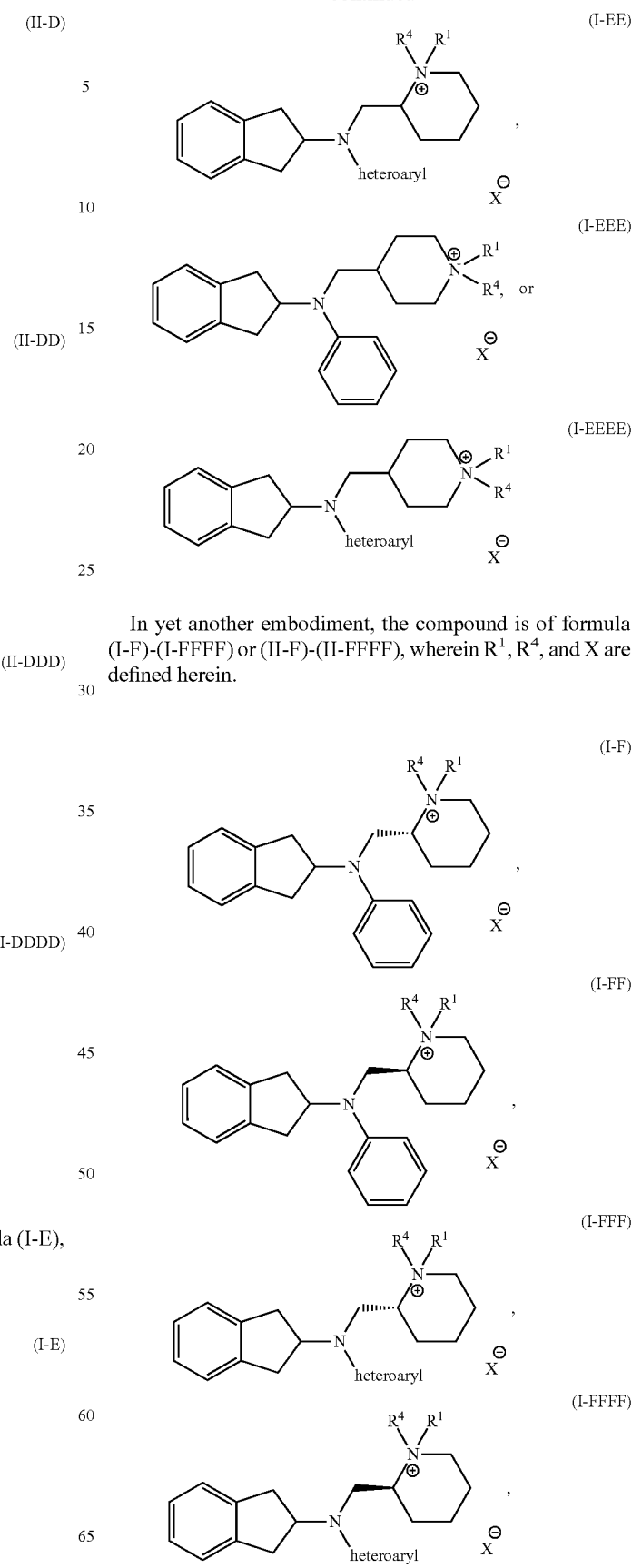
In yet another embodiment, the compound is of formula (I-F)-(I-FFFF) or (II-F)-(II-FFFF), wherein $R^1$, $R^4$, and X are defined herein.

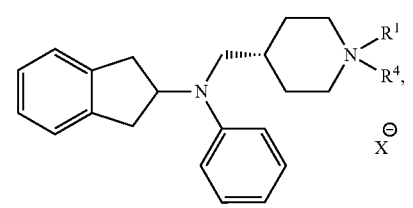
(II-F)

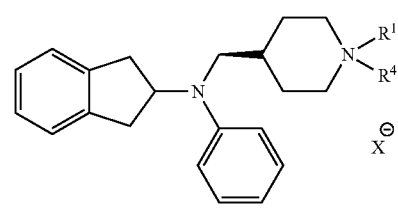
(II-FF)

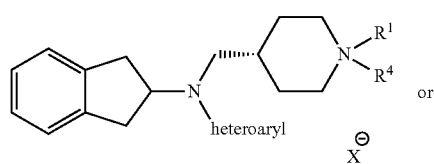
(II-FFF)

or

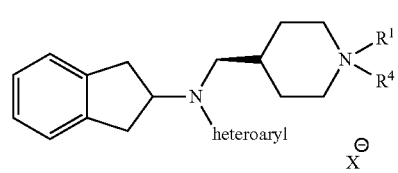
(II-FFFF)

In still a further embodiment, the compound is of formula (I-G), (I-GG), or (II-G), wherein $R^1$, $R^4$, A, X, m, and n are defined herein. In one example, m is 2 or 3.

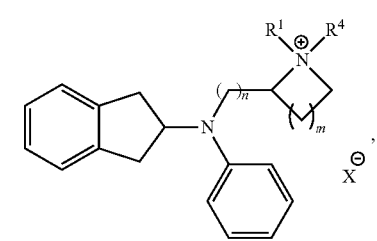
(I-G)

(I-GG)

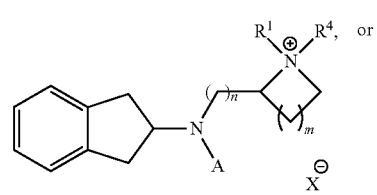
(II-G)

In another embodiment, the compound is of formula (I-H), wherein $R^1$, $R^4$, X, m, and n are defined herein. In one example, m is 2 or 3.

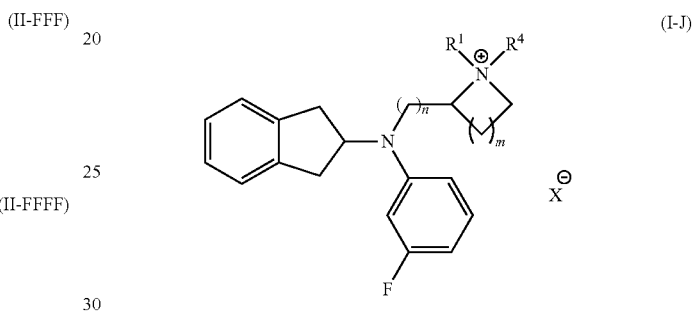
(I-H)

In still a further embodiment, the compound is of formula (I-J), wherein $R^1$, $R^4$, X, m, and n are defined herein. In one example, m is 2 or 3.

(I-J)

In still a further embodiment, the compound is of formula (I-K), wherein $R^1$, $R^4$, X, m, and n are defined herein. In one example, m is 2 or 3.

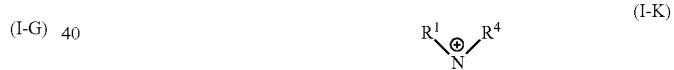
(I-K)

In yet another embodiment, the compound is of formula (I-L) or (II-L), wherein $R^1$, $R^4$, X, m, and n are defined herein. In one example, m is 2 or 3.

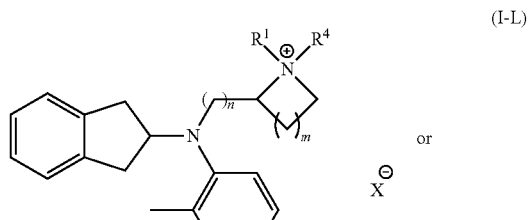
(I-L)

or

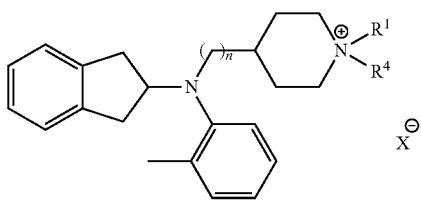
(II-L)

In a further embodiment, the compound is of formula (I-M) or (II-M), wherein $R^1$, $R^4$, X, m, and n are defined herein. In one example, m is 2 or 3.

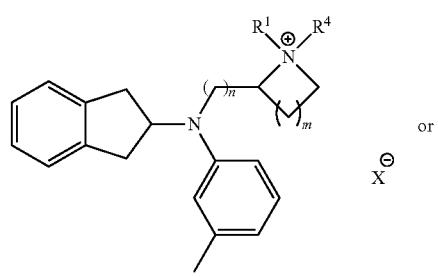
(I-M)

or

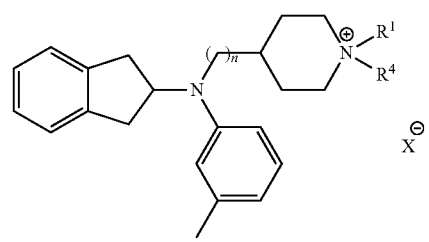
(II-M)

In yet a further embodiment, the compound is of formula (I—N) or (II-N) wherein $R^1$, $R^4$, X, m, and n are defined herein. In one example, m is 2 or 3.

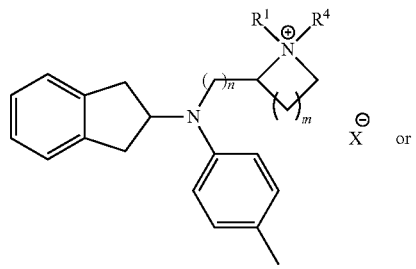
(I-N)

or

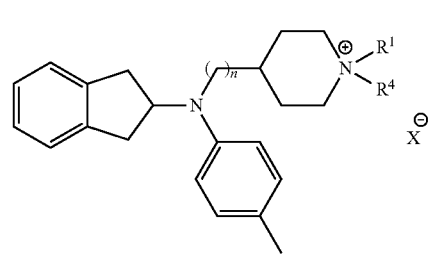
(II-N)

In another embodiment, the compound is of formula (I-O), (I-OO), (II-O), or (II-OO), wherein $R^1$, $R^4$, X, m, and n are defined herein. In one example, m is 2 or 3.

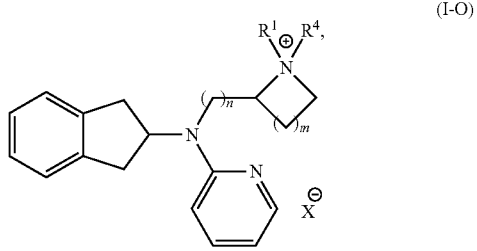
(I-O)

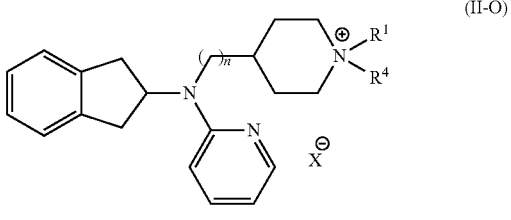
(II-O)

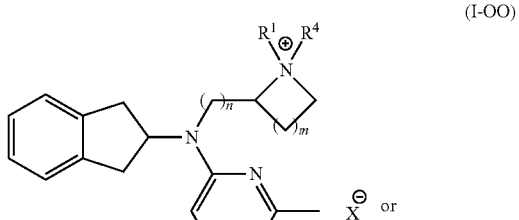
(I-OO)

or

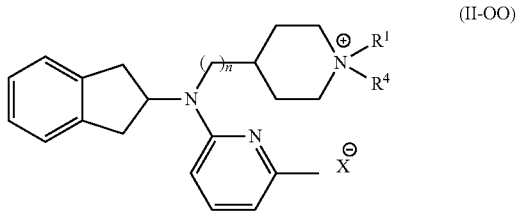
(II-OO)

In still a further embodiment, the compound is of formula (I-P) or (II-P) wherein $R^1$, $R^4$, X, m, and n are defined herein. In one example, m is 2 or 3.

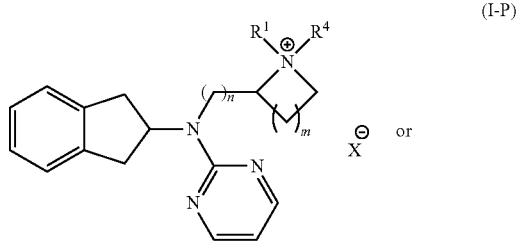
(I-P)

or

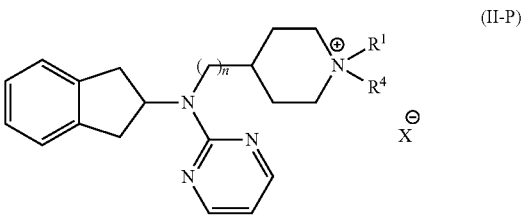
(II-P)

In yet another embodiment, the compound is of formula (I-Q) or (II-Q) wherein $R^1$, $R^4$, X, m, and n are defined herein. In one example, m is 2 or 3.

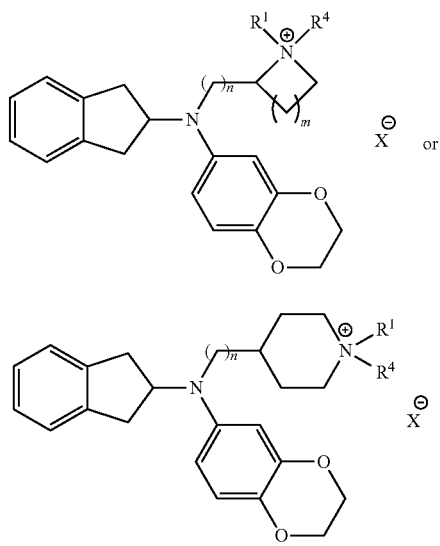

In a further embodiment, the compound is of formula (I-R) or (II-R) wherein $R^1$, $R^4$, X, m, and n are defined herein. In one example, m is 2 or 3.

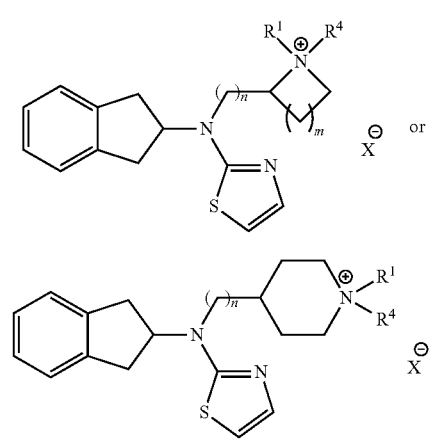

In still a further embodiment, the compound is of formula (I-S) or (II-S) wherein $R^1$, $R^4$, X, m, and n are defined herein. In one example, m is 2 or 3.

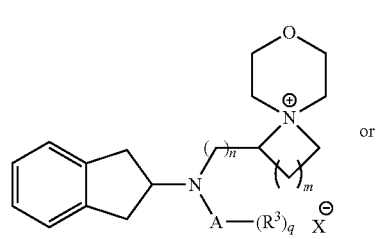

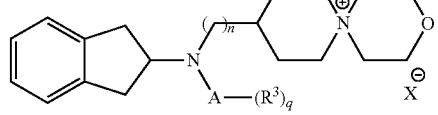

In yet another embodiment, the compound is of formula (I-T) or (II-T) wherein $R^1$, $R^4$, X, m, and n are defined herein. In one example, m is 2 or 3.

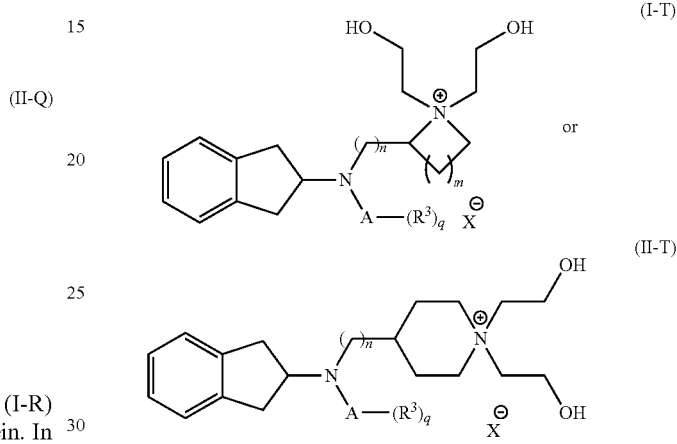

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched. In one embodiment, an alkyl contains 1 to 6 (inclusive) carbon atoms. In another embodiment, an alkyl contains 1 to 5 (inclusive) carbon atoms. In a further embodiment, an alkyl contains 1 to 4 (inclusive) carbon atoms. In yet another embodiment, an alkyl contains 1 to 3 (inclusive) carbon atoms. In still a further embodiment, an alkyl contains 1 or 2 carbon atoms. Examples of alkyl groups that are hydrocarbon chains include, but are not limited to, methyl, ethyl, propyl, butyl, pentyl, and hexyl, where all isomers of these examples are contemplated.

Alkyl groups may also consist of or contain a cyclic alkyl radical, i.e., "carbocyclic ring". Examples of carbocyclic rings include, but are not limited to, cyclopropyl, cyclobutyl, cyclopentyl, cyclohexyl, and the like. In one embodiment, the carbocyclic ring is 3- to 6-membered. In a further embodiment, the carbocyclic ring is 3- to 5-membered. In still a further embodiment, the carbocyclic ring is 4- to 6-membered. In another embodiment, the carbocyclic ring is 3- or 4-membered, i.e., cyclopropyl or cyclobutyl. Unless specifically noted, the alkyl groups are unsubstituted, i.e., they contain carbon and hydrogen atoms only. However, when the alkyl group or carbocyclic ring is substituted, it is prefaced with the term "optionally substituted" or "substituted". The optional substituents of the alkyl groups or carbocyclic rings include, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkyl-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH ($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl), or NHC(O)$NH_2$.

"Alkenyl" refers to hydrocarbon chain which is straight or branched and contains at least one degree of unsaturation (i.e., with one or more carbon-carbon double bonds), or to a hydrocarbon group that consists of or contains a cyclic alkenyl radical. Each alkenyl double bond may exist in the E or Z conformation. In one embodiment, an alkenyl contains 2 to about 6 (inclusive) carbon atoms or integers or ranges there between. In another embodiment, an alkenyl contains 2 to 5 (inclusive) carbon atoms. In a further embodiment, an alkenyl contains 2 to 4 (inclusive) carbon atoms. In yet another embodiment, an alkenyl contains 2 or 3 carbon atoms. An alkenyl contains at least 1 double bond. In one embodiment, the alkenyl may contain 1 to 3 double bonds, or integers there between. Examples of alkenyl hydrocarbon chain include, but are not limited to, ethene, propene, butene, pentene and hexene. Examples of alkenyl that consist of or contain a cyclic alkenyl radical include, but are not limited to, cyclopentene, and cyclohexene. An alkenyl can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkynyl" refers to a hydrocarbon chain which is straight or branched chain and contains at least one degree of unsaturation, i.e., with one or more carbon-carbon triple bond. In one embodiment, an alkynyl contains 2 to about 6 (inclusive) carbon atoms or integers or ranges there between. In another embodiment, an alkynyl contains 2 to 5 (inclusive) carbon atoms. In a further embodiment, an alkynyl contains 2 to 4 (inclusive) carbon atoms. In yet another embodiment, an alkynyl contains 2 or 3 carbon atoms. An alkynyl contains at least 1 triple bond. In one embodiment, the alkynyl may contain 1 to 3 triple bonds, or integers there between. Examples of alkynyl include, but are not limited to, ethyne, propyne, butyne, pentyne, and hexyne. An alkynyl can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkoxy" refers to ∼O(alkyl), where the alkyl is optionally substituted and is defined above. In one embodiment, an alkoxy contains 1 to 6 (inclusive) carbon atoms or integers or ranges there between. In another embodiment, an alkoxy contains 1 to 5 (inclusive) carbon atoms or ranges there between. In a further embodiment, an alkoxy contains 1 to 4 (inclusive) carbon atoms. In yet another embodiment, an alkoxy contains 1 to 3 (inclusive) carbon atoms. In still a further embodiment, an alkoxy contains 1 or 2 carbon atoms. Examples of alkoxy include, but are not limited to, methoxy, ethoxy, propoxy, and butoxy. The alkyl radical of an alkoxy group can be unsubstituted or substituted as defined above for "alkyl".

"Alkynyloxy" refers to ∼O(alkynyl), where the alkynyl is optionally substituted and is defined above. Examples of alkynyloxy include, but are not limited to, propynyloxy, butynyloxy, pentynyloxy, and hexynyloxy.

"Heterocyclyloxy" refers to ∼O(heterocycle), where the heterocycle is optionally substituted and is defined below.

"Heteroaryloxy" refers to ∼O(heteroaryl), where the heteroaryl is optionally substituted and is defined below.

"Aryl" refers to an aromatic hydrocarbon group containing carbon atoms. In one embodiment, the aryl contains 6 to 10 carbon atoms, i.e., 6-, 7-, 8-, 9- or 10-membered. In another embodiment, aryl is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Halogen" refers to F, Cl, Br and I.

The term "heteroatom" refers to a sulfur, nitrogen, or oxygen atom.

"Heteroaryl" refers to a monocyclic aromatic 5- or 6-membered ring containing at least one ring heteroatom. In one embodiment, the heteroaryl contains 1 to 5 carbon atoms (inclusive) or integers or ranges there between. In a further embodiment, the heteroaryl contains 2 to 5 carbon atoms (inclusive). In another embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In yet a further embodiment, the bicyclic heteroaryl is a pyridine fused to a 5- or 6-membered monocyclic heteroaryl. In still another embodiment, the heteroaryl ring has 1 or 2 nitrogen atoms in the ring. In a further embodiment, the heteroaryl ring has 1 nitrogen atom and 1 oxygen atom. In yet another embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, pyrazole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), NHSO$_2$($C_1$ to $C_6$ alkyl), N($C_1$ to $C_6$ alkyl)SO$_2$($C_1$ to $C_6$ alkyl), $NH_2$, NH(aryl), N($C_1$ to $C_6$ alkyl)($C_1$ to $C_6$ alkyl) or NHC(O)$NH_2$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges there between. In a further embodiment, the heterocycle contains 4 to 7 carbon atoms (inclusive). In another embodiment, the heterocycle contains 4 to 6 carbon atoms (inclusive). In still a further embodiment, the heterocycle contains 5 or 6 carbon atoms (inclusive). Examples of heterocycles include, but are not limited to, aziridine, oxirane, thiirane, morpholine, thiomorpholine, pyrroline, pyrrolidine, azepane, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In yet another embodiment, the heterocycle contains 1 or 2 nitrogen atoms, 3 to 6 carbon atoms, and 1 oxygen atom. In a further embodiment, the heterocycle is 5- to 8-membered. In another embodiment, the heterocycle is 5-membered. In still a further embodiment, the heterocycle is 6-membered. In yet another embodiment, the heterocycle is 8-membered. A heterocycle may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), NHSO$_2$($C_1$ to $C_6$ alkyl), N($C_1$ to $C_6$ alkyl)SO$_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkylthio" refers to ~S(alkyl) where the alkyl is optionally substituted and is defined above. In one embodiment, an alkylthio contains 1 to 6 (inclusive) carbon atoms or integers or ranges therebetween. Examples of alkylthio include, but are not limited to, $SCH_2CH_3$, $SCH_2CH_2CH_3$, $SCH_2CH_2CH_3$, $SCH_2CH_2CH_2CH_3$, $SCH_2CH_2CH_2CH_3$ and $SCH_2CH_2CH_2CH_3$.

"Heteroarylthio" refers to ~S(heteroaryl) where the heteroaryl is optionally substituted and is defined below.

"Alkylsulfonyl" refers to ~$SO_2$(alkyl) where the alkyl is optionally substituted and defined above. Examples of alkylsulfonyl include, but are not limited to, $CH_3SO_2$, $CH_3CH_2CH_2SO_2$, $CH_3CH(CH_3)SO_2$, $CH_3CH_2CH_2CH_2SO_2$, $CH_3CH(CH_3)CH_2SO_2$, $(CH_3)_3CSO_2$, and the like.

"Alkynylsulfonyl" refers to ~$SO_2$(alkynyl) where the alkynyl is optionally substituted and defined above. Examples of alkynylsulfonyl include, but are not limited to, CH≡C$SO_2$, CH≡CHCH$_2$SO$_2$, and the like.

"Heterocyclesulfonyl" refers to ~$SO_2$(heterocycle) where the heterocycle is optionally substituted and defined above.

"Alkylamino" refers to an NH or N group, the nitrogen atom of the group being attached to 1 or 2 alkyl substituents, respectively, wherein the alkyl is optionally substituted and defined above. The alkylamino is bound through the nitrogen atom of the group. In one embodiment, alkylamino refers to ~NH(alkyl). In another embodiment, alkylamino refers to ~N(alkyl)(alkyl), i.e., a "dialkylamino". In a further embodiment, alkylamino refers to ~N($C_1$ to $C_6$ alkyl)($C_1$ to $C_6$ alkyl). In yet another embodiment, alkylamino refers to ~N(alkyl)(heterocycle). In still a further embodiment, alkylamino refers to ~N(alkyl)(aryl). In another embodiment, alkylamino refers to ~N(alkyl)(heteroaryl). In yet a further embodiment, alkylamino refers to ~N(alkyl)(alkenyl). When the nitrogen atom is bound to two alkyl groups, each alkyl group may be independently selected. In another embodiment, two alkyl groups on the nitrogen atom may be taken together with the nitrogen to which they are attached to form a 3- to 4-membered nitrogen-containing heterocycle where up to two of the carbon atoms of the heterocycle can be replaced with N(H), N($C_1$ to $C_6$ alkyl), N(aryl), N(heteroaryl), O, S(O), or S(O)$_2$. Examples of alkylamino include, but are not limited to N($CH_3$)$_2$, N($CH_2CH_3$)($CH_3$), N($CH_2CH_3$)$_2$, N($CH_2CH_2CH_3$)$_2$, N($CH_2CH_2CH_3$)$_2$, N(CH($CH_3$)$_2$)($CH_3$), and the like.

"Arylamino" refers to an NH or N group, the nitrogen atom of the group being attached to 1 or 2 aryl substituents, respectively, wherein the aryl is optionally substituted and defined above. The arylamino is bound through the nitrogen atom of the group. In one embodiment, arylamino refers to ⁓NH(aryl). In another embodiment, arylamino refers to ⁓N(aryl)(aryl), i.e., a "diarylamino". When the nitrogen atom is bound to two aryl groups, each aryl may be independently selected.

"Alkylcarbonylamino" refers to ⁓NHC(O)(alkyl) or ⁓N(alkyl)C(O)(alkyl) where the alkyl groups are independently defined and independently optionally substituted as described above. Examples of alkylcarbonylamino include, but are not limited to, $CH_3CONH$, $CH_3CH_2CONH$, $CH_3CH_2CH_2CONH$, $CH_3CH(CH_3)CONH$, and the like.

"Arylcarbonylamino" refers to ⁓NHC(O)(aryl) where the aryl group is defined and optionally substituted as described above.

"Heteroarylcarbonylamino" refers to ⁓NHC(O)(heteroaryl) where the heteroaryl group is defined and optionally substituted as described above.

"Alkylsulfonylamino" refers to ⁓NHSO$_2$(alkyl) where the alkyl group is defined and optionally substituted as described above. Examples of alkylsulfonylamino include, but are not limited to $CH_3SO_2NH$, $CH_3CH_2SO_2NH$, $CH_3CH_2CH_2SO_2NH$, $CH_3CH(CH_3)SO_2NH$, and the like.

"Ester" refers to ⁓C(O)O(alkyl), which is bound through the carbon atom. The alkyl group is defined and optionally substituted as described above. Examples of ester include, without limitation, $C(O)OCH_3$, $C(O)O(CH_2CH_3)$, $C(O)O(CH_2CH_2CH_3)$, $C(O)(0)(CH_2CH_2CH_3)$, and the like.

"Carbamate" refers to ⁓NHC(O)O(alkyl) or ⁓N(alkyl)C(O)O(alkyl) where the alkyl groups are independently defined and independently optionally substituted as described above. Examples of carbamate include, but are not limited to, $NHC(O)OCH_3$, $NHC(O)OCH_2CH_3$, $NHC(O)OCH_2CH_2CH_3$, $NHC(O)OCH_2CH_2CH_2CH_3$, and the like.

"Urea" refers to a group having a ⁓NHC(O)NH⁓ where one of the nitrogen atoms is bound to an alkyl or heteroaryl group. The alkyl or heteroaryl groups are defined and optionally substituted as described above. Examples of urea include, without limitation, NHC(O)NHCH$_3$, NHC(O)NHCH$_2$CH$_3$, NHC(O)NHCH$_2$CH$_2$CH$_3$, NHC(O)NHCH$_2$CH$_2$CH$_2$CH$_3$, and the like.

"Alkylaminocarbonyl" refers to ⁓C(O)NH(alkyl) or ⁓C(O)N(alkyl)(alkyl) where the alkyl groups are independently defined and independently optionally substituted as described above. Examples of alkylaminocarbonyl include, but are not limited to, $CH_3NHCO$, $CH_3CH_2NHCO$, $CH_3CH_2CH_2NHCO$, $CH_3CH(CH_3)NHCO$, and the like.

"Arylaminocarbonyl" refers to ⁓C(O)NH(aryl) or ⁓C(O)N(aryl)(aryl) where the aryl groups are independently defined and independently optionally substituted as described above.

"Heteroarylaminocarbonyl" refers to ⁓C(O)NH(heteroaryl) or ⁓C(O)N(heteroaryl)(heteroaryl) where the heteroaryl groups are independently defined and independently optionally substituted as described above.

"Heterocycleaminocarbonyl" refers to ⁓C(O)NH(heterocycle) or ⁓C(O)N(heterocycle)(heterocycle) where the heterocycle groups are independently defined and independently optionally substituted as described above.

"Alkylaminosulfonyl" refers to ⁓SO$_2$NH(alkyl) or ⁓SO$_2$N(alkyl)$_2$ where the alkyl groups are independently defined and independently optionally substituted as described above. Examples of alkylaminosulfonyl include, but are not limited to, $SO_2NHCH_3$, $SO_2NHCH_2CH_3$, $SO_2NHCH_2CH_3CH_3$, $SONHC(CH_3)CH_3$, $SO_2N(CH_3)_2$, $SO_2NH(CH_3)(CH_2CH_3)$, and the like.

"Alkynylaminosulfonyl" refers to ⁓SO$_2$NH(alkynyl) where the alkynyl group is defined and optionally substituted as described above. Examples of alkynylaminosulfonyl include, but are not limited to, CH≡CNHSO$_2$, CH≡CCH$_2$NHSO$_2$, and the like.

"Heteroarylaminosulfonyl" refers to ⁓SO$_2$NH(heteroaryl) or ⁓SO$_2$N(heteroaryl)$_2$ where the heteroaryl groups are independently defined and independently optionally substituted as described above.

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term % enantiomeric excess (% ee) as used herein is recognized by those skilled in the art to refer to the enantiomeric purity of the sample, i.e., the percentage of one enantiomer over other enantiomers in the sample. In one embodiment, a "high" % ee of at least 90, at least 91, at least 92, at least 93, at least 94, at least 95, at least 96, at least 97, at least 98, or 100% may be obtained.

The terms "comprise", "comprises", and "comprising" are to be interpreted inclusively rather than exclusively. The terms "consist", "consisting", and its variants, are to be interpreted exclusively, rather than inclusively.

As used herein, the term "about" means a variability of 10% from the reference given, unless otherwise specified.

Methods useful for making the compounds of formulae (I) and (II) are set forth in the Examples below and generalized in Schemes 1-27. One of skill in the art will recognize that Schemes 1-27 can be adapted to produce the other compounds of formulae (I) and (II) according to the present invention.

The following methods outline the synthesis of the compounds of formulae (I) and (II). The following examples are presented to illustrate certain embodiments of the present invention, but should not be construed as limiting the scope of this invention.

Scheme 1

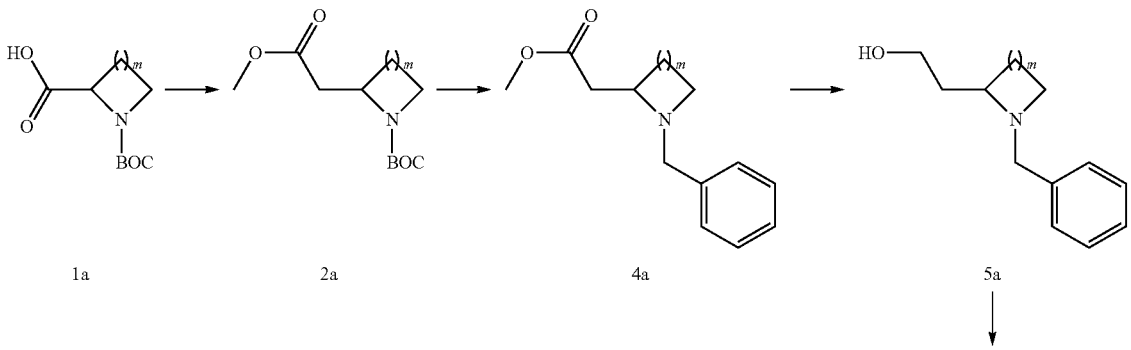

1a      2a      4a      5a

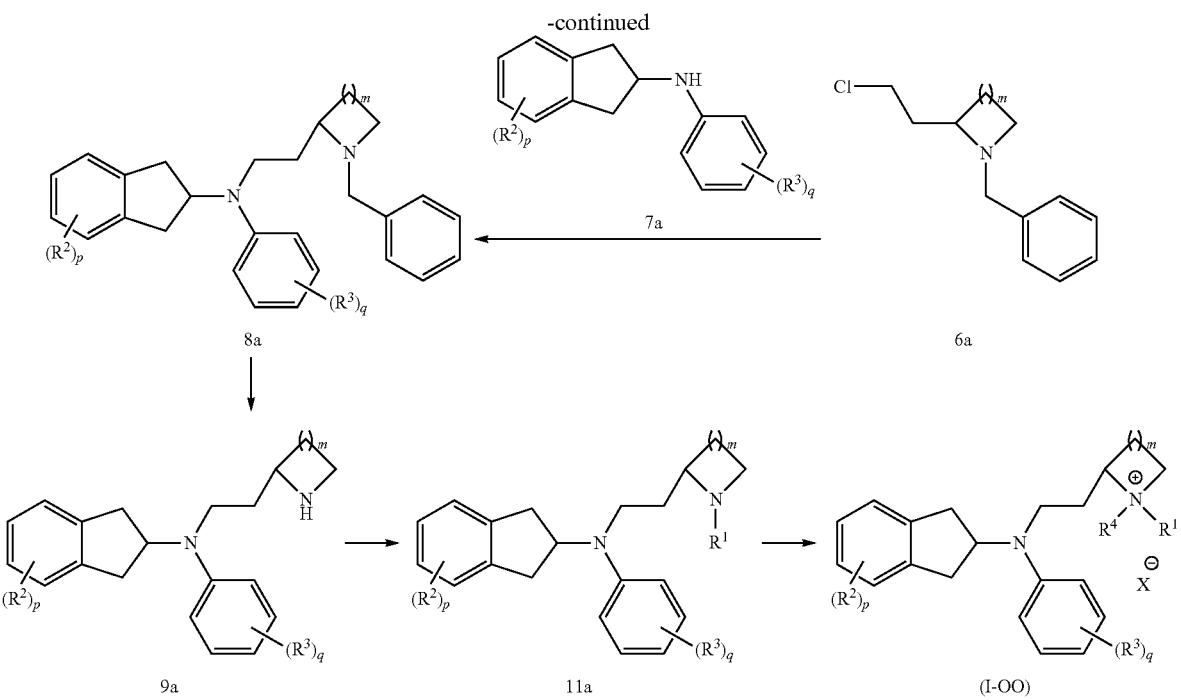

In one aspect, compounds of formula (I-OO) are prepared using the synthetic steps provided in Scheme 1, wherein $R^1$-$R^4$, X, m, q, and p are defined herein. In this scheme, an acid 1a bearing a protecting group such as a butoxycarbonyl (BOC) group, is converted to the corresponding ester 2a. In one embodiment, ester 2a is formed using isobutyl chloroformate, diazomethane, and silver benzoate or silver oxide. In another embodiment, protected acid 1a is N-Boc-azetidine-2-carboxylic acid (BOC Sciences, Shirley, N.Y.), Boc-pyrrolidine-2-carboxylic acid, Boc-L-pipecolic acid, or N-Boc-azepane-2-carboxylic acid (AstaTech, Inc., Bristol, Pa.). Ester 2a is then converted to benzylamine 4a. In one embodiment, the conversion is performed using trifluoroacetic acid, followed by benzyl bromide. Compound 4a is then reduced to the corresponding alcohol 5a. In one embodiment, the reduction is performed using diisobutyl aluminum hydride (DIBAL-H) or lithium aluminum hydride (LAH). Alcohol 5a is then converted to the corresponding chloride 6a using a suitable chlorinating agent. In one embodiment, the chlorinating agent is thionyl chloride, phosphorus oxychloride, phosphorus pentachloride, or a combination of carbontetrachloride and triphenylphosphine. Chloride 6a is then coupled with substituted aminoindane 7a to provide compound 8a. In one embodiment, chloride 6a is coupled with aminoindane 7a in the presence of $NaNH_2$, potassium t-butoxide, sodium t-butoxide, or butyl lithium, among others. The benzyl group of compound 8a is then removed via hydrogenation to provide compound 9a. In one embodiment, the hydrogenation is performed using ammonium formate, hydrogen gas and Pd/C, or $Pd(OH)_2$. The N-atom of the heterocyclic ring of compound 9a is then substituted to provide compound 11a. In one embodiment, the N-atom of the heterocyclic ring of compound 9a is substituted with an $R^1$ group. In another embodiment, the substitution is an alkylation. In a further embodiment, the alkylation is performed using an aldehyde such as propanaldehyde, acetaldehyde, or formaldehyde, and $NaCNBH_3$. The same N-atom is further substituted with a $R^4$ group to provide a compound of formula (I-OO). In one embodiment, the further substitution is an alkylation. In another embodiment, the further substitution is performed using an alkyl halide, alkyl triflate, or alkyl besylate. In a further embodiment, the further substitution is performed using 1-iodopropane, ethyl iodide, methyl iodide, methyl triflate, ethyl triflate, propyl triflate, or methyl besylate, among others.

Scheme 2

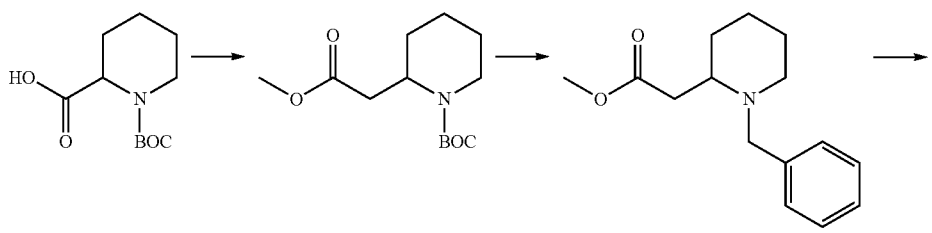

-continued

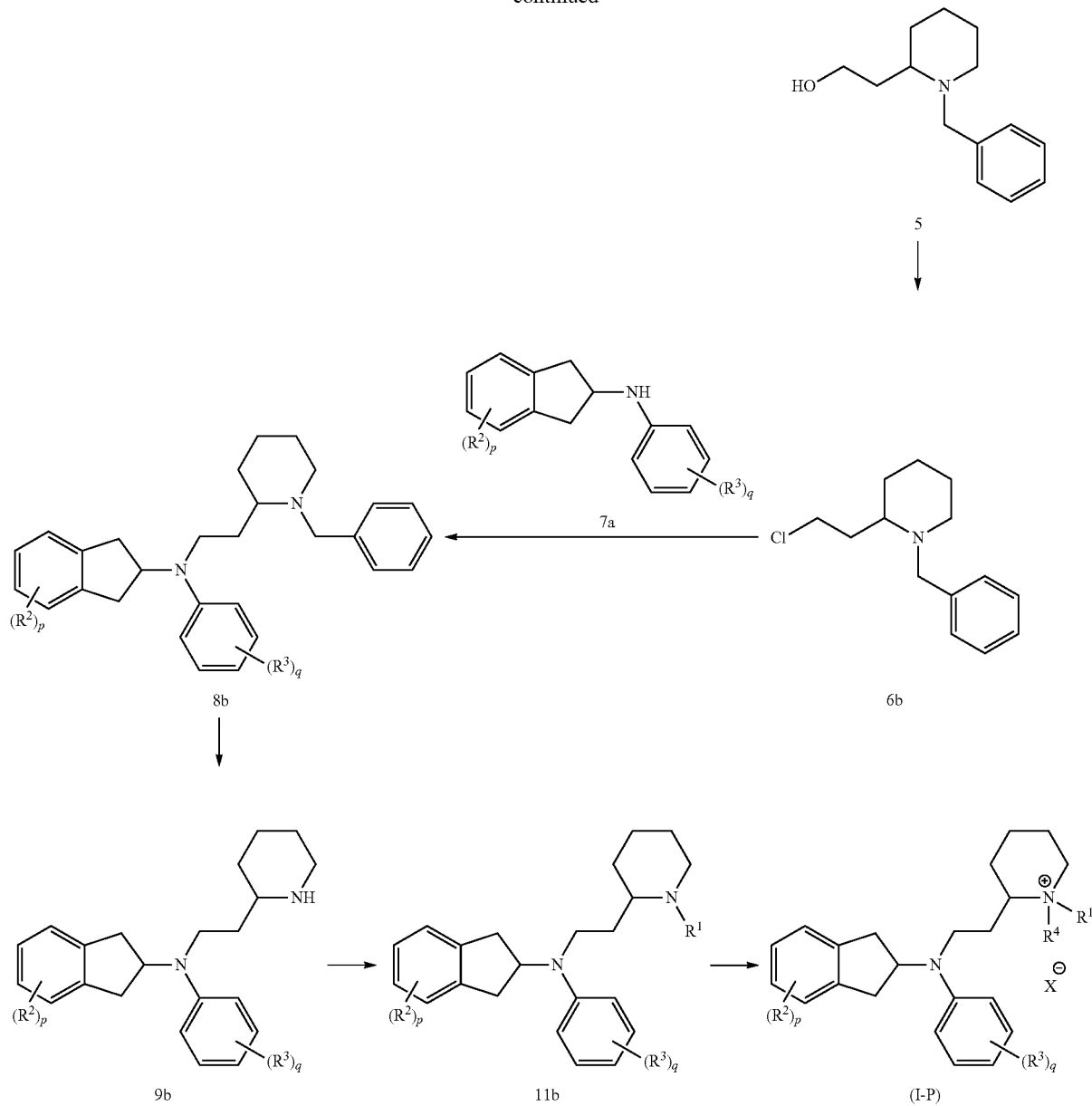

Scheme 2, wherein R¹-R⁴, X, q, and p are defined herein, depicts the synthesis of compounds of formula (I-P). In this scheme, Boc-L-pipecolic acid 1 is converted to corresponding ester compound 2, i.e., (S)-2-(methoxycarbonylmethyl) piperidine-1-carboxylic acid tert-butyl ester. In one embodiment, (S)-2-(Methoxycarbonylmethyl)piperidine-1-carboxylic acid tert-butyl ester is formed using isobutyl chloroformate, diazomethane, and silver benzoate. (S)-2-(Methoxycarbonylmethyl)piperidine-1-carboxylic acid tert-butyl ester is then converted to benzylamine 4, i.e., (S)-2-(1-benzyl-piperidin-2-yl)acetic acid methyl ester. In one embodiment, the conversion is performed using trifluoroacetic acid, followed by treatment with benzyl bromide. Compound 4 is then reduced to the corresponding alcohol 5, i.e., (S)-2-(1-benzyl-piperidin-2-yl)-ethanol. In one embodiment, the reduction is performed using diisobutyl aluminum hydride (DIBAL-H). Alcohol 5 is then converted to the corresponding chloride 6, i.e., (S)-1-benzyl-2-(2-chloroethyl)-piperidine, using thionyl chloride. Chloride 6 is then coupled with aminoindane 7a to provide compound 8b. In one embodiment, chloride 6a is coupled with aminoindane 7a in the presence of $NaNH_2$. The benzyl group of compound 8b is then removed via hydrogenation to provide compound 9b. In one embodiment, the hydrogenation is performed using ammonium formate and Pd/C. The N-atom of the heterocyclic ring of compound 9b is then substituted to provide compound 11b. In one embodiment, the N-atom of the heterocyclic ring of compound 9b is substituted with an R¹ group. In another embodiment, the substitution is an alkylation. In a further embodiment, the alkylation is performed using propanaldehyde and $NaCNBH_3$. The same N-atom of compound 11b is further substituted with a R⁴ group to provide a compound of formula (I-P). In one embodiment, the further substitution is an alkylation. In another embodiment, the further substitution is performed using an alkyl halide. In a further embodiment, the further substitution is performed using 1-iodopropane.

Scheme 3

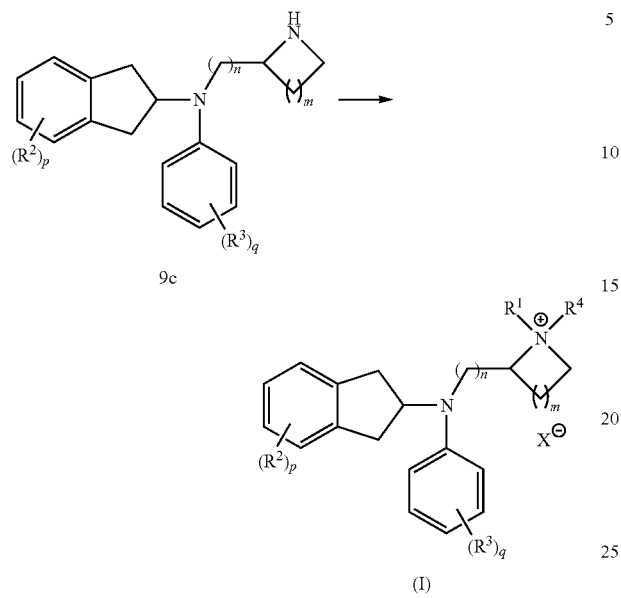

9c (I)

Scheme 3 depicts a direct conversion of compound 9c to a compound of formula (I), where $R^1$ and $R^4$ are the same and $R^1$-$R^4$, m, n, p, q, and X are defined herein. By doing so, the generation of intermediate compound 11a or 11b can be circumvented. This conversion is performed using at least 2 equivalents of $R^1X$ or $R^4X$, where X is iodine, bromine, or chlorine. In one embodiment, at least 5 equivalents, at least 10 equivalents, at least 20 equivalents, at least 30 equivalents, at least 40 equivalents, at least 50 equivalents, at least 60 equivalents, at least 70 equivalents, at least 80 equivalents, at least 90 equivalents, and at least 100 equivalents of $R^1X$ or $R^4X$ are utilized. In another embodiment, the conversion is performed using an alkylating agent. In a further embodiment, the conversion is performed using methyl iodide, ethyl iodide, propyl iodide, benzyl iodide, methyl triflate, ethyl triflate, propyl triflate, or methyl besylate.

Scheme 4

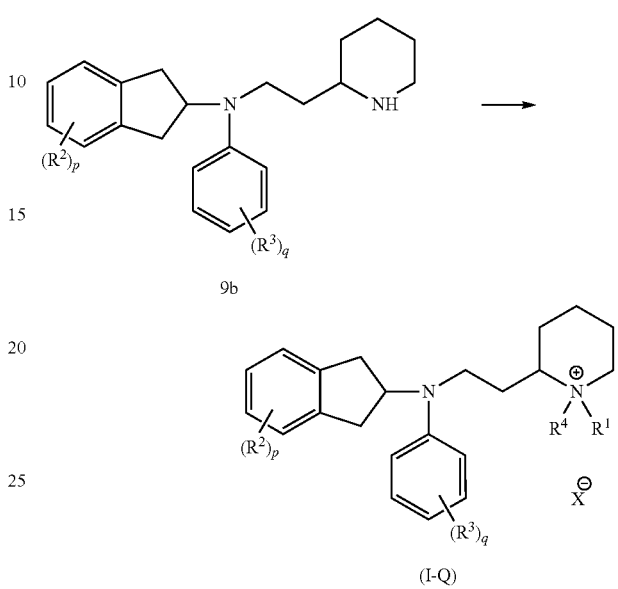

9b (I-Q)

Similarly, scheme 4 depicts a direct conversion of compound 9b to a compound of formula (I-Q), where $R^1$ and $R^4$ are the same and $R^1$-$R^4$, p, q, and X are defined herein. This conversion is performed using at least 2 equivalents of $R^1X$ or $R^4X$, where X is iodine, bromine, or chlorine. In one embodiment, the conversion is performed using an alkylating agent. In a further embodiment, the conversion is performed using methyl iodide, ethyl iodide or propyl iodide.

Scheme 5

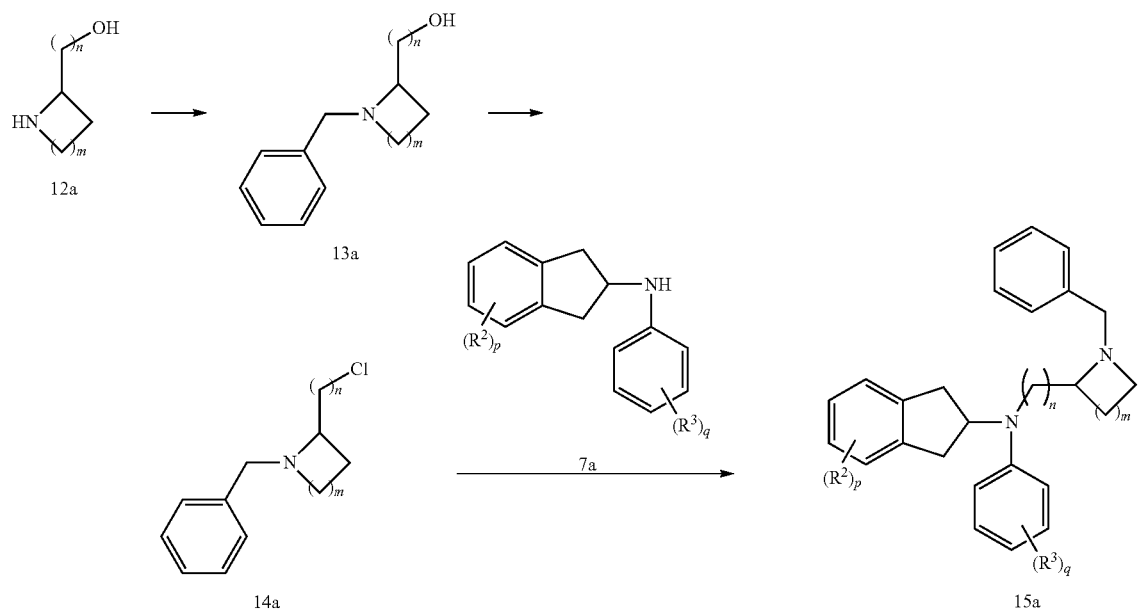

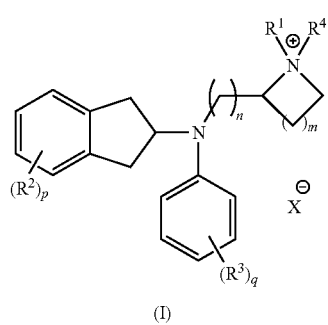

(I)

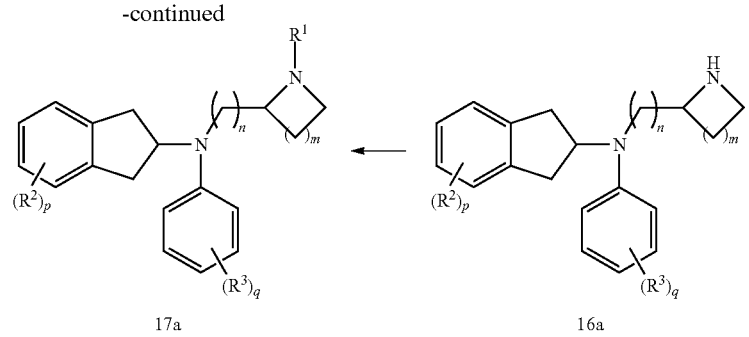

17a 16a

Compounds of formula (I), wherein $R^1$-$R^4$, m, n, p, q, and X are defined herein, may also be prepared according to the transformations noted in Scheme 5. The initial step of this scheme entails protecting the N-atom of a compound 12a to form protected compound 13a. In one embodiment, the N-atom of compound 12a is protected using an optionally substituted benzyl or carbamate group. In another embodiment, the N-atom of compound 12a is protected with a benzyl, p-methoxy benzyl, or BOC. In a further embodiment, the N-atom of compound 12a is protected using a benzyl halide such as benzyl bromide, p-methoxy benzyl bromide, or boc-anhydride. Compound 13a is then converted to chloride 14a using reagents and techniques known in the art. In one embodiment, compound 13a is chlorinated using thionyl chloride, phosphorus oxychloride, phosphorus pentachloride, or a combination of carbon tetrachloride, and triphenylphosphine. Compound 14a is then coupled with an aminoindane to form compound 15a. In one embodiment, compound 14a is coupled with aminoindane compound 7a to provide compound 15a. The N-atom of compound 15a is then deprotected using reagents and techniques standard in the art.

In one embodiment, the N-atom is deprotected using ammonium formate, hydrogen gas in the presence of a catalyst such as Pd—C, Pd(OH)$_2$, trifluoroacetic acid, or dioxane-HCl. Desirably, the deprotection is performed at elevated temperatures to provide compound 16a. The N-atom of compound 16a may then be $R^1$ substituted using reagents and techniques known by those of skill in the art to provide compound 17a. In one embodiment, the N-atom of compound 16a is $R^1$ substituted using an appropriately substituted aldehyde or alkyl halide to provide compound 17a. In one embodiment, the N-atom of compound 16a may be $R^1$ substituted using formaldehyde and NaCNBH$_3$. Compound 17a may then be further substituted at the N-atom with $R^4$ to provide a compound of formula (I). In one embodiment, the further substitution is an alkylation. In another embodiment, the further substitution is performed using an alkyl halide, alkyl triflate, or alkyl besylate, such as $R^4X$, where X is halogen, such as iodine, chlorine, or bromine, triflate, or besylate. In a further embodiment, the further substitution is performed using 1-iodopropane, ethyl iodide, methyl iodide, methyl triflate, ethyl triflate, propyl triflate, or methyl besylate.

Scheme 6

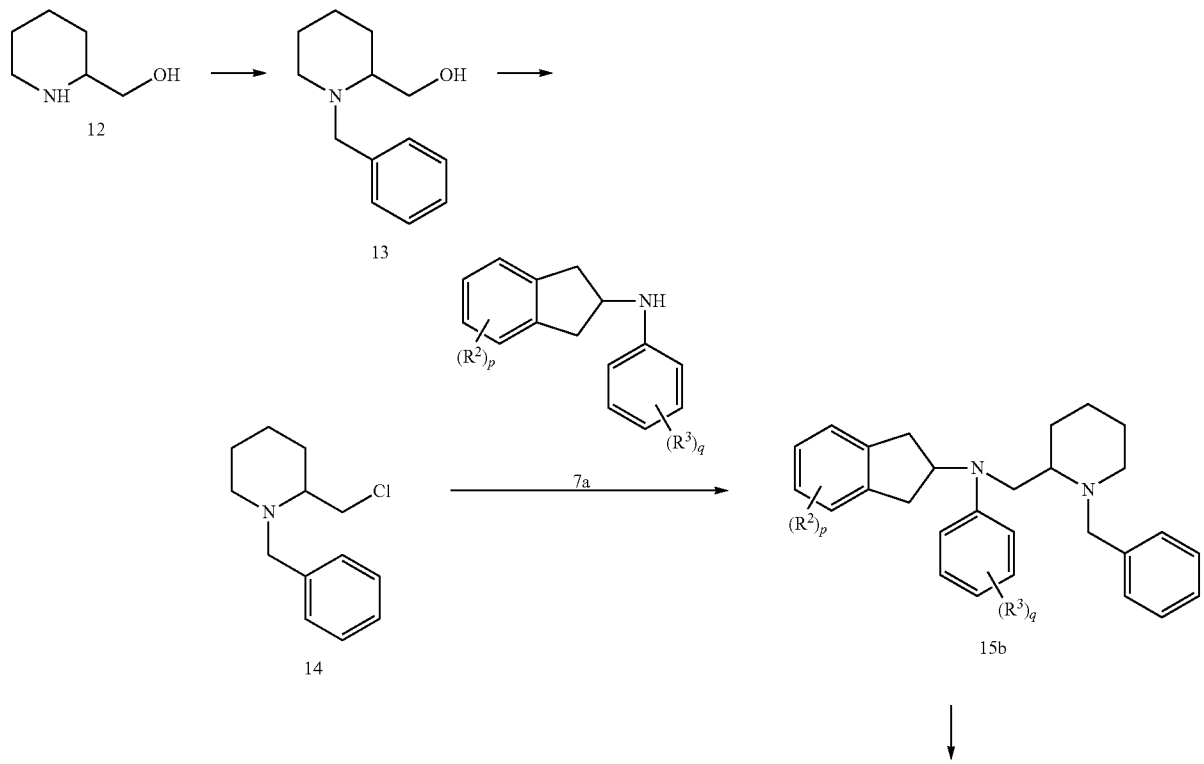

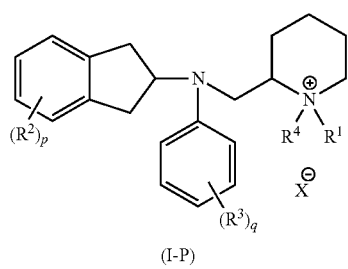 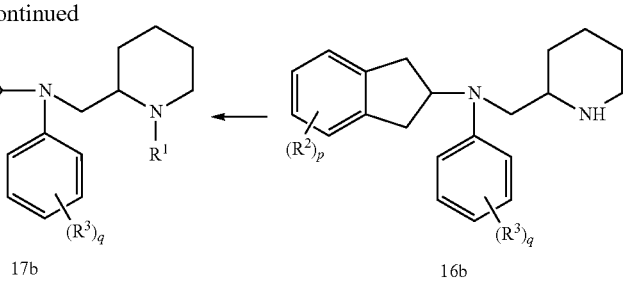

(I-P)  17b  16b

In a similar fashion, compounds of formula (I-P), wherein $R^1$-$R^4$, p, q, and X are defined herein, may be prepared according to the transformations noted in Scheme 6. The initial step includes protecting the N-atom of piperidine-2-methanol (12) to form protected (1-benzylpiperidin-2-yl)-methanol (13). In one embodiment, the N-atom of piperidine-2-methanol is protected using an optionally substituted benzyl group. In another embodiment, the N-atom of piperidine-2-methanol is protected with a benzyl group. In a further embodiment, the N-atom of piperidine-2-methanol is protected using a benzyl halide such as benzyl bromide. (1-Benzylpiperidin-2-yl)-methanol is then converted to 1-benzyl-2-(chloromethyl)piperidine (14) using reagents and techniques known in the art. In one embodiment, (1-benzylpiperidin-2-yl)-methanol is chlorinated using thionyl chloride. Compound 14 is then coupled with an aminoindane to form compound 15b. In one embodiment, compound 14 is coupled with aminoindane 7a to provide compound 15b. The N-atom of compound 15b is then deprotected using reagents and techniques standard in the art. In one embodiment, the N-atom is deprotected using ammonium formate in the presence of a catalyst such as Pd—C. Desirably, the deprotection is performed at elevated temperatures to provide compound 16b. The N-atom of compound 16b may then be $R^1$ substituted using reagents and techniques known by those of skill in the art to provide compound 17b. In one embodiment, the N-atom of compound 16b is $R^1$ substituted using an appropriately substituted aldehyde to provide compound 17b. In one embodiment, the N-atom of compound 16b may be $R^1$ substituted using formaldehyde. Compound 17b may then be further substituted at the N-atom with $R^4$ to provide a compound of formula (I-P). In one embodiment, the further substitution is an alkylation. In another embodiment, the further substitution is performed using an alkyl halide such as $R^4X$, where X is iodine, chlorine, or bromine. In a further embodiment, the further substitution is performed using 1-iodopropane.

-continued

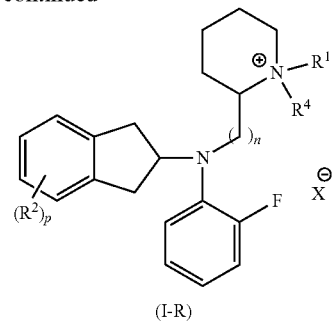

(I-R)

Scheme 7 illustrates the embodiment whereby a compound of formula (I-R) is formed from compound 9d, i.e., a compound of formula (I) when $R^3$ is F, p is 1, and $R^1$ and $R^4$ are the same and $R^1$, $R^2$, $R^4$, n, p, and X are defined herein. In this scheme, compound 9d is $R^1$ or $R^4$ substituted at the N-atom. In one embodiment, at least 2 equivalents of $R^1X$ or $R^4X$, where X is a leaving group such as iodine, chlorine, bromine, triflate, or besylate, are reacted with compound 9d. In another embodiment, at least 2 equivalents of an alkyl halide are reacted with compound 9d. In a further embodiment, at least 2 equivalents of methyl iodide, ethyl iodide, propyl iodide, methyl triflate, ethyl triflate, or propyl triflate are reacted with compound 9d.

Scheme 8

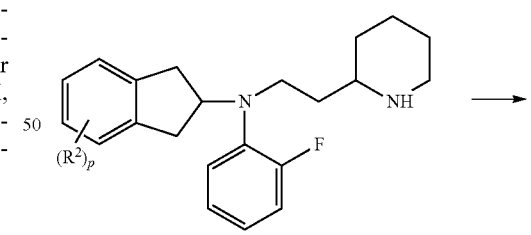

9e

Scheme 7

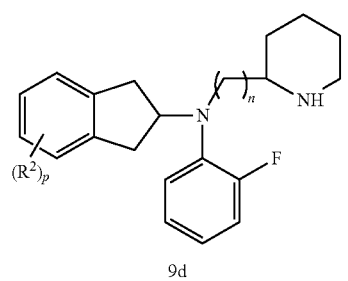

9d

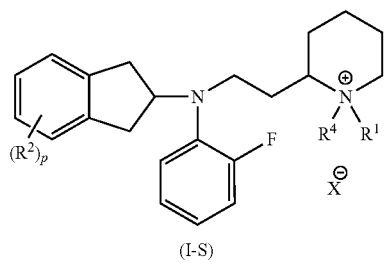

(I-S)

Scheme 8 provides a summary of the preparation of a compound of formula (I-S), wherein $R^1$, $R^2$, $R^4$, p, and X are defined herein from compound 9e. In this scheme, compound 9e is $R^1$ or $R^4$ substituted at the N-atom. In one embodiment, at least 2 equivalents of $R^1X$ or $R^4X$, where X is a leaving group such as iodine, chlorine, or bromine, are reacted with compound 9e. In another embodiment, at least 2 equivalents of an alkyl halide are reacted with compound 9e. In a further embodiment, at least 2 equivalents of methyl iodide, ethyl iodide, or propyl iodide are reacted with compound 9e.

formed using $R^4X$, wherein X is a leaving group such as iodine, chlorine, or bromine 1n a further embodiment, the $R^4$ substitution is performed using an alkyl halide such as methyl iodide, ethyl iodide, or propyl iodide. Doing so provides the compound of formula (I).

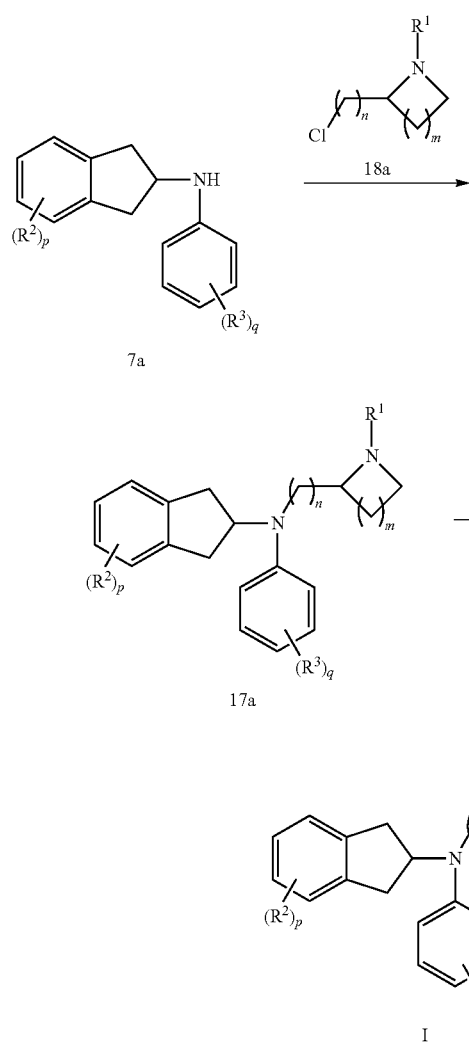

Scheme 9

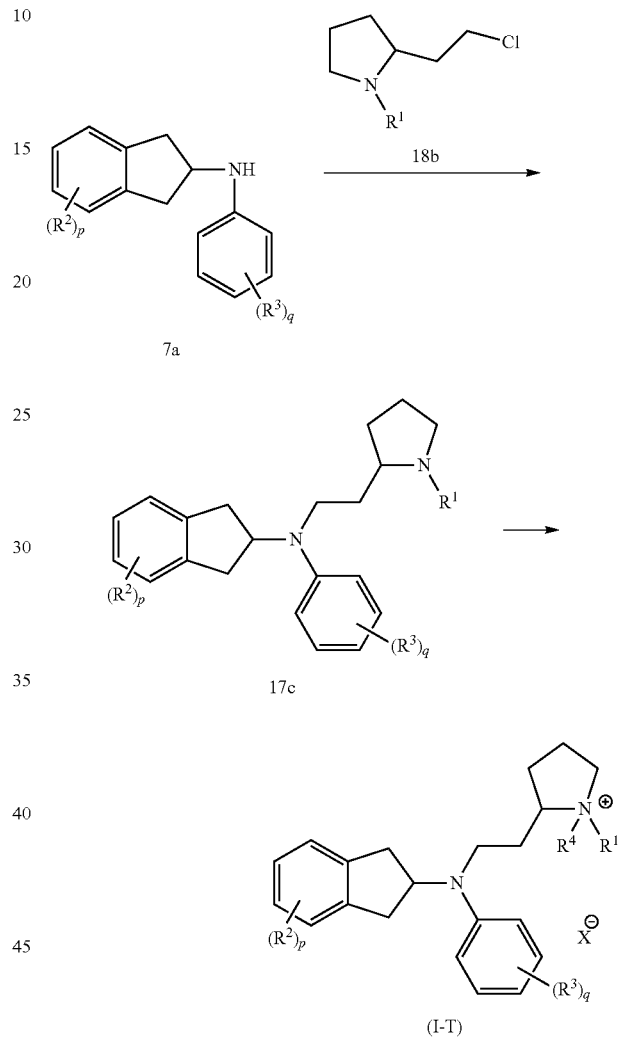

Scheme 10

Scheme 9 provides an alternate route to a compound of formula (I), where $R^1$ and $R^4$ are the same or different and $R^1$-$R^4$, m, n, p, q, and X are defined herein, via the use of reagent 18a. Specifically, compound 7a is reacted with compound 18a to provide compound 17a. In one embodiment, the reaction between compounds 7a and 18a is performed in the presence of sodamide, potassium t-butoxide, sodium t-butoxide, or butyl lithium. $R^4$ substitution of the N-atom may then be performed to provide a compound of formula (I). In one embodiment, the $R^4$ substitution is an alkylation at the N-atom. In another embodiment, the $R^4$ substitution is per- Scheme 10 provides an alternate route to a compound of formula (I-T), where $R^1$ and $R^4$ are the same or different and $R^1$-$R^4$, p, q, and X are defined herein, via the use of reagent 18b. Specifically, compound 7a is reacted with compound 18b to provide compound 17c. In one embodiment, the reaction between compounds 7a and 18b is performed in the presence of sodamide. $R^4$ substitution of the N-atom may then be performed to provide a compound of formula (I-T). In one embodiment, the $R^4$ substitution is an alkylation at the N-atom. In another embodiment, the $R^4$ substitution is performed using $R^4X$, wherein X is a leaving group such as iodine, bromine, or chlorine. In a further embodiment, the $R^4$ substitution is performed using an alkyl halide such as methyl iodide, ethyl iodide, or propyl iodide. Doing so provides the compound of formula (I-T).

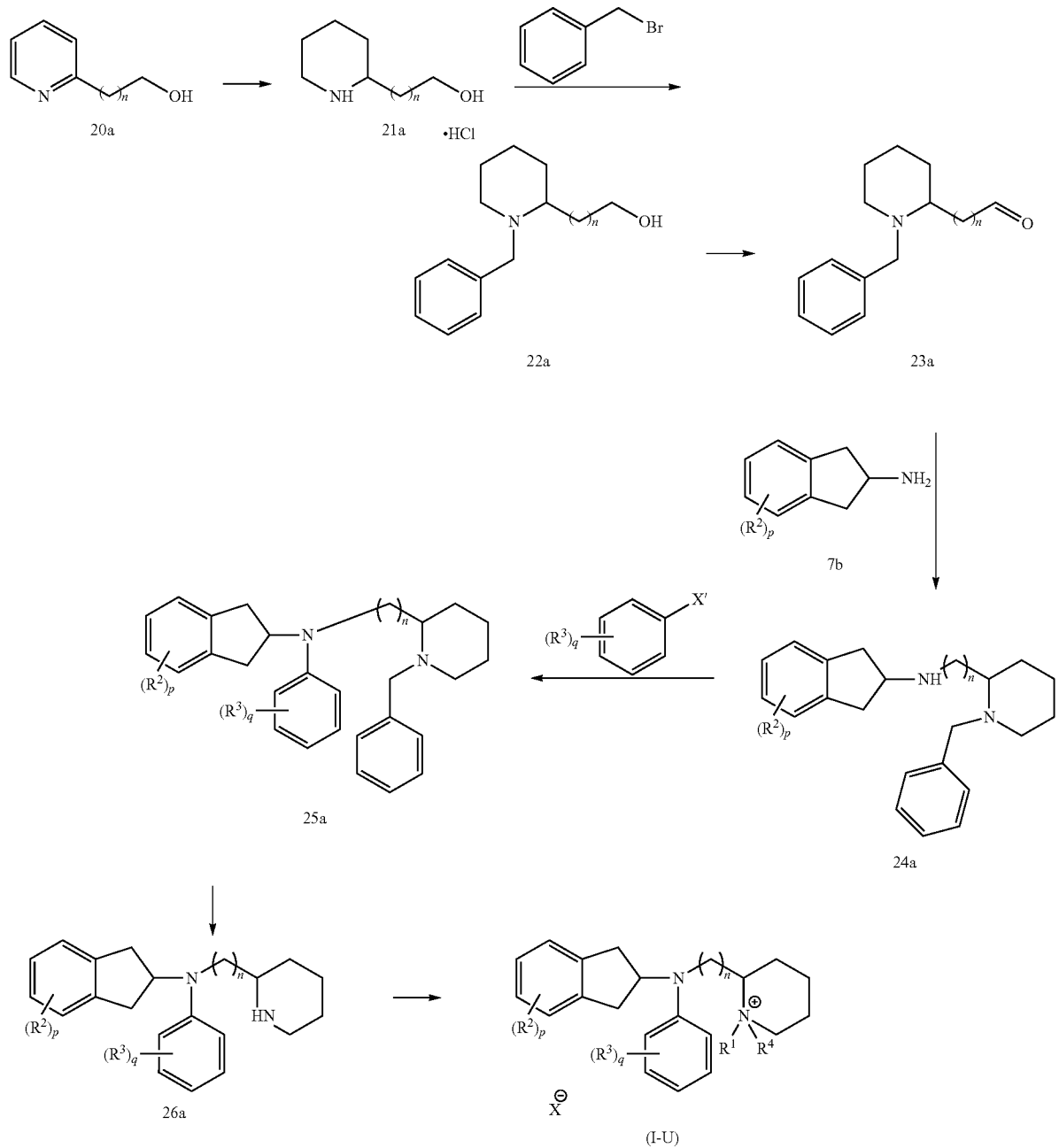

Scheme 11 provides the preparation of a compound of formula (I-U), where $R^1$ and are the same and $R^2$, $R^3$, X, n, p, and q are defined herein, via the use of reagent 20a. Specifically, compound 20a is reduced in the presence of an acid to form compound 21a. In one embodiment, the reduction is performed using standard reagents and conditions such as hydrogen gas in the presence of a catalyst. In one embodiment, the catalyst is $PtO_2$. Compound 20a is then protected using a suitable protecting group to provide compound 22a. In one embodiment, the protecting group is a benzyl group. In another embodiment, compound 22a is prepared using a benzyl halide such as benzyl bromide, or p-methoxy benzyl bromide. Compound 22a is then oxidized to form the corresponding aldehyde 23a. This oxidation is performed using reagents and conditions known to those of skill in the art. In one embodiment, the oxidation is performed using oxalyl chloride, dimethylsulfoxide (DMSO) and triethylamine Compound 23a is then coupled with aminoindane 7b to provide compound 24a. This reaction is typically performed in the presence of sodium triacetoxy borohydride. The nitrogen-atom of the aminoindane is then substituted with a $R^3$-substituted phenyl group. In one embodiment, the substitution is performed using bromobenzene. In another embodiment, the substitution is performed in the presence of catalytic reagents such as a t-butoxide, such as potassium, sodium, or lithium t-butoxide, a phosphate agent such as 2-dicyclohexylphosphino-2'-(N,N-dimethylamino)biphenyl (DavePhos), and a palladium reagent such as $Pd_2(dba)_3$. The benzyl group of compound 25a is then removed using standard deprotection reagents. In one embodiment, compound 25a is converted to compound 26a using ammonium formate and a palladium catalyst such as Pd/C or $Pd(OH)_2$. Compound 26a is then $R^1/R^4$ substituted using an alkylating agent to provide compound (I-U). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

Scheme 12 provides the synthesis to compound (I-UU), wherein $R^1$-$R^4$, X, p, and q are defined herein, starting with pyridine-2-propanol (20). Specifically, compound 20 is reduced using hydrogen gas in the presence of $PtO_2$ and hydrochloric acid to provide 3-cyclohexyl-propan-1-ol hydrochloride (21). Compound 21 is then protected with a benzyl group using benzyl bromide to provide 3-(1-benzyl-piperidin-2-yl)-propan-1-ol (22). Compound 22 is thereby oxidized to form the corresponding 3-(1-benzyl-piperidin-2-yl)-propionaldehyde (23) using oxalyl chloride, DMSO and triethylamine Compound 23 is then coupled with aminoindane 7b to provide compound 24b, which reaction is per-

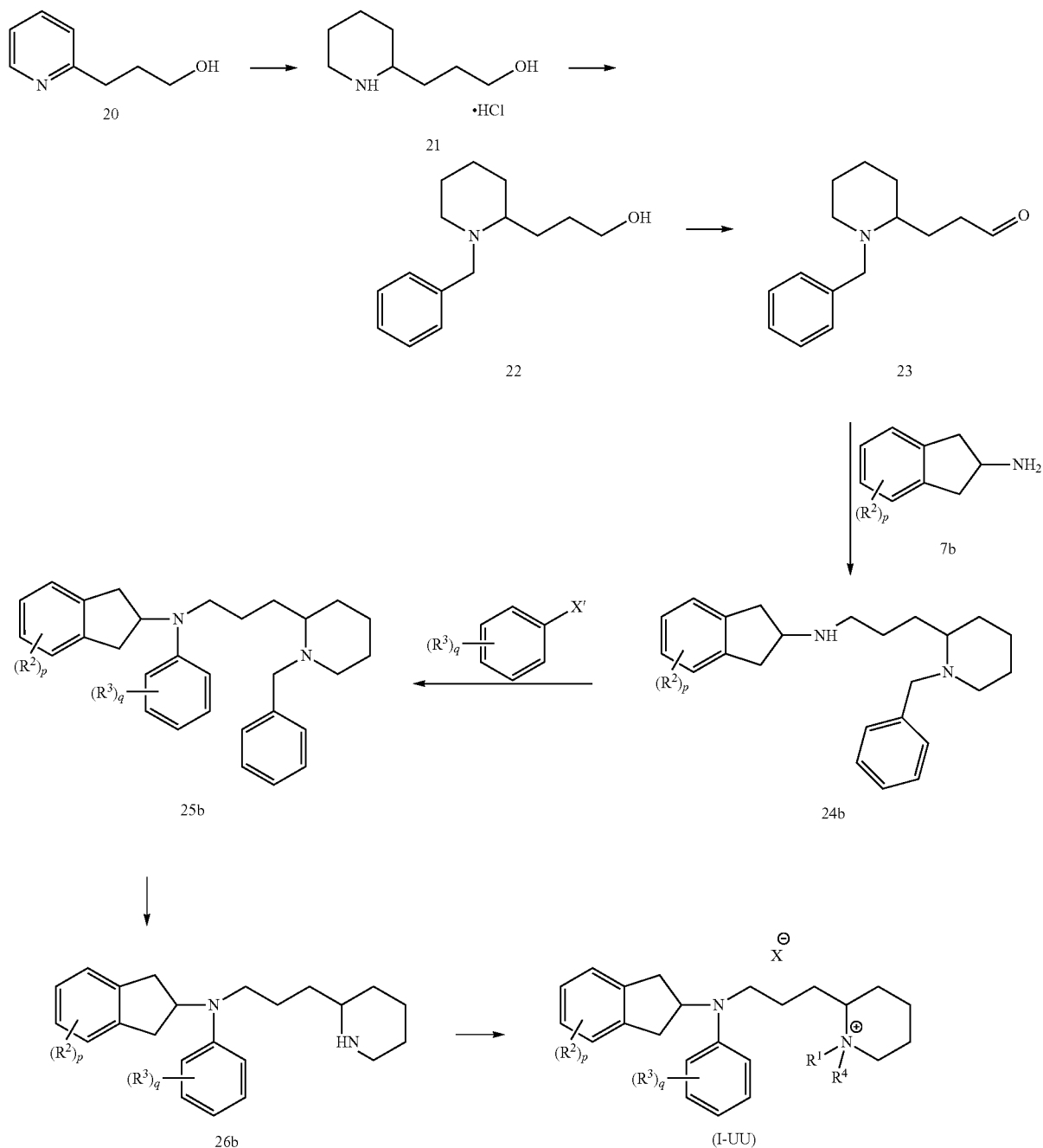

formed in the presence of sodium triacetoxy borohydride. The nitrogen-atom of the aminoindane moiety is then substituted with a phenyl group using bromobenzene, potassium t-butoxide, DavePhos, and Pd$_2$(dba)$_3$ to provide compound 25b. The benzyl group of compound 25a is then removed using standard deprotection reagents such as ammonium formate to provide compound 26a. Compound 26a is alkylated to provide compound (I-UU). In one embodiment, the alkylating agent is an alkyl halide, alkyl triflate, or alkyl besylate such as 1-iodopropane, ethyl iodide, methyl iodide, methyl triflate, ethyl triflate, propyl triflate, or methyl besylate, among others.

Scheme 13

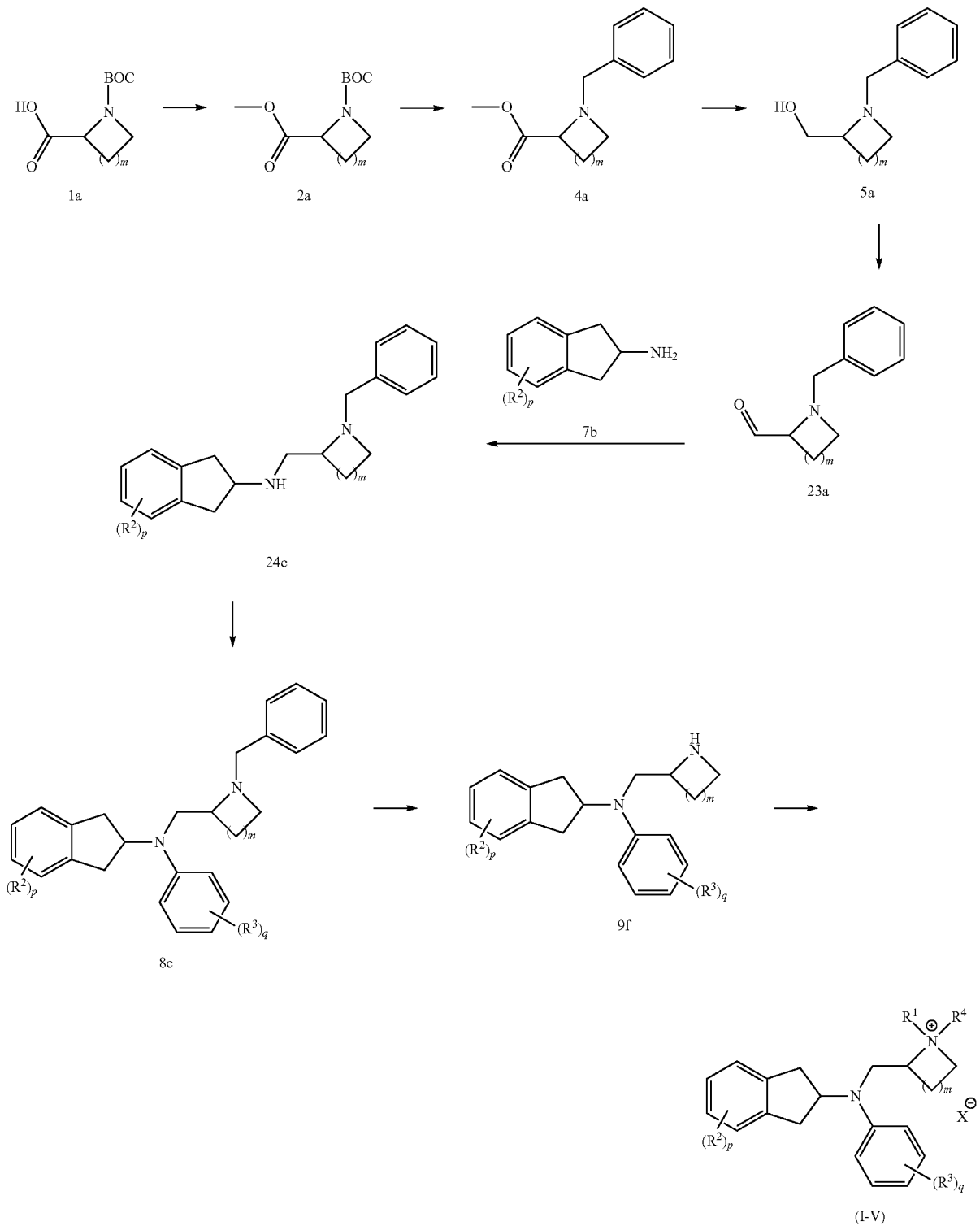

Scheme 13 depicts the preparation of the compound of formula (I-V), where $R^1$ and $R^4$ are the same and $R^1$-$R^4$, X, p, and q are defined herein. In this scheme, a Boc protected acid 1a is converted to corresponding ester 2a via methylation of the acid moiety. In one embodiment, compound 1a is reacted with a methylating agent to provide compound 2a. In another embodiment, compound 1a is reacted with methyl iodide, methyl triflate, or methyl besylate, among others. Ester 2a is then converted to benzylamine 4a. In one embodiment, the conversion is performed using trifluoroacetic acid, followed by benzyl bromide. Compound 4a is then reduced to the corresponding alcohol 5a. In one embodiment, the reduction is performed using DIBAL-H or LAH. Alcohol 5a is then converted to the corresponding aldehyde 23a using an oxidizing agent. In one embodiment, the oxidizing agent is oxalyl 8c is substituted with bromobenzene. The benzyl group of compound 8c is then removed via hydrogenation to provide compound 9f. In one embodiment, the hydrogenation is performed using ammonium formate, hydrogen gas and Pd/C, or $Pd(OH)_2$. The N-atom of the heterocyclic ring of compound 9f is then substituted to provide compound (I-V). In one embodiment, the substitution is performed using an alkylating agent. In a further embodiment, the substitution is performed using an alkyl halide, alkyl triflate, or alkyl besylate. In yet a further embodiment, the substitution is performed using 1-iodopropane, ethyl iodide, methyl iodide, methyl triflate, ethyl triflate, propyl triflate, or methyl besylate, among others. In still another embodiment, the substitution is performed using at least 2 equivalents of the alkylating agent.

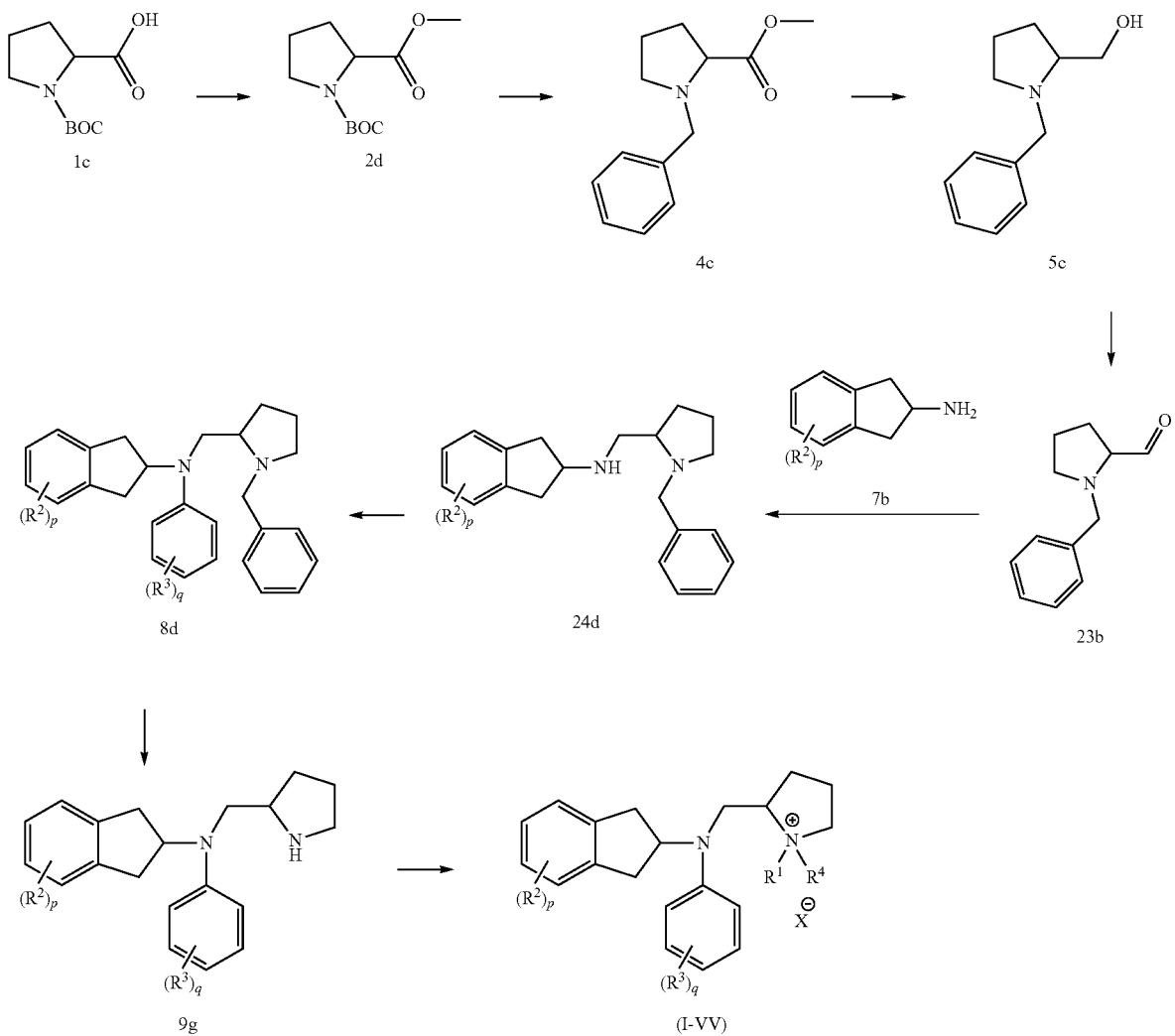

Scheme 14 chloride, DMSO and triethylamine Compound 23a is then coupled with substituted aminoindane 7b to provide compound 24c. In one embodiment, compound 23a is coupled with aminoindane 7b in the presence of sodium triacetoxy borohydride. The N-atom of compound 24c is then substituted with an optionally substituted phenyl group to provide compound 8c. In one embodiment, the N-atom of compound Scheme 14 provides the synthesis of a compound of formula (I-VV), wherein $R^1$-$R^4$, X, p, and q are defined herein. In this scheme, Boc-pyrrolidine-2-carboxylic acid (1c) is converted to pyrrolidine-1,2-dicarboxylic acid 1-tert-butyl ester 2-methyl ester (2d) via methylation of the acid moiety using methyl iodide, methyl triflate, or methyl besylate, among others. Ester 2d is then converted to 1-benzyl-pyrrolidine-2-carboxylic acid methyl ester (4c) using trifluoroacetic acid, followed by benzyl bromide. Compound 4c is then reduced to the corresponding (1-benzyl-pyrrolidin-2-yl)-methanol (5c) using DIBAL-H or LAH. Alcohol 5c is then converted to the corresponding 1-benzyl-pyrrolidine-2-carbaldehyde (23b) using an oxidizing agent. In one embodiment, the oxidizing agent is oxalyl chloride, DMSO and triethylamine Compound 23b is then coupled with substituted aminoindane 7b to provide compound 24d. In one embodiment, compound 23b is coupled with aminoindane 7b in the presence of sodium triacetoxy borohydride. The N-atom of compound 24d is then substituted with a phenyl group to provide compound 8d. In one embodiment, substitution of the N-atom of compound 24d is accomplished using bromobenzene. The benzyl group of compound 8d is then removed via hydrogenation to provide compound 9g. In one embodiment, the hydrogenation is performed using ammonium formate, hydrogen gas and Pd/C, or Pd(OH)$_2$. The N-atom of the heterocyclic ring of compound 9g is then alkylated using an alkyl halide, alkyl triflate, or alkyl besylate to provide the compound of formula (I-VV). In one embodiment, the substitution is performed using 1-iodopropane, ethyl iodide, methyl iodide, methyl triflate, ethyl triflate, propyl triflate, or methyl besylate, among others. In still another embodiment, the substitution is performed using at least 2 equivalents of the alkylating agent.

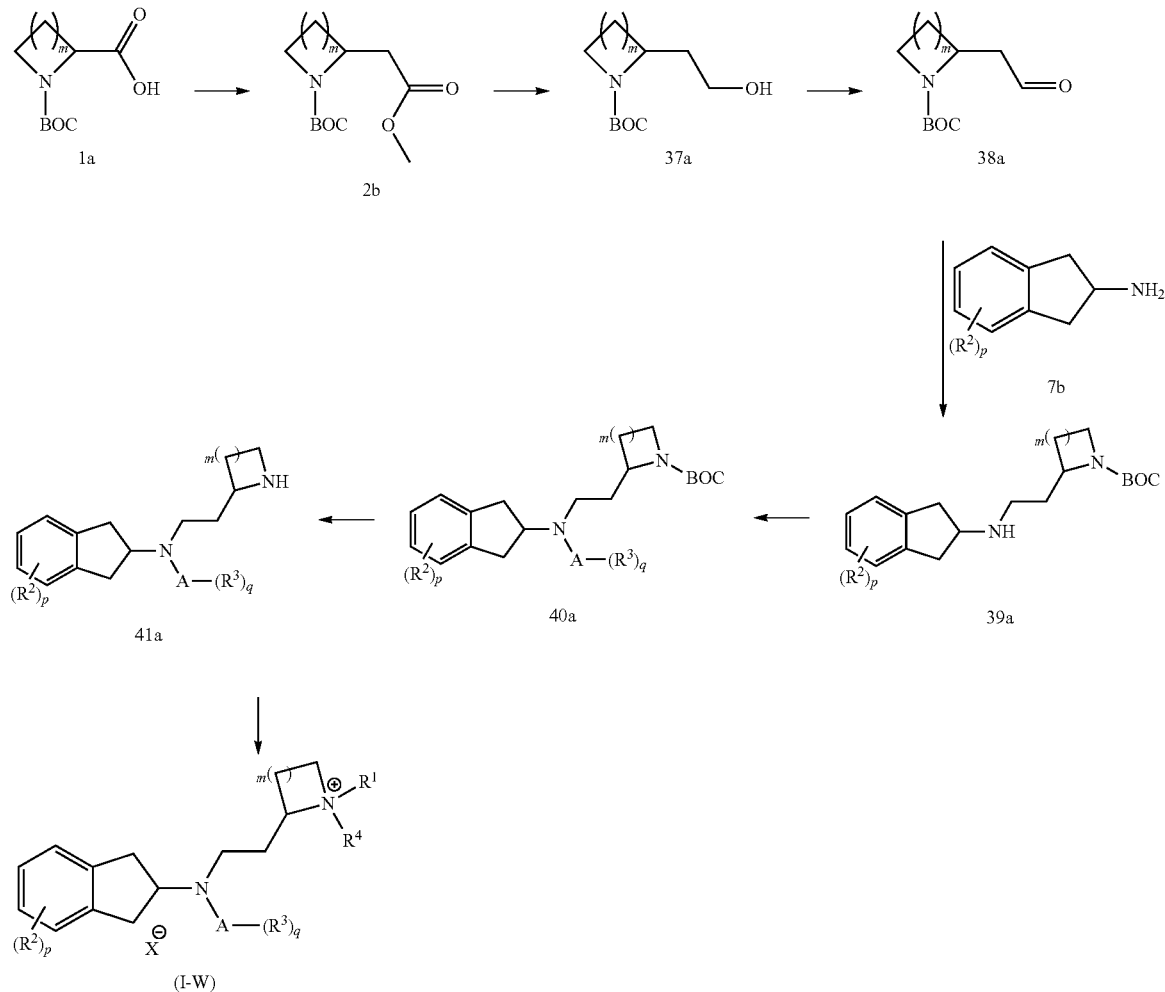

In another aspect, compounds of formula (I-W) are prepared, wherein $R^1$-$R^4$, A, X, m, q, and p are defined herein. In this scheme, acid 1a is converted to the corresponding ester 2b as described in Scheme 1. Ester 2b is then reduced to corresponding alcohol 37a using a suitable reducing agent. In one embodiment, the reducing agent is a hydride agent such as lithium aluminum hydride or DIBAL-H. Alcohol 37a is then oxidized to form aldehyde 38a. This oxidation may be performed using reagents and conditions known to those of skill in the art. In one embodiment, the oxidation is performed using oxalyl chloride, DMSO and triethylamine Compound 38a is then coupled with aminoindane 7b to provide compound 39a. This reaction may be performed in the presence of a mild reducing agent such as sodium triacetoxy borohydride. The nitrogen-atom of compound 39a is then substituted with an A-($R^3$)$_q$ group to provide compound 40a. In one embodiment, compound 39a is substituted with an optionally substituted phenyl group. In another embodiment, compound 39a is substituted with an optionally substituted heteroaryl. In a further embodiment, the substitution is performed using bromobenzene. In another embodiment, the substitution is performed in the presence of catalytic reagents such as a t-butoxide, such as potassium, sodium, or lithium t-butoxide, a phosphate agent such as DavePhos, and a palladium reagent such as $Pd_2(dba)_3$. The t-butoxycarbonyl group of compound 40a is then removed using standard deprotection reagents. In one embodiment, compound 40a is converted to compound 41a using an acidic medium such as dioxane-HCl or trifluoroacetic acid. Compound 41a is then $R^1/R^4$ substituted, where $R^1$ and $R^4$ are the same, using an alkylating agent to provide compound (I-W) as described for Scheme 1.

ethyl)pyrrolidine-1-carboxylic acid tert-butyl ester (37) using a reducing agent. In one embodiment, the reducing agent is a hydride agent such as lithium aluminum hydride. Compound 37 is then oxidized to form 2-(2-oxoethyl)pyrrolidine-1-carboxylic acid tert-butyl ester (38). This oxidation is performed using oxalyl chloride, DMSO and triethylamine Compound 38 is then coupled with aminoindane 7b to provide compound 39b. This reaction may be performed in the presence of sodium triacetoxy borohydride. The nitrogen-atom of compound 39b is then substituted with an $A-(R^3)_q$ group to pro-

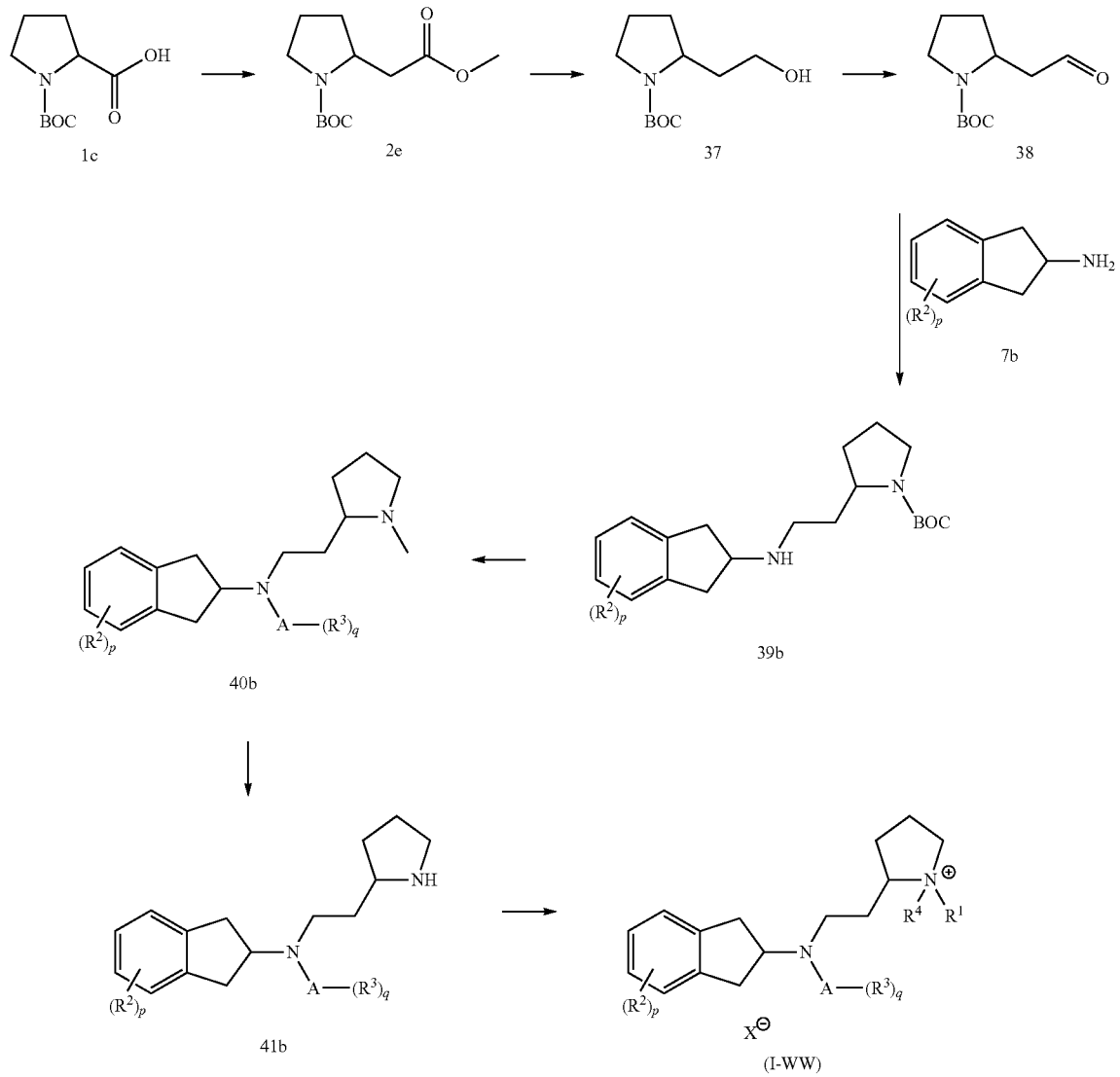

Scheme 16 provides the preparation of compounds of formula (I-WW), wherein $R^1$-$R^4$, A, p, q, and X are defined herein. In this scheme, pyrrolidine-1,2-dicarboxylic acid 1-tert-butyl ester (1c) is converted to corresponding 2-methoxycarbonylmethylpyrrolidine-1-carboxylic acid tert-butyl ester (2e). In one embodiment, 2-methoxycarbonylmethylpyrrolidine-1-carboxylic acid tert-butyl ester is formed using isobutyl chloroformate, diazomethane, and silver benzoate. 2-Methoxycarbonylmethylpyrrolidine-1-carboxylic acid tert-butyl ester (2e) is then reduced to 2-(2-hydroxyvide compound 40b. In one embodiment, the substitution is performed using bromobenzene optionally in the presence of catalytic reagents such as a t-butoxide, such as potassium, sodium, or lithium t-butoxide, a phosphate agent such as DavePhos, and a palladium reagent such as $Pd_2(dba)_3$. The t-butoxycarbonyl group of compound 40b is then removed using dioxane-HCl or trifluoroacetic acid to provide compound 41b. Compound 41b is then $R^1/R^4$ substituted using an alkylating agent such as an alkyl halide, to provide compound (I-WW).

Scheme 17

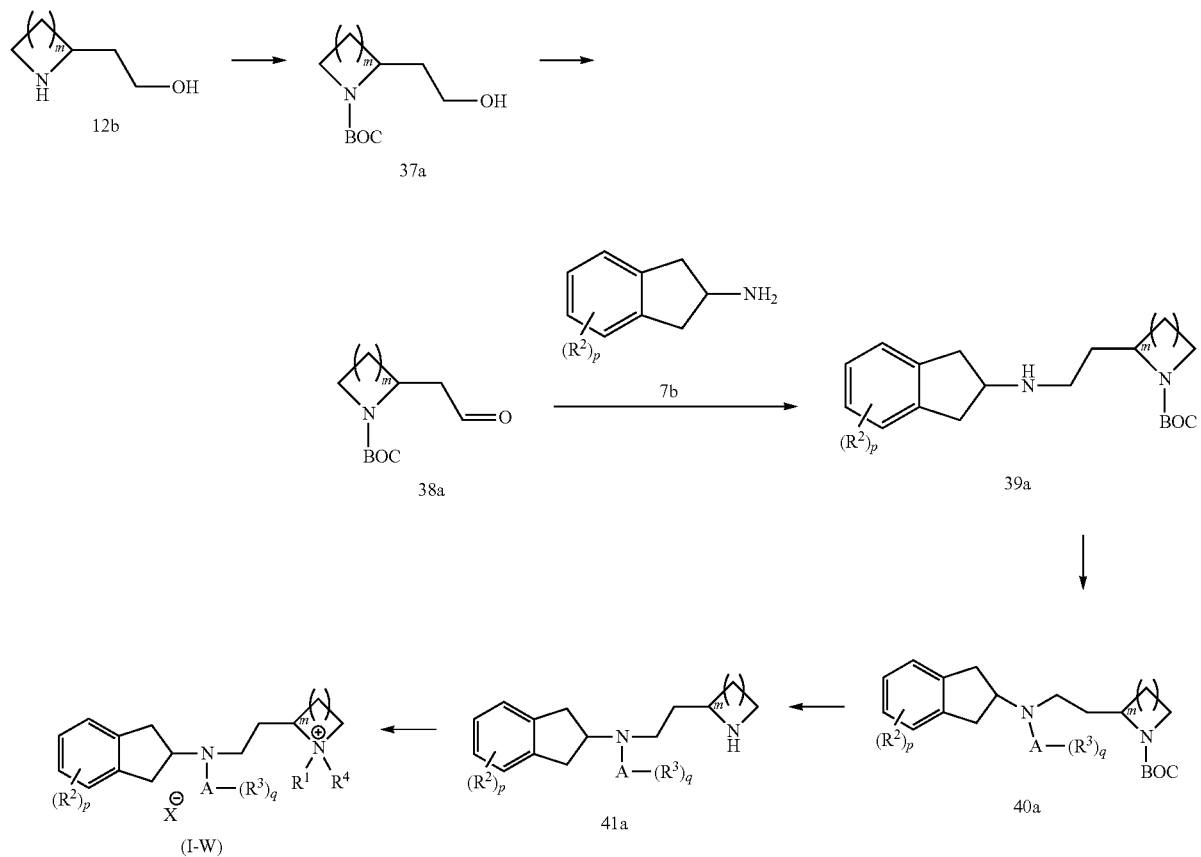

Scheme 17 provides a second route to prepare a compound of formula (I-W), where $R^1$ and $R^4$ are the same and $R^1$-$R^4$, A, m, p, q, and X are defined herein. Specifically, the nitrogen atom of compound 12b is protected to provide compound 37a. In one embodiment, the nitrogen atom is protected with a protecting group such as a t-butoxycarbonyl group. Compound 37a is then oxidized to form the corresponding aldehyde 38a. This oxidation is performed using reagents and conditions known to those of skill in the art. In one embodiment, the oxidation is performed using oxalyl chloride, DMSO and triethylamine Compound 38a is then coupled with aminoindane 7b to provide compound 39a. This reaction may be typically performed in the presence of a mild reducing agent such as sodium triacetoxy borohydride. The nitrogen-atom of compound 39a is then substituted with an A-$(R^3)_q$ group to provide compound 40a. In one embodiment, compound 39a is substituted with an optionally substituted phenyl group. In another embodiment, compound 39a is substituted with an optionally substituted heteroaryl. In a further embodiment, the substitution is performed using bromobenzene or bromopyridine such as 2-bromo-pyridine, 3-bromo-pyridine, or 4-bromo-pyridine. In another embodiment, the substitution is performed in the presence of catalytic reagents such as a t-butoxide, such as potassium, sodium, or lithium t-butoxide, a phosphine catalyst such as P(i-BuNCH$_2$CH$_2$)$_3$N, and a palladium reagent such as Pd$_2$(dba)$_3$. The protecting group, i.e., the t-butoxycarbonyl group, of compound 40a is then removed using standard deprotection reagents to provide compound 41a. In one embodiment, the deprotection is performed using an acidic medium such as dioxane-HCl or trifluoroacetic acid. Compound 26a is then $R^1$/$R^4$ substituted, where $R^1$ and $R^4$ are the same, using an alkylating agent to provide compound (I-W). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

Scheme 18

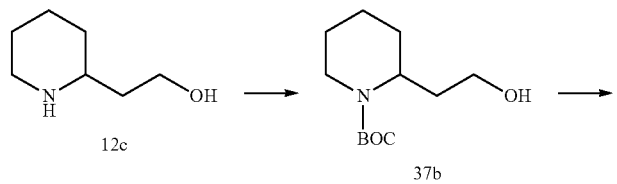

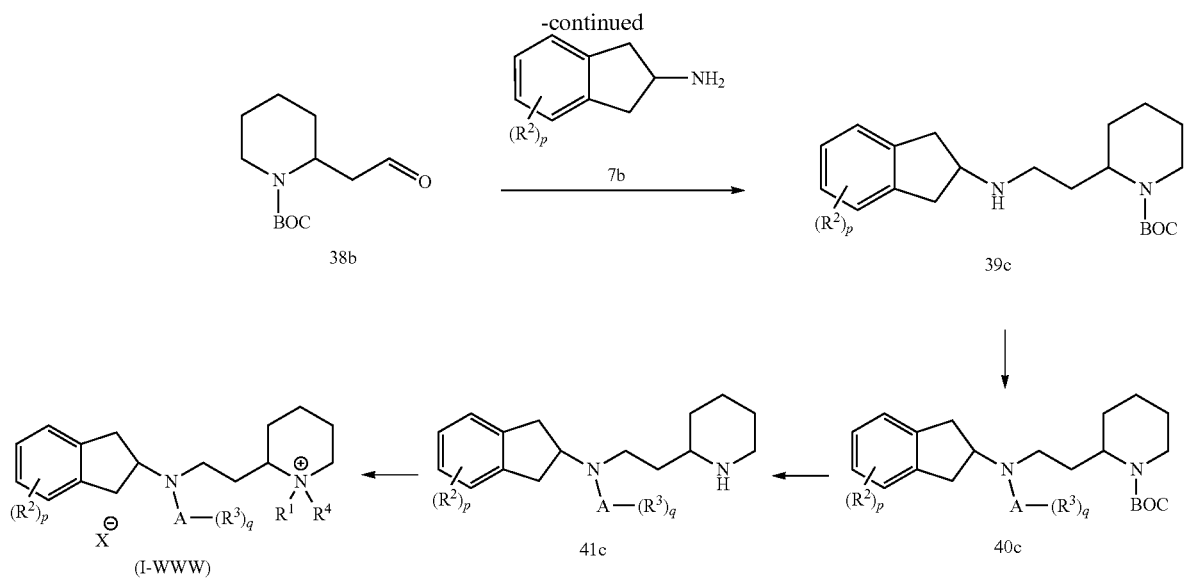

Scheme 18 provides the preparation of a compound of formula (I-WWW), where $R^1$ and $R^4$ are the same and $R^1$-$R^4$, A, p, q, and X are defined herein. Specifically, the nitrogen atom of piperidine-2-ethanol (12c) is protected with a t-butoxycarbonyl group to provide 2-(2-hydroxyethyl)piperidine-1-carboxylic acid tert-butyl ester (37b). Compound 37b is then oxidized to form 2-(2-oxoethyl)piperidine-1-carboxylic acid tert-butyl ester (38b). In one embodiment, the oxidation is performed using oxalyl chloride, DMSO and triethylamine Compound 38b is then coupled with aminoindane 7b to provide compound 39c. This reaction is typically performed in the presence of sodium triacetoxy borohydride. The nitrogen-atom of compound 39c is then substituted with an A-$(R^3)_q$ group to provide compound 40c. In one embodiment, the substitution is performed using an optionally substituted phenyl. In another embodiment, the substitution is performed using an optionally substituted heteroaryl. In a further embodiment, the substitution is performed using bromobenzene or bromopyridine such as 2-bromo-pyridine, 3-bromo-pyridine, or 4-bromo-pyridine. In another embodiment, the substitution is performed in the presence of catalytic reagents such as a t-butoxide, such as potassium, sodium, or lithium t-butoxide, a phosphine catalyst such as P(i-BuNCH$_2$CH$_2$)$_3$N, and a palladium reagent such as Pd$_2$(dba)$_3$. The protecting group, i.e., the t-butoxycarbonyl group, of compound 40c is then removed using standard deprotection reagents to provide compound 41c. In one embodiment, the deprotection is performed using an acidic medium such as dioxane-HCl or trifluoroacetic acid. Compound 41c is then $R^1/R^4$ substituted, where $R^1$ and $R^4$ are the same, using an alkylating agent to provide compound (I-WWW). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

Scheme 19

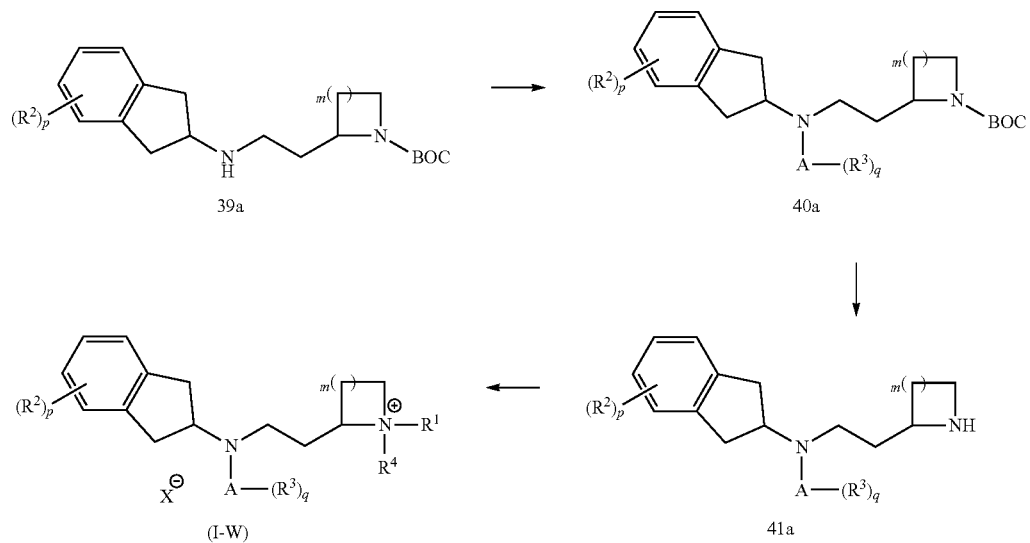

Scheme 19 provides a third route in the preparation of compound (1-W), wherein $R^1$-$R^4$, A, m, p, q, and X are defined herein, via compound 39a, which may be prepared as described herein. The nitrogen atom of compound 39a is A-$(R^3)_q$ substituted to provide compound 40a. In one embodiment, compound 39a is substituted with an optionally substituted phenyl. In another embodiment, compound 39a is substituted with an optionally substituted heteroaryl. In a further embodiment, the substitution is performed using bromobenzene, bromopyridine, or bromopyrimidine. In another embodiment, the substitution is performed in the presence of catalytic reagents such as a t-butoxide, such as potassium, sodium, or lithium t-butoxide, a phosphine catalyst such as P(i-BuNCH$_2$CH$_2$)$_3$N, or a strong base such as Verkade's super base, and a palladium reagent such as Pd$_2$(dba)$_3$. The protecting group, i.e., the t-butoxycarbonyl group, of compound 40a is then removed using standard deprotection reagents to provide compound 41a. In one embodiment, the deprotection is performed using an acidic medium such as dioxane-HCl or trifluoroacetic acid. Compound 41a is then $R^1$/$R^4$ substituted, where $R^1$ and $R^4$ are the same, using an alkylating agent to provide compound (I-W). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

Scheme 20

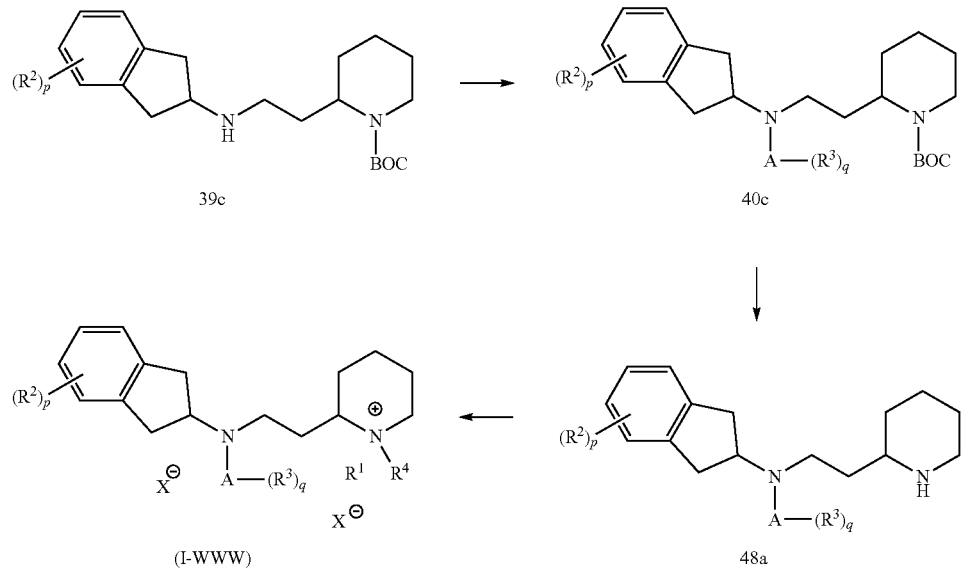

Scheme 20 provides another preparation of compound (1-WWW), wherein $R^1$-$R^4$, A, p, q, and X are defined herein, via compound 39c where the nitrogen atom of compound 39c is A-$(R^3)_q$ substituted to provide compound 40c. In one embodiment, the substitution is performed using bromobenzene, bromopyridine, or bromopyrimidine. In another embodiment, the substitution is performed in the presence of sodium t-butoxide, P(i-BuNCH$_2$CH$_2$)$_3$N, and Pd$_2$(dba)$_3$. The protecting group, i.e., the t-butoxycarbonyl group, of compound 40c is then removed using standard deprotection reagents to provide compound 48a. In one embodiment, the deprotection is performed using dioxane-HCl or trifluoroacetic acid. Compound 48a is then $R^1$/$R^4$ substituted, where $R^1$ and $R^4$ are the same, using an alkylating agent to provide compound (I-WWW). In one embodiment, the alkylating agent is an alkyl halide such as 1-iodopropane, ethyl iodide, methyl iodide, methyl triflate, ethyl triflate, propyl triflate, or methyl besylate, among others.

Scheme 21

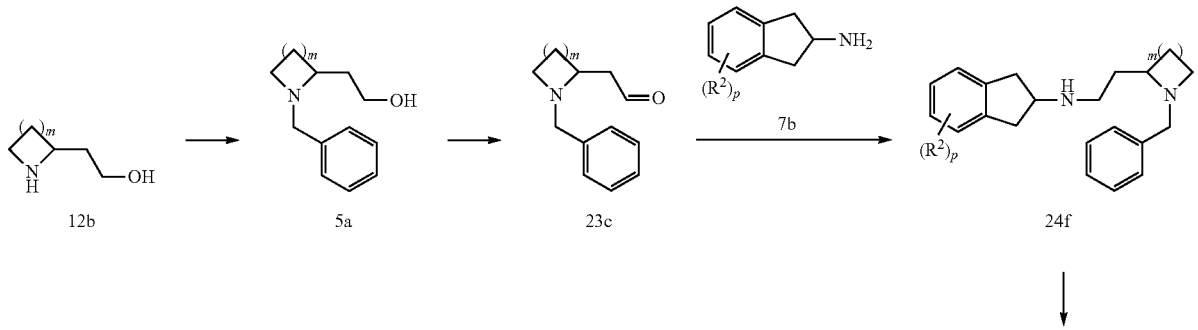

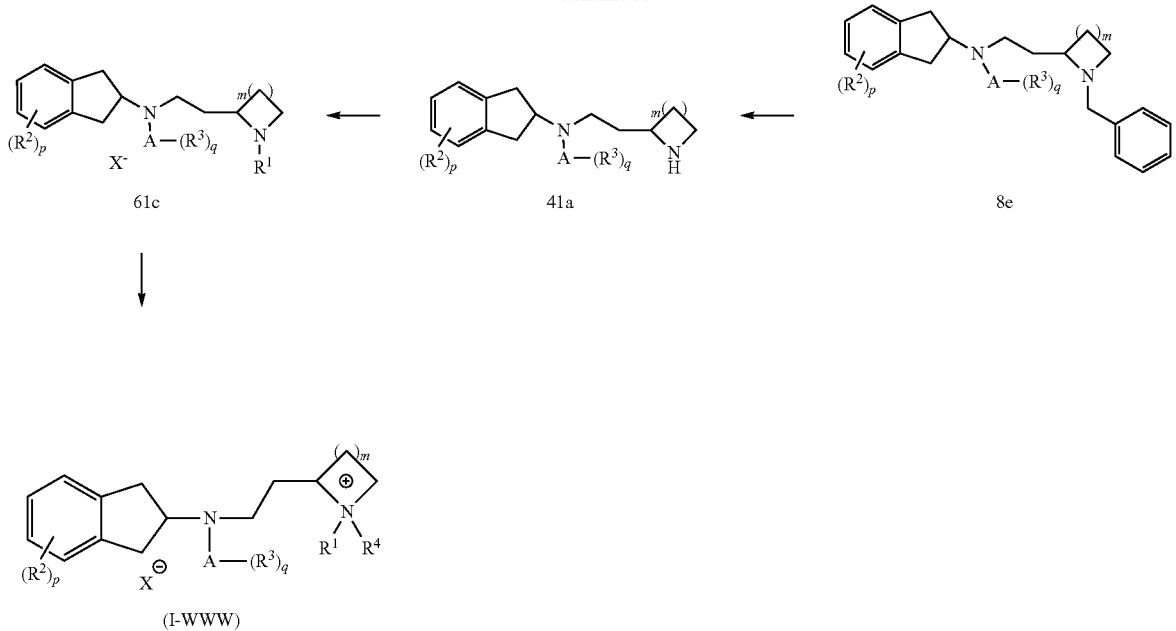

(I-WWW)

Scheme 21 provides a further preparation of compound (1-WWW), wherein R¹-R⁴, A, m, p, q, and X are defined herein. Specifically, the nitrogen atom of compound 12b is protected to provide compound 5a. In one embodiment, the nitrogen atom is protected with a protecting group such as a benzyl group using a reagent such as benzyl bromide. Compound 5a is then oxidized to form the corresponding aldehyde 23c. This oxidation is performed using reagents and conditions known to those of skill in the art. In one embodiment, the oxidation is performed using an oxidizing agent such as oxalyl chloride/DMSO, and a strong base such as triethylamine Compound 23c is then coupled with aminoindane 7b to provide compound 24f. This reaction is typically performed in the presence of a mild reducing agent such as sodium triacetoxy borohydride. The nitrogen-atom of compound 24f is then substituted with an A-(R³)$_q$ group to provide compound 8e. In one embodiment, the compound 24f is substituted with an optionally substituted phenyl. In another embodiment, compound 24f is substituted with an optionally substituted heteroaryl. In a further embodiment, the substitution is performed using a bromo-aryl or bromo-heterocyclic group. In another embodiment, the substitution is performed using bromobenzene, bromopyridine, or bromothioazole. In another embodiment, the substitution is performed in the presence of catalytic reagents such as a t-butoxide, such as potassium, sodium, or lithium t-butoxide, a base such as Verkade's super base, and a palladium reagent such as Pd$_2$(dba)$_3$. The protecting group, i.e., the benzyl group, of compound 8e is then removed using standard deprotection reagents to provide compound 41a. In one embodiment, the deprotection is performed using isobutyl chloroformate. Compound 41a is then R¹ substituted to provide compound 61c. In one embodiment, the R¹ substitution is an alkylation. In another embodiment, the alkylation is performed using an aldehyde such as propanaldehyde, acetaldehyde, or formaldehyde. Compound 61c is then R⁴ substituted using an alkylating agent. In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

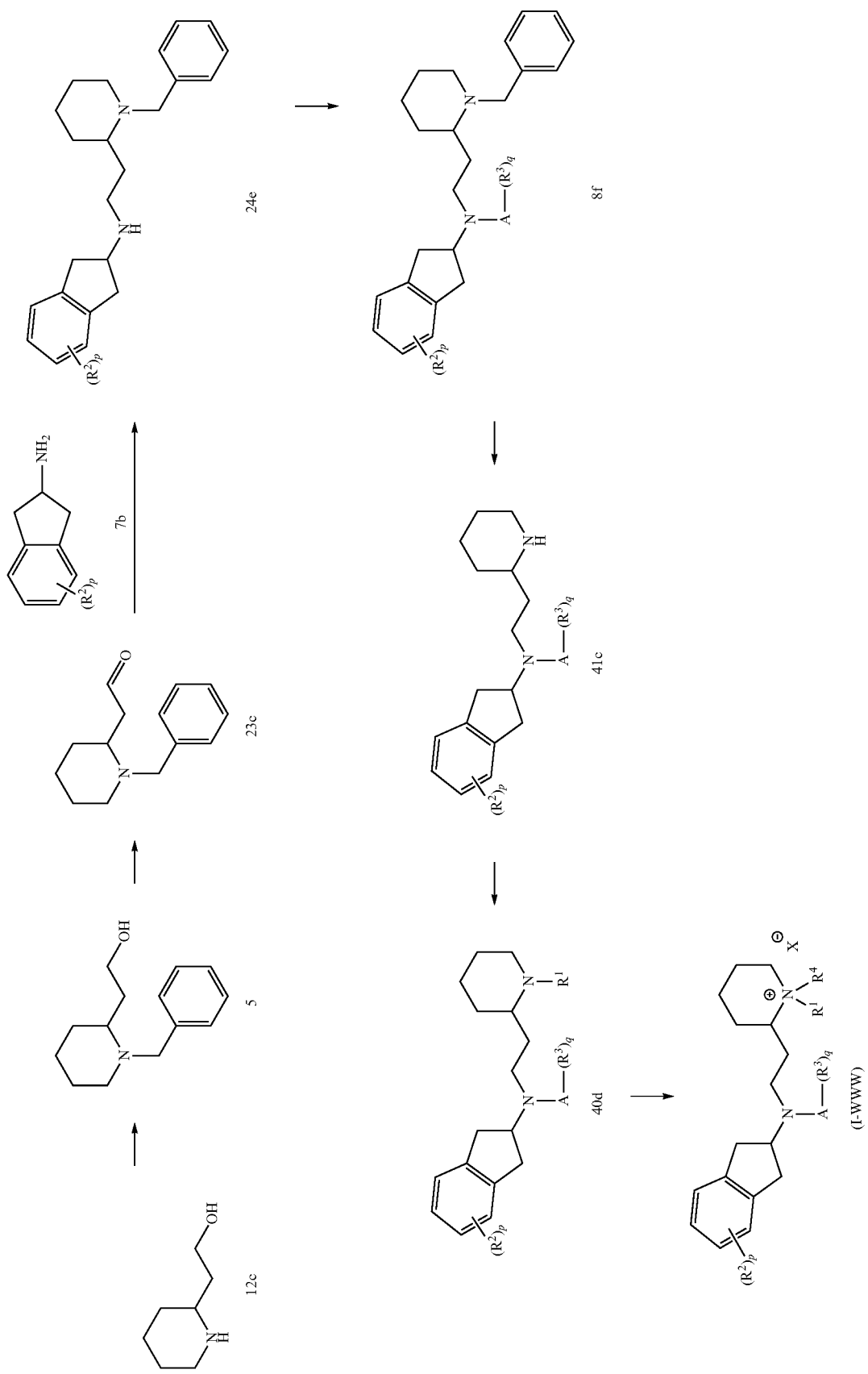
Scheme 22

Scheme 22 provides yet another preparation of compound (1-WWW), wherein $R^1$-$R^4$, A, X, p, and q are defined herein. Specifically, the nitrogen atom of piperidine-2-ethanol (12c) is protected to provide 2-(1-benzylpiperidin-2-yl)ethanol (5). In one embodiment, the nitrogen atom is protected with a benzyl group using benzyl bromide. 2-(1-Benzylpiperidin-2-yl)ethanol is then oxidized to form (1-benzylpiperidin-2-yl) acetaldehyde (23c). In one embodiment, the oxidation is performed using oxalyl chloride, DMSO and triethylamine (1-Benzylpiperidin-2-yl)acetaldehyde is then coupled with aminoindane 7b to provide compound 24e. In one embodiment, the reaction is performed in the presence of sodium triacetoxy borohydride. The nitrogen-atom of compound 24e is then substituted with a A-$(R^3)_q$ group to provide compound 8f. In one embodiment, the substitution is performed using bromobenzene, bromopyridine, or bromothioazole, a catalytic reagent such as a t-butoxide, such as potassium, sodium, or lithium t-butoxide, a base such as Verkade's super base, and a palladium reagent such as $Pd_2(dba)_3$. The protecting group, i.e., the benzyl group, of compound 8f is then removed using isobutyl chlorformate. Compound 41c is then $R^1$ substituted to provide compound 61d. In one embodiment, the $R^1$ substitution is performed using an aldehyde such as propionaldehyde, acetaldehyde, or formaldehyde. Compound 61d is then $R^4$ substituted using an alkylating agent such as an alkyl halide, alkyl triflate, or alkyl besylate to provide compound (I-WWW).

Scheme 23 provides a synthesis of a compound whereby $R^1$ and $R^4$ are joined and $R^2$, $R^3$, A, m, p, q, Y, and X are defined herein, i.e., compound (1-Y). Specifically, the nitrogen atom of compound 41a may be substituted with an optionally substituted —$CH_2YCH_2$— group to form a compound of formula (I-Y). In one embodiment, $R^1$ and $R^4$ are joined to form a carbocyclic, i.e., where Y is a carbon atom. In another embodiment, $R^1$ and $R^4$ are joined to form a heterocyclic ring. In a further embodiment, $R^1$ and $R^4$ are joined to form a cyclic ether. In still a further embodiment, substitution of the nitrogen atom is performed using a 1-halo-2-(2-chloro-alkoxy)-alkane such as 1-chloro-2-(2-chloro-ethoxy)-ethane.

Scheme 24

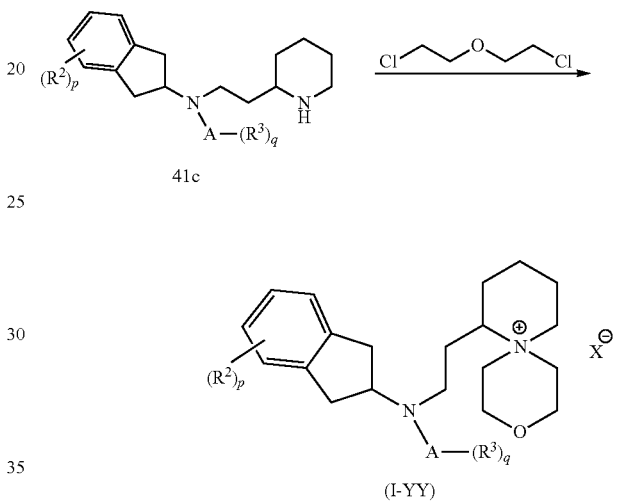

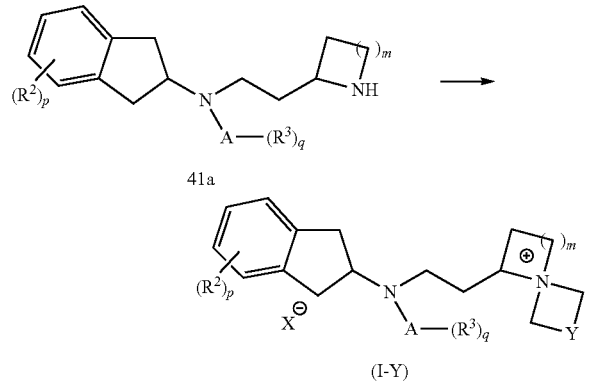

Scheme 24 provides a synthesis of a compound, i.e., compound (I-YY), whereby $R^1$ and $R^4$ are joined to form a heterocyclic ring and $R^2$, $R^3$, A, p, q, and X are defined herein. In one embodiment, $R^1$ and $R^4$ are joined to form a cyclic ether. In a further embodiment, alkylation of the nitrogen atom is performed using a 1-halo-2-(2-chloro-alkoxy)-alkane such as 1-chloro-2-(2-chloro-ethoxy)-ethane.

Scheme 25
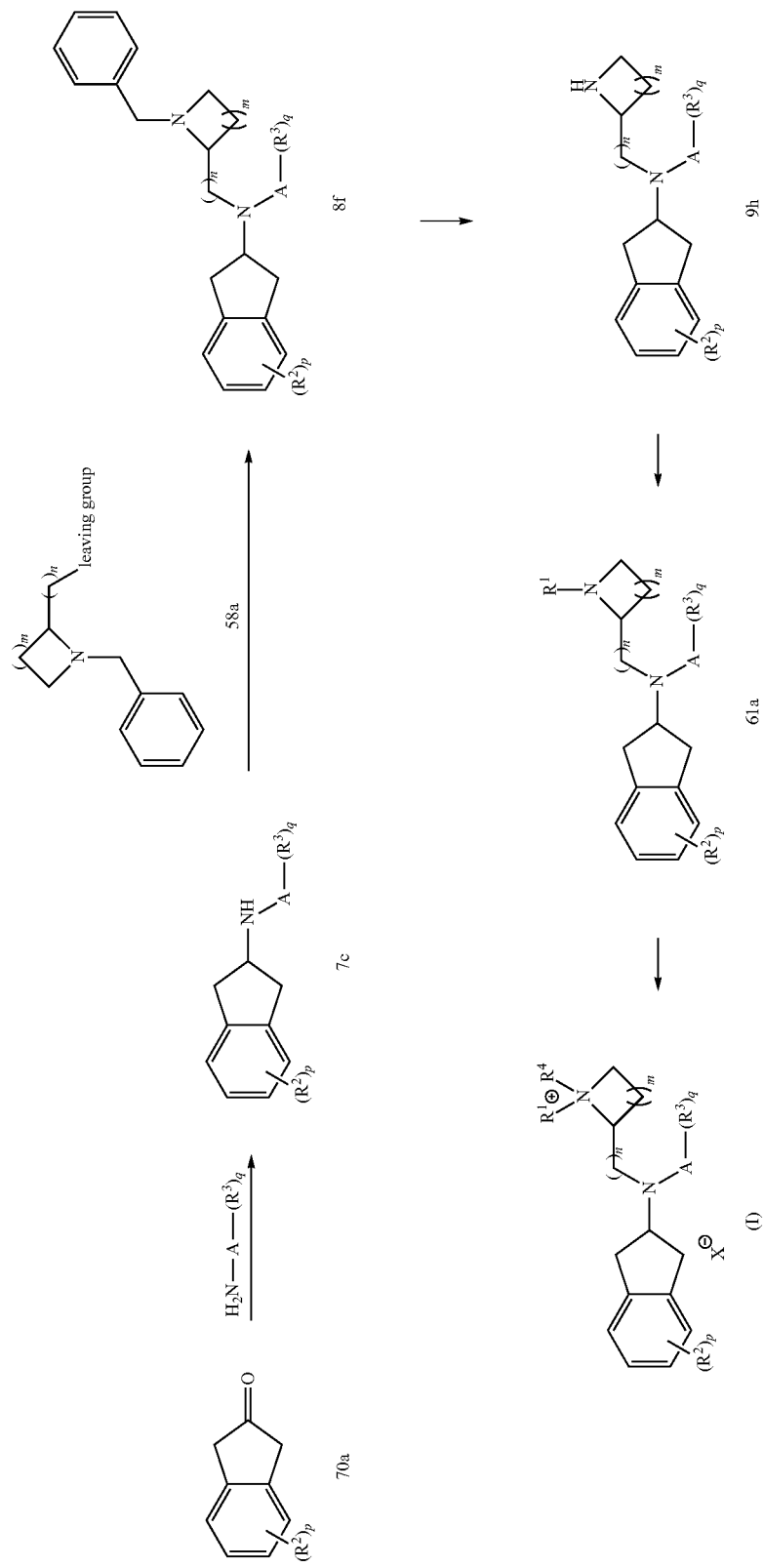

Scheme 25 provides the preparation of compounds of formula (I), wherein $R^1$-$R^4$, A, m, n, p, q, and X are defined herein. These compounds are prepared by first aminating ketone 70a to provide compound 7c. In one embodiment, ketone 70a is aminated using a primary amine 1n another embodiment, ketone 70a is aminated using $H_2N$-A-$(R^3)_q$. This transformation is performed in the presence of a mild reducing agent such as Na(OAc)$_3$BH. Compound 7c is then coupled with amine 58a to provide compound 8f. The leaving group of amine 58a may be selected by one of skill in the art. In one embodiment, the leaving group is a halogen, mesylate, tosylate, or triflate. In another embodiment, coupling of compounds 7c and 58a is performed using an alkoxide, such as those described above. Compound 8f is then deprotected by removal of the benzyl group using techniques and reagents known in the art to provide compound 9h. In one embodiment, the deprotection is performed via a hydrogenation. In another embodiment, the hydrogenation is performed using ammonium formate, hydrogen gas and Pd/C, or Pd(OH)$_2$. The nitrogen-ring atom is then successively $R^1$ and then $R^4$ substituted using the reagents and conditions described above, e.g., the descriptions for Schemes 1-24, to provide compounds 61a and (I), respectively.

Scheme 26

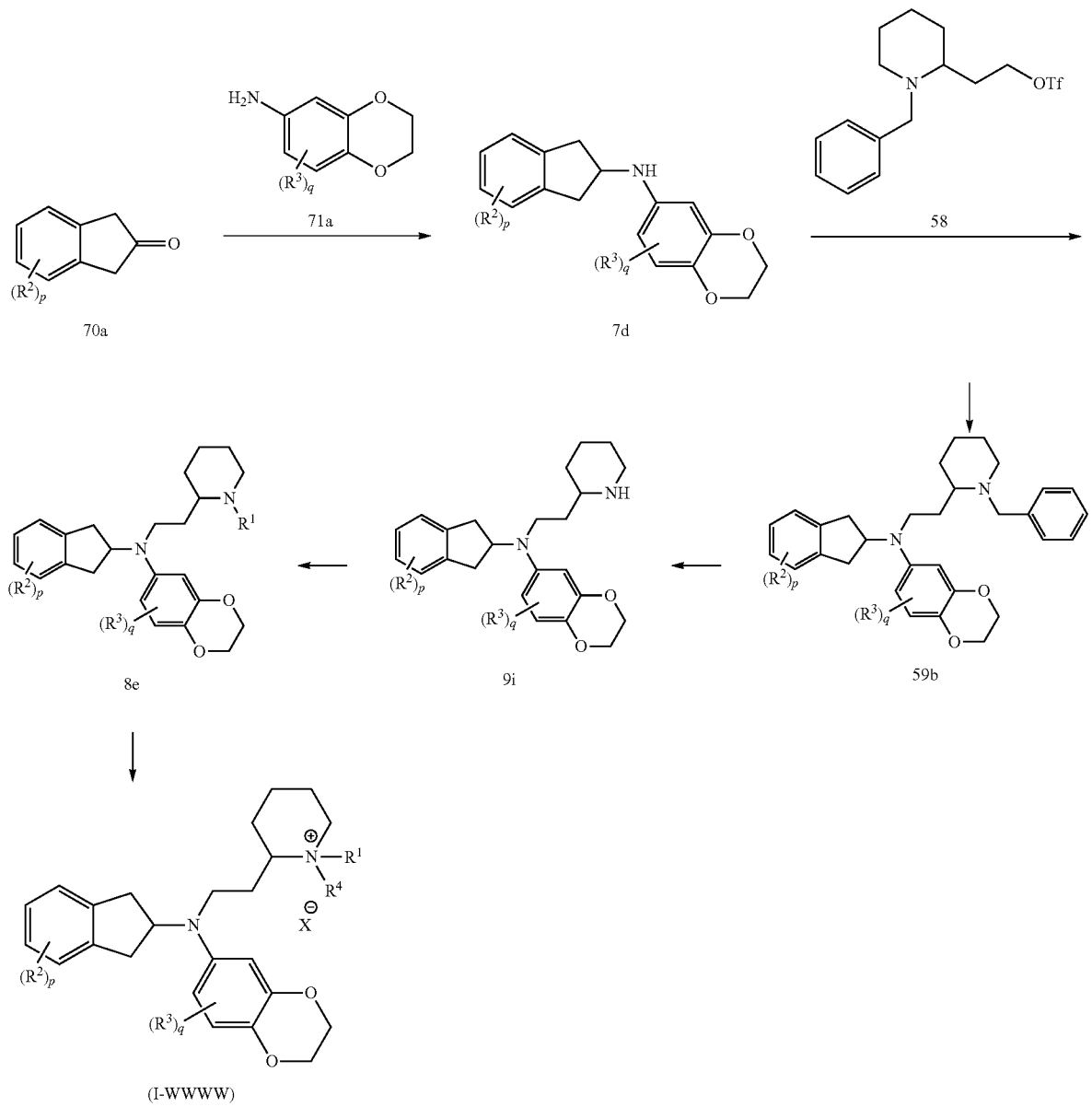

Scheme 26 provides the preparation of compounds of formula (I-WWWW), wherein $R^1$-$R^4$, p, q, and X is defined herein. These compounds are prepared by aminating ketone 70a to provide compound 7d. In one embodiment, ketone 70a is aminated using primary amine 71a in the presence of a mild reducing agent such as Na(OAc)$_3$BH. Compound 7d is then coupled with amine 58 in the presence of an alkoxide to provide compound 8e. Compound 8e is then deprotected via hydrogenation to provide compound 9i. The nitrogen-ring atom of compound 9I is then successively $R^1$ and then $R^4$ substituted using the reagents and conditions described above, to provide compounds 61b and (I-WWWW), respectively.

Scheme 27

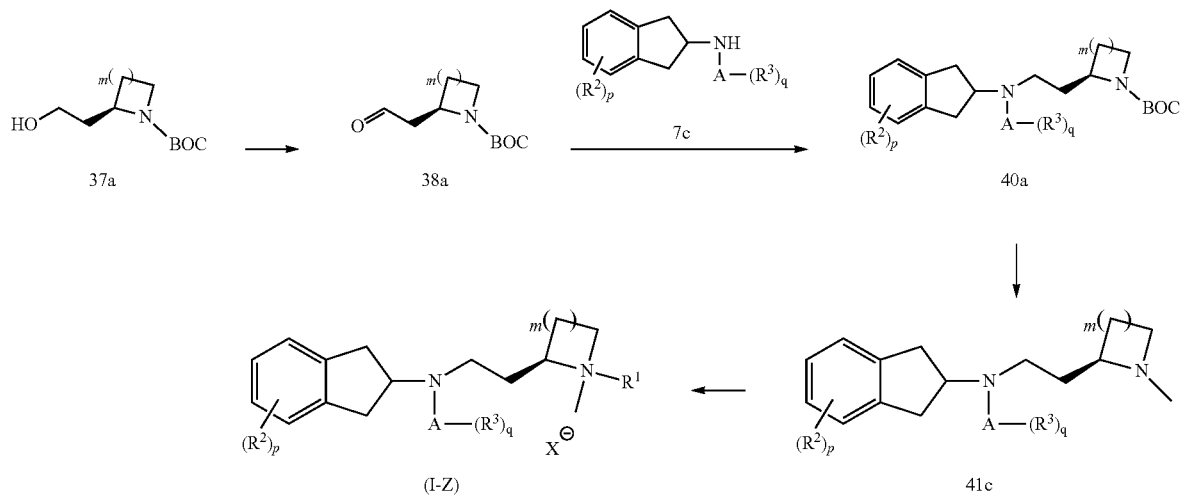

Scheme 27 provides an alternate route to compound (I-Z), wherein R¹-R³, A, m, p, q, and X are defined herein, via compound 40a. Compound 37a may be prepared as discussed in Tetrahedran, 2007, 63:3000-3005, which is hereby incorporated by reference, and is then oxidized to form compound 38a. The oxidation may be performed using an oxidizing agent such as sodium hypochlorite and 2,2,6,6-tetramethylpiperidin-1-yl)oxidanyl (TEMPO) catalyst. Compound 40a is then prepared by adding compound 38a to a solution of compound 7c and Na(OAc)$_3$BH. The inventors found that this order of addition afforded the production of compound 40a in a high enantiomeric excess (ee). Compound 40a is then deprotected by reduction of the BOC group using standard reducing agents to form diamine 41c. In one embodiment, the BOC group is reduced to a methyl group using lithium aluminium hydride. The nitrogen atom of compound 41c is then R¹-substituted as discussed above for other R¹/R⁴ substitutions to provide a compound of formula (I-Z). In one embodiment, the alkylation is performed using an alkyl halide such as methyl bromide or methyl iodide in a solvent such as dichloroethane or methyl t-butyl ether. This route may also be used to prepare the (S)-enantiomer of compound (I-Z).

In one embodiment, a method for preparing the compound of formula (I), wherein A is phenyl, is provided and includes (i) converting

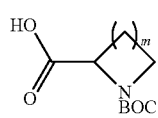

to

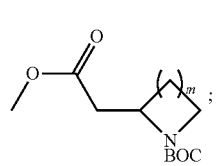

2a (ii) converting compound 2a to

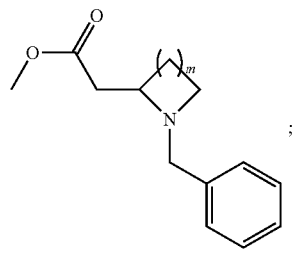

4a (iii) reducing compound 4a to

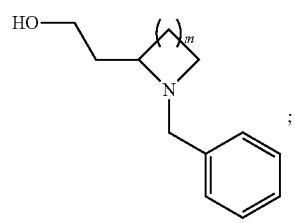

5a (iv) chlorinating compound 5a to form

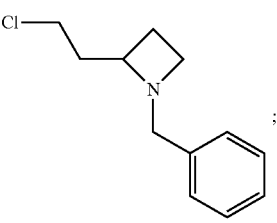

6a (v) coupling compound 6a with

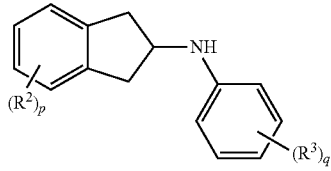
7a to form

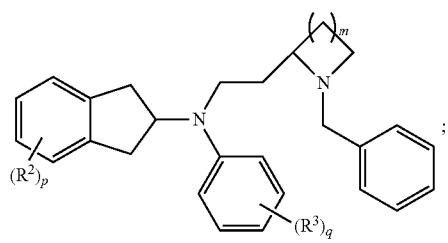
8a (vi) removing the benzyl group of compound 8a via hydrogenation to form

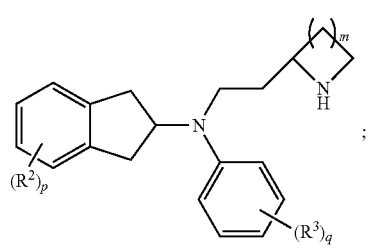
9a (vii) R¹ substituting compound 9a to form

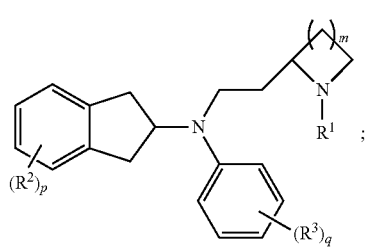
11a and (viii) R⁴ substituting compound 11a.

In another embodiment, a method for preparing the compound of the invention, wherein A is phenyl, is provided and includes (i) converting

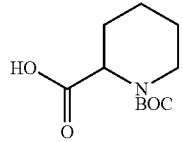

to

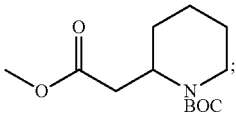
2a (ii) converting compound 2a to

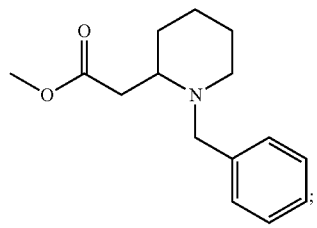
4a (iii) reducing compound 4a

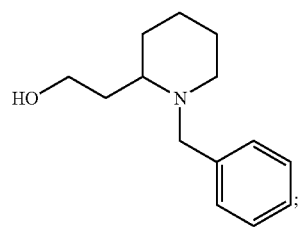
5a to (iv) chlorinating compound 5a to form

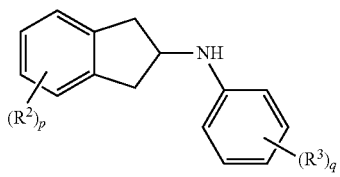
6a (v) coupling compound 6a with

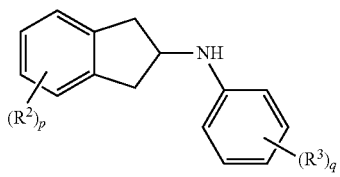
7a to form

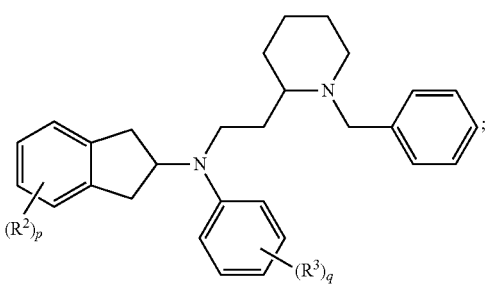
8a (vi) removing the benzyl group of compound 8a via hydrogenation to form

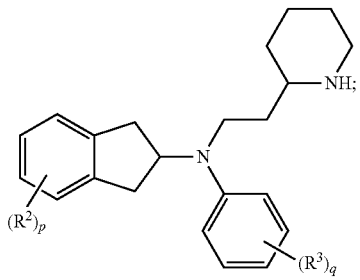
9a (vii) R¹ substituting compound 9a to form

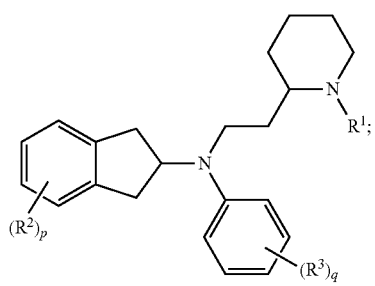
11a and (viii) R⁴ substituting compound 11a.

In a further embodiment, a method for preparing a compound of the invention, wherein A is phenyl and the method includes R¹ and R⁴ substituting

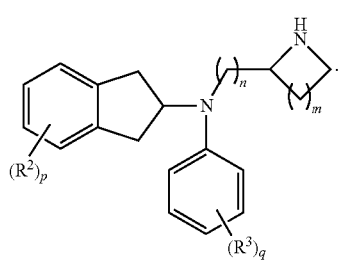
9c

In one aspect, compound 9c is

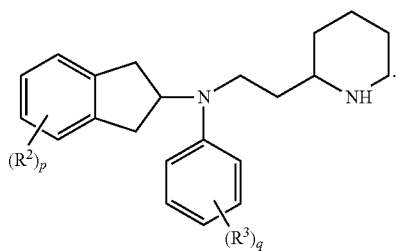

In yet another embodiment, a method for preparing a compound of the invention, wherein A is phenyl, is provided and includes (i) protecting the nitrogen atom of

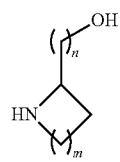

to form

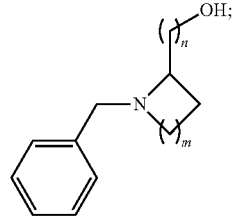
13a (ii) chlorinating compound 13a to form

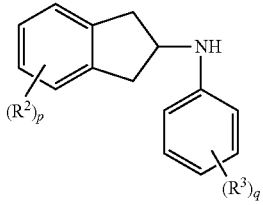
14a (iii) coupling compound 14a with

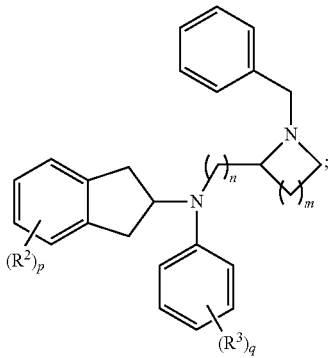
7a to form

15a (iv) deprotecting compound 15a to form

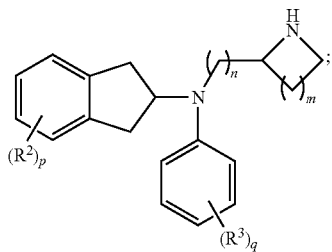
16a (v) R¹ substituting compound 16a to form

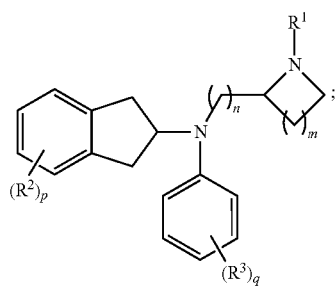
17a and (vi) R⁴ substituting compound 17a.

In still a further embodiment, a method for preparing a compound of the invention, wherein A is phenyl, is provided and includes (i) protecting the nitrogen atom of piperidine-2-methanol to form

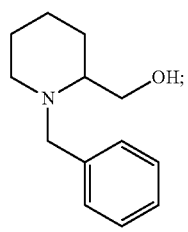
13a (ii) chlorinating compound 13a to form

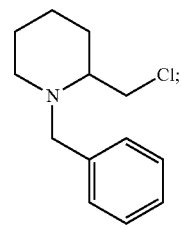
14a (iii) coupling compound 14a with

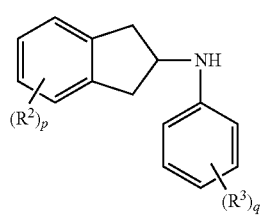
7a to form

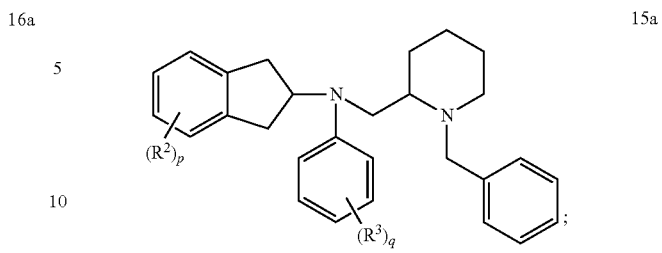
15a (iv) deprotecting compound 15a to form

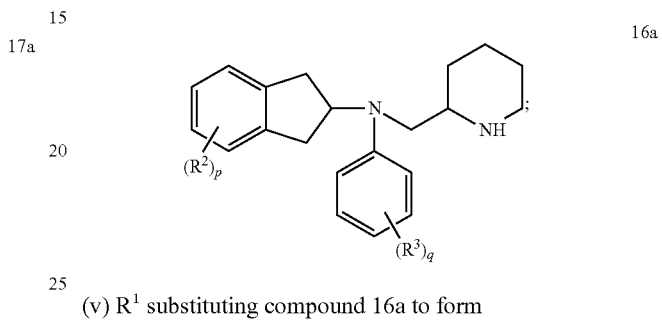
16a (v) R¹ substituting compound 16a to form

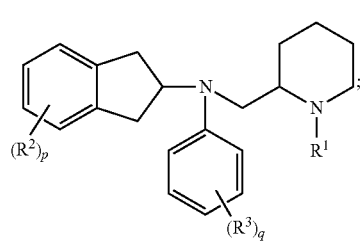
17a and (vi) R⁴ substituting compound 17a.

In yet another embodiment, a method for preparing a compound of the invention, wherein A is phenyl, R³ is 2-F, m is 2, and q is 1, is provided and includes R¹ and R⁴ substituting

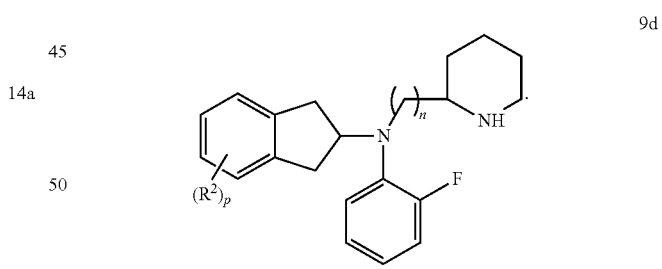
9d

In one aspect, compound 9d is

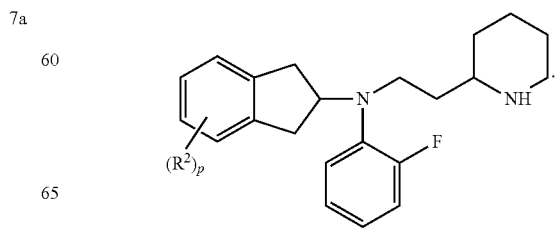

In yet a further embodiment, a method for preparing a compound of the invention, wherein A is phenyl, is provided and includes (i) coupling

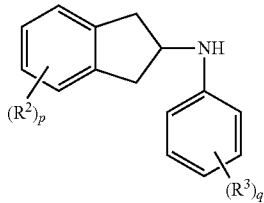

and

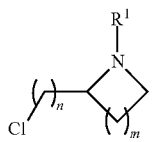

to form

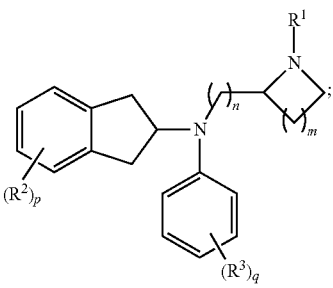

and (ii) R⁴ substituting compound 17a.

In still another embodiment, a method for preparing a compound of the invention, wherein A is phenyl, is provided and includes (i) coupling

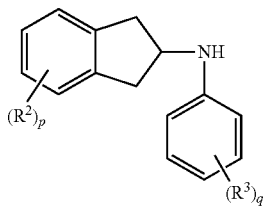

and

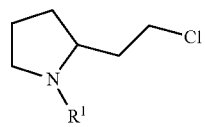

to form

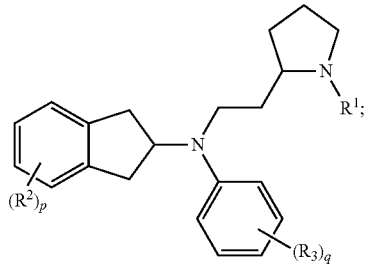

17a and (ii) R⁴ substituting compound 17a.

In a further embodiment, a method for preparing a compound of the invention, wherein m is 3, is provided and includes (i) reducing

using an acid to form

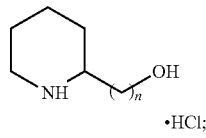

21a

·HCl;

(ii) protecting compound 21a with a benzyl group to provide

22a

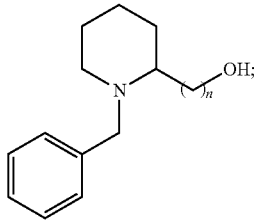

(iii) oxidizing compound 22a to provide

23a (iv) coupling compound 23a with

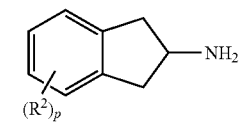

7b to provide

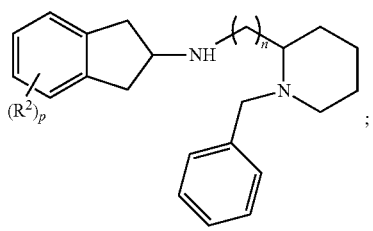

(v) substituting the nitrogen atom of compound 24a with a R³-substituted phenyl group to form

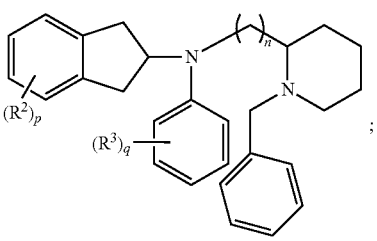

(vi) deprotecting compound 25a to provide

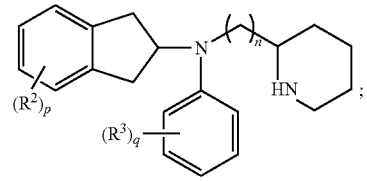

and (v) R¹ and R⁴ substituting compound 26a.

In yet a further embodiment, a method for preparing a compound of the invention, wherein m is 3, is provided and includes (i) reducing

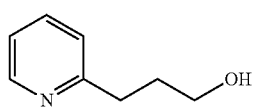

using an acid to form

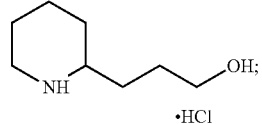

(ii) protecting compound 21a with a benzyl group to provide

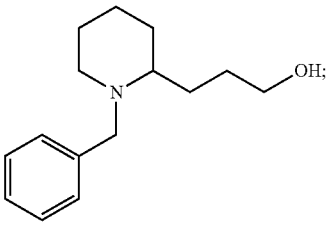

(iii) oxidizing compound 22a to provide

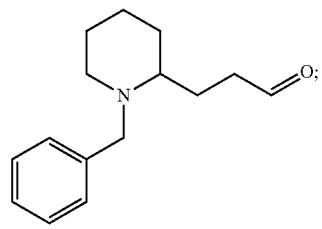

(iv) coupling compound 23a with

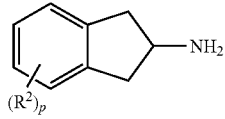

to provide

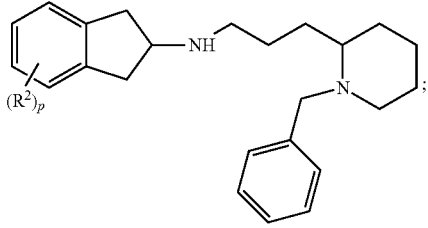

(v) substituting the nitrogen atom of compound 24a with a R³-substituted phenyl group to form

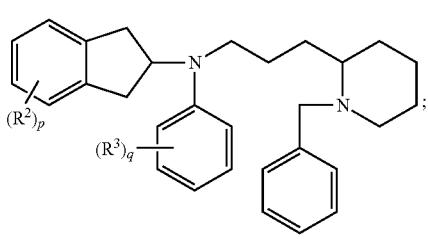

(vi) deprotecting compound 25a to provide

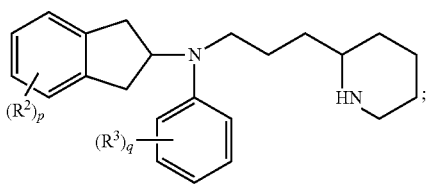
26a and (v) R¹ and R⁴ substituting compound 26a.

In another embodiment, a method for preparing a compound of the invention, wherein A is phenyl, is provided and includes (i) converting

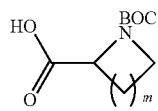

to

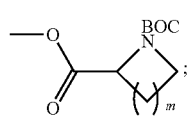
2a (ii) converting compound 2a to

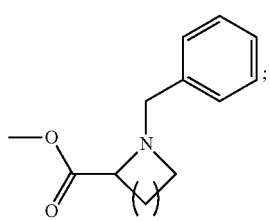
4a (iii) reducing compound 4a to

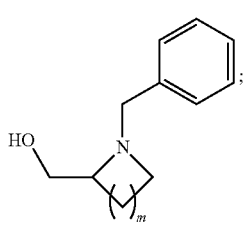
5a (iv) oxidizing compound 5a to provide

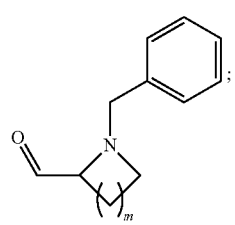
23a (v) coupling compound 23a with

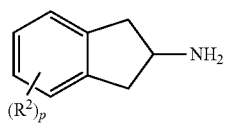
7b to provide

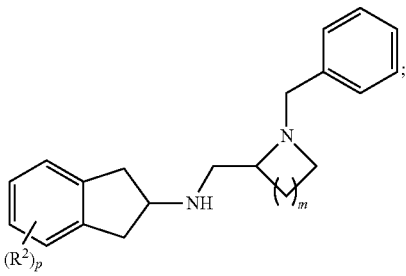
24c (v) substituting the nitrogen atom of compound 24c with an R³-substituted phenyl group to provide

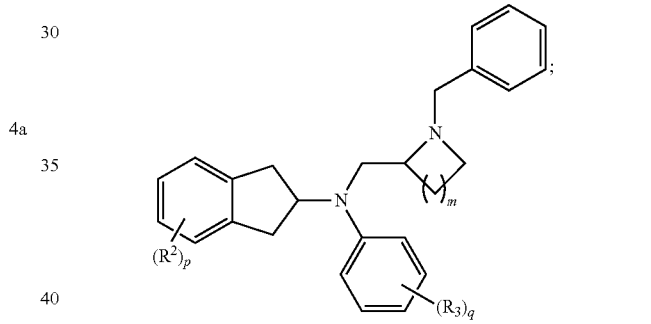
8c (vi) deprotecting compound 8c to form

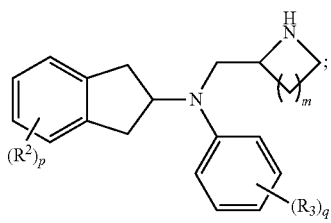
9f and (vii) R¹ and R⁴ substituting the nitrogen ring.

In still another embodiment, a method for preparing a compound of the invention, wherein A is phenyl, is provided and includes (i) converting

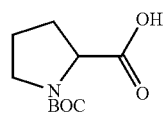

to

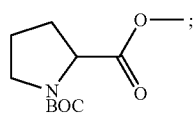

(ii) converting compound 2c to

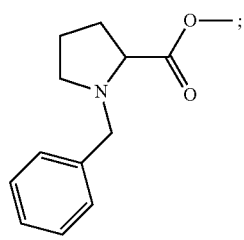

(iii) reducing compound 4c to

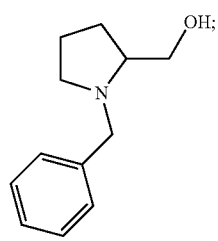

(iv) oxidizing compound 5c to provide

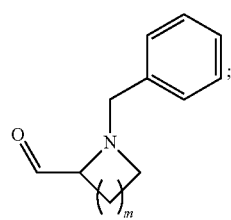

(v) coupling compound 23a with

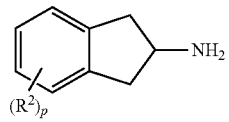

to provide

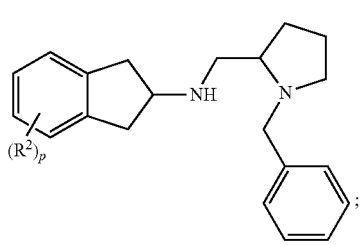

(v) substituting the nitrogen atom of compound 24c with an $R^3$-substituted phenyl group to provide

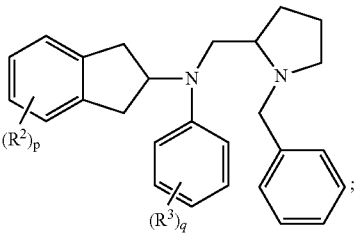

(vi) deprotecting compound 8c to form

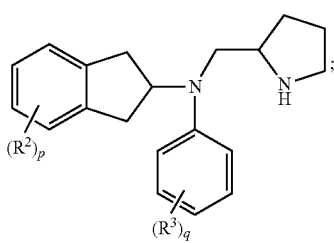

and (vii) $R^1$ and $R^4$ substituting the nitrogen ring.

In still a further embodiment, a method for preparing a compound of the invention is provided and includes (i) converting

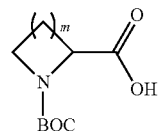

to

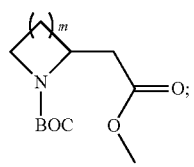

(ii) reducing compound 2b to

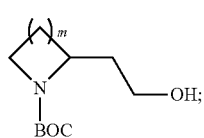

(iii) oxidizing compound 37a to

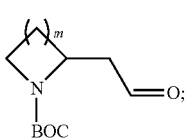

(iv) coupling coupling compound 38a with

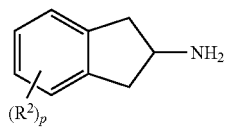
7b to

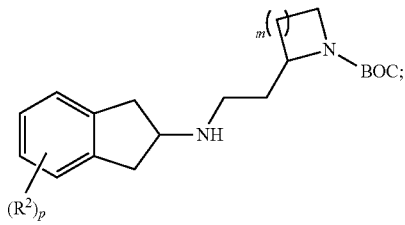
39a (v) coupling compound 39a with an A-(R³)$_q$ group to form

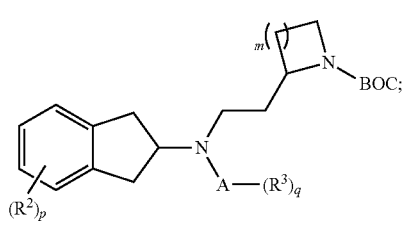
40a (vi) deprotecting compound 40a to form

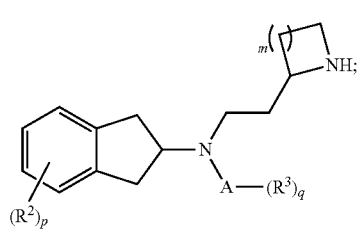
41a and (vii) R¹ and R⁴ substituting compound 41a.

In yet a further embodiment, a method for preparing a compound of the invention is provided and includes (i) converting

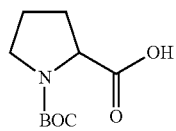 [SMILES: CC(C)(C)OC(=O)N1CCCC1C(=O)O]

to

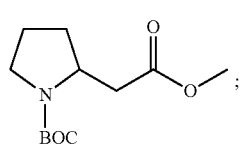
2b;

(ii) reducing compound 2b to

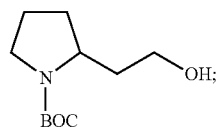
37a (iii) oxidizing compound 37a to

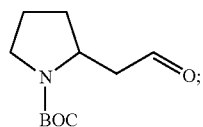
38a;

(iv) coupling coupling compound 38a with

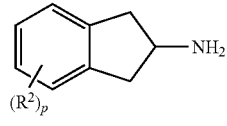
7b to

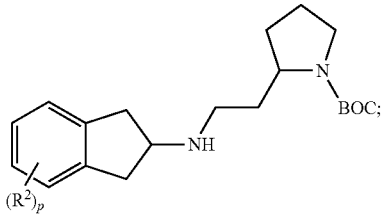
39a (v) coupling compound 39a with an A-(R³)$_q$ group to form

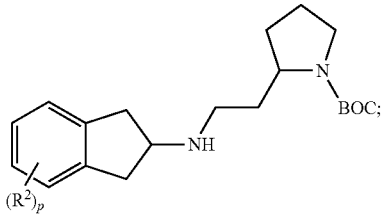
40a (vi) deprotecting compound 40a to form

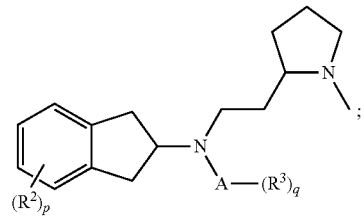
41a and (vii) R¹ and R⁴ substituting compound 41a.

In another embodiment, a method for preparing a compound of the invention is provided and includes (i) BOC protecting

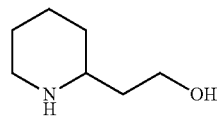

to form

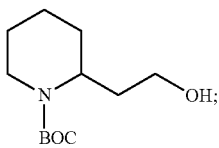

(ii) oxidizing compound 37a to form

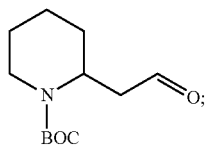

(iii) coupling compound 38a with

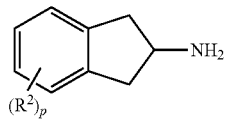

to form

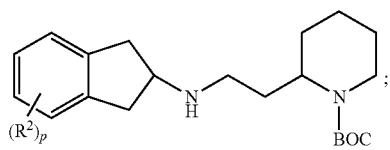

(iv) substituting compound 39a with A-$(R^3)_q$ to form

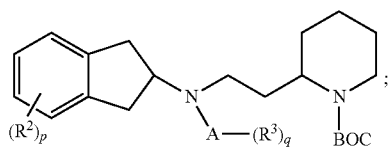

(v) deprotecting compound 40a to form

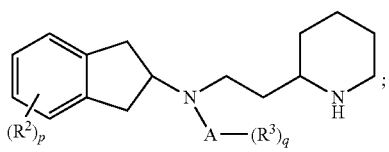

and (vi) $R^1$ and $R^4$ substituting compound 41a.

In yet another embodiment, a method for preparing a compound of the invention is provided, wherein n is 2, and includes (i) substituting

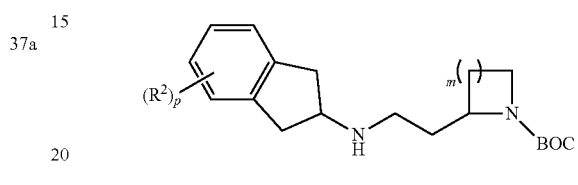

with A-$(R^3)_q$ to form

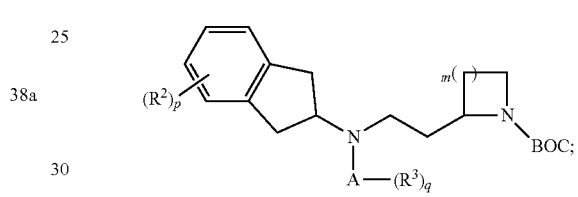

deprotecting compound 40a to form

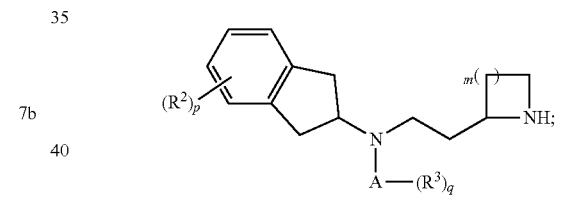

and (iii) $R^1$ and $R^4$ substituting compound 41a.

In still another embodiment, a method for preparing a compound of the invention is provided, wherein n is 2, and includes (i) substituting

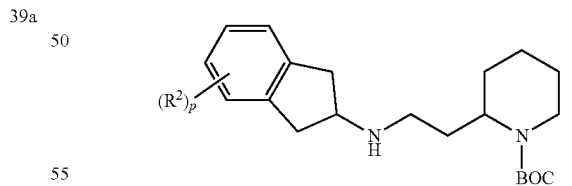

with A-$(R^3)_q$ to form

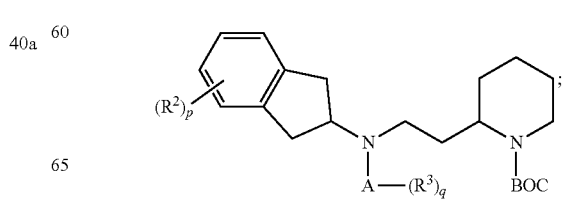

(ii) deprotecting compound 40a to form

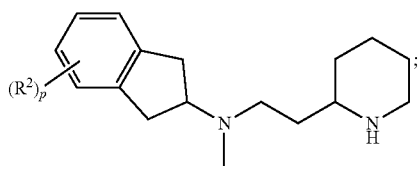
41a and (iii) R¹ and R⁴ substituting compound 41a.

In a further embodiment, a method for preparing a compound of the invention is provided and includes (i) protecting

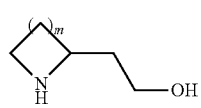
12b to form

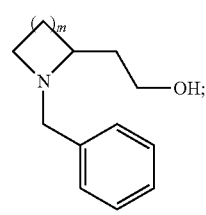
5a (ii) oxidizing compound 5a to form

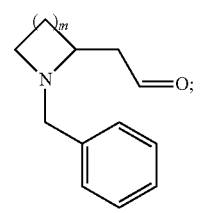
23c (iii) coupling compound 23a with

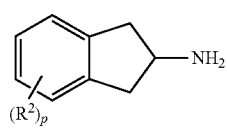
7b to form

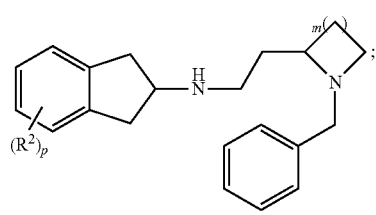
24f (iv) substituting compound 24f with A-(R³)$_q$ to form

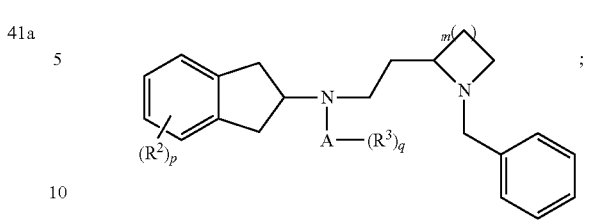
8e (v) deprotecting compound 8e to form

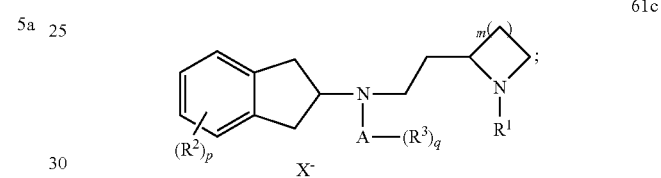
41a (vi) R¹ substituting compound 41a to form

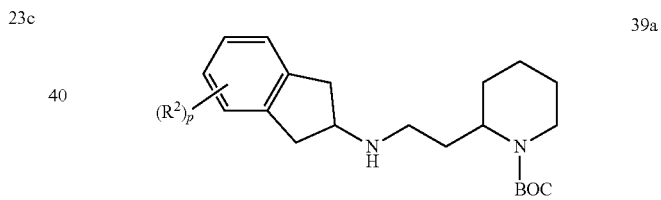
61c and (vii) R⁴ substituting compound 61c.

In a further embodiment, a method for preparing a compound of the invention is provided, wherein n is 2, and includes (i) substituting

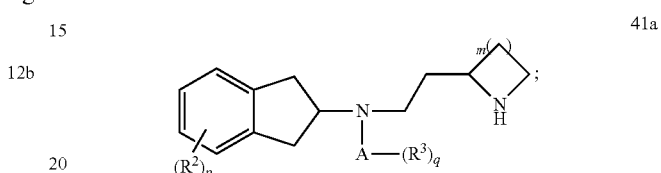
39a with A-(R³)$_q$ to form

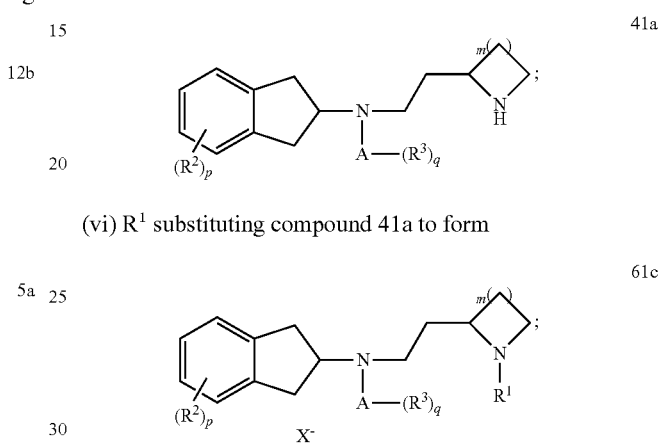
40a (ii) deprotecting compound 40a to form

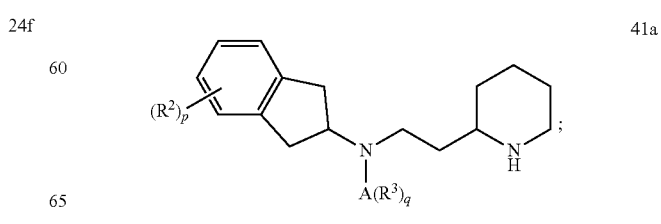
41a and (iii) R¹ and R⁴ substituting compound 41a.

In a further embodiment, a method for preparing a compound of the invention is provided and includes (i) protecting

*[structure: 2-(2-hydroxyethyl)piperidine]* to form

5a

*[structure: N-benzyl-2-(2-hydroxyethyl)piperidine]*

(ii) oxidizing compound 5a to form

23a

*[structure: N-benzyl piperidine-2-acetaldehyde]*

(iii) coupling compound 23a with

*[structure: 2-aminoindane with $(R^2)_p$]* to form

24f

*[structure: indane-NH-CH$_2$CH$_2$-piperidine-N-benzyl with $(R^2)_p$]*

(iv) substituting compound 24f with $A-(R^3)_q$ to form

8e

*[structure: indane-N(A-(R$^3$)$_q$)-CH$_2$CH$_2$-piperidine-N-benzyl with $(R^2)_p$]*

(v) deprotecting compound 8e to form

41a

*[structure: indane-N(A-(R$^3$)$_q$)-CH$_2$CH$_2$-piperidine-NH with $(R^2)_p$]*

(vi) R$^1$ substituting compound 41a to form

61c

*[structure: indane-N(A-(R$^3$)$_q$)-CH$_2$CH$_2$-piperidine-NR$^1$ with $(R^2)_p$]* and (vii) R$^4$ substituting compound 61c.

In another embodiment, a method for preparing a compound of the invention is provided and includes reacting

41a

*[structure: indane-N(A-(R$^3$)$_q$)-CH$_2$CH$_2$-azetidine-NH, with $(R^2)_p$ and $(\ )_m$]* with X"—(CH$_2$)$_r$—Y—(CH$_2$)$_n$—X", wherein r is 1 to 4; s is 1 to 4; Y is CH$_2$, O, or S; and X" is a leaving group.

In still another embodiment, a method for preparing a compound of the invention is provided and includes reacting

7b

*[structure: indane-N(A-(R$^3$)$_q$)-CH$_2$CH$_2$-piperidine-NH with $(R^2)_p$]* with ClCH$_2$CH$_2$OCH$_2$CH$_2$Cl.

In a further embodiment, a method for preparing a compound of the invention is provided and includes (i) reacting

70a

*[structure: indanone with $(R^2)_p$]* with H$_2$N-A-(R$^3$)$_q$ to form

7c

*[structure: indane-NH-A-(R$^3$)$_q$ with $(R^2)_p$]*

(ii) coupling compound 7c with
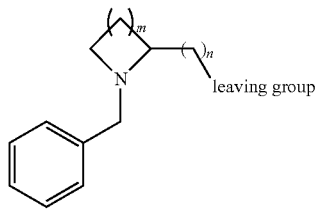
to form
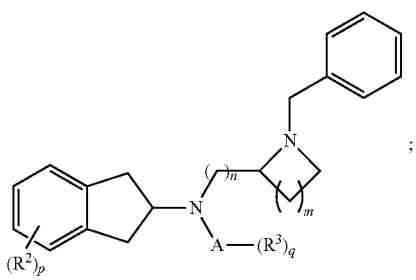
8f
(iii) deprotecting compound 8f to form
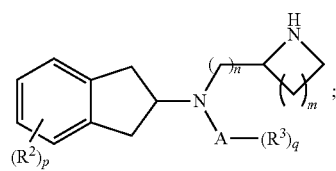
9h
(iv) R¹ substituting compound 9h to form
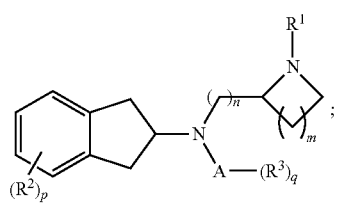
61a
and (v) R⁴ substituting compound 61a.
In yet a further embodiment, a method for preparing a compound of the invention is provided and includes (i) reacting
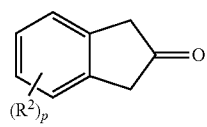
70a
with
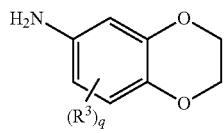
5
to form
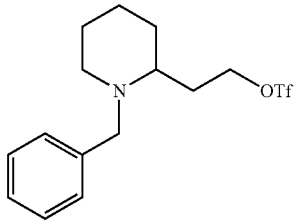
7c
(ii) coupling compound 7c with
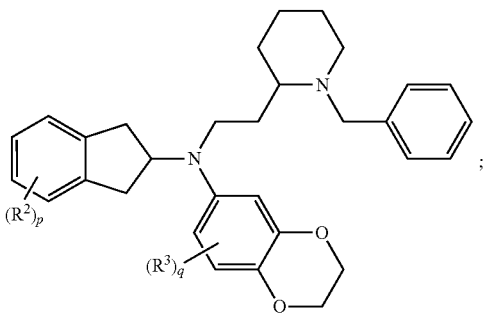
58a
to form
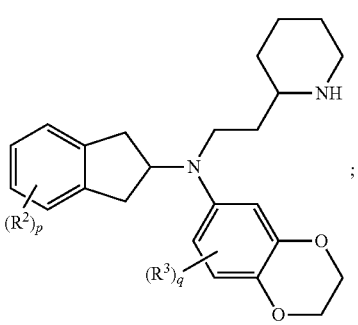
8f
(iii) deprotecting compound 8f to form
9h (iv) R[1] substituting compound 9h to form

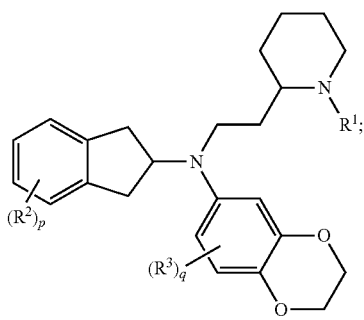

and (v) R[4] substituting compound 61a.

In still another embodiment, a method for preparing a compound of the invention is provided, wherein R[4] is CH$_3$, and includes (i) oxidizing

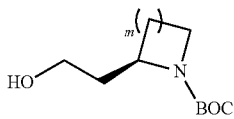

to

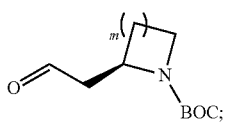

(ii) coupling compound 38a with

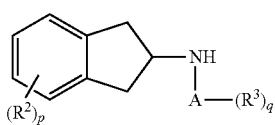

to

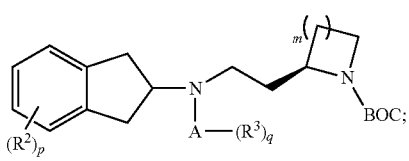

(iii) reducing compound 40a to

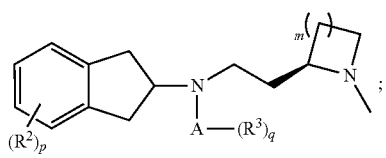

and (iv) R[1] substituting compound 41c. In one aspect, compound 40a is prepared by adding compound 38a to a solution containing compound 7c and a mild reducing agent. In another aspect, the mild reducing agent is Na(OAc)$_3$BH. In a further aspect, the % ee of compound 40a is at least about 97% ee.

Pharmaceutical compositions/regimens of the invention contain a compound of formulae (I) and/or (II) optionally with other pharmaceutically inert or inactive ingredients. In one embodiment, the pharmaceutically inert or inactive ingredient is one or more pharmaceutically acceptable carriers or excipients. The present invention also contemplates combining the compound of formulae (I) and/or (II) with one or more therapeutic agents, i.e., active ingredients, as described below. In a further embodiment, a compound of formulae (I) and/or (II) is combined with one or more inert/inactive ingredients and one or more therapeutic agents.

The pharmaceutical compositions of the invention contain an amount of a compound of formulae (I) and/or (II) that is effective for treating pain or itch in a subject. Specifically, the dosage of the compound of formulae (I) and/or (II) to achieve a therapeutic effect will depend on factors such as the formulation, pharmacological potency of the drug, age, weight and sex of the patient, condition being treated, severity of the patient's symptoms, specific compound of formulae (I) and/or (II), route of delivery, and response pattern of the patient. It is also contemplated that the treatment and dosage of the compound of formulae (I) and/or (II) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect.

In one embodiment, the therapeutically effective amount is about 0.0001% to about 25% w/w. In another embodiment, the therapeutically effective amount is less than about 20% w/w, about 15% w/w, about 10% w/w, about 5% w/w, or about 1% w/w. In another embodiment, the therapeutically effective amount is about 0.0001% to about 10% w/w. In a further embodiment, the therapeutically effective amount is about 0.005 to about 5% w/w. In yet another embodiment, the therapeutically effective amount is about 0.01 to about 5% w/w. In still a further embodiment, the therapeutically effective amount is about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.8% w/w, about 0.9% w/w, about 1% w/w, about 2% w/w, about 3% w/w, about 4% w/w, or about 5% w/w.

The therapeutically effective amounts may be provided on regular schedule, i.e., on a daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy will be determined according to the judgment of a health-care practitioner. The therapeutically effective amounts described herein refer to total amounts administered for a given time period; that is, if more than one compound of formulae (I) and/or (II) is administered, the therapeutically effective amounts correspond to the total amount administered.

The compound of formulae (I) and/or (II) may be administered by any route, taking into consideration the specific condition for which it has been selected. The compounds of formulae (I) and/or (II) may be delivered orally, by injection, inhalation (including orally, intranasally and intratracheally), ocularly, transdermally (via simple passive diffusion formulations or via facilitated delivery using, for example, iontophoresis, microporation with microneedles, radio-frequency ablation or the like), intravascularly, subcutaneously, intramuscularly, sublingually, intracranially, epidurally, intrathecally, rectally, intravesically, and vaginally, among others. Desirably, the compound of formulae (I) and/or (II) may be administered by injection, transdermally or topically. In one embodiment, the amount of the compound of formulae (I) and/or (II) is about 0.05% w/w to about 10% w/w of the preparation depending on the route of administration. When for ocular use, the amount of the compound of formulae (I) and/or (II) can be about 0.05% w/w to about 2.5% w/w.

When used for dermal anesthesia, the amount of the compound of formulae (I) and/or (II) is about 0.1% w/w to about 10% w/w. When used for non-ocular, topical (e.g., oral, nasal, rectal, urethral, vaginal) administration the amount of the compound of formula (I) and/or (II) is about 0.5% w/w to about 5% w/w. When used as in an injection, the amount of the compound of formulae (I) and/or (II) is about 0.25% w/w to about 3% w/w for injections. When used for infusions (e.g., for epidural, spinal or regional anesthesia), the amount of the compound of formulae (I) and/or (II) is about 0.1% w/w to about 3% w/w.

In one embodiment, the compound of formulae (I) and/or (II) may be administered topically to the eye, e.g., as solutions, suspensions or ointments. Examples of ophthalmically compatible carriers which may be used include, without limitation, an aqueous solution, such as saline solution, oil solution or ointments containing ophthalmically compatible preservatives, surfactants, buffers, and viscosity regulators. These compositions may also contain stabilizing agents, antibacterial agents, and may be manufactured in different dosage units, suitable for ocular administration. Drug inserts, either soluble or insoluble, may also be used.

In another embodiment, the compound of formulae (I) and/or (II) may be administered by injection. Solutions for injection or infusion may be prepared as aqueous solutions. Desirably, the compound of formulae (I) and/or (II) is present in a concentration of about 0.1% w/w to about 3% w/w. These solutions may also contain stabilizing agents, antibacterial agents, buffers and may be manufactured in different dosage unit ampoules or bottles.

In a further embodiment, the compound of formulae (I) and/or (II) may be administered rectally. Dosage units for rectal administration may be prepared in the form of ointments or suppositories, which contain the compound of formulae (I) and/or (II) in a mixture with a neutral fat base, or they may be prepared in the form of gelatin-rectal capsules that contain the compound of formulae (I) and/or (II) in a mixture with, e.g., a vegetable oil or paraffin oil. Ointments, suppositories or creams containing at least one compound of formulae (I) and/or (II) are useful for the treatment of hemorrhoids.

In still another embodiment, the compound of formulae (I) and/or (II) may be administered transdermally. A variety of transdermal delivery systems are known. For use in these systems, a compound of formula (I) and/or (II) may be admixed with a variety of excipients which may include, e.g., pH adjusters, preservatives, and/or penetration enhancers in order to form a solution, ointment, cream, lotion, or gel. Such a composition may form a constituent of a transdermal delivery system ("patch" etc.).

A transdermal delivery system may be selected which permits or assists a compound of the invention in passing though the dermal layer and to the targeted area, such as muscular tissues or a perineural space. Such systems may include formulation with skin penetration enhancers. Examples of skin penetration enhancers include physical enhancers (ultrasound, iontophoresis, electroporation, magnetophoresis, microneedle), vesicles, particulate systems (liposome, niosome, transfersome, microemulsion, solid lipid nanoparticle), and chemical enhancers (sulphoxides, azones, glycols, alkanols, terpenes, etc.). Further examples of chemical enhancers include, e.g., propylene glycol, polyethylene glycol, isopropanol, ethanol, oleic acid, N-methylpyrrolidone, which increase the permeability of the skin to the compounds, and permit the compounds to penetrate through the skin to deeper tissues. See, Sagie & Kohane, "Prolonged Sensory-Selective Nerve Blockade", PNAS, 2010(8): 3740-3745, 2010, which is herein incorporated by reference, for additional examples of chemical enhancers.

The pharmaceutical compositions containing a compound of formulae (I) and/or (II) may be formulated neat or with one or more pharmaceutical carriers for administration. The amount of the pharmaceutical carrier(s) is determined by the solubility and chemical nature of the compound of formulae (I) and/or (II), chosen route of administration and standard pharmacological practice. The pharmaceutical carrier(s) may be solid or liquid and may incorporate both solid and liquid carriers. A variety of suitable liquid carriers is known and may be readily selected by one of skill in the art. Such carriers may include, e.g., dimethylsulfoxide (DMSO), saline, buffered saline, cyclodextrin, hydroxypropylcyclodextrin (HPβCD), n-dodecyl-β-D-maltoside (DDM) and mixtures thereof. Similarly, a variety of solid carriers and excipients are known to those of skill in the art.

The compounds of formulae (I) and/or (II) can also be administered together with other-membrane stabilizers (local anesthetics), for example to form eutectic mixtures.

Although the compound of formulae (I) and/or (II) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formulae (I) and/or (II) is dissolved a liquid carrier. In another embodiment, the compound of formulae (I) and/or (II) is suspended in a liquid carrier. One of skill in the art of formulations would be able to select a suitable liquid carrier, depending on the route of administration. The compound of formulae (I) and/or (II) may alternatively be formulated in a solid carrier. In one embodiment, the composition may be compacted into a unit dose form, i.e., tablet or caplet.

In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formulae (I) and/or (II). For example, the unit dosage can be packaged compositions, e.g., packeted powders, vials, ampoules, prefilled syringes or sachets containing liquids.

Examples of excipients which may be combined with one or more compound of formulae (I) and/or (II) include, without limitation, adjuvants, antioxidants, binders, buffers, coatings, coloring agents, compression aids, diluents, disintegrants, emulsifiers (e.g., polyoxyethylene fatty acid esters), emollients, encapsulating materials, fillers, flavoring agents, glidants, granulating agents, lubricants, metal chelators, osmo-regulators, pH adjustors (e.g., sodium hydroxide), preservatives, solubilizers, sorbents, stabilizing agents, sweeteners (such as saccharin), surfactants, suspending agents, syrups, thickening agents (e.g., carboxypolymethylene or hydroxypropylmethylcellulose), penetration enhancers (e.g., hydroxypolyethoxydodecane, DMSO, DMAC, DDM, etc) or viscosity regulators (such as polymers to increase viscosity). See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formulea (I) and/or (II) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a modified-release delivery device. "Modified-release" as used herein refers to delivery of a compound of formula (I) and/or (II) which is controlled, for example over a period of at least about 8 hours (e.g., extended delivery) to at least about 12 hours (e.g., sustained delivery). Such devices may also permit immediate release (e.g., therapeutic levels achieved in under about 1 hour, or in less than about 2 hours). Those of skill in the art know suitable modified-release delivery devices. For use in such modified-release delivery devices, the compound of formulae (I) and/or (II) is formulated as described herein.

In still a further embodiment, the compositions may be administered transdermally, i.e., via the use of a drug-eluting patch. In one embodiment, the patch is an "iontophoretic" transdermal patch in which one or more medication(s) is delivered using a simple or more sophisticated (e.g. microprocessor-controlled) electrical current using, for example, an on-board battery. In still a further embodiment, the patch is a "microneedle" transdermal patch which contains microneedles coated with or containing (in dissolvable or non-dissolvable form) a pharmaceutical composition of the invention. See, e.g., U.S. Pat. Nos. 7,798,987 and 7,537,795, the disclosures of which are herein incorporated by reference. The microneedles can themselves be dissolvable or non-dissolvable; see, for example, the "microneedle" technology described in Sullivan et al., "Dissolving Polymer Microneedle Patches for Influenza Vaccination", Nature Medicine, 16:915-920 (Jul. 18, 2010 online publication) and Lee et al., "Dissolving Microneedle Patch for Transdermal Delivery of Human Growth Hormone", Small, Jan. 4, 2011 online publication, which are herein incorporated by reference. Other suitable transdermal delivery systems include the radio-frequency ablations systems described in Sintov et al., "Radiofrequency-Driven Skin Microchanneling as a New Way for Electrically Assisted Transdermal Delivery of Hydrophilic Drugs", Controlled Release 89: 311-320 (2003), and U.S. Pat. No. 7,558,625, the disclosures of which are herein incorporated by reference.

Further examples of transdermal patches useful for administration of the compounds of formula (I) and/or (II) include those described in U.S. Pat. Nos. 5,411,738 and 5,827,528 and Prausnitz and Langer, "Transdermal drug delivery", Nature Biotechnology, 26(11):1261-1268, November 2006, which are herein incorporated by reference. Desirably, a patch is applied via a suitable adhesive on the skin, where it remains in place for at least one hour. In one embodiment, the patch remains in place for about 1 hour and is replaced weekly, for a total of about 2 or about 3 hours wear time. In another embodiment, the patch remains in place for about 2 hours. In a further embodiment, the patch remains in place for about 3 hours. In still another embodiment, the patch remains in place for about 4 hours. In yet another embodiment, the patch remains in place for longer or shorter periods of time.

Also contemplated is the administration of the compounds of formulae (I) and/or (II) with other medication(s) or therapeutic agent(s). In one embodiment, the compounds of formulae (I) and/or (II) are combined with other medications or therapeutic agents in a single composition. However, the present invention is not so limited. In other embodiments, the compounds of formulae (I) and/or (II) may be administered in one or more separate formulations from other compounds of formulae (I) and/or (II), or other medications or therapeutic agents as described below.

In one embodiment, the compounds of the invention may be utilized for treating pain or itch when combined a TRPV1 receptor activator. The term "TRPV1 receptor activator" as used herein refers to any agent or stimulus that activates TRPV1 receptors on nociceptors and allows for entry of at least one inhibitor of voltage-gated ion (e.g., sodium or calcium) channels. In one embodiment, the TRPV1 receptor activator includes, but is not limited to, capsaicin, dihydrocapsaicin and nordihydrocapsaicin, lidocaine, articaine, procaine, tetracaine, mepivicaine, bupivicaine, eugenol, camphor, clotrimazole, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), Cl 8 N-acylethanolamines, lipoxygenase derivatives (such as 12-hydroperoxyeicosatetraenoic acid), inhibitor cysteine knot (ICK) peptides (vanillotoxins), pipeline, MSK1 95 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-α-sanshool, 2-aminoethoxydiphenyl borate, 10-shogaol, oleylgingerol, oleylshogaol, SU200 (N-(4-tert-butylbenzyl)-N'-(4-hydroxy-3-methoxybenzyl)thiourea) nonivamide, and fatty acyl amides of tetrahydroisoquinolines. In another embodiment, the TRPV1 receptor activator is lidocaine, aprindine, benzocaine, butacaine, cocaine, dibucaine, encamide, mexiletine, oxetacaine (oxethazaine), prilocalne, proparacaine, procainamide, n-acetylprocainamide, chloroprocaine (nesacaine, nescaine), dyclonine, etidocaine, levobupivacaine, ropivacaine, cyclomethycaine, dimethocaine (larocaine), propoxycaine, trimecaine, and sympocaine. In a further embodiment, the TRPV1 receptor activator is lidocaine. In another embodiment, the TRPV1 activator may be a detergent or a surfactant, examples of which may be found in commonly-used hygiene products such as soaps and shampoos (e.g. sodium lauryl sulfate). See, Lilja et al. "Surfactant-Induced TRPV1 activity—A Novel Mechanism for Eye Irritation?" Technological Sciences, 99(1):174-180, 2007, which is incorporated herein by reference. In another embodiment, the TRPV1 receptor activator is heat or inflammation.

When utilized as described herein, the TRPV1 receptor activator may utilized in amounts greater or less than the compound of formula (I) or (II), or a combination thereof. In one embodiment, the ratio of TRPV1 receptor activator to the compound of formula (I), formula (II), or a combination thereof, is at least about 0.5:1. In a further embodiment, the ratio of TRPV1 receptor activator to the compound of formula (I), formula (II), or a combination thereof, is at least about 1:1. In still a further embodiment, the ratio of TRPV1 receptor activator to the compound of formula (I), formula (II), or a combination thereof, is 25:1 or lower. In another embodiment, the ratio of TRPV1 receptor activator to the compound of formula (I), formula (II), or a combination thereof, is about 0.5:1 to about 25:1. In yet another embodiment, the ratio of TRPV1 receptor activator to the compound of formula (I), formula (II), or a combination thereof, is less than about 1:1. In a further embodiment, the ratio of TRPV1 receptor activator to the compound of formula (I), formula (II), or a combination thereof, is at least about 2:1. In still a further embodiment, the ratio of TRPV1 receptor activator to the compound of formula (I), formula (II), or a combination thereof, is at least about 3:1. In yet another embodiment, the ratio of TRPV1 receptor activator to the compound of formula (I), formula (II), or a combination thereof, is at least about 4:1. In still a further embodiment, the ratio of TRPV1 receptor activator to the compound of formula (I), formula (II), or a combination thereof, is about 10:1. In yet another embodiment, the ratio of TRPV1 receptor activator to the compound of formula (I), formula (II), or a combination thereof, is about 0.5 to about 1 to about 25 to about 1.

Also contemplated for use in the pharmaceutical combinations and methods described below are inhibitors of voltage-gated ion channels. In one embodiment, the voltage-gated ion channels are sodium or calcium ion channels. In a further embodiment, the voltage-gated sodium channel inhibitor includes, without limitation, QX-314, N-methyl-procaine (QX-222), N-octyl-guanidine, 9-aminoacridine, and pancuronium. In another embodiment, the inhibitor of voltage-gated calcium channels includes, but is not limited to, D-890 (quaternary methoxyverapamil) and CERM 1 1888 (quaternary bepridil). In a further embodiment, voltage-gated ion channel inhibitors such as riluzole, mexilitine, phenyloin, carbamazepine, procaine, tocamide, prilocalne, diisopyramide, bencyclane, quinidine, bretylium, lifarizine, lamotrigine, flunarizine, articaine, bupivicaine, mepivicaine, fluspirilene, orphenadrine, phenbenzamine, bepridil, pimozide, penfluridol, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine may be combined with the compound of formulae (I) and/or (II).

Membrane permeable inhibitors of voltage-gated ion channels may also be utilized in combination with the compound of formulae (I) and/or (II) in the compositions, combinations, or methods described herein. In one embodiment, the membrane permeable inhibitor of voltage-gated ion channels includes, but is not limited to, cocaine, carbamazepine, disopyramide, lamotrigine, procainamide, phenyloin, oxcarbazepine, topiramate, zonisamide, tetracaine, ethyl aminobenzoate, prilocalne, disopyramide phosphate, flecamide acetate, mexiletine, propafenone, quinidine gluconate, quinidine polygalacturonate, chloroprocaine, dibucaine, dyclonine, mepivacaine, pramoxine, procaine, tetracaine, oxethazaine, propitocaine, levobupivacaine, bupivacaine, lidocaine, moricizine, tocamide, proparacaine, ropivacaine, quinidine sulfate, encamide, ropivacaine, etidocaine, moricizine, quinidine, encamide, flecamide, tocamide, fosphenyloin, chloroprocaine, dyclonine, L-(-)-1-butyl-2',6'-pipecoloxylidide, and pramoxine.

Additionally, one or more agents typically used to treat pain, i.e., analgesics, may be used in conjunction with a combination of the invention in the methods, compositions, and kits described herein. Such agents include, but are not limited to, non-steroidal anti-inflammatory drugs (NSAIDs), opioids, tricyclic antidepressants, amine transporter inhibitors, and anticonvulsants (such as gabapentinoids).

The compound of formulae (I) and/or (II) may be administered together with a vasoconstrictor (e.g., epinephrine or vasopressin) when utilized in injectable solutions.

The compound of formulae (I) and/or (II) may be combined with glucose or dextrose when utilized for infusion or as a regional analgesic or anti-pruritic.

Further, the compound of formulae (I) and/or (II) may be combined with thickening agents to form a jelly, or may also contain penetration enhancers, for use in topical or dermal applications such as for urogenital topical procedures.

Sprays for topical anesthesia of the mouth and oropharynx may contain the compound of formulae (I) and/or (II), saccharin and/or alcohol.

Finally, the compound of formulae (I) and/or (II) may be formulated as an ointment for administration to accessible mucous membranes.

One or more additional agents typically used to treat itch may be used in conjunction with a combination of the invention in the methods, compositions, and kits described herein. Such agents include topical or oral steroids and antihistamines.

In one embodiment, the combination comprises the following compounds:

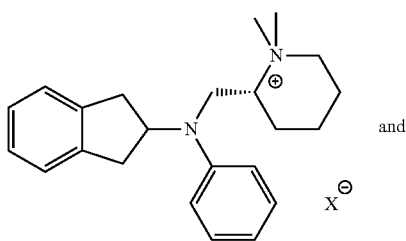

and

-continued

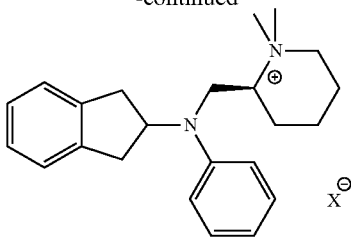

In another embodiment, the combination comprises the following compounds:

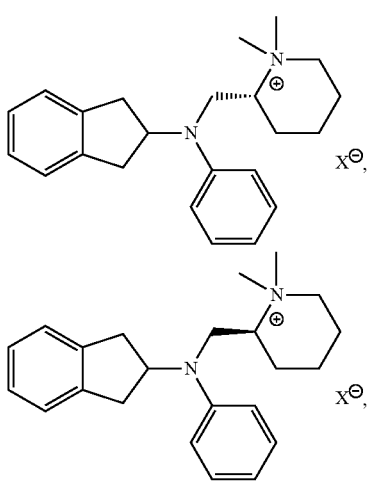

and lidocaine.

In a further embodiment, the combination comprises lidocaine and the

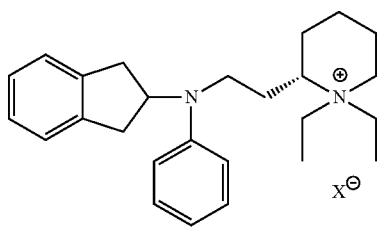

Also provided herein are regimens, kits or packages of pharmaceutical formulations containing the compounds of formulae (I) and/or (II) or compositions described herein. The kits may be organized to indicate a single formulation or combination of formulations to be taken at each desired time.

Suitably, the kit contains packaging or a container with the compound of formulae (I) and/or (II) formulated for the desired delivery route. Suitably, the kit contains instructions on dosing and an insert regarding the compound of formulae (I) and/or (II). Optionally, the kit may further contain instructions for monitoring local or circulating levels of product and materials for performing such assays including, e.g., reagents, well plates, containers, markers or labels, and the like. Such kits are readily packaged in a manner suitable for treatment of a desired indication. For example, the kit may also contain instructions for use of a patch, spray pump or other delivery device. Other suitable components to include in such kits will be readily apparent to one of skill in the art, taking into consideration the desired indication and the delivery route.

The compounds of formulae (I) and/or (II) or compositions described herein can be a single dose or for continuous or periodic discontinuous administration. For continuous administration, a package or kit can include the compound of formulae (I) and/or (II) in each dosage unit (e.g., solution, lotion, tablet, pill, drug-eluting patch or other unit described above or utilized in drug delivery), and optionally instructions for administering the doses less-than-daily, daily, weekly, or monthly, for a predetermined length of time or as prescribed. When the compound of formulae (I) and/or (II) is to be delivered periodically in a discontinuous fashion, a package or kit can include placebos during periods when the compound of formulae (I) and/or (II) is not delivered. When varying concentrations of a composition, of the components of the composition, or the relative ratios of the compounds of formulae (I) and/or (II) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a foil or blister package, labeled ampoule, vial or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

One or more components of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials or other suitable packaging means in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forceps, measuring spoon, eye dropper or any such medically approved delivery means.

In one embodiment, a kit is provided and contains a compound of formulae (I) and/or (II). The compound of formulae (I) and/or (II) may be in the presence or absence of one or more of the carriers or excipients described above. The kit may optionally contain instructions for administering the compound of formulae (I) and/or (II) to a subject having pain or itching.

In a further embodiment, a kit is provided and contains a compound of formulae (I) and/or (II) in a second dosage unit, and one or more of the carriers or excipients described above in a third dosage unit. The kit may optionally contain instructions for administering the compound of formulae (I) and/or (II) to a subject having pain or itching.

As discussed above, the methods, compositions, and kits of the invention can be used to treat pain or itch resulting from a number of conditions. The term "pain" as used herein includes all types of pain. In one embodiment, the pain may be acute or chronic. In another embodiment, the pain may be nociceptive, dysfunctional, idiopathic, neuropathic, somatic, visceral, inflammatory, and/or procedural. For example, the pain may be from a migraine, back pain, neck pain, gynecological pain, pre-labor or labor pain, orthopedic pain, post-stroke pain, post-surgical or procedural pain, post herpetic neuralgia, sickle cell crises, interstitial cystitis, urological pain (such as urethritis), dental pain, headache, pain from a wound or from a medical procedure such as surgery (such as bunionectomy or hip, knee or other joint replacement), suturing, setting a fracture, biopsy, and the like. Pain may also occur in patients with cancer, which may be due to multiple causes, such as inflammation, nerve compression, and mechanical forces resulting from tissue distension as a consequence of invasion by a tumor and tumor metastasis into bone or other tissues.

In one embodiment, the pain is neuropathic pain, such as post-herpetic neuralgia. In another embodiment, the pain is inflammatory pain. In a further embodiment, the pain is nociceptive pain. In still another embodiment, the pain is procedural pain. In yet a further embodiment, the pain is caused by esophageal cancer, colitis, cystitis, irritable bowel syndrome, colitis or idiopathic neuropathy.

"Somatic pain" includes pain from bone, joint, muscle, skin, or connective tissue.

"Central pain" includes pain arising as a consequence of brain trauma, stroke, or spinal cord injury.

"Visceral pain" includes pain from visceral organs, such as the respiratory or gastrointestinal tract and pancreas, the urinary tract and reproductive organs. In one embodiment, visceral pain results from tumor involvement of the organ capsule. In another embodiment, visceral pain results from obstruction of hollow viscus. In a further embodiment, visceral pain results from inflammation as in cystitis or reflux esophagitis.

"Idiopathic pain" refers to pain which has no underlying cause or refers to pain caused by condition which remains undiagnosed.

"Dysfunctional pain" refers to pain which occurs in the absence of a noxious stimulus, tissue damage or a lesion to the nervous system. In one embodiment, dysfunctional pain results from rheumatologic conditions such as arthritis and fibromyalgia, tension type headache, irritable bowel disorders and erythermalgia.

"Nociceptive pain" includes pain caused by noxious stimuli that threaten to or actually injure body tissues. In one embodiment, nociceptive pain results from a cut, bruise, bone fracture, crush injury, burn, trauma, surgery, labor, sprain, bump, injection, dental procedure, skin biopsy, or obstruction. In another embodiment, nociceptive pain is located in the skin, musculoskeletal system, or internal organs.

"Neuropathic pain" is pain due to abnormal processing of sensory input by the peripheral or central nervous system consequent on a lesion to these systems. In one embodiment, neuropathic pain is chronic and non-malignant. In one embodiment, neuropathic pain is due to trauma, surgery, herniation of an intervertebral disk, spinal cord injury, diabetes, infection with herpes zoster (shingles), HIV/AIDS, late-stage cancer, amputation (such as mastectomy), carpal tunnel syndrome, chronic alcohol use, exposure to radiation, and as an unintended side-effect of neurotoxic treatment agents, such as certain anti-HIV and chemotherapeutic drugs. In another embodiment, neuropathic pain is may be described as "burning," "electric," "tingling," or "shooting".

The phrase "inflammatory pain" includes pain resulting from inflammation caused by any number of factors. In one embodiment, inflammatory pain occurs due to tissue damage or inflammation. In another embodiment, inflammatory pain is due to injury (including joints, muscle, and tendons injuries), surgical procedures, infection, and/or arthritis.

"Procedural pain" includes refers to pain arising from a medical procedure. The medical procedure may include any type of medical, dental or surgical procedure. In one embodiment, the procedural pain is postoperative. In another embodiment, the pain is associated with an injection, draining an abscess, surgery, dermatological, dental procedure, ophthalmic procedure, arthroscopy and use of other medical instrumentation, and/or cosmetic surgery.

A "migraine" is a headache due to activation of sensory fibers innervating the meninges of the brain.

The term "itch" refers to all types of itching and stinging sensations that may be localized or generalized, and may be acute, intermittent or persistent. The itch may be idiopathic, allergic, metabolic, infectious, drug-induced, or due to specific disease states due to liver or kidney disease, or cancer. "Pruritus" is severe itching, but as used herein can include "itch" as defined above. In one embodiment, the itching may result from stress, anxiety, UV radiation from the sun, metabolic and endocrine disorders (e.g., liver or kidney disease, hyperthyroidism), cancer, drug reactions, reactions to food, parasitic infections, fungal infections, allergic reactions, diseases of the blood (e.g., polycythemia vera), insect bites, pregnancy, metabolic disorders, liver or renal failure, eczema, and dermatological conditions such as dermatitis, eczema, or psoriasis.

The term "treat", "treating", or any variation thereof is meant to include therapy utilized to remedy a health problem or condition in a patient or subject. In one embodiment, the health problem or condition may be eliminated permanently or for a short period of time. In another embodiment, the severity of the health problem or condition, or of one or more symptoms characteristic of the health problem or condition, may be lessened permanently, or for a short period of time. The effectiveness of a treatment of pain or itch can be determined using any standard pain or itch index, such as those described herein, or can be determined based on the patient's subjective pain or itch assessment. A patient is considered "treated" if there is a reported reduction in pain or itch, or a reduced reaction to stimuli that should cause pain or itch.

In order to measure the efficacy of any of the methods, compositions, or kits described herein, a measurement index may be used. Indices that are useful for the measurement of pain associated with musculoskeletal, immunoinflammatory and neuropathic disorders include a visual analog scale (VAS), a Likert scale, categorical pain scales, descriptors, the Lequesne index, the WOMAC index, and the AUSCAN index, each of which is well known in the art. Such indices may be used to measure pain, itch, function, stiffness, or other variables.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain or itch by choosing the spot on the line that best corresponds to the sensation of pain or itch, where one end of the line corresponds to "no pain" (score of 0 cm) or "no itch" and the other end of the line corresponds to "unbearable pain" or "unbearable itch" (score of 10 cm). This procedure provides a simple and rapid approach to obtaining quantitative information about how the patient is experiencing pain or itch. VAS scales and their use are described, e.g., in U.S. Pat. Nos. 6,709,406 and 6,432,937, the relevant disclosures of which are herein incorporated by reference.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced. Likert scales and their use are described, e.g., in U.S. Pat. Nos. 6,623,040 and 6,766,319, the relevant disclosures of which are herein incorporated by reference.

The Lequesne index and the Western Ontario and McMaster Universities (WOMAC) osteoarthritis (OA) index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert scale. Both the WOMAC index and the Lequesne index questionnaires have been extensively validated in OA, including in surgical settings (e.g., knee and hip arthroplasty). Their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index may utilize, e.g., a Likert or a VAS scale.

Other suitable indices that are useful for the measurement of pain include the Pain Descriptor Scale (PDS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

Itch can also be measured by subjective measures known to those skilled in the art (VAS, Likert, descriptors and the like). Another approach is to measure scratch which is an objective correlate of itch using a vibration transducer or movement-sensitive meters.

In one embodiment, the treatment methods described herein include administering a compound of formulae (I) and/or (II) to a patient. Additional, optional agents, such as those described above for use in the combination, may be administered to the patient prior to, concurrently with, or subsequent to the compound of formulae (I) and/or (II).

In another embodiment, the methods described herein thereby include administering a compound of formulae (I) and/or (II) and a TRPV1 receptor activator to a patient. In one embodiment, the compound of formulae (I) and/or (II) is administered to the patient prior to the TRPV1 receptor activator. In another embodiment, the TRPV1 receptor activator is administered to the patient prior to the compound of formulae (I) and/or (II). In a further embodiment, the compound of formulae (I) and/or (II) and TRPV1 receptor activator are administered to the patient concurrently.

Also contemplated by the present invention is administration of a compound of formulae (I) and/or (II) after the TRPV1 receptor has been activated. Specifically, this method is performed after the TRPV1 receptor is activated. Such activation may result from administration of an exogenous activating compound or stimulus, or may arise as a result of endogenous activation induced by a pathophysiological state, such as inflammation, that activates TRPV1 receptors.

A variety of in vivo assays and animal models are useful for assessing the ability of compounds to inhibit pain via internal sodium channel inhibition. These models may or may not involve opening (activation) of TRPV1 channels via inducing pain through physical, mechanical, or chemical (e.g., capsaicin) means. Examples of suitable models include, e.g., those described in Khan et al., Anesthesiology, January 2002, 96(1): 109-116; AM Binshtok et al., Anesthesiology, July 2009, 111(1):127-137; CR Reis et al., Anesthesiology, July 2009, 111(1):122-126; P Gerner et al., Anesthesiology, November 2008, 109(5):872-878; and AM Binshtok et al., Nature, October 2007, 449:607-610, which are incorporated by reference herein. However, for a variety of reasons which will be readily apparent to those of ordinary skill in the art, it is desirable to provide in vitro assays which allow for the identification of compounds with the desired properties. Described herein are two such in vitro assays.

In one embodiment, a modified FLIPR® (Fluorometric Imaging Plate Reader) based assay system was developed which is capable of discriminating between non-specific versus hTRPV1-mediated entry of test compounds. Advantageously, the assay system utilizes heat activated opening of hTRPV1 channels followed by an assessment of internal sodium channel block. The assay allows a permanently charged compound to selectively enter through opened hTRPV1 channels and that compound's potency in inhibiting sodium channels from the cytoplasm side of the same cell can be assessed and quantified.

The modified FLIPR® assay utilizes cells which functionally express hTRPV1.

As used herein, the term "functionally express" includes those cells which express the human TRPV1 protein and which respond to stimuli which naturally open this channel, including, e.g., the thermal (e.g., heat) or chemical (e.g., capsaicin, lidocaine) means described herein. Suitable assays may include the calcium or membrane potential assays described herein (see, e.g., Example 36). However, other functional assays are known in the art (e.g. voltage-clamp electrophysiology such as used by Binshtok et al., Nature 449(4) 607-610, 2007)

A suitable cell may be selected for expression of TRPV1 in cis or in trans and constructed using known techniques. In one embodiment, a neuroblastoma cell line such as N1E115 [CRL-2263] or ND7/23 [ECACC catalog code: 92090903] is selected for expression of the hTRPV1. However, another neuroblastoma cell line may be selected, e.g., such as IMR-32 [CRL-127]; Neuro-2a [CRL-131]; NB41A3 [CRL-147]; B104-1-1 [CRL-1887]; SK-N-AS [CRL-2137]; SK-N-F1 [CRL-2142]; SK-N-DZ [CRL-2149]; SH-SY5Y [CRL-2266]; BE(2)-M17 [CRL-2267]; BE(2)-C [CRL-2268]; MC-IXC [CRL-2270]; SK-N-BE(2) (CRL-2271); CHP-212 (CRL-2273]; B35 [CRL-2754], which are available from the American Type Culture Collection, Manassas, Va. (US). Still other cell lines may be selected.

For a generation description of how the cells are produced, see generally, e.g., Sambrook et al, Molecular Cloning: A Laboratory Manual, Cold Spring Harbor Press, Cold Spring Harbor, N.Y. (US) 2001. In one embodiment, a stable cell line may be prepared using the techniques in Sambrook et al, using wild-type (wt) or recombinant hTRPV1 coding sequences. For example, preparation of one such cell line is described in detail herein (see Example 32). Preparation of another cell line is described in WO 2007/0066068; the LipofectAMINE® method may be employed for transfection of TRPV1 and hTRPV1 into Human Embryonic Kidney cells (HEK293) according to the manufacturers protocol (Gibco). To create a permanently expressing cell line, wt-TRPV1 transfected HEK cells can be subcloned in geneticin (0.6 mg/mL) containing medium (DMEM containing 10% FCS, 100 U/mL penicillin, 100 U/mL streptomycin, and 250 ng/mL amphotericin B) and propagated for two weeks to allow selection. To obtain a TRPV1 permanently expressing single cell line, transfected cells can be plated in 96 well plates (1 cell per well) and colonies grown from single cells were subsequently tested for capsaicin responsiveness by measuring increases in intracellular calcium. The final clones selected, are taken through three further rounds of single cell cloning to ensure the cell lines are derived from a single cell. Variations on this methodology will be readily apparent to one of skill in the art. In another embodiment, a cells may be selected from a stable cell line to express the hTRPV1, in trans, e.g., from a viral vector or another suitable genetic element.

In one embodiment, the hTRPV1 protein is selected which has the sequence of SEQ ID NO:1 [NCBI Accession Number NM_080706.3].

However, one of skill in the art that minor modifications may be made to this sequence while retaining the desired functionality of the protein. Alternatively, one could select another TRPV1 protein (e.g., from a guinea pig, mouse, or other species) and modify that sequence for use in the present invention. Such modifications may be made for a variety of reasons, including, e.g., to improve yield or purification.

In order to prepare an hTRPV1-expressing cell, a construct containing the coding sequence for the above-identified hTRVP1 sequence is selected. In one embodiment, the coding sequence is any sequence which encodes the above-identified protein. In another embodiment, the coding sequence is selected from one of the four transcript variants reported in NCBI for human TRPV1 (hTRPV1), (NM_018727.5, NM_080704.3, NM_080705.3, and NM_080706.3). The functional protein coding sequence (ORF—Open Reading Frame) for all the four transcripts is same. In the examples below, the construct contains the functional protein coding sequence only. However, in another embodiment, another variant, including the longest variant (variant 3, NCBI Accession No: NM_080706.3) may also be used. In still another embodiment, another ORF, or another sequence containing the ORF, is selected. In one embodiment, the sequence is cloned from an existing construct such as described in the examples below. In another embodiment, a recombinant sequence is used.

While the use of cells which are infected or transfected such that they express hTRPV1 in trans is possible, the use of a cell line which stably expresses the hTRPV1 channel is desirable. Such cell lines can be generated by one of skill in the art utilizing the information available herein and known in the art.

In one embodiment, in order to prepare the cell line, hTRPV1 is amplified by PCR from IMR322 cDNA (a neuroblastoma cell line). The PCR product obtained containing the protein coding sequence of hTRPV1 is cloned into a production vector under the control of a strong promoter. As illustrated below, the human cytomegalovirus promoter was used. However, another promoter with strong constitutive expression in mammalian host cells may also be used. Optionally, the sequence may be verified by PCR. The cells which are to be transduced (e.g., the N1E115 cells) are pre-

```
  1 MKKWSSTDLG AAADPLQKDT CPDPLDGDPN SRPPPAKPQL STAKSRTRLF GKGDSEEAFP

61 VDCPHEEGEL DSCPTITVSP VITIQRPGDG PTGARLLSQD SVAASTEKTL RLYDRRSIFE

121 AVAQNNCQDL ESLLLFLQKS KKHLTDNEFK DPETGKTCLL KAMLNLHDGQ NTTIPLLLEI

181 ARQTDSLKEL VNASYTDSYY KGQTALHIAI ERRNMALVTL LVENGADVQA AAHGDFFKKT

241 KGRPGFYFGE LPLSLAACTN QLGIVKFLLQ NSWQTADISA RDSVGNTVLH ALVEVADNTA

301 DNTKFVTSMY NEILMLGAKL HPTLKLEELT NKKGMTPLAL AAGTGKIGVL AYILQREIQE

361 PECRHLSRKF TEWAYGPVHS SLYDLSCIDT CEKNSVLEVI AYSSSETPNR HDMLLVEPLN

421 RLLQDKWDRF VKRIFYFNFL VYCLYMIIFT MAAYYRPVDG LPPFKMEKTG DYFRVTGEIL

481 SVLGGVYFFF RGIQYFLQRR PSMKTLFVDS YSEMLFFLQS LFMLATVVLY FSHLKEYVAS

541 MVFSLALGWT NMLYYTRGFQ QMGIYAVMIE KMILRDLCRF MFVYIVFLFG FSTAVVTLIE

601 DGKNDSLPSE STSHRWRGPA CRPPDSSYNS LYSTCLELFK FTIGMGDLEF TENYDFKAVF

661 IILLLAYVIL TYILLLNMLI ALMGETVNKI AQESKNIWKL QRAITILDTE KSFLKCMRKA

721 FRSGKLLQVG YTPDGKDDYR WCFRVDEVNW TTWNTNVGII NEDPGNCEGV KRTLSFSLRS

781 SRVSGRHWKN FALVPLLREA SARDRQSAQP EEVYLRQFSG SLKPEDAEVF KSPAASGEK
``` pared using Lipofectamine 2000 (Invitrogen, Catalog No. 11668-019), as described herein. The transduced cells are passaged using conventional methods and standard transfection techniques where utilized. By the end of second week, transfected stable colonies appear, which are then expanded and tested functionally. Final clonal candidate for the study was selected based on the functional assay data. These assays assess the ability of the cell to express hTRPV1 in a functional manner, i.e., such that upon being contacted with at least one of stimuli to which wt hTRPV1 respond, the hTRPV1 channel opens. For example, a cell expressing a functional hTRPV1 may respond to capsaicin, or to heat, or to other chemical, mechanical or physical stimuli characteristic of hTRPV1 in its natural setting. Examples of suitable assays are described in Example 36 below and include the membrane potential and calcium assays. Other suitable assays include standard single-cell voltage-clamp electrophysiology approaches such as used by Binshtok et al., Nature 449(4) 607-610, 2007. The TRPV1 assay is performed using a FLIPR®-384 fluorescence measurement platform (Molecular Devices, Inc.) operating in a membrane potential assay mode, or another suitable system, using hTRPV1-expressing cells as described herein. FLIPR® Membrane Potential Assay Kits (both blue and red) are available from Molecular Devices Corp (Sunnyvale, Calif., USA), which provides many of the dyes and materials used in the following assay. However, similar materials may be obtained from other sources as needed or desired.

The assay described herein used a method of activation for the TRPV1 channel which differs from that typically described in the literature and the art (i.e., capsaicin). The use of capsaicin to open the hTRPV1 channel in the cells proved to be unsuitable since it eroded the signal-to-noise window of the subsequent sodium channel response component of the assay in the hTRPV1-N1E115 cell line. Alternatively, it is anticipated that another cell line prepared as described herein could be substituted for this cell line. Therefore, another method to open the channel had to be developed. The heat activation method used herein has been found to yield robust and reproducible performance.

The assay is readily performed in multi-well assay plates into which cells in growth media are added and incubated under conditions which permit the formation of a confluent monolayer over a period of hours prior to the start of the assay. Conventional culture media and conditions may be utilized. Duplicate cell assay plates are prepared for each experiment.

The spent media from the cell seeded plates is removed on the day of the assay and replaced with Membrane potential Dye-Blue (Molecular Devices). The dye was prepared in assay buffer following manufacturer's instructions. The dye-loaded plate is incubated at room temperature (about 25° C.) for about 30 minutes in order to pre-load the cells with dye. Optionally, the cells may be loaded with the dye simultaneously with adding the test compounds.

An illustrative assay buffer is prepared using purified, deionized water according to Table 1. While the precise components may be varied, the ionic nature of the assay buffer is desirable for use in the assay. The pH is adjusted to 7.4 using potassium hydroxide and the volume is made up with Milli-Q water (Millipore) up to 500 mL. Unless otherwise mentioned, all the dilutions were done in Assay Buffer.

TABLE 1

| Salt | Concentration (mM) |
| --- | --- |
| NaCl | 150 |
| KCl | 3.25 |
| $CaCl_2$ 2 $H_2O$ | 2 |
| $MgCl_2$ 6 $H_2O$ | 3 |
| HEPES | 10 |
| Glucose | 11 (198 mg/100 mL) |

The test compounds are diluted in the Assay Buffer and added to each well of a specific 384-well 'compound plate', which serves as a source plate for compound addition using the FLIPR® platform. The concentration of compounds in the compound-plate was adjusted to achieve the desired final concentration when added to the cells in the 'cell-plate'. After completion of the dye incubation period, the dye loaded cell-plates and the compound source plates are inserted into the FLIPR® Tetra™ device with a 384 FLIPR® tip box (Molecular Devices, Inc.) according to manufacturer's instructions. The compounds are robotically added to the dye loaded cell-plates using software integral to the FLIPR® Tetra™ instrument.

Immediately following compound addition, hTRPV1 is activated, in one of the duplicate cell plates, by heating. Specifically, entire multi-well plate containing the compound-cells mixture is incubated at 47° C. for 10 minutes, after which they are returned to room temperature (about 25° C.) for a further 30 minutes. Heat activation of hTRPV1 was omitted from the replicate cell plate which was simply maintained at room temperature for the entire 40 minutes.

A membrane potential response is elicited in the dye- and compound-loaded cells by the addition of veratridine which is a known sodium channel 'agonist'. As illustrated in an example herein, an agonist plate containing veratridine (Sigma) is prepared in advance and is inserted into suitable devices such as, e.g., the FLIPR® TETRA® device for a "$2^{nd}$ addition" as instructed by the manufacturer. The concentration of veratridine in the 'agonist plate' was adjusted to achieve a final concentration of 100 µM when added to the cells in the cell-plate. Final concentrations of veratridine greater or lesser than 100 µM may also be used but the signal measured by the FLIPR®$^{Tetra}$™ device or another suitable device may vary accordingly.

The exposure of the cells in the cell-plate to veratridine induces sodium channels in the cells to open and the resulting ion flux produces a membrane potential depolarization that is detected as a fluorescence signal by the FLIPR® $^{Tetra}$™ Device. The activity of test compounds is determined by their ability to attenuate the veratridine-induced fluorescence signal, the most promising compounds are those that show an enhanced activity in the heat-activated cell plate over the non-heat-activated cell plate. This differential activity reflects enhanced compound uptake via the heat activated and open hTRPV1 channels and rests on the fact that sodium channel block requires test compounds to act from the cytoplasmic side of the cell membrane.

Once assessed using these screening assays, compounds may be selected for study in animal models. Routine evaluation of the analgesic effect of compounds was performed using a rodent pinch-pain test apparatus (Bioseb (France)). Skin pinch provides a mechanical stimulus that can be graded and which is particularly suitable for assessing acute mechanical (as described by AM Binshtok et al., Anesthesiology, July 2009, 111(1):127-137, which is incorporated by reference herein). Another rodent pain model typically used is the Hargreaves plantar test apparatus (IITC (USA)) which is particularly suitable for assessing thermal nociception. Yet another model utilizes a pin-prick-evoked cutaneous trunci muscle reflex response (the so-called CTMR model) to assess cutaneous analgesia after localized subcutaneous injections of an anesthetic agent (Khan et al., Anesthesiology, January 2002, 96(1): 109-116, which is incorporated by reference herein).

The following examples are illustrative only and are not intended to limit the present invention.

EXAMPLES

Unless otherwise stated, all the raw materials are purchased from commercially available common suppliers. $^1$H-NMR spectra were recorded using trimethylsilane (TMS) as the internal reference for $CDCl_3$ dissolved compounds. For DMSO-$d_6$, MeOD and $D_2O$ dissolved compounds the instrument was calibrated at δ 2.5, 3.3 and 4.82 ppm respectively. The chemical shift values are quoted in δ (parts per million).

For LCMS analysis LCMS/MS API 2000 (Applied Biosystem) instrument was used. The columns included:
Column V: Zorbax® C18 column, 4.6×50 mm, 5μ.
Column W: Zorbax® Extend C18 column, 4.6×50 mm, 5μ.
Column X: Gemini® NX C18 column, 4.6×50 mm, 5μ.
Column Y: Xbridge® C18 column, 4.6×50 mm, 5μ.
Column Z. Reprosil® column, 4.6×50 mm, 5μ.

The eluent (solvent) typically included (acidic or basic buffer as aqueous phase):
A channel: (i) 0.05% formic acid in water;
  (ii) 10 mM ammonium acetate in water; or
  (iii) 0.05% TFA in water.
B channel: acetonitrile (organic phase).

The detector was UV measured at dual wavelengths: 220 and 260 nm.

The LCMS gradients were one of the following:
1. LCMS Reaction Monitoring and Final Compound Analysis Method (for General Polarity Compounds)
  Gradient condition: 5 minutes run time
  Time Programs: P1: 10 mM ammonium acetate in water/acetonitrile
    Q1: 0.05% TFA in water/acetonitrile,
    R1: 0.05% formic acid in water/acetonitrile.
  The gradient varied acetonitrile from 10% to 90% to 10%.
  Flow rate: 1.2 mL/minute
2. LCMS Reaction Monitoring and Final Compound Analysis Method in 12 Minutes Run (for Close Eluting Compounds):
  Gradient condition: 12 minutes run time
  Time Programs: P2: 10 mM ammonium acetate in water/acetonitrile
    Q2: 0.05% TFA in water/acetonitrile
    R2: 0.05% formic acid in water/acetonitrile
  The gradient varied acetonitrile from 5% to 90% to 5%
  Flow rate: 1.0 mL/minute
3. LCMS after method development in HPLC—gradient conditions are as per HPLC.

Mass spectral data was obtained using the following:
Ionization technique: ESI (Electron Spray Ionization) using API (Atmospheric pressure Ionization) source
Declustering Potential: 10-70 V depending on the ionization of compound
Mass range: 100-800 amu
Scan type: Q1
Polarity: +/−ve
Ion Source: Turbo spray
Ion spray voltage: +5500 for +ve mode and −4500 for −ve mode
Mass Source temperature: 200° C.

HPLC analysis was carried out using the Shimadzu® LC-2010, the Agilent® 1200 series, and Waters® Alliance® HT instruments. The columns included:
  (i) Zorbax® SB C18 column (50×4.6 mm) 1.8μ
  (ii) Atlantis® dC18 column (150×4.6 mm) 5μ
  (iii) Gemini® NX C18 column (50×4.6 mm) 3μ
  (iv) XBridge® C18 column (50×4.6 mm) 3μ
  (v) XBridge® C18 column (50×4.6 mm) 5μ
  (vi) XTerra® C18 column (250×4.6 mm) 5μ
  (vii) Gemini® C18 column (50×4.6 mm) 5μ
  (viii) Zorbax® SB-C18 column (4.6×50 mm) 5μ
  (ix) Sunfire®-C18 column (150×4.6 mm) 5μ

The mobile phases included the following and the mobile phase gradients were changed from A. 90% to 10% to 90%. Flow rate was 1 mL/minute.
  A. 0.05% TFA in water, 0.05% HCOOH in water, 0.05% Acetic acid in water, 10 mM ammonium acetate in water (acidic or basic buffer); and
  B. acetonitrile or methanol (organic phase).

Ultra Performance Liquid Chromatography (HPLC) analysis was carried out using Agilent® 1100 series and 1200 series instruments. The columns included:
  (i) Zorbax® SB C18 column (50×4.6 mm) 1.8μ
  (ii) Zorbax® XDB C18 column (50×4.6 mm) 1.8μ
  (iii) Gemini® NX C18 column (50×4.6 mm) 5μ
  (iv) XBridge® C18 column (50×4.6 mm) 5μ
operating at ambient temperature. The mobile phase included the following and mobile phase gradients were changed from A. 95% to 5% to 95%. Flow rate varied from 0.8 to 1 mL/minute.
  A. 0.05% TFA in water, 0.05% HCOOH in water
  B. Acetonitrile Example 1

General Procedure A1—Preparation of (S)-1,1,-dipropyl-2-[2-((indan-2-yl)(phenyl)amino)ethyl] piperidinium iodide

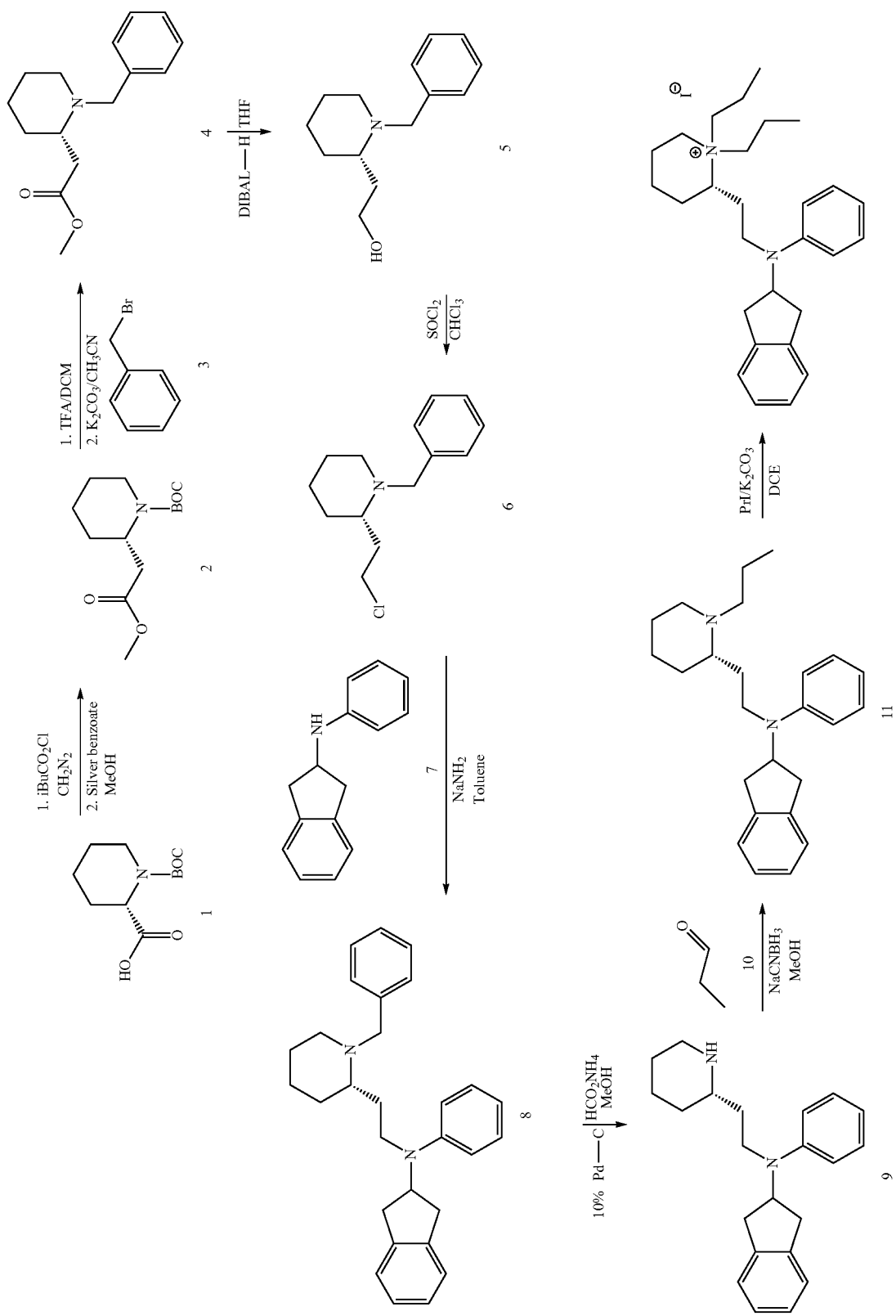

A. (S)-2-(Methoxycarbonylmethyl)piperidine-1-carboxylic acid tert-butyl ester (Compound 2)

To a stirred solution of boc-L-pipecolic acid (1; 15g, 68.10 mmol) in tetrahydrofuran (THF; 175 mL) was added N-methyl morpholine (9.4 mL, 85.12 mmol) at −30° C., followed by the addition of isobutyl chloroformate (9.8 mL, 74.90 mmol) dropwise at −30° C. The resulting mixture was stirred at that temperature for 1 hour. A solution of diazomethane in diethyl ether was then added to the reaction mixture and the mixture was stirred at room temperature (rt) for 16 hours. The reaction mixture was quenched by adding glacial acetic acid (10 mL) and was then concentrated. The residue was dissolved in diethyl ether (500 mL), washed with water (100 mL) and brine (25 mL). The combined organic layers were dried, filtered and concentrated.

The crude material was dissolved in methanol (130 mL), silver benzoate (4 g) was added portion-wise at ice cold conditions and the mixture was stirred at rt for 16 hours. Brine solution (50 mL) was added to the reaction mixture and filtered through the Celite® reagent and washed with methanol. The organic layer was evaporated in vacuo, the residue was diluted with ethyl acetate (EtOAc, 470 mL) and washed with water (50 mL) and brine (20 mL). The organic layer was dried, filtered and concentrated. The crude material was purified by chromatography using 230-400 mesh silica gel eluting with 3% EtOAc in hexane to provide compound 2 as a liquid.

Yield: 10.2 g (58.28%);

$^1$H-NMR (400 MHz, DMSO-d$_6$): δ 4.51 (s, 1H), 3.81 (d, J=11 Hz, 1H), 3.57 (s, 3H), 2.77-2.74 (m, 1H), 2.55 (d, J=7 Hz, 2H), 1.58-1.52 (m, 6H), 1.37 (s, 9H);

LCMS: [M+H]=258.2, RT=3.55 minutes, (Program R1, Column X).

B. (S)-2-(1-Benzyl-piperidin-2-yl)acetic acid methyl ester (Compound 4)

To a stirred solution of compound 2 (10 g, 38.91 mmol) in dichloromethane (DCM; 70 mL) was added trifluoroacetic acid (TFA; 20 mL) dropwise at ice cold conditions and the reaction mixture was stirred at rt for 4 hours. The solvent of the reaction mixture was evaporated in vacuo. The crude material was dissolved in acetonitrile (130 mL), K$_2$CO$_3$ (27 g, 194.55 mmol) was added portion-wise at ice cold conditions, and the reaction mixture was stirred for 15 minutes. Benzyl bromide (3; 7 mL, 58.37 mmol) was then added dropwise and the resulting mixture was heated at 100° C. for 16 hours. The mixture was filtered and washed with EtOAc. The organic layer was washed with water (75 mL) and brine (30 mL). The combined organic layers were dried, filtered and concentrated. The crude material was purified by Combiflash® chromatography eluting with 4.5% EtOAc-hexane to provide compound 4 as a liquid.

Yield: 6.1 g (63.47%);

$^1$H-NMR (400 MHz, DMSO-d$_6$): δ 7.32-7.21 (m, 5 H), 3.75 (d, J=14 Hz, 1 H), 3.58 (s, 3 H), 3.30 (d, J=14 Hz, 1H), 2.87-2.84 (m, 1 H), 2.69 (dd, J=15, 5 Hz, 1 H), 2.56-2.52 (m, 1 H), 2.47-2.41 (m, 1H), 2.15-2.10 (m, 1H), 1.64-1.52 (m, 2H), 1.44-1.32 (m, 4H);

LCMS: [M+H]=248.0, RT=3.61 minutes (Program P1, Column Y).

C. (S)-2-(1-Benzyl-piperidin-2-yl)ethanol (Compound 5)

To a stirred solution of compound 4 (6 g, 24.29 mmol) in dry THF (200 mL) was added diisobutylaluminum hydride (DIBAL-H, 1.2 M in toluene, 81 mL, 97.16 mmol) drop-wise at −30° C. The reaction mixture was then stirred at 0-5° C. for 4 hours. The reaction mixture was quenched by adding saturated NH$_4$Cl solution (15 mL) at −50° C. The reaction mixture was concentrated and diluted with EtOAc. The organic layer was washed with water and brine, dried over Na$_2$SO$_4$, filtered and concentrated to provide compound 5.

Yield: 5.1 g (95.87%);

$^1$H-NMR (400 MHz, DMSO-d$_6$): δ 7.30-7.18 (m, 5H), 4.40 (s, 1H), 3.87 (d, J=14 Hz, 1H), 3.51-3.44 (m, 2H), 3.23 (d, J=14 Hz, 1H), 2.62-2.58 (m, 1H), 2.44-2.42 (m, 1H), 2.05-2.00 (m, 1H), 1.82-1.77 (m, 1H), 1.66-1.59 (m, 3H), 1.40-1.23 (m, 5H);

LCMS: [M+H]=220.5, RT=1.78 minutes (Program P1, Column Y).

D. (S)-1-Benzyl-2-(2-chloroethyl)piperidine (Compound 6)

A solution of compound 5 (3.5 g, 15.98 mmol), thionyl chloride (6 mL) and four drops of concentrated HCl in chloroform (40 mL) was heated at 75° C. for 16 hours. The reaction mixture was concentrated, saturated sodium bicarbonate solution (50 mL) was added, and the product extracted with EtOAc. The organic layer was separated and washed with water and brine, dried over Na$_2$SO$_4$, filtered and concentrated. The crude material was purified by Combiflash® chromatography eluting with 3.5% EtOAc in hexane to provide compound 6 as a liquid.

Yield: 3.1 g (81.85%);

$^1$H-NMR (400 MHz, DMSO-d$_6$): δ 7.30-7.22 (m, 5H), 3.82 (d, J=14 Hz, 1H), 3.72-3.62 (m, 2H), 3.32-3.30 (m, 1H), 2.63-2.55 (m, 2H), 2.12-2.04 (m, 2H), 1.99-1.89 (m, 1H), 1.66-1.59 (m, 2H), 1.42-1.32 (m, 4H);

LCMS: [M+H]=237.8, RT=3.78 minutes (Program P1, Column Y).

E. (S)—N-[2-(1-Benzyl-piperidin-2-yl)ethyl]-N-phenylindan-2-yl-amine (Compound 8)

To a stirred solution of NaNH$_2$ (0.74 g, 18.99 mmol) in toluene (80 mL) was added a solution of compound 7 (2.91 g, 13.92 mmol) in toluene (10 mL) dropwise at ice cold conditions and the mixture was stirred at rt for 3 hours. A solution of compound 6 (3 g, 12.66 mmol) in toluene (10 mL) was then added to the reaction mixture dropwise at ice cold conditions and the mixture was heated at 110° C. for 16 hours. This reaction mixture was diluted with EtOAc (70 mL) and washed with water and brine. The organic layer was dried over Na$_2$SO$_4$, filtered and concentrated. The crude material was purified by Combiflash® chromatography eluting with 11.2% EtOAc in hexane to provide compound 8, which was isolated as a sticky solid.

Yield: 1.5 g (28.90%);

$^1$H-NMR (400 MHz, DMSO-d$_6$): δ 7.30-7.10 (m, 11H), 6.79 (d, J=8 Hz, 2H), 6.64 (t, J=7 Hz, 1H), 4.64-4.61 (m, 1H), 3.67 (d, J=14 Hz, 1H), 3.23-3.15 (m, 5H), 2.95-2.90 (m, 2H), 2.53-2.50 (m, 1H), 2.31 (brs, 1H), 2.02-1.98 (m, 1H), 1.67-1.60 (m, 2H), 1.51-1.49 (m, 2H), 1.35-1.17 (m, 4H);

LCMS: [M+H]=411.0, RT=3.20 minutes (Program P1, Column Y).

F. (S)-2-N-Phenyl-N-[2-(piperidin-2-yl)ethyl]indan-2-yl-amine (Compound 9)

A stirred solution of compound 8 (0.55 g, 1.34 mmol) and ammonium formate (0.85 g, 13.41 mmol) in methanol (30 mL) was purged with $N_2$ for 30 minutes. Ten percent Pd—C (0.07 g) was added and purging was continued for 5 additional minutes. The resulting mixture was heated at 100° C. for 3 hours. The reaction mixture was filtered through the Celite® reagent and washed with methanol. The filtrate was concentrated and the crude material was dissolved in 50% acetonitrile-water mixture and lyophilized to provide compound 9.

Yield: 0.4 g (93.14%);

$^1$H-NMR (DMSO-$d_6$): δ 7.24-7.10 (m, 6 H), 6.81 (d, J=8 Hz, 2 H), 6.63 (t, J=7 Hz, 1 H), 4.68-4.60 (m, 1 H), 3.38-3.36 (m, 1 H), 3.24-3.11 (m, 3 H), 2.96 (dd, J=16, 8 Hz, 2 H), 2.93-2.88 (m, 1 H), 2.45-2.35 (m, 2 H), 1.66-1.65 (m, 1 H), 1.47-1.45 (m, 4 H), 1.27-1.23 (m, 2 H), 0.96-0.93 (m, 1 H);

LCMS: [M+H]=320.8, RT=3.03 minutes (Program P1, Column Y).

G. (S)—N-Phenyl-N-[2-(1-propyl-piperidin-2-yl)ethyl]indan-2-yl-amine (Compound 11)

To a stirred solution of compound 9 (0.35 g, 1.09 mmol) in methanol (15 mL) was added NaCNBH$_3$ (0.082 g, 1.2 mmol) at ice cold conditions and the mixture was then stirred at rt for 30 minutes. Propanaldehyde (10; 0.1 mL, 1.37 mmol) was added to the reaction mixture drop-wise at ice cold conditions and the mixture was stirred at rt for 16 hours. The reaction mixture was concentrated using a rotavapour. The crude material was purified by Combiflash® chromatography eluting with 4.6% MeOH in DCM to provide compound 11.

Yield: 0.37 g (93.59%);

$^1$H-NMR (400 MHz, DMSO-$d_6$): δ 7.22-7.15 (m, 6H), 6.89-6.87 (m, 2H), 6.73-6.70 (m, 1H), 4.63-4.61 (m, 1H), 3.33-3.31 (m, 1H), 3.23-3.16 (m, 6H), 2.99-2.94 (m, 4H), 1.99-1.97 (m, 1H), 1.72-1.53 (m, 10H), 0.85-0.82 (m, 6H);

LCMS: [M+H]=363.0, RT=3.44 minutes (Program P1, Column Y).

H. (S)-1,1-Dipropyl-2-[2-((indan-2-yl)(phenyl)amino)ethyl]piperidinium iodide To a stirred solution of compound 11 (0.25 g, 0.69 mmol) in dichloroethane (DCE, 5 mL) were added K$_2$CO$_3$ (1.15 g, 8.29 mmol) and 1-iodopropane (3 mL) in a sealed tube and the mixture was heated at 65° C. for 16 hours. The reaction mixture was filtered and washed with DCM. The organic layer was concentrated using a rotavapour. The crude material was purified by Combiflash® chromatography eluting with 5.3% methanol (MeOH) in DCM to provide (S)-1,1-dipropyl-2-[2-((indan-2-yl)(phenyl)amino)ethyl]piperidinium iodide.

Yield: 0.12 g (31.32%);

$^1$H-NMR (400 MHz, DMSO-$d_6$): δ 7.25-7.16 (m, 6H), 6.87 (d, J=8 Hz, 2H), 6.73 (t, J=7 Hz, 1H), 4.67-4.64 (m, 1H), 3.40-3.35 (m, 2H), 3.27-3.13 (m, 8H), 3.01-2.95 (m, 3H), 1.95-1.82 (m, 2H), 1.70-1.50 (m, 10H), 0.87 (t, J=7 Hz, 3H), 0.80 (t, J=7 Hz, 3H);

LCMS: [M$^+$]=405.4, RT=3.49 minutes;

UPLC: 98.00%, RT=4.03 minutes, λ$_{200nm}$, Mobile Phase (i) 0.05% TFA in water, (ii) acetonitrile; Column. Zorbax® SB 1.8μ.

Alternatively, the compound of Example 1 may be prepared by the method described in Scheme 27.

Example 2

General Procedure A2—Preparation of (S)-1,1-diethyl-2-[2-((indan-2-yl)(phenyl)amino)ethyl]piperidinium iodide

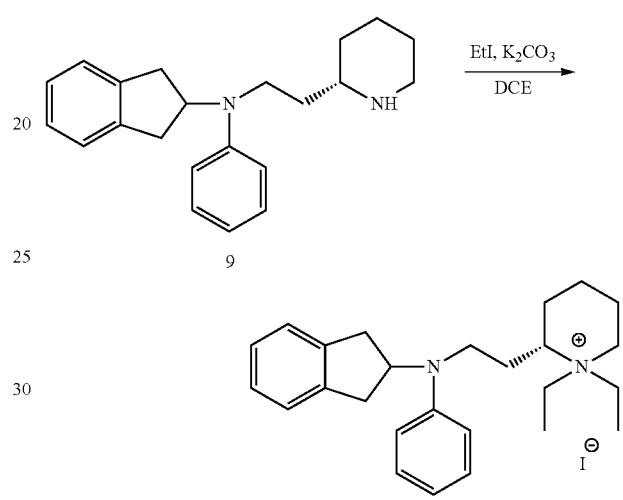

To a stirred mixture of compound 9 (0.15 g, 0.47 mmol) and K$_2$CO$_3$ (0.78 g, 5.63 mmol) in DCE (2 mL) was added ethyl iodide (2 mL) and heated at 65° C. in a sealed tube for 16 hours. The reaction mixture was filtered, washed with MeOH-DCM and concentrated using a rotavapour. The brownish solid crude material was purified using a 230-400 mesh silica gel column chromatograph eluting with 4% MeOH in DCM. The solid material was triturated with ether-hexane to provide (S)-1,1-diethyl-2-[2-((indan-2-yl)(phenyl)amino)-ethyl]piperidinium iodide.

Yield: 0.17 g (71.62%);

$^1$H-NMR (400 MHz, DMSO-$d_6$): δ 7.26-7.16 (m, 6H), 6.87 (d, J=8 Hz, 2H), 6.72 (t, J=7 Hz, 1H), 4.68-4.61 (m, 1H), 3.52-3.47 (m, 1H), 3.39-3.16 (m, 9H), 3.04-2.92 (m, 3H), 1.88-1.85 (m, 2H), 1.66-1.47 (m, 6H), 1.19-1.08 (m, 6H);

LCMS: [M$^+$]=377.8, RT=3.33 minutes;

HPLC: 97.43%, RT=2.73 minutes, λ$_{200nm}$, Mobile Phase (i) 0.05% HCOOH in water, (ii) acetonitrile; Column. Zorbax® SB-C18 (4.6×50 mm) 1.8μ.

Alternatively, the compound of Example 2 may be prepared by the method described in Scheme 27.

Example 3

Procedure B1—Preparation of 1,1-dimethyl-2-[((indan-2-yl)(phenyl)amino)methyl]piperidinium iodide

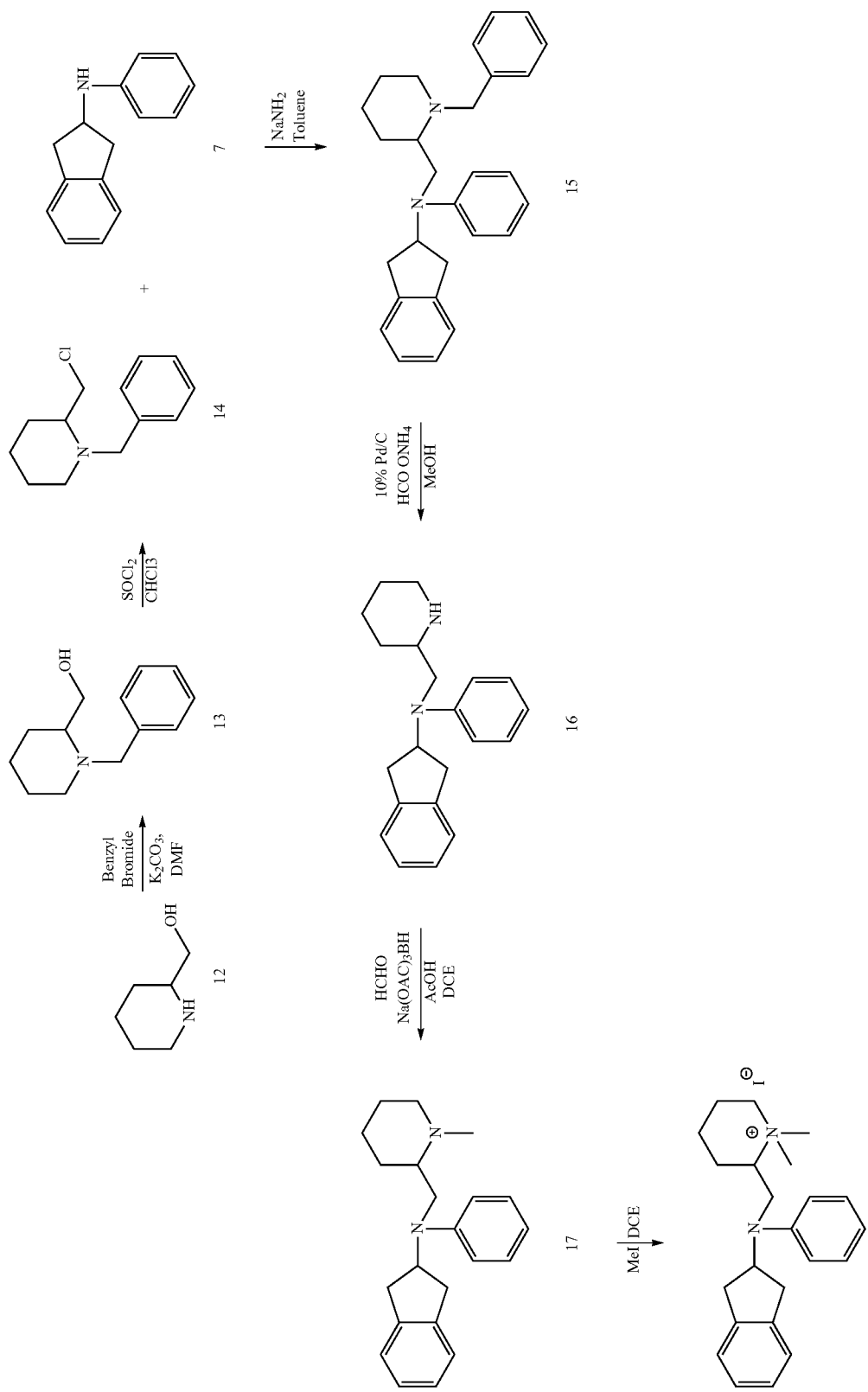

A. (1-Benzylpiperidin-2-yl)methanol (compound 13)

To a stirred solution of piperidine-2-methanol (12; 6 g, 52.09 mmol) in dimethylformamide (DMF, 50 mL) were added successively $K_2CO_3$ (10.78 g, 78.14 mmol) and benzyl bromide (6.85 mL, 57.30 mmol) at 0° C. and the mixture stirred at rt for 16 hours. The reaction mixture was then filtered and the filtrate was concentrated. The residue was dissolved in EtOAc and the organic layer was washed with water and brine solution. The organic layer was dried over $Na_2SO_4$, filtered and concentrated. The crude material was purified by chromatography on 230-400 mesh silica gel eluting with 30% EtOAc-hexane to provide compound 13.

Yield: 6.0 g (56.6%);

$^1$H-NMR (400 MHz, $CDCl_3$): δ 7.37-7.21 (m, 5H), 4.05 (d, J=13 Hz, 1H), 3.85 (dd, J=11, 4 Hz, 1H), 3.50 (dd, J=11, 4 Hz, 1H), 3.30 (d, J=13 Hz, 1H), 2.88-2.83 (m, 1H), 2.69 (brs, 1H), 2.47-2.43 (m, 1H), 2.17-2.11 (m, 1H), 1.70-1.54 (m, 4H), 1.40-1.33 (m, 2H).

B. 1-Benzyl-2-(chloromethyl)piperidine (compound 14)

To a stirred solution of compound 13 (3.6 g, 15.00 mmol) in chloroform (50 mL) was added thionyl chloride (1.34 mL) at 0° C. The reaction mixture was heated at reflux for 2 hours and then concentrated. The residue was dissolved in EtOAc and washed with saturated sodium bicarbonate solution, water and brine. The organic layer was dried over $Na_2SO_4$, filtered and concentrated. The crude material was purified by chromatography on 230-400 mesh silica gel eluting with 10% EtOAc-hexane to provide compound 14 as an oil.

Yield: 3.2 g (82.0%);

$^1$H-NMR (400 MHz, $CDCl_3$): δ 7.37-7.28 (m, 4H), 7.23-7.21 (m, 1H), 4.01-3.96 (m, 1H), 3.79-3.66 (m, 2H), 3.32 (d, J=13 Hz, 1H), 2.76-2.72 (m, 1H), 2.61 (brs, 1H), 2.13-2.11 (m, 1H), 1.73-1.50 (m, 5H), 1.42-1.33 (m, 1H);

LCMS: [M+H]=224.2, RT=3.77 minutes (Program P1, Column Y).

C. N-[(1-Benzyl-piperidin-2-yl)methyl]-N-phenylindan-2-yl-amine (compound 15)

To a stirred suspension of sodamide (706 mg, 18.1 mmol) in toluene (10 mL) was added a solution of compound 7 (2.76 g, 13.2 mmol) in toluene (10 mL) at 0° C. The reaction mixture was stirred at rt for 3 hours. A solution of compound 14 (2.69 g, 12.1 mmol) in toluene was added to the reaction mixture and the resulting mixture was heated at reflux for 16 hours. The reaction mixture was diluted with EtOAc and washed with water and brine. The organic layer was dried over $Na_2SO_4$, filtered and concentrated. The crude material was purified by chromatography on 230-400 mesh silica gel eluting with 15% EtOAc-hexane to provide compound 15.

Yield: 1.5 g (31.9%);

$^1$H-NMR (400 MHz, $CDCl_3$): δ 7.32-7.27 (m, 4H), 7.23-7.13 (m, 7H), 6.89 (d, J=8 Hz, 2H), 6.80 (d, J=7 Hz, 1H), 4.54-4.50 (m, 1H), 4.11 (d, J=14 Hz, 1H), 3.57 (dd, J=14, 4 Hz, 1H), 3.32 (d, J=14 Hz, 1H) 3.24-3.04 (m, 5H), 2.76-2.71 (m, 1H), 2.64-2.62 (m, 1H), 2.16-2.10 (m, 1H), 1.82-1.76 (m, 1H), 1.63-1.61 (m, 1H), 1.48-1.31 (m, 4H).

D. N-Phenyl-N-(piperidin-2-ylmethyl)indan-2-yl-amine (compound 16)

A solution of compound 15 (1.5 g, 3.79 mmol) in methanol (50 mL) was purged with argon for 20 minutes. Ammonium formate (2.33 g, 37.87 mmol) was then added and the solution was purged for another 10 minutes. Pd—C (10%; 216 mg) was added and the reaction mixture was heated at reflux for 3 hours. The reaction mixture was filtered through the Celite® reagent and washed with methanol. The filtrate was concentrated and the crude material was purified by chromatography on 230-400 mesh silica gel eluting with 2% methanol-DCM to provide compound 16.

Yield: 1.06 g (92.1%);

$^1$H-NMR (400 MHz, DMSO-$d_6$): δ 7.21-7.13 (m, 6H), 6.95 (d, J=8 Hz, 2H), 6.73 (t, J=7 Hz, 1H), 4.67-4.63 (m, 1H), 3.15-2.93 (m, 7H), 2.68-2.66 (m, 1H), 2.45-2.42 (m, 1H), 1.70-1.60 (m, 2H), 1.51-1.48 (m, 1H), 1.33-1.19 (m, 2H), 1.06-1.00 (m, 1H).

E. N-[(1-Methyl-piperidin-2-yl)methyl]-N-phenylindan-2-yl-amine (compound 17)

To a stirred solution of compound 16 (0.2 g, 0.65 mmol) in DCE (10 mL) were added successively formaldehyde (35% in $H_2O$, 0.08 mL, 0.98 mmol), $Na(OAc)_3BH$ (0.415 g, 1.95 mmol) and acetic acid (AcOH, 0.1 mL) at ice-cold conditions. The resulting mixture was allowed to stir at rt for 16 hours. The reaction mixture was diluted with DCM and basified with NaOH (1N). The organic layer was separated and washed with water and brine, dried over $Na_2SO_4$, filtered and concentrated. The crude material was purified by chromatography on 230-400 mesh silica gel eluting with 5% methanol-DCM to provide compound 17.

Yield: 0.12 g (57.4%);

$^1$H-NMR (400 MHz, DMSO-$d_6$): δ 7.22-7.13 (m, 6H), 6.88 (d, J=8 Hz, 2H), 6.70 (t, J=7 Hz, 1H), 4.61-4.56 (m, 1H), 3.54 (dd, J=14, 4 Hz, 1H), 3.15-2.96 (m, 5H), 2.71-2.66 (m, 1H), 2.21 (s, 3H), 2.11-2.03 (m, 1H), 2.00-1.91 (m, 1H), 1.70-1.59 (m, 2H), 1.47-1.35 (m, 2H), 1.13-1.06 (m, 2H);

LCMS: [M+H]=321.0, RT=3.32 minutes (Program P1, Column Y).

F. 1,1-Dimethyl-2-[((indan-2-yl)(phenyl)amino)methyl]piperidinium iodide

To a stirred solution of compound 17 (0.1 g, 0.31 mmol) in DCE (5 mL) was added methyl iodide (0.058 mL, 0.94 mmol) and the resulting mixture was stirred at rt for 16 hours. The reaction mixture was concentrated under reduced pressure and the crude material was purified by crystallization from methanol-ether to provide 1,1-dimethyl-2-[((indan-2-yl)(phenyl)amino)methyl]piperidinium iodide.

Yield: 0.06 g (41.62%).

$^1$H-NMR (400 MHz, DMSO-$d_6$): δ 7.27 (t, J=7.76 Hz, 2H), 7.22-7.19 (m, 2H), 7.15-7.13 (m, 2H), 7.04 (d, J=7.96 Hz, 2H), 6.90 (t, J=7 Hz, 1H), 4.50-4.46 (m, 1H), 3.83 (d, J=12 Hz, 1H), 3.41-3.35 (m, 4H), 3.19 (s, 3H), 3.06 (d, J=8 Hz, 2H), 3.00-2.98 (m, 5H), 1.95-1.92 (m, 1H), 1.79-1.64 (m, 4H), 1.33-1.30 (m, 1H);

LCMS: [M$^+$]=335.0, RT=3.26 minutes; HPLC: 99.72%, RT=3.92 minutes, $\lambda_{200nm}$, Mobile Phase (i) 0.05% TFA in water, (i) acetonitrile; Column: Zorbax® SB-C18 (4.6×50 mm) 1.8μ.

121

Example 4

General Procedure B2—Preparation of 1,1-dimethyl-2-[2-((2-fluorophenyl)(indan-2-yl)amino)ethyl]piperidinium iodide

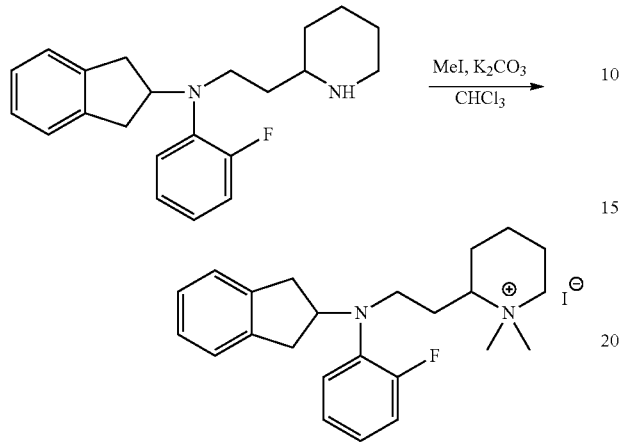

To a stirred solution of (2-fluoro-phenyl)-indan-2-yl-(2-piperidin-2-yl-ethyl)-amine (100 mg, 0.30 mmol) in CHCl₃ (3 mL) in a sealed tube were added methyl iodide (97 μL, 1.48 mmol) and potassium carbonate (204 mg, 1.48 mmol) and the reaction mixture was stirred at 50° C. for 16 hours. The reaction mixture was then filtered through a sintered funnel. The filtrate was concentrated in vacuo and purified by 230-400 silica gel column chromatography using MeOH-DCM (1-5%) as the eluent. The solid was lyophilized to provide 1,1-dimethyl-2-[2-((2-fluorophenyl)(indan-2-yl)amino)-ethyl]piperidinium iodide.

Yield: 84 mg (57.47%);

¹H-NMR (400 MHz, DMSO-d₆): δ 7.33 (t, J=15 Hz, 1 H), 7.22-7.11 (m, 7 H), 4.23-4.19 (m, 1 H), 3.42 (d, J=13 Hz, 1 H), 3.31-3.22 (m, 2 H), 3.10-3.07 (m, 1 H), 3.05-3.03 (m, 1 H), 3.01-2.99 (m, 1 H), 2.91 (s, 3 H), 2.88-2.85 (m, 2 H), 2.80 (s, 3 H), 2.01-1.97 (m, 1 H), 1.86-1.76 (m, 2 H), 1.69-1.66 (m, 2 H), 1.56-1.53 (m, 2 H), 1.41-1.34 (m, 3 H);

LC-MS: [M⁺]=367, RT=2.64 minutes;

UPLC: 98.63%, RT=3.96 minutes, λ₂₀₀ₙₘ, Mobile phase: (i) 0.05% TFA in water, (ii) acetonitrile; Column. Zorbax® SB C18 (50×4.6 mm) 1.8μ)

Example 5

General Procedure C—Preparation of 1,1-dimethyl-2-[2-((indan-2-yl)(phenyl)amino)ethyl]pyrrolidinium iodide

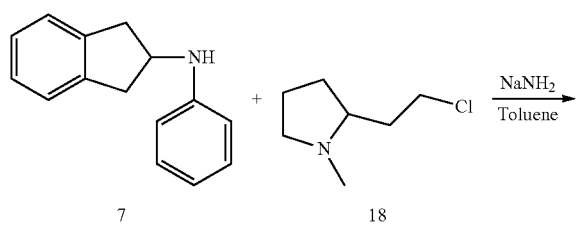

122

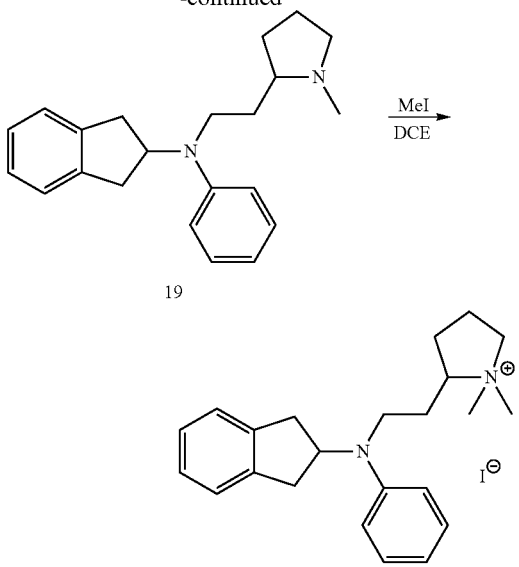

A. Indan-2-yl-[2-(1-methyl-pyrrolidin-2-yl)-ethyl]phenylamine (compound 19)

To a stirred suspension of sodamide (256 mg, 6.58 mmol) in toluene (10 mL) was added a solution of indan-2-yl-phenyl-amine (7; 1.0 g, 4.78 mmol) in toluene (5 mL) at 0° C. The reaction mixture was stirred at rt for 3 hours. A solution of 2-(2-chloroethyl)-1-methyl-pyrrolidine hydrochloride (18; 0.808 g, 4.39 mmol) in toluene (5 mL) was added to the reaction mixture and the resulting mixture was refluxed for 16 hours. The reaction mixture was diluted with EtOAc and washed with water and brine. The organic layer was dried over Na₂SO₄, filtered and concentrated. The crude material was purified by column chromatography on neutral alumina eluting with 0.8% methanol-DCM to provide compound 19.

Yield: 0.1 g (7.1%);

¹H-NMR (400 MHz, DMSO-d₆): δ 7.26-7.14 (m, 6H), 6.81 (d, J=8 Hz, 2H), 6.65 (t, J=7 Hz, 1H), 4.65-4.62 (m, 1H), 3.22-3.14 (m, 4H), 2.97-2.88 (m, 3H), 2.10 (s, 3H), 1.94-1.91 (m, 2H), 1.77-1.68 (m, 2H), 1.57-1.53 (m, 2H), 1.29-1.23 (m, 2H);

LCMS: [M+H]=321.0, RT=3.22 minutes (Program P1, Column Y).

B. 1,1-Dimethyl-2-[2-((indan-2-yl)(phenyl)amino)ethyl]pyrrolidinium iodide

To a stirred solution of compound 19 (0.1 g, 0.31 mmol) in DCE (3 mL) was added methyl iodide (0.058 mL, 0.94 mmol) and the resulting mixture was stirred at rt for 16 hours. The reaction mixture was concentrated under reduced pressures and the crude material was purified by column chromatography on neutral alumina eluting with 1% methanol-DCM to provide 1,1-dimethyl-2-[2-((indan-2-yl)(phenyl)amino)ethyl]pyrrolidinium iodide.

Yield: 0.06 g (41.8%);

¹H-NMR (400 MHz, DMSO-d₆): δ 7.24-7.15 (m, 6H), 6.90 (d, J=8 Hz, 2H), 6.74 (t, J=7 Hz, 1H), 4.65-4.61 (m, 1H), 3.59-3.55 (m, 1H), 3.45-3.39 (m, 6H), 3.24-3.13 (m, 4H), 2.98-2.94 (m, 5H), 2.74 (s, 3H), 2.30-2.21 (m, 1H), 2.02-1.94 (m, 3H), 1.67-1.62 (m, 1H), 1.54-1.50 (m, 1H);

LCMS: [M⁺]=335.4, RT=3.65 minutes;

UPLC: 97.93%, RT=3.37 minutes, λ₂₀₀ₙₘ, Mobile Phase (i) 0.05% TFA in water, (ii) acetonitrile; Column. Zorbax® SB-C18 (4.6×50 mm) 1.8μ.

Example 6

General procedure for preparation of N-(indan-2-yl)phenylamine (compound 7)

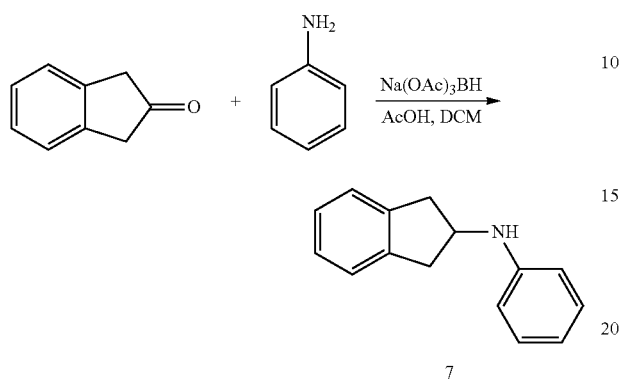

To a stirred solution of 2-indanone (5 g, 37.83 mmol) in DCM (135 mL) were successively added aniline (3.4 mL, 37.83 mmol), AcOH (2.16 mL, 37.83 mmol) and Na(OAc)$_3$BH (11.22 g, 52.96 mmol) portion-wise at ice cold conditions. The reaction mixture was stirred at rt for 16 hours. The reaction mixture was then diluted with EtOAc (450 mL) and washed with water (150 mL) and brine (50 mL). The organic layer was dried over Na$_2$SO$_4$, filtered and concentrated. The crude material was purified by Combiflash® chromatography and eluted with 1.7% EtOAc in hexane to obtain compound 7.

Yield: 7.1 g (89.80%);

$^1$H-NMR (400 MHz, DMSO-d$_6$): δ 7.24-7.21 (m, 2H), 7.15-7.13 (m, 2H), 7.08 (t, J=8 Hz, 2H), 6.61 (d, J=8 Hz, 2H), 6.53 (t, J=7 Hz, 1H), 5.83 (d, J=7 Hz, 1H), 4.24-4.16 (m, 1H), 3.28 (dd, J=16, 7 Hz, 2H), 2.79 (dd, J=16, 7 Hz, 2H);

LCMS: [M+H]=210.2, RT=3.72 minutes (Program P1, Column Y).

Example 7

General Procedure D—Preparation of 1,1-dimethyl-2-[3-((indan-2-yl)phenyl)amino)propyl]piperidinium iodide

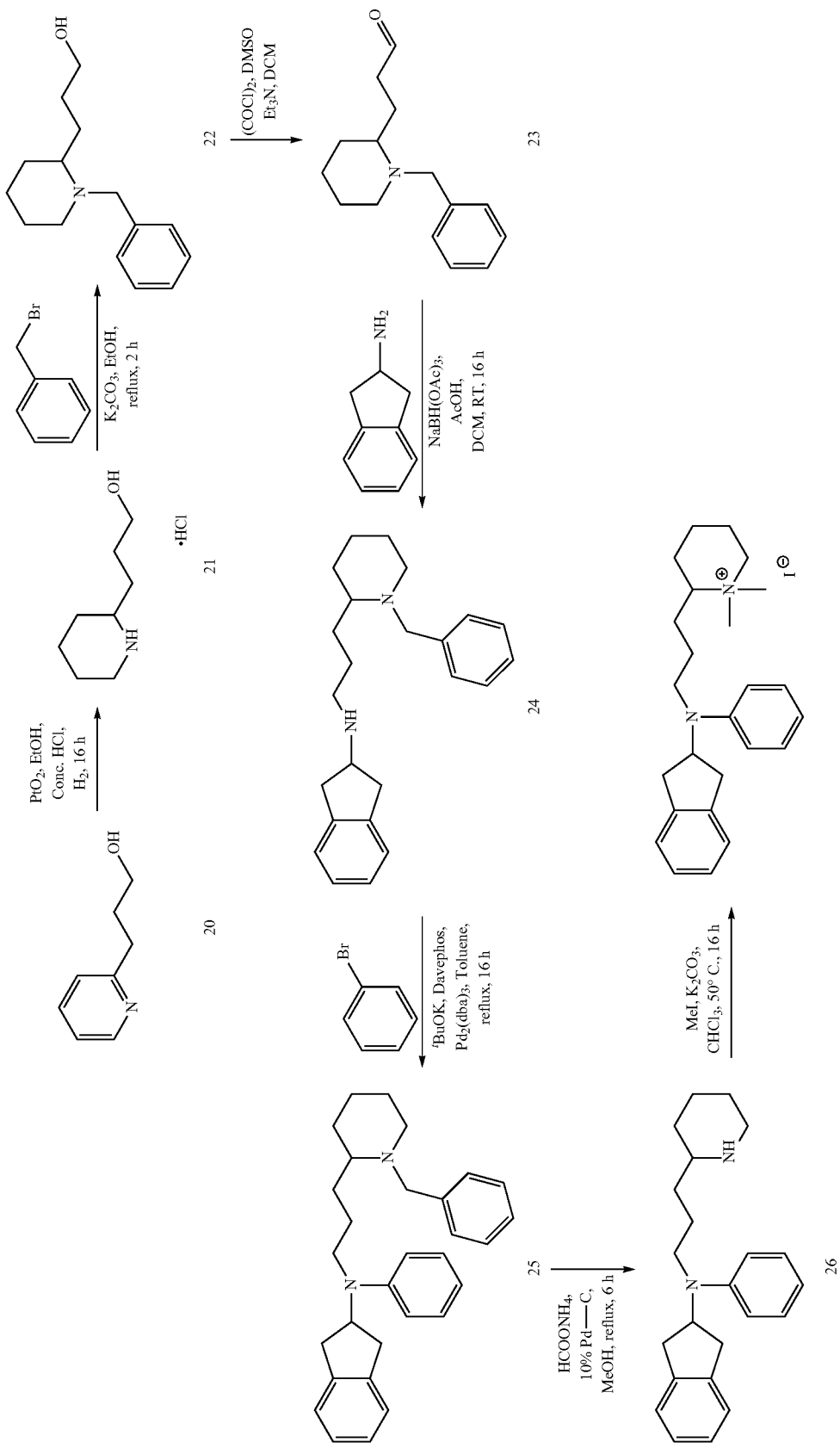

A: 3-(Piperidin-2-yl)propan-1-ol hydrochloride (compound 21)

To a stirred solution of compound 20 (5 g, 36.4 mmol) in ethanol (32 mL) was added concentrated HCl (3.2 mL) and the reaction mixture was degassed with $N_2$ for 15 minutes. Platinum oxide ($PtO_2$; 1 g) was then added and degassed for 5 minutes. Finally, the reaction mixture was hydrogenated at rt in a Parr apparatus for 16 hours under 45 psi $H_2$ pressure. The reaction mixture was filtered through the Celite® reagent, and was washed with ethanol. The filtrate was concentrated to yield the crude product 21 which was used as such for the next step.

Yield: 6.2 g (94.8%);
$^1$H-NMR (400 MHz, DMSO-$d_6$): δ 8.88 (brs, 1 H), 8.71 (brs, 1 H), 4.57 (s, 1 H), 3.40 (d, J=4 Hz, 2 H), 3.17 (d, J=12 Hz, 1 H), 2.96 (brs, 1 H), 2.81-2.79 (m, 1 H), 1.84 (d, J=13 Hz, 1 H), 1.71-1.65 (m, 3 H), 1.62-1.58 (m, 1 H), 1.56-1.43 (m, 3 H), 1.40-1.38 (m, 1 H).

B: 3-(1-Benzyl-piperidin-2-yl)propan-1-ol (compound 22)

To a stirred solution of compound 21 (3 g, 16.71 mmol) in ethanol (23 mL) was added $K_2CO_3$ (11.5 g, 83.55 mmol) portion-wise at ice cold conditions. Benzyl bromide (2 mL, 16.71 mmol) was then added and the reaction mixture was heated at reflux for 2 hours. The reaction mixture was filtered, and washed with EtOAc. The filtrate was concentrated, the residue was dissolved in EtOAc, washed with saturated $NaHCO_3$ solution and brine, dried over $Na_2SO_4$, filtered and concentrated. The crude material was purified by 230-400 silica gel column chromatography using 1-3% MeOH-DCM as eluent to yield compound 22.

Yield: 2.6 g (66.7%);
$^1$H-NMR (400 MHz, DMSO-$d_6$): δ 7.30-7.29 (m, 4 H), 7.23-7.21 (m, 1 H), 4.40 (s, 1 H), 3.91 (d, J=14 Hz, 1 H), 3.37 (s, 2 H), 3.16 (d, J=14 Hz, 1 H), 2.62 (d, J=12 Hz, 1 H), 2.28 (s, 1 H), 1.99-1.94 (m, 1 H), 1.60-1.48 (m, 4 H), 1.43-1.24 (m, 4 H);
LCMS [M+H]: 234.2, RT=2.07 minutes, (Program P1, Column Y).

C: 3-(1-Benzyl-piperidin-2-yl)propionaldehyde (compound 23)

Oxalyl chloride (0.55 mL, 6.44 mmol) was added to a stirred solution of DMSO (0.92 mL, 12.87 mmol) in dry DCM (40 mL) at −78° C. and the reaction mixture was stirred for 15 minutes. Compound 22 (1 g, 4.29 mmol) dissolved in DCM (15 mL) was the added drop-wise and the reaction mixture was stirred at −78° C. for 1 hour. The reaction mixture was then quenched by adding $Et_3N$ (2.9 mL, 21.45 mmol) drop-wise and the solution was stirred at rt for 15 minutes. Water was then added to the solution and the reaction mixture was extracted with DCM. The organic layer was dried over $Na_2SO_4$, filtered and concentrated to yield crude compound 23 which was used as such for the next step.

Yield: 820 mg (83%);
$^1$H-NMR (400 MHz, DMSO-$d_6$): δ 9.68 (s, 1 H), 7.52-7.31 (m, 5 H), 3.88-3.84 (m, 1 H), 3.55-3.47 (m, 1 H), 3.20-3.16 (m, 1 H), 2.67 (brs, 1 H), 2.33 (brs, 1 H), 2.10-2.01 (m, 1 H), 1.88-1.76 (m, 2 H), 1.72-1.61 (m, 3 H), 1.45-1.21 (m, 4 H).

D: [3-(1-Benzyl-piperidin-2-yl)-propyl]indan-2-yl-amine (compound 24)

To a stirred solution of compound 23 (820 mg, 3.55 mmol) in DCM (15 mL) was added 2-amino-indane (472 mg, 3.55 mmol) drop-wise at ice cold conditions. Acetic acid (0.2 mL) was added to the reaction mixture, followed by sodium triacetoxy borohydride (2.2 g, 10.65 mmol) portion-wise at ice cold conditions. The reaction mixture was stirred at rt for 16 hours. The reaction mixture was diluted with DCM, washed with saturated $NaHCO_3$ solution and brine. The organic layer was dried over $Na_2SO_4$, filtered and concentrated. The crude material was purified by 230-400 silica gel column chromatography using 1-3% MeOH-DCM as eluent to yield compound 24.

Yield: 500 mg (40.5%);
$^1$H-NMR (400 MHz, DMSO-$d_6$): δ 7.29 (d, J=4 Hz, 4 H), 7.22-7.17 (m, 3 H), 7.12-7.11 (m, 2 H), 3.91 (d, J=14 Hz, 1 H), 3.59 (t, J=7 Hz, 1 H), 3.18 (d, J=13 Hz, 1 H), 3.11-3.05 (dd, J=7, 16 Hz, 2 H), 2.75-2.70 (dd, J=6, 16 Hz, 2 H), 2.63 (brs, 3 H), 2.29 (brs, 1 H), 2.04-1.97 (m, 1 H), 1.58 (brs, 4 H), 1.45-1.28 (m, 5 H), 1.23 (s, 1 H);
LCMS [M+H]=349.2, RT=2.89 minutes, (Program P1, Column Y)

E: [3-(1-Benzyl-piperidin-2-yl)-propyl]indan-2-yl-phenylamine (compound 25)

To a stirred solution of compound 24 (400 mg, 1.15 mmol) in dry toluene (12 mL) was added bromo-benzene (0.12 mL, 1.15 mmol) and potassium tertiary butoxide (322 mg, 2.87 mmol). The reaction mixture was purged with nitrogen for 30 minutes. Finally, DavePhos (90 mg, 0.23 mmol) and $Pd_2$(dba)$_3$ (136 mg, 0.15 mmol) were added and the reaction mixture was heated to 110° C. for 16 hour. Thin layer chromatography (TLC) showed that the reaction was completed. The reaction mixture was then diluted with ethyl acetate, washed with water and brine, dried over $Na_2SO_4$ and concentrated. The crude reaction mixture was purified by 230-400 silica gel column chromatography using 5-20% EtOAc-hexane as eluent yield compound 25.

Yield: 290 mg (59.5%);
$^1$H-NMR (400 MHz, DMSO-$d_6$): δ 7.29-7.21 (m, 6 H), 7.16-7.12 (m, 5 H), 6.79 (d, J=8 Hz, 2 H), 6.63 (t, J=7 Hz, 1 H), 3.86 (d, J=14 Hz, 1 H), 3.17-3.07 (m, 5 H), 2.96-2.90 (dd, J=6, 16 Hz, 2 H), 2.60-2.58 (m, 1 H), 2.20 (brs, 1 H), 1.98-1.89 (m, 1 H), 1.56 (brs, 2 H), 1.48-1.40 (m, 5 H), 1.30-1.23 (m, 3 H);
LCMS [M+H]=424.8, RT=3.14 minutes, (Program P1, Column Y).

F: Indan-2-yl-phenyl-(3-piperidin-2-yl-propyl)amine (compound 26)

Compound 25 (340 mg, 0.80 mmol) and ammonium formate (506 mg, 8.02 mmol) in methanol (20 mL) was purged with $N_2$ for 15 minutes, 10% Pd—C catalyst (68 mg) was added, purging was continued for another 5 minutes and the mixture was heated at 110° C. for 6 hours. The reaction mixture was filtered through the Celite® reagent and washed with methanol. The combined organic layer was concentrated in rotavapour. A small amount of water was added to the residue and the product was extracted with EtOAc. The organic layer was dried, filtered and concentrated to yield compound 26.

Yield: 248 mg (92.6%);
$^1$H-NMR (400 MHz, DMSO-$d_6$): δ 7.24-7.23 (m, 2 H), 7.19-7.15 (m, 4 H), 6.81 (d, J=8 Hz, 2 H), 6.66 (t, J=7 Hz, 1 H), 4.64 (t, J=7 Hz, 1 H), 3.16-3.13 (m, 4 H), 3.06 (d, J=13 Hz, 1 H), 2.99-2.93 (dd, J=7, 16 Hz, 2 H), 2.67-2.61 (m, 2 H), 1.70-1.58 (m, 3 H), 1.51-1.45 (m, 2 H), 1.42-1.27 (m, 4 H), 1.14-1.09 (m, 1 H);
LCMS [M+H]=335.2, RT=3.73 minutes, (Program P1, Column Z).

G: 1,1-Dimethyl-2-[3-(indan-2-yl)phenyl)amino) propyl]piperidinium iodide

To a stirred solution of compound 26 (100 mg, 0.30 mmol) in CHCl$_3$ (3 mL) in a sealed tube were added methyl iodide (97 µL, 1.50 mmol) and potassium carbonate (207 mg, 1.50 mmol) and the reaction mixture was stirred at 50° C. for 16 hours. The reaction mixture was filtered through a sintered funnel. The filtrate was concentrated in a rotavapour and purified by 230-400 silica gel column chromatography using MeOH-DCM (1-3%) as the eluent to yield 2-[3-(Indan-2-yl-phenyl-amino)-propyl]-1,1-dimethyl-piperidinium iodide.

Yield: 51 mg (46.9%);

$^1$H-NMR (400 MHz, CDCl$_3$) δ 7.28 (s, 1 H), 7.25 (s, 3 H), 7.16 (t, J=3 Hz, 2H), 6.89-6.82 (m, 3 H), 4.52 (t, J=7 Hz, 1 H), 3.99 (d, J=13 Hz, 1 H), 3.66-3.50 (m, 1 H), 3.38-3.33 (m, 4 H), 3.27-3.13 (m, 4 H), 3.04-2.97 (m, 5 H), 1.87-1.81 (m, 5 H), 1.68-1.61 (m, 1 H), 1.48-1.42 (m, 2 H), 1.29-1.23 (m, 2 H);

LCMS [M$^+$]=363, RT=3.32 minutes.

UPLC: 98.11%, RT=3.11 minutes, λ$_{200nm}$, Mobile phase: (i) 0.05% TFA in Water, (ii) Acetonitrile; Column: Zorbax® SB C18 (50×4.6 mm) 1.8µ

Example 8

General Procedure E—Preparation of 1,1-dimethyl-2-[((indan-2-yl)phenyl)amino)methyl]pyrrolidinium iodide

A: Pyrrolidine-1,2-dicarboxylic acid 1-tert-butyl ester 2-methyl ester

To a stirred solution of pyrrolidine-1,2-dicarboxylic acid 1-tert-butyl ester (5.0 g, 23.25 mmol) and methyl iodide (6.0 mL, 93.02 mmol) in DMF (25 mL) was added NaH (60% w/w, 2.3 g, 57.09 mmol) portion-wise at 0° C. The resulting mixture was allowed to stir at rt for 24 hours. The reaction mixture was poured into cold water and extracted with ethyl acetate. The organic layer was washed with water and brine. Drying over Na$_2$SO$_4$, filtering and concentration provided crude compound 2d.

Yield: 5.0 g (93.91%);

$^1$H-NMR (400 MHz, DMSO-d$_6$): δ 4.18-4.13 (m, 1 H), 3.65 (s, 3 H), 3.38-3.32 (m, 2 H), 2.22-2.18 (m, 1 H), 1.87-1.78 (m, 3 H), 1.32 (s, 9 H);

LCMS [M+H]=230.2, RT=3.28 minutes (Program P1, Column Z).

B: 1-Benzyl-pyrrolidine-2-carboxylic acid methyl ester

To a stirred solution of compound 2d (6.8 g, 29.69 mmol) in DCM (55 mL) was added TFA (15.2 mL, 203.94 mmol) drop-wise at ice-cold conditions. The resulting mixture was allowed to stir at rt for 4 hours. The reaction mixture was concentrated under reduced pressure, the crude material was dissolved in acetonitrile (100 mL) and the mixture was cooled

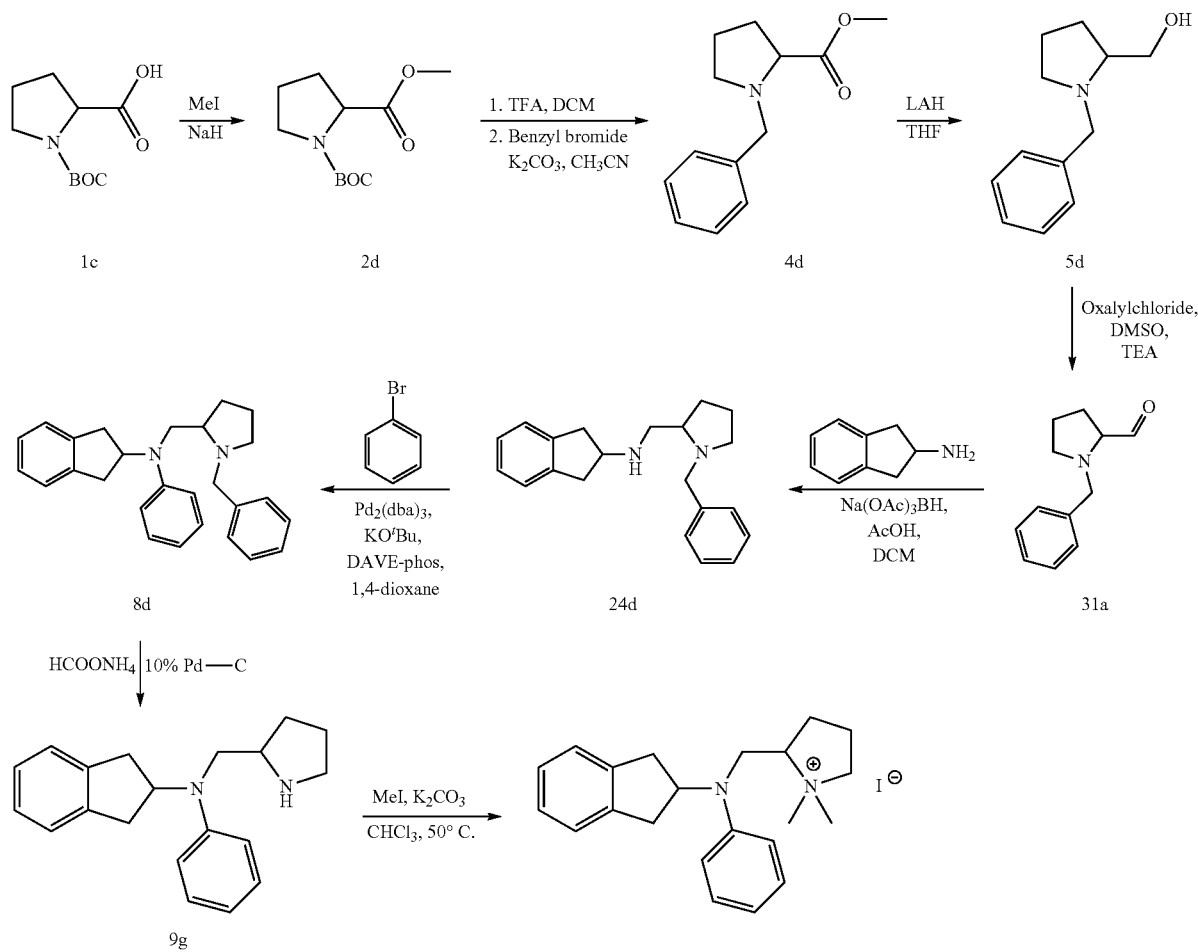

to 0° C. K$_2$CO$_3$ (20.48 g, 148.47 mmol) was then added (pH was adjusted to basic) and the mixture stirred at 0° C. for 15 minutes. Benzyl bromide (5.2 mL, 44.54 mmol) was added and the resulting mixture was heated at reflux for 16 hours. The reaction mixture was filtered and the filtrate was concentrated. The residue was dissolved in ethyl acetate and the organic layer was washed with water and brine. Drying over Na$_2$SO$_4$, filtering, and concentrating provided crude compound 4d.

Yield: 3.0 g (46.11%);
$^1$H-NMR (400 MHz, DMSO-d$_6$): δ 7.32-7.21 (m, 5 H), 3.85 (d, J=13 Hz, 1H), 3.58 (s, 3 H), 3.50 (d, J=13 Hz, 1 H), 3.28-3.24 (m, 1 H), 2.86-2.81 (m, 1 H), 2.38-2.32 (m, 1 H), 2.08-2.03 (m, 1 H), 1.84-1.69 (m, 3 H);
LCMS [M+H]=219.6, RT=3.35 minutes (Program P1, Column X).

C: (1-Benzyl-pyrrolidin-2-yl)methanol

To a stirred suspension of LAH (1.03 g, 27.39 mmol) in THF (120 mL) was added a solution of compound 4d (3.0 g, 13.69 mmol) in THF (30 mL) at ice-cold conditions. The resulting mixture was allowed to stir at rt for 4 hours. The reaction mixture was quenched by adding brine solution and filtered through a Celite® pad. The filtrate was dried over Na$_2$SO$_4$, filtered and concentrated to get crude compound 5d.

Yield: 2.5 g (95.54%);
$^1$H-NMR (400 MHz, DMSO-d$_6$): δ 7.30-7.19 (m, 5 H), 4.37 (t, J=5 Hz, 1 H), 4.04 (d, J=13 Hz, 1 H), 3.47-3.41 (m, 1 H), 3.32 (d, J=13 Hz, 1 H), 3.27-3.24 (m, 1 H), 2.76-2.74 (m, 1 H), 2.58-2.55 (m, 1 H), 2.16-2.10 (m, 1 H), 1.86-1.80 (m, 1 H), 1.60-1.55 (m, 3 H);
LCMS: [M+H]=192.0, RT=1.67 minutes (Program P1, Column Y).

D: 1-Benzylpyrrolidine-2-carboxaldehyde

To a stirred solution of DMSO (2.79 mL, 39.27 mmol) in DCM (120 mL) was added oxalyl chloride (1.69 mL, 19.63 mmol) drop-wise at −78° C. and the mixture stirred for 15 minutes. A solution of compound 5d (2.5 g, 13.08 mmol) in DCM (30 mL) was then slowly added and stirred at −78° C. for 1 hour. Triethyl amine (TEA; 9.1 mL, 65.44 mmol) was added to the reaction mixture and the reaction mixture was diluted with DCM. The organic layer was washed with water and brine. Drying over Na$_2$SO$_4$, filtering and concentrating provided crude compound 31a.

Yield: 2.59 g;
$^1$H-NMR (400 MHz, DMSO-d$_6$): δ 9.26 (d, J=4 Hz, 1 H), 7.32-7.23 (m, 5 H), 3.73 (d, J=13 Hz, 1 H), 3.63 (d, J=13 Hz, 1 H), 2.98-2.94 (m, 2 H), 2.39-2.32 (m, 1 H), 1.97-1.90 (m, 1 H), 1.83-1.72 (m, 3 H).

E: (1-Benzyl-pyrrolidin-2-ylmethyl)indan-2-yl-amine

To a stirred solution of compound 31a (1.6 g, 8.46 mmol) in DCM (30 mL) were added successively 2-aminoindane (1.12 g, 8.46 mmol), Na(OAc)$_3$BH (5.38 g, 25.40 mmol) and acetic acid (0.5 mL) at 0° C. The resulting mixture was allowed to stir at rt for 16 hours. The reaction mixture was diluted with DCM and the organic layer was washed with saturated NaHCO$_3$ solution, water and brine, dried over Na$_2$SO$_4$, filtered and concentrated and the crude material was purified by Combiflash® eluting 8% ethyl acetate-hexane to provide sticky compound 24d.

Yield: 1.5 g (57.94%);
$^1$H-NMR (400 MHz, DMSO-d$_6$): δ 7.30-7.09 (m, 9 H), 3.96 (d, J=13 Hz, 1 H), 3.46-3.42 (m, 1 H), 3.25 (d, J=13 Hz, 1 H), 3.07-2.99 (m, 2 H), 2.78-2.74 (m, 1 H), 2.68-2.55 (m, 5 H), 2.15-2.08 (m, 1 H), 1.87-1.82 (m, 1 H), 1.67-1.55 (m, 3 H);
LCMS [M+H]=307.0, RT=3.23 minutes (Program P1, Column X).

F: (1-Benzylpyrrolidin-2-ylmethyl)indan-2-yl-phenylamine (compound 33)

The stirred mixture of compound 24d (1.0 g, 3.26 mmol), bromobenzene (0.6 mL, 6.53 mmol), KO$^t$Bu (0.92 g, 8.16 mmol) and DavePhos (0.26 g, 0.65 mmol) in 1,4-dioxane (30 mL) was purged with nitrogen for 15 minutes. Pd$_2$(dba)$_3$ (0.3 g, 0.33 mmol) was then added and the resulting mixture was heated at 100° C. for 1 hour under microwave conditions. The reaction mixture was diluted with ethyl acetate and the organic layer was washed with water and brine. Drying over Na$_2$SO$_4$, filtering, concentrating, and Combiflash® chromatography eluting using 6% ethyl acetate-hexane provided sticky compound 8d.

Yield: 0.24 g (9.62%);
$^1$H-NMR (400 MHz, DMSO-d$_6$): δ 7.30-7.27 (m, 2 H), 7.23-7.13 (m, 9 H), 6.88-6.86 (m, 2 H), 6.76-6.68 (m, 1 H), 4.64-4.60 (m, 1 H), 4.00 (d, J=13 Hz, 1 H), 3.26-3.22 (m, 2 H), 3.15-3.09 (m, 4 H), 3.04-2.98 (m, 1 H), 2.80-2.77 (m, 2 H), 2.15-2.09 (m, 1 H), 1.82-1.77 (m, 1 H), 1.62-1.57 (m, 2 H), 1.51-1.48 (m, 1 H);
LCMS [M+H]=383.2, RT=2.69 minutes (Program P1, Column Y).

G: Indan-2-yl-phenylpyrrolidin-2-yl-methylamine (compound 34)

The stirred mixture of compound 8d (0.7 g, 1.83 mmol) and HCOONH$_4$ (2.32 g, 36.79 mmol) in MeOH (30 mL) was purged with nitrogen for 15 minutes. Ten percent Pd—C (0.28 g) was added and the resulting mixture was heated at reflux for 6 hours. The reaction mixture was filtered through a Celite® pad and washed with methanol. The filtrate was concentrated and the residue was taken in ethyl acetate. The organic layer was washed with water and brine. Drying over Na$_2$SO$_4$, filtering, concentrating, and Combiflash® chromatography eluting with 10% methanol-DCM provided compound 9g.

Yield: 0.35 g (65.50%);
$^1$H-NMR (400 MHz, DMSO-d$_6$): δ 7.23-7.20 (m, 4 H), 7.15-7.13 (m, 2 H), 6.97 (d, J=8 Hz, 2 H), 6.78 (t, J=7 Hz, 1 H), 4.61-4.57 (m, 1 H), 3.33-3.30 (m, 1 H), 3.16-3.06 (m, 4 H), 3.01-2.89 (m, 4 H), 1.86-1.67 (m, 3 H), 1.44-1.38 (m, 1 H);
LCMS [M+H]=293.0, RT=2.90 minutes (Program P1, Column Y).

H: 1,1-Dimethyl-2-[((indan-2-yl)phenyl)amino)methyl]pyrrolidinium iodide

To a stirred solution of compound 9g (0.12 g, 0.41 mmol) in CHCl$_3$ (4 mL) were added successively K$_2$CO$_3$ (0.57 g, 4.1 mmol) and methyl iodide (0.3 mL, 4.1 mmol). The resulting mixture was heated at 50° C. for 40 hours in a sealed tube. The reaction mixture was filtered and washed with methanol. The filtrate was concentrated and the crude material was purified by Combiflash® chromatography eluting with 2.5% methanol-DCM to get a yellow solid which was triturated with pentane and ether to provide 2-[(indan-2-yl-phenyl-amino)-methyl]-1,1-dimethyl-pyrrolidinium iodide.

Yield: 0.056 g (30.48%);

$^1$H-NMR (400 MHz, DMSO-$d_6$): δ 7.32-7.28 (m, 2 H), 7.20-7.10 (m, 6 H), 6.96 (t, J=7 Hz, 1 H), 4.43-4.38 (m, 1 H), 3.79-3.74 (m, 1 H), 3.60-3.54 (m, 2 H), 3.52-3.46 (m, 2 H), 3.16 (s, 3 H), 3.09-2.99 (m, 4 H), 2.92 (s, 3 H), 2.18-2.15 (m, 1 H), 1.97-1.90 (m, 3 H);

LCMS [M$^+$]=321.2, RT=2.99 minutes;

UPLC: 97.43%, RT=4.44 minutes, $\lambda_{200nm}$, Mobile Phase (i) 0.05% HCOOH in water, (ii) acetonitrile; Column: Gemini® NX C18 (50×4.6 mm), 3μ.

Examples 9-35

Additional compounds listed in Table 2 were prepared in a similar manner, using the methods described for Examples 1 to 8 and in Schemes 1 to 27. Yields and $^1$H-NMR, LCMS, and HPLC characterization data for Examples 9 to 35 are provided immediately following Table 2.

Example 36

General Procedure F—Preparation of 1,1-diethyl-2-[2-((indan-2-yl)(phenyl)amino)ethyl]pyrrolidinium iodide A: 2-Methoxycarbonylmethylpyrrolidine-1-carboxylic acid tert-butyl ester (compound 36)

To a stirred solution of pyrrolidine-1,2-dicarboxylic acid 1-tert-butyl ester 35 (10 g, 46.46 mmol) in dry THF were added drop wise N-methyl morpholine (6.4 mL, 58.1 mmol) and isobutyl chloroformate (6.7 mL, 65.1 mmol) at −30° C. The reaction mixture was stirred at same temperature for one hour and diazomethane solution (prepared in situ) was added at −30° C. The resulting mixture was allowed to stir at rt overnight. Excess diazomethane was quenched with acetic acid (15 mL) and evaporated under reduced pressure. The residue was dissolved in ether and washed with water and brine. The organic layer was dried over anhydrous Na$_2$SO$_4$, filtered and evaporated. The residue was dissolved in methanol (100 mL) and Ag$_2$O (5.5 g) was added portion-wise at ice-cold conditions, and then allowed to stir at rt for 2 hours. Chloroform was added, filtered through Celite® reagent and washed with methanol. The filtrate was concentrated and the crude material was purified by chromatography on silica-gel (230-400 mesh) eluting with 1-5% of ethyl acetate-hexane to get light yellow liquid compound 36.

Yield: 4.0 g (45%);

$^1$H-NMR (400 MHz, DMSO-$d_6$): δ 3.99-3.95 (m, 1 H), 3.59 (s, 3 H), 3.23-3.21 (m, 2 H), 2.72-2.65 (m, 1 H), 2.38-2.34 (m, 1 H), 1.98-1.95 (m, 1 H), 1.81-1.72 (m, 2 H), 1.65-1.63 (m, 1 H), 1.39 (s, 9 H).

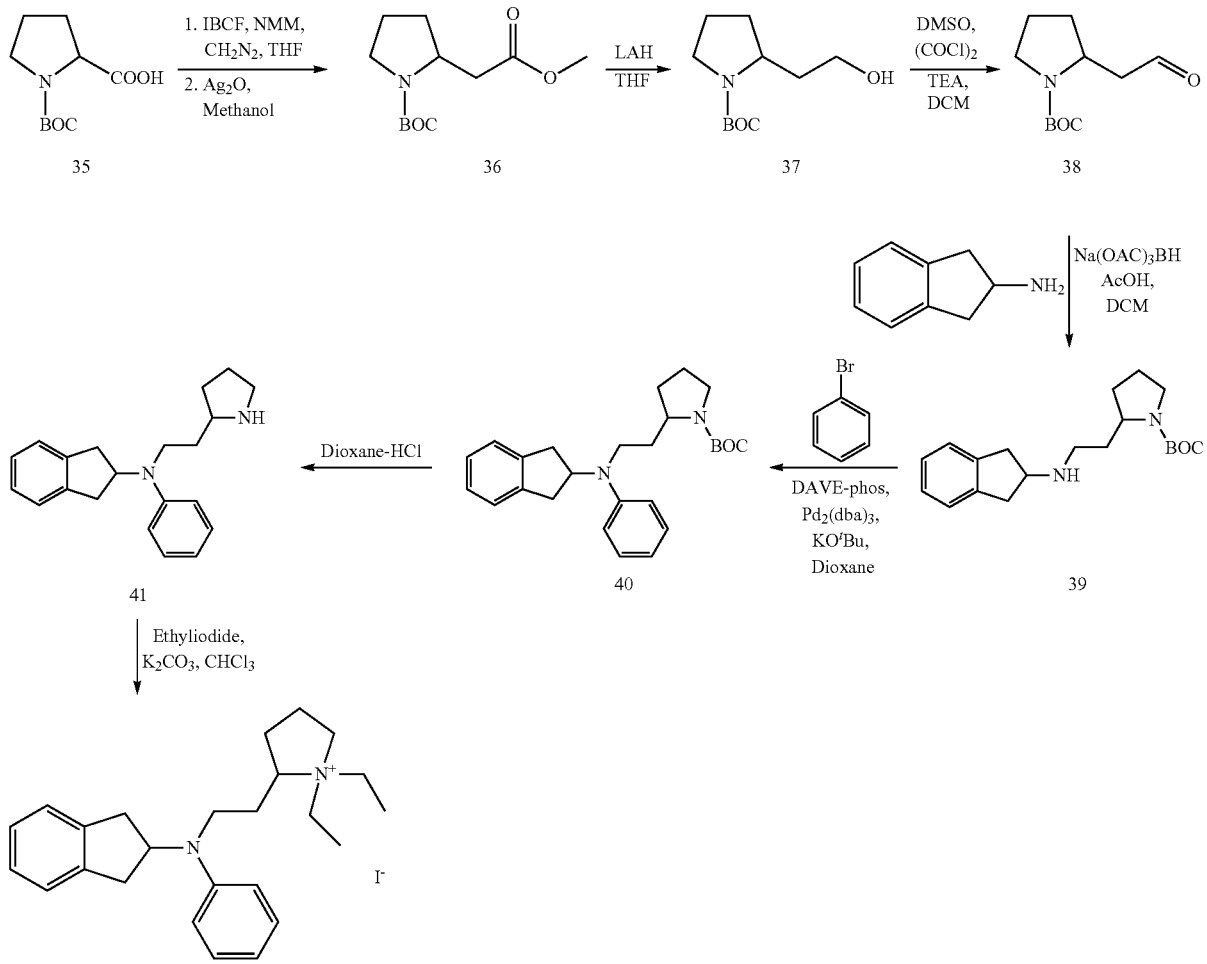

B: 2-(2-Hydroxyethyl)pyrrolidine-1-carboxylic acid tert-butyl ester (compound 37)

To a stirred solution of LAH (0.94 g, 24.69 mmol) in dry THF (100 mL) was added solution of compound 36 (3.0 g 12.34 mmol) in THF (40 mL) at 0° C. and stirred at rt for 16 hours. The reaction mixture was quenched with brine solution and filtered through a Celite® bed. The organic layer was dried over anhydrous $Na_2SO_4$ and evaporated. The crude was purified by Combiflash® chromatography eluting with 2-3% of methanol-DCM to provide liquid compound 37.

Yield: 1.4 g (52.8%);

$^1$H-NMR (400 MHz, DMSO-$d_6$): δ 4.37 (t, J=5 Hz, 1 H), 3.73-3.71 (m, 1 H), 3.42-3.37 (m, 2 H), 3.22-3.19 (m, 2 H), 1.83-1.64 (m, 5 H), 1.43-1.41 (m, 1 H), 1.39 (s, 9 H);

LCMS [M+H]=216.0, RT=2.83 minutes, (Program P1, Column Y)

C: 2-(2-Oxoethyl)pyrrolidine-1-carboxylic acid tert-butyl ester (compound 38)

To a stirred solution of DMSO (2.08 mL, 29.30 mmol) in DCM (60 mL) was added oxalyl chloride (1.26 mL, 14.65 mmol) at −78° C. and stirred for 15 minutes. Then a solution of compound 37 (2.1 g, 9.76 mmol) in DCM (30 mL) was added at −78° C. and stirred at same temperature for 1 hour. TEA (4.9 mL, 48.83 mmol) was added and the reaction mixture was allowed to warm to rt. The reaction mixture was diluted with DCM and washed with water and brine. The organic layer was dried over anhydrous $Na_2SO_4$, filtered and evaporated to provide crude compound 38.

Yield: 2.3 g (crude)

D: 2-[2-((Indan-2-yl)amino)ethyl]pyrrolidine-1-carboxylic acid tert-butyl ester (compound 39)

To a stirred solution of compound 38 (2.3 g, 10.80 mmol) in DCM (90 mL) were added successively 2-aminoindane (1.4 mL, 10.80 mmol), Na(OAC)$_3$BH (6.86 g, 32.39 mmol) and acetic acid (2 mL) at 0° C. The resulting mixture was allowed to stir at rt for 16 hours. The reaction mixture was diluted in DCM and washed with 1N NaOH, water and brine solution. The organic layer was dried over anhydrous $Na_2SO_4$, filtered and evaporated. The crude material was purified by Combiflash® chromatography eluting with 3-4% of methanol-DCM to provide compound 39.

Yield: 3.0 g (84.26%).

E: 2-[2-(((Indan-2-yl)phenyl)amino)-ethyl]pyrrolidine-1-carboxylic acid tert-butyl ester (compound 40)

To a stirred solution of compound 39 (1.5 g, 4.54 mmol) in dioxane (22 mL) were added bromobenzene (1 mL, 9.09 mmol), DavePhos (0.36 g, 0.91 mmol), and KO$^t$Bu (1.28 g, 11.36 mmol) and purged with argon for 15 minutes. Then Pd$_2$(dba)$_3$ (0.42 g, 0.45 mmol) was added and the solution was again purged for 15 minutes. The reaction mixture was heated in a microwave for 1 hour at 100° C. The reaction mixture was diluted in ethyl acetate and washed with water and brine. The organic layer was dried over anhydrous $Na_2SO_4$, filtered and evaporated. The crude product was purified by Combiflash® chromatography eluting with 5-6% of ethyl acetate-hexane to provide compound 40.

Yield: 1.7 g (94.44%);

$^1$H-NMR (400 MHz, DMSO-$d_6$): δ 7.24-7.22 (m, 2 H), 7.18-7.14 (m, 4 H), 6.81 (d, J=8 Hz, 2 H), 6.65 (t, J=7 Hz, 1 H), 4.66-4.64 (m, 1 H), 3.62-3.60 (m, 1 H), 3.21-3.14 (m, 6 H), 2.97-2.90 (m, 2 H), 1.82-1.77 (m, 2 H), 1.67-1.65 (m, 2 H), 1.40-1.35 (m, 11 H);

LCMS [M+H]=407.0, RT=2.53 minutes, (Program P1, Column Y).

F: 2-[2-(((Indan-2-yl)phenyl)amino)ethyl]pyrrolidine (compound 41)

Dioxane-HCl (25 mL) was added to compound 40 (1 g, 2.46 mmol) at 0° C. and allowed to stir at rt for 4 hours. The reaction mixture was evaporated, diluted in ethyl acetate, and washed with sodium bicarbonate solution, water and brine. The organic layer was dried over anhydrous $Na_2SO_4$ and evaporated to provide crude compound 41.

Yield: 0.6 g (crude).

$^1$H-NMR (400 MHz, DMSO-$d_6$): δ 7.25-7.22 (m, 2 H), 7.18-7.14 (m, 4 H), 6.83 (d, J=8 Hz, 2 H), 6.63 (t, J=7 Hz, 1 H), 4.67-4.63 (m, 1 H), 3.21-3.13 (m, 3 H), 3.00-2.95 (m, 2 H), 2.83-2.75 (m, 2 H), 2.66-2.64 (m, 1 H), 1.74-1.71 (m, 1 H), 1.57-1.50 (m, 4 H), 1.08-1.07 (m, 1 H);

LCMS [M+H]=307.0, RT=3.01 minutes, (Program P1, Column Y).

G: 1,1-Diethyl-2-[2-((indan-2-yl)(phenyl)amino) ethyl]pyrrolidinium iodide

To a stirred solution of compound 41 (0.3 g, 0.98 mmol) in chloroform (6 mL) were added K$_2$CO$_3$ (0.68 g, 4.90 mmol) and ethyl iodide (0.75 mL, 9.8 mmol). The reaction mixture was heated at 50° C. for 16 hours in a sealed tube. The reaction mixture was filtered and evaporated. The crude product was purified by flash column chromatography eluting with 1-2% of methanol-DCM to provide a sticky compound.

The compound was lyophilized and dried under high vacuum to get the desired compound.

Yield: 0.12 g (24.99%);

$^1$H-NMR (400 MHz, DMSO-$d_6$): δ 7.25-7.16 (m, 6 H), 6.89 (d, J=8 Hz, 2 H), 6.73 (t, J=7 Hz, 1 H), 4.65-4.61 (m, 1 H), 3.59-3.55 (m, 1 H), 3.45-3.36 (m, 2 H), 3.25-3.05 (m, 8 H), 3.02-2.94 (m, 2 H), 2.22-2.20 (m, 1 H), 1.92-1.90 (m, 3 H), 1.69-1.64 (m, 2 H), 1.18-1.08 (m, 6 H);

LCMS [M$^+$]=363.0, RT=3.07 minutes, (Program P1, Column Y); HPLC: 98.00% (RT=4.97 minutes, $\lambda_{200nm}$, Mobile Phase A. 0.05% TFA in water, B. Acetonitrile; Column: Zorbax® SB-C18 (50×4.6 mm) 1.8μ).

Example 37

General Procedure G—Preparation of 1,1-dimethyl-2-[2-((indan-2-yl)(pyridine-2-yl)amino)ethyl]piperidinium iodide

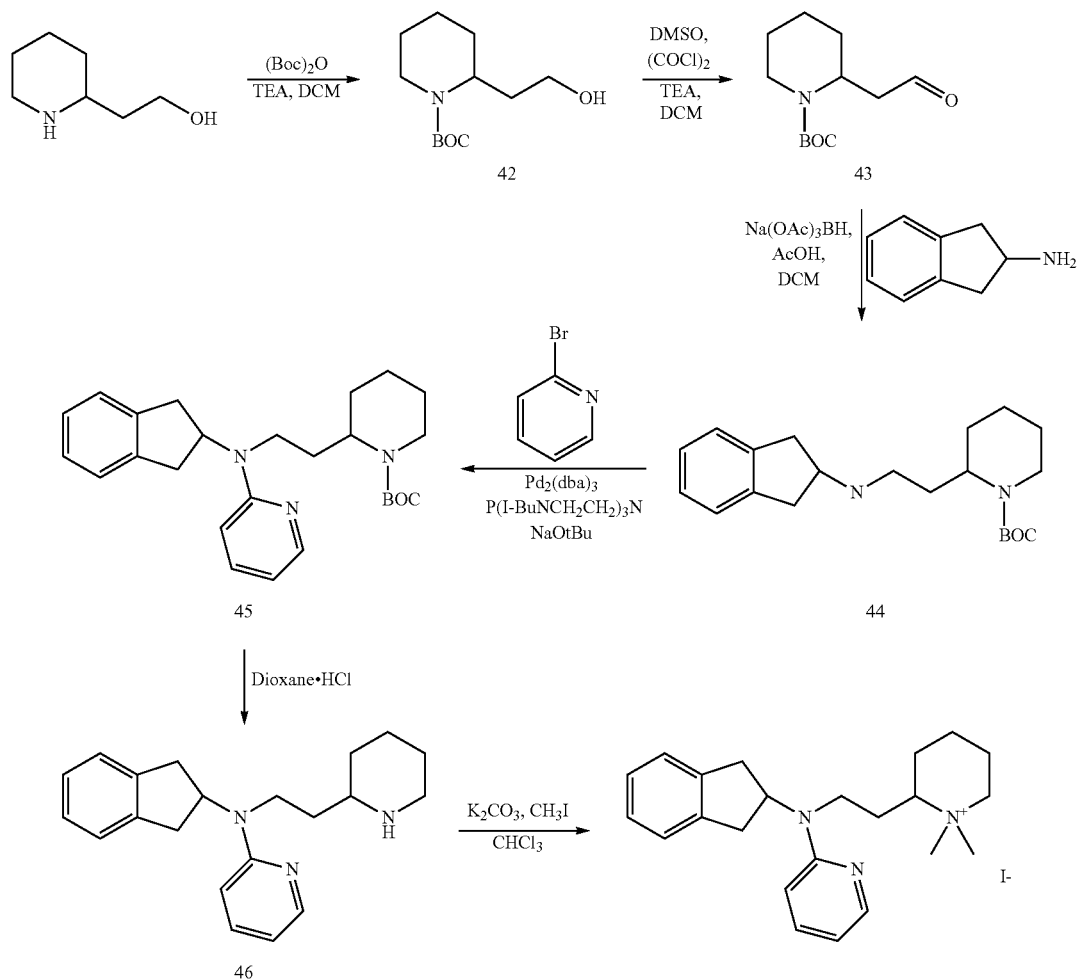

A. 2-(2-Hydroxyethyl)piperidine-1-carboxylic acid tert-butyl ester (compound 42)

To a stirred solution of piperidine-2-ethanol (5 g, 38.69 mmol) in DCM (80 m:) was added TEA (6.5 mL, 46.43 mmol), followed by BOC anhydride (9.8 mL, 42.56 mmol) at 0° C. and the reaction mixture was stirred at rt for 16 hours. The reaction mixture was diluted with ethyl acetate and the organic layer was washed with water and brine solution then dried over anhydrous $Na_2SO_4$, filtered and concentrated to get crude compound 42.

Yield: 10 g (crude);

$^1$H-NMR (400 MHz, DMSO-$d_6$): δ 4.33 (t, J=5 Hz, 1 H), 4.20-4.18 (m, 1 H), 3.82-3.79 (m, 2 H), 3.37-3.34 (m, 1 H), 2.73 (t, J=13 Hz, 1 H), 1.79-1.72 (m, 1 H), 1.61-1.47 (m, 7 H), 1.38 (s, 9 H), 1.26-1.22 (m, 1 H);

LCMS [M+H]=230.2, RT=2.95 minutes, (Program P1, Column Y).

B. 2-(2-Oxoethyl)piperidine-1-carboxylic acid tert-butyl ester (compound 43)

To a stirred solution of DMSO (1.86 mL, 26.2 mmol) in DCM (60 mL) was added $(COCl)_2$ (1.13 mL, 13.1 mmol) at −78° C. and the reaction mixture was stirred at −78° C. for 15 minutes. Compound 42 (2 g, 8.733 mmol) in DCM (20 mL) was then added dropwise at −78° C. and the solution then stirred at same temperature for 1 hour. TEA (6.06 mL, 43.66 mmol) was then added and the reaction mixture was stirred at rt. The reaction mixture was diluted with DCM and the organic layer was washed with water and brine solution, dried over $Na_2SO_4$, filtered and concentrated to provide sticky crude compound 43.

Yield: 2.4 g (crude).

C. 2-[2-((Indan-2-yl)amino)ethyl]piperidine-1-carboxylic acid tert-butyl ester (compound 44)

To a stirred solution of compound 43 (2.4 g, 10.57 mmol) in DCM (50 mL) were added successively 2-aminoindane (1.37 mL, 10.57 mmol), sodium triacetoxyborohydride (6.72 g, 31.72 mmol) and acetic acid (2 drops) at 0° C. The reaction mixture was stirred at rt for 16 hours. The reaction mixture was diluted with DCM and basified with 1N NaOH. The organic layer was washed with water and brine, dried over anhydrous Na$_2$SO$_4$, filtered and concentrated. The crude compound was purified by column chromatography (using 230-400 silica mesh) eluting with 4-5% methanol-DCM to provide the desired compound 44.

Yield: 1.6 g (44.4%);

$^1$H-NMR (400 MHz, DMSO-d$_6$): δ 7.18-7.13 (m, 2 H), 7.11-7.08 (m, 2 H), 4.19 (brs, 1 H), 3.84-3.81 (m, 1 H), 3.52-3.49 (m, 1 H), 3.07-3.02 (m, 2 H), 2.76-2.60 (m, 5 H), 1.86-1.83 (m, 1 H), 1.57-1.50 (m, 7 H), 1.39 (s, 9 H), 1.25-1.23 (m, 1 H);

LCMS [M+H]=345.0, RT=3.04 minutes, (Program P1, Column Y).

D: 2-[2-((Indan-2-yl)(pyridin-2-yl)amino)ethyl]piperidine-1-carboxylic acid tert-butyl ester (compound 45)

The stirred mixture of compound 44 (0.6 g, 1.74 mmol), 2-bromo-pyridine (0.17 mL, 1.74 mmol) and NaO$^t$Bu (0.23 g, 2.44 mmol) in toluene (20 mL) was purged with argon for 15 minutes. Pd$_2$(dba)$_3$ (0.08 g, 0.09 mmol) and P(i-BuNCH$_2$CH$_2$)$_3$N (0.12 mL, 0.35 mmol) were then added. The resulting mixture was again degassed with argon for 15 minutes and heated at 110° C. for 16 hours. The reaction mixture was diluted with ethyl acetate and washed with water and brine. The organic layer was dried over anhydrous sodium sulphate and concentrated under reduced pressure. The crude compound was purified by column chromatography (using 230-400 mesh silica gel) eluting with 1-2% of ethyl acetate-hexane to provide the desired compound 45.

Yield: 0.32 g (43.6%);

$^1$H-NMR (400 MHz, DMSO-d$_6$): δ 8.10-8.08 (m, 1 H), 7.51-7.47 (m, 1 H), 7.25-7.23 (m, 2 H), 7.17-7.15 (m, 2 H), 6.62 (d, J=9 Hz, 1 H), 6.57-6.54 (m, 1 H), 5.29-5.26 (m, 1 H), 4.10-4.08 (m, 1 H), 3.78-3.75 (m, 1 H), 3.36-3.34 (m, 1 H), 3.22-3.13 (m, 3 H), 2.98-2.91 (m, 2 H), 2.65-2.59 (m, 1 H), 1.83-1.80 (m, 1 H), 1.67-1.61 (m, 1 H), 1.54-1.50 (m, 1 H), 1.45-1.42 (m, 4 H), 1.32 (s, 9 H), 1.26-1.17 (m, 1 H);

LCMS [M+H]=422.6, RT=3.18 minutes, (Program R1, Column X).

E. 2-[2-((Indan-2-yl)(pyridin-2-yl)amino)ethyl]piperidine (compound 46)

Dioxane-HCl (10 mL) was added to compound 45 (0.35 g, 0.83 mmol) at 0° C. The reaction mixture was stirred at rt for 3 hours. The reaction mixture was dried under reduced pressure. The crude compound was dissolved in ethyl acetate and washed with saturated sodium bicarbonate, water and brine. The organic layer was dried over anhydrous sodium sulphate and concentrated to provide the desired compound 46.

Yield: 0.23 g (87%);

LCMS [M+H]=322.4, RT=2.25 minutes, (Program R1, Column Z).

F. 1,1-Dimethyl-2-[2-((indan-2-yl)(pyridine-2-yl)amino)ethyl]piperidinium iodide To a stirred solution of compound 46 (0.12 g, 0.37 mmol) in chloroform (5 mL) were added K$_2$CO$_3$ (0.257 g, 1.87 mmol) and methyl iodide (0.12 mL, 1.87 mmol). The resulting mixture was heated at 50° C. for 16 hours in a sealed tube. The reaction mixture was filtered and the filtrate was concentrated. The crude material was purified by column chromatography (using 230-400 mesh silica) eluting with 2-3% of methanol-DCM to provide the desired compound.

Yield: 0.08 g (44.96%);

$^1$H-NMR (400 MHz, DMSO-d$_6$): δ 8.11 (d, J=3 Hz, 1 H), 7.52 (t, J=7 Hz, 1 H), 7.27-7.25 (m, 2 H), 7.19-7.17 (m, 2 H), 6.74 (d, J=10 Hz, 1 H), 6.63-6.60 (m, 1 H), 5.17-5.10 (m, 1 H), 3.46-3.43 (m, 3 H), 3.28-3.25 (m, 2 H), 3.20-3.13 (m, 2 H), 3.07-2.99 (m, 5 H), 2.85 (s, 3 H), 2.12-2.09 (m, 1 H), 1.92-1.89 (m, 1 H), 1.82-1.76 (m, 1 H), 1.70-1.67 (m, 2 H), 1.60-1.50 (m, 2 H), 1.40-1.37 (m, 1 H);

LCMS [M$^+$]=350.4, RT=1.72 minutes (Program R1, Column Z)

UPLC: 99.57% (RT=2.70 minutes, λ$_{200nm}$, Mobile Phase A. 0.05% TFA in water, B. Acetonitrile; Column: Zorbax® XDB-C18 (4.6×50 mm), 1.8μ).

Example 38

General Procedure H—Preparation of 1,1-dimethyl-2-[2-((indan-2-yl)(pyrimidine-2-yl)amino)ethyl]piperidinium iodide

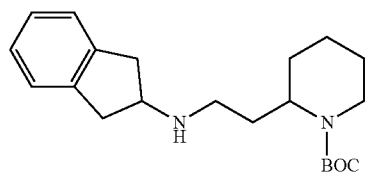

44

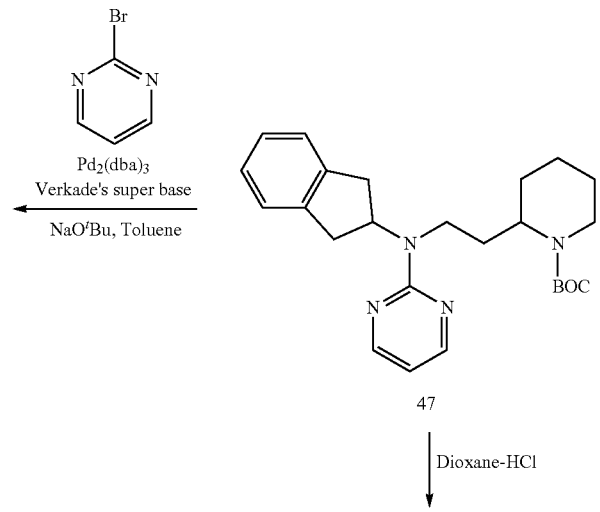

47

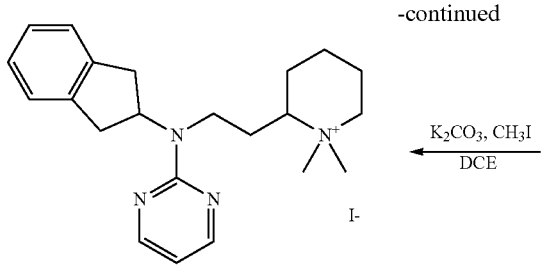 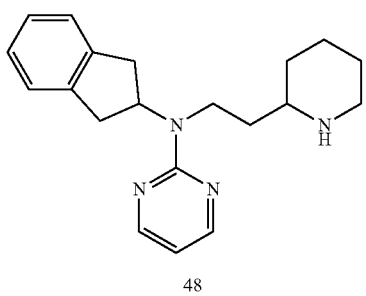

A. 2-[2-((Indan-2-yl)(pyrimidin-2-yl)amino)ethyl] piperidine-1-carboxylic acid tert-butyl ester (compound 47)

To a stirred solution of compound 44 (1.2 g, 3.48 mmol) in dry toluene (35 mL) were added 2-bromo-pyrimidine (0.55 g, 3.48 mmol) and NaO$^t$Bu (0.47 g, 4.88 mmol) and the solution was purged with argon for 30 minutes. Pd$_2$(dba)$_3$ (0.159 g, 0.17 mmol) and Verkade's super base (0.24 g, 0.70 mmol) were then added and the solution refluxed overnight. The reaction mixture was filtered through Celite®reagent and washed with ethyl acetate. The filtrate was washed with water and brine solution, dried over anhydrous Na$_2$SO$_4$, filtered and concentrated. The crude material was purified by Combiflash® chromatography eluting with 14-15% ethyl acetate-hexane to get compound 47.

Yield: 0.303 g (20.6%);
$^1$H-NMR (DMSO-d$_6$): δ 8.35 (d, J=5 Hz, 2 H) , 7.22 (s, 2 H) , 7.16-7.14 (m, 2 H), 6.61 (t, J=5 Hz, 1 H) , 5.47-5.43 (m, 1 H) , 4.07 (s, 1 H) , 3.77-3.74 (m, 1 H) , 3.42-3.39 (m, 1 H) , 3.18-3.11 (m, 2 H) , 3.03-2.97 (m, 2 H) , 2.65 (t, J=12 Hz, 1 H) , 1.89-1.87 (m, 1 H) , 1.66-1.63 (m, 1 H) , 1.55-1.37 (m, 6 H) , 1.31 (s, 9 H) , 1.26-1.17 (m, 1 H);
LCMS [M+H]=423.2, RT=2.62 minutes, (Program P1, Column Y).

B. 2-[2-((Indan-2-yl)(pyrimidin-2-yl)amino)ethyl] piperidine (compound 48)

To compound 47 (0.303 g, 0.72 mmol) was added dioxane-HCl (20 mL) at ice-cold condition and the solution was stirred for 4 hours at rt. The solution was then concentrated under reduced pressure and dissolved in ethyl acetate. The organic layer was washed with saturated NaHCO$_3$ solution, water and brine, dried over anhydrous Na$_2$SO$_4$, filtered and concentrated under reduced pressure to provide sticky compound 48.

Yield: 0.21 g (90.83%);
$^1$H-NMR (400 MHz, DMSO-d$_6$): δ 8.34 (d, J=5 Hz, 2 H) , 7.22-7.21 (m, 2 H), 7.16-7.14 (m, 2 H) , 6.59 (t, J=9 Hz, 1 H) , 5.37-5.34 (m, 1 H) , 4.07 (s, 1 H) , 3.77-3.74 (m, 1 H) , 3.55-3.53 (m, 2 H) , 3.16-3.01 (m, 4 H) , 2.9-2.88 (m, 1 H) , 1.53-1.45 (m, 5 H) , 1.35-1.23 (m, 3 H) ;
LCMS [M+H]=322.8, RT=3.08 minutes, (Program P1, Column Y).

C. 1,1-Dimethyl-2-[2-((indan-2-yl)(pyrimidine-2-yl)amino)ethyl]piperidinium iodide To a stirred solution of compound 48 (0.21 g, 0.65 mmol) in CHCl$_3$ (5 mL) was added K$_2$CO$_3$ (0.45 g, 3.26 mmol) followed by addition of methyl iodide (0.2 mL, 3.26 mmol. The solution was stirred at 50° C. for 16 hours in a sealed tube. The reaction mixture was filtered through a sintered funnel and concentrated. The crude material was purified by column chromatography on neutral alumina eluting with 1-1.5% methanol-DCM to get the desired compound.

Yield: 0.16 g (51.34%);
$^1$H-NMR (400 MHz, DMSO-d$_6$): δ 8.39 (d, J=5 Hz, 2 H) , 7.25-7.24 (m, 2 H) , 7.18-7.16 (m, 2 H) , 6.68-6.66 (m, 1 H) , 5.45-5.41 (m, 1 H) , 3.55-3.51 (m, 2 H) , 3.46-3.42 (m, 1 H) , 3.26-3.23 (m, 2 H) , 3.12-3.05 (m, 7 H) , 2.86 (s, 3 H) , 2.20-2.17 (m, 1 H), 1.93-1.36 (m, 7 H) ;
LCMS [M$^+$]=351, RT=2.90 minutes, (Program P1, Column Y); HPLC: 99.9% (RT=4.70 minutes, λ$_{220nm}$, Mobile Phase; A. 0.05% TFA in water, B. Acetonitrile; Column: Zorbax® SB-C18 (50×4.6 mm) 1.8μ).

Example 39

General Procedure I—Preparation of 1,1-dimethyl-2-[2-((indan-2-yl)(thiazol-2-yl)amino)ethyl]piperidinium iodide

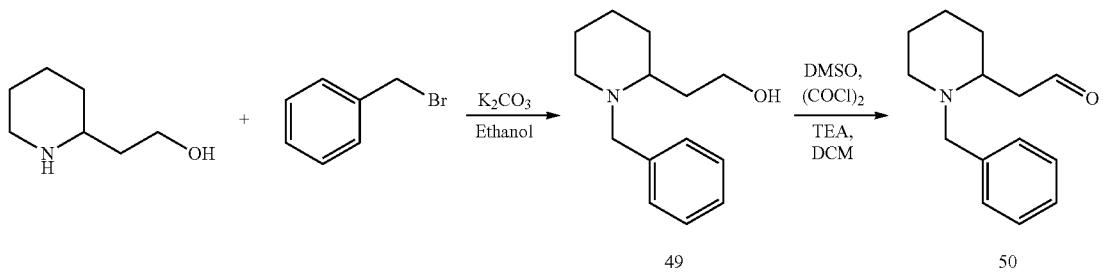

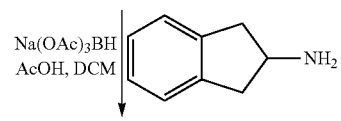

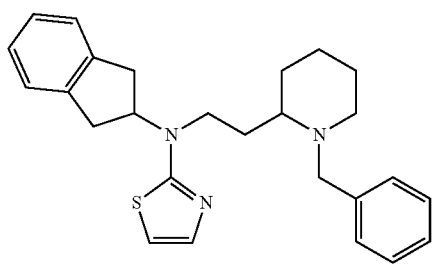

52

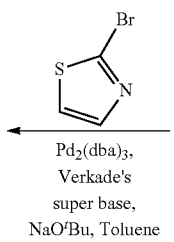

-continued

Pd₂(dba)₃,
Verkade's
super base,
NaO'Bu, Toluene

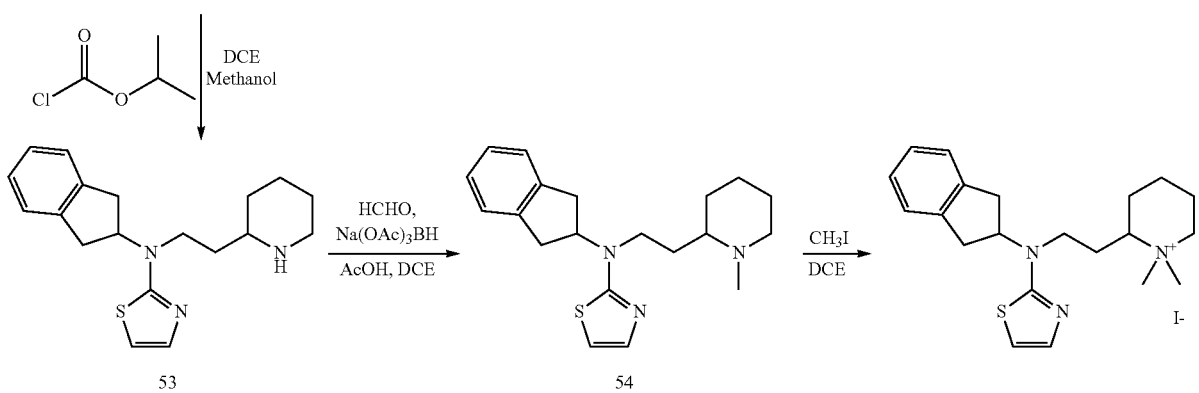

A. 2-(1-Benzylpiperidin-2-yl)ethanol (compound 49)

To a stirred solution of piperidine-2-ethanol (20 g, 155 mmol) in ethanol (240 mL) was added K₂CO₃ (106 g, 775.1 mmol) followed by addition of benzyl bromide (18.4 mL, 155.04 mmol) at 0° C. The reaction mixture was stirred at rt overnight, filtered through a sintered funnel and concentrated. The crude material was dissolved in ethyl acetate, the organic layer was washed with water and brine, dried over anhydrous Na₂SO₄, filtered and concentrated to get liquid compound 49.

Yield: 25 g (73.65%);

¹H-NMR (400 MHz, DMSO-d₆): δ 7.31 (d, J=13 Hz, 4 H), 7.24-7.19 (m, 1 H), 4.41 (s, 1 H), 3.88 (d, J=14 Hz, 1 H), 3.54-3.41 (m, 2 H), 3.31-3.23 (m, 1 H), 2.62-2.58 (m, 1 H), 2.45 (s, 1 H), 2.06-2.01 (m, 1 H), 1.83-1.76 (m, 1 H), 1.66-1.57 (m, 3 H), 1.42-1.26 (m, 4 H);

LCMS [M+H]=220.4, RT=2.35 minutes, (Program P1, Column Y).

B. (1-Benzylpiperidin-2-yl)acetaldehyde (compound 50)

To a stirred solution of DMSO (5.84 mL, 82.2 mmol) in dry DCM (220 mL) was added (COCl)₂ (3.55 mL, 41.1 mmol) at −78° C. and the mixture stirred at same temperature for 20 minutes. A solution of compound 49 (6 g, 27.4 mmol) in DCM (30 mL) was then added slowly and the reaction mixture was stirred at −78° C. for 1 hour. TEA (13.8 mL, 137 mmol) was added at −78° C. and the reaction mixture was stirred and allowed to come to rt. The reaction mixture was diluted with DCM and the organic layer was washed with water and brine, dried over anhydrous Na₂SO₄, filtered and concentrated to provide sticky compound 50.

Yield: 7.0 g (Crude);

¹H-NMR (400 MHz, DMSO-d₆): δ 9.76 (s, 1 H), 7.43-7.21 (m, 5 H), 3.81 (d, J=13 Hz, 1 H), 3.24 (d, J=8 Hz, 1 H), 3.06 (d, J=6 Hz, 1 H), 2.92 (s, 1 H), 2.71-2.62 (m, 2 H), 2.58-2.49 (m, 3 H), 2.13-2.03 (m, 1 H), 1.79-1.59 (m, 3 H), 1.44-1.35 (m, 4 H), 1.23-1.16 (m, 1 H).

C. 2-[1-Benzyl-2-((indan-2-yl)amino)ethyl]piperidine (compound 51)

To a stirred solution of compound 50 (7 g, 32.2 mmol) in DCM (120 mL) were added successively 2-aminoindane (4.29 mL, 32.2 mmol), Na(OAc)₃BH (20.5 g, 96.7 mmol) and acetic acid (3 mL) at 0° C. The resulting mixture was allowed to stir at RT for 16 hours. The reaction mixture was diluted with DCM and basified by 1N NaOH solution. The organic layer was separated and washed with water and brine, dried over anhydrous Na₂SO₄, filtered and concentrated. The crude material was purified by Combiflash® chromatography eluting with 1-2% methanol-DCM to afford compound 51.

Yield: 6.6 g (61.37%);

¹H-NMR (400 MHz, DMSO-d₆): δ 7.29-7.0 (m, 9 H), 3.91 (d, J=14 Hz, 1 H), 3.48-3.46 (m, 1 H), 3.21 (s, 1 H), 3.18-3.12 (m, 1 H), 3.05-2.99 (m, 2 H), 2.64 (d, J=8 Hz, 1 H), 2.62-2.55 (m, 5 H), 2.38 (s, 1 H), 2.01-1.95, (m, 1 H), 1.78 (s, 1 H), 1.74-1.70 (m, 1 H), 1.67-1.60 (m, 3 H), 1.41-1.27 (m, 6 H);

LCMS [M+H]=334.8, RT=3.0 minutes, (Program P1, Column Y).

D. 2-[1-Benzyl-2-((indan-2-yl)(thiazol-2-yl)amino)ethyl]piperidine (compound 52)

To a stirred solution of compound 51 (2 g, 5.98 mmol) in dry toluene (35 mL) were added 2-bromo-thiazole (0.53 mL, 5.98 mmol) and NaO'Bu (0.805 g, 8.38 mmol) and the solution was degassed with argon for 30 minutes. Pd₂dba₃ (0.274 g, 0.30 mmol) and Verkade's super base (0.42 mL, 1.19 mmol) were then added and the resulting mixture was refluxed for 16 hours. The reaction mixture was filtered through a Celite® pad and was washed with ethyl acetate. The organic layer was washed with water and brine, dried over anhydrous Na$_2$SO$_4$, filtered and concentrated. The crude material was purified by Combiflash® chromatography eluting with 20-22% ethyl acetate-hexane to provide compound 52.

Yield: 0.688 g (27.42%);
$^1$H-NMR (DMSO-d$_6$): δ 7.29-7.20 (m, 9 H) , 7.12 (m, 1 H) , 6.73 (d, J=4 Hz, 1 H), 4.79-4.75 (m, 1 H) , 3.82 (d, J=14 Hz, 1 H) , 3.40-3.37 (m, 1 H) , 3.35-3.25 (m, 2 H), 3.23-3.07 (m, 3 H) , 2.67-2.61 (m, 1 H) , 2.5-2.49 (m, 1 H) , 2.32-2.26 (m, 1 H) , 2.22-1.98 (m, 1 H) , 1.97-1.95 (m, 1 H) , 1.93-1.82 (m, 3 H) , 1.73-1.51 (m, 4 H) ;
LCMS [M+H]=418.1, RT=3.95 minutes, (Program P1, Column Y).

E. 2-[2-((Indan-2-yl)(thiazol-2-yl)amino)ethyl]piperidine (compound 53)

To a stirred solution of compound 52 (0.688 g, 1.64 mmol) in DCE (15 mL) was added isobutyl chloroformate (0.53 mL, 4.94 mmol) at 0° C. and the solution was refluxed for 9.5 hours. Methanol (30 mL) was added and the mixture was allowed to stir at rt for 16 hours. The reaction mixture was concentrated under reduced pressure to provide compound 53.

Yield: 0.53 g (98.78%);
$^1$H-NMR (400 MHz, DMSO-d$_6$): δ 7.4-7.18 (m, 4 H) , 7.0 (d, J=4 Hz, 1 H) , 6.52-6.48 (m, 1 H) , 4.75 (s, 1 H) , 4.70-4.67 (m, 1 H) , 3.78 (s, 3 H) , 3.73-3.59 (m, 1 H), 3.28-3.10 (m, 3 H) , 3.08-2.98 (m, 1 H) , 2.78-2.75 (m, 1 H) , 1.99-1.97 (m, 1 H) , 1.86-1.82 (m, 1 H) , 1.78-1.75 (m, 2 H) , 1.7-1.68 (m, 2 H) , 1.58-1.55 (m, 1 H) , 1.39-1.34 (m, 2 H) ;
LCMS [M+H]=328, RT=3.08 minutes, (Program P1, Column X).

F. 2-[2-((Indan-2-yl)(thiazol-2-yl)amino)ethyl]-1-methylpiperidine (compound 54)

To a stirred solution of compound 53 (0.53 g, 1.62 mmol) in DCE (25 mL) were added successively formaldehyde (35% solution in H$_2$O, 0.2 mL, 2.43 mmol), Na(OAc)$_3$BH (1.03 g, 4.86 mmol) and acetic acid (0.2 mL) at 0° C., and the solution was allowed to stir at rt for 16 hours. The reaction mixture was diluted with ethyl acetate and basified with 1N NaOH solution. The organic layer was separated and washed with water and brine, dried over anhydrous Na$_2$SO$_4$, filtered and concentrated. The crude material was purified by chromatography on neutral alumina eluting 1% methanol-DCM to get compound 54.

Yield: 0.25 g (45.25%);
$^1$H-NMR (400 MHz, DMSO-d$_6$): δ 7.26-7.24 (m, 2 H) , 7.18-7.15 (m, 2 H) , 7.13 (d, J=4 Hz, 1 H) , 6.74 (d, J=4 Hz, 1 H) , 4.80-4.76 (m, 1 H) , 3.35-3.31 (m, 1 H), 3.31-3.20 (m, 3 H) , 3.12-3.06 (m, 2 H) , 2.67-2.64 (m, 1 H) , 2.03 (s, 3 H) , 1.87-1.84 (m, 1 H) , 1.75-1.69 (m, 2 H) , 1.61-1.55 (m, 2 H) , 1.45-1.38 (m, 1 H) , 1.35-1.32 (m, 2 H) , 1.23-1.11 (m, 3 H) ;
LCMS [M+H]=342, RT=2.91 minutes, (Program P1, Column Y).

G. 1,1-Dimethyl-2-[2-((indan-2-yl)(thiazol-2-yl)amino)ethyl]piperidinium iodide To a stirred solution of compound 54 (0.25 g, 0.733 mmol) in DCE (5 mL) was added methyl iodide (0.2 mL, 2.93 mmol) and the reaction mixture was stirred at rt for 16 hours in a sealed tube. The reaction mixture was concentrated and the crude material purified by column chromatography on neutral alumina eluting with 1% methanol-DCM to provide a solid compound. The solid material crystallized from methanol-ether to provide the desired compound as an off white solid.

Yield: 0.146 g (41.24%);
$^1$H-NMR (400 MHz, DMSO-d$_6$): δ 7.28-7.22 (m, 2 H) , 7.19-7.16 (m, 3 H) , 6.83 (d, J=4 Hz, 1 H) , 3.39-3.32 (m, 3 H) , 3.2-3.08 (m, 6 H) , 3.01 (s, 3 H) , 2.84 (s, 3 H), 2.32-2.21 (m, 1 H) , 1.86-1.78 (m, 2 H) , 1.67 (d, J=12 Hz, 2 H) , 1.52-1.49 (m, 2 H), 1.38-1.35 (m, 1 H) ;
LCMS [M$^+$]=356.2, RT=2.44 minutes, (Program R1, Column Z);
UPLC: 99.28% (RT=4.56 minutes, λ$_{260nm}$, Mobile Phase A. 0.05% TFA in water, B. Acetonitrile; Column: Zorbax® SB-C18 (4.6×50 mm) 1.8µ).

Example 40

General Procedure J—Preparation of 1,1-dimethyl-4-[2-((indan-2-yl)(2-methylphenyl)amino)ethyl]piperidinium bromide

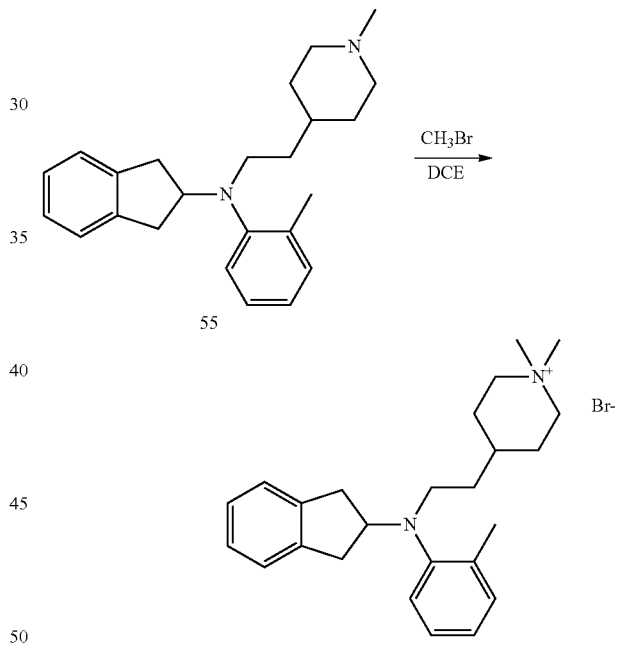

To a stirred solution of compound 55, which is prepared according to general procedure A1 for the preparation of compound 8 (except substituting compound 7e for compound 7 and 4-(2-hydroxyethyl)-1-methylpiperidine for compound 5, (1.2 g, 3.45 mmol) in DCE (20 mL) was added a solution of methyl bromide (25% solution in toluene, 5.23 mL, 13.79 mmol) and the reaction mixture was stirred at rt for 16 hours in a sealed tube. The reaction mixture was concentrated and the crude material was purified by chromatography on silica-gel (230-400 mesh) eluting with 10% methanol-DCM and then crystallized from methanol-ether to provide the desired compound.

Yield: 1.5 g (98.15%);
$^1$H-NMR (400 MHz, DMSO-d$_6$): δ 7.28 (d, J=8 Hz, 1 H) , 7.21 (t, J=8 Hz, 2 H), 7.17-7.14 (m, 2 H) , 7.11-7.09 (m, 2 H), 7.03 (t, J=7 Hz, 1 H), 3.98-3.94 (m, 1 H), 3.37-3.33 (m, 2 H), 3.24-3.18 (m, 2 H), 3.06 (s, 3 H), 3.02-2.92 (m, 7 H), 2.79 (dd, J=15, 8 Hz, 2 H), 2.28 (s, 3 H), 1.69-1.66 (m, 2 H), 1.51-1.46 (m, 3 H), 1.27-1.25 (m, 2 H);

LCMS: [M$^+$]=363.2, RT=3.30 minutes, (Program P1, Column Y);

UPLC: 99.54% (RT=3.21 minutes, $\lambda_{200nm}$, Mobile Phase: A 0.05% TFA in water, B Acetonitrile; Column: Zorbax® SB C18 (4.6×50 mm) 1.8μ).

Example 41

General Procedure K—Preparation of 7-[2-((indan-2-yl)(2-methylphenyl)amino)ethyl]-3-oxa-6-azaspiro[5.5]undecan-6-ium chloride

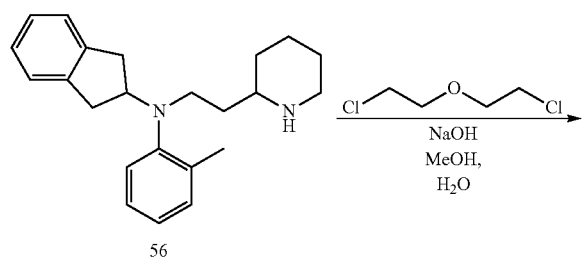

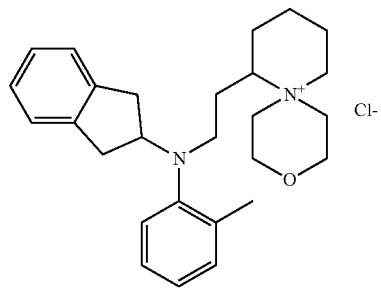

To a stirred solution of NaOH (78 mg, 1.95 mmol) in water (16 mL) was added 1-chloro-2-(2-chloro-ethoxy)ethane (0.3 mL, 2.6 mmol) and the solution was refluxed for 1 hour. Then a solution of compound 56 (435 mg, 1.3 mmol) in methanol (4-5 drops) and water (4 mL) was added and the resultant solution refluxed for 16 hours. 40% NaOH was added to the reaction mixture at ice salt conditions and extracted with chloroform. The solution was then dried over anhydrous Na$_2$SO$_4$, filtered and concentrated. The crude material was purified by column chromatography on neutral alumina eluting with 2-3% methanol-DCM to provide a solid. The solid material was triturated with dry ether and dried under vacuum to get the desired compound as a white solid.

Yield: 88 mg (15.35%);

$^1$H-NMR (400 MHz, DMSO-d$_6$): δ 7.33-7.31 (m, 1 H), 7.26-7.21 (m, 4 H), 7.19-7.10 (m, 2 H), 7.07-7.03 (m, 1 H), 4.06-4.02 (m, 1 H), 3.96-3.90 (m, 1 H), 3.84-3.73 (m, 3 H), 3.59-3.49 (m, 5 H), 3.12-3.10 (m, 2 H), 3.02-2.95 (m, 3 H), 2.92-2.81 (m, 3 H), 2.30 (s, 3 H), 1.97 (brs, 1 H), 1.88 (brs, 1 H), 1.71 (brs, 2 H), 1.58-1.48 (m, 4 H);

LCMS [M$^+$]=405, RT=3.32 minutes, (Program P1, Column Y);

UPLC: 98.59% (RT=5.47 minutes, $\lambda_{220nm}$, Mobile Phase A. 0.05% TFA in water, B. Acetonitrile; Column: Zorbax® XDB-C18 (4.6×50 mm) 1.8μ).

Example 42

General Procedure L—Preparation of 1,1-dimethyl-2-[2-((2,3-dihydrobenzo[b][1,4]dioxin-6-yl)(indan-2-yl)amino)ethyl]piperidinium iodide

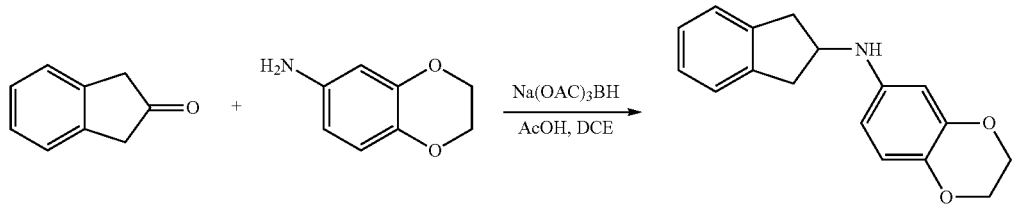

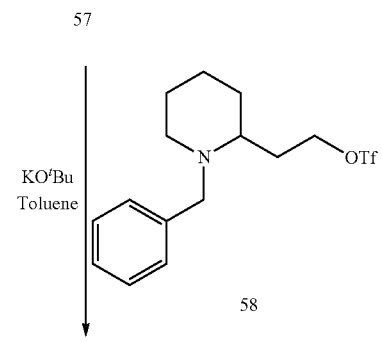

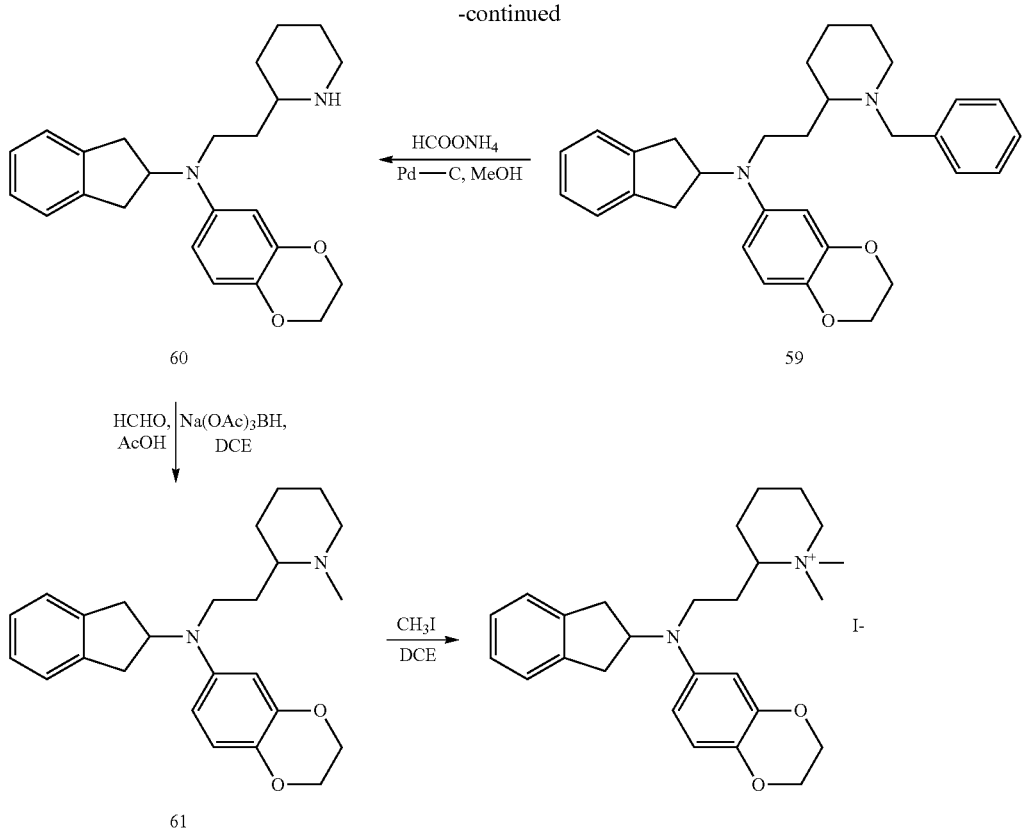

A. N-2,3-Dihydro-benzo[1,4]dioxin-6-yl-N-indan-2-ylamine (compound 57)

To a stirred solution of 2-indanone (2 g, 15.1 mmol) in DCE (50 mL) were added 2,3-dihydro-benzo[1,4]dioxin-6-ylamine (2.28 g, 15.1 mmol), Na(OAc)$_3$BH (4.81 g, 22.6 mmol), AcOH (1.8 mL) successively at 0° C. and the mixture was stirred overnight at rt. The reaction mixture was dissolved in ethyl acetate and was washed with 1N NaOH, water and brine. The solution was dried over Na$_2$SO$_4$, filtered and concentrated. The crude material was purified by Combiflash® chromatography eluting with 9-10% ethyl acetate-hexane to get compound 57.

Yield: 3.9 g (96.5%);
$^1$H-NMR (400 MHz, DMSO-d$_6$): δ 7.21-7.11 (m, 4 H), 6.60-6.56 (m, 1 H), 6.14-6.11 (m, 2 H), 5.41 (d, J=7 Hz, 1 H), 4.16-4.02 (m, 6 H), 3.32-3.21 (m, 2 H), 2.77-2.71 (m, 2 H);
LCMS [M+H]=268.2, RT=3.54 minutes, (Program P1, Column Y).

B. 2-[1-Benzyl-2-((2,3-dihydrobenzo[b][1,4]dioxin-6-yl)(indan-2-yl)amino)ethyl]piperidine (compound 59)

To a stirred solution of compound 57 (1 g, 3.74 mmol) in dry toluene (25 mL) was added KO$^t$Bu (0.63 g, 5.61 mmol) at 0° C. and the solution was heated at 50° C. for 5 hours. A solution of trifluoromethanesulfonic acid 2-(1-benzyl-piperidin-2-yl)-ethyl ester (58) (1.4 g, 4.11 mmol) in dry toluene (5 mL) was then added at 0° C. and refluxed for 16 hours. TLC showed incomplete conversion of the starting material, hence another 0.5 eq of compound 58 was added and refluxed for 16 hours. The reaction mixture was diluted with ethyl acetate and the organic layer was washed with water and brine. The solution was dried over anhydrous Na$_2$SO$_4$, filtered and concentrated. The crude material was purified by Combiflash® chromatrography eluting with 7-8% methanol-DCM to get compound 59.

Yield: 1.8 g (68.46%);
$^1$H-NMR (400 MHz, DMSO-d$_6$): δ 7.28-7.10 (m, 9 H), 6.69-6.67 (m, 1 H), 6.38 (m, 2 H), 4.35-4.34 (m, 1 H), 4.17-4.14 (m, 4 H), 3.67-3.63 (m, 1 H), 3.14-3.07 (m, 4 H), 2.87-2.81 (m, 3 H), 2.49-2.5 (m, 1 H), 2.32-2.28 (m, 1 H), 2.00-1.95 (m, 2 H), 1.61-1.23 (m, 8 H);
LCMS [M+H]=468.8, RT=4.37 minutes, (Program P1, Column Y).

C. 2-[2-((2,3-Dihydrobenzo[b][1,4]dioxin-6-yl)(indan-2-yl)amino)ethyl]piperidine (compound 60)

To a stirred solution of compound 59 (1.55 g, 3 31 mmol) in methanol (30 mL) was added HCOONH$_4$ (2.08 g, 33.11 mmol) and the solution was purged with nitrogen for 30 minutes. 10% Pd—C (0.4 g) was then added and the solution was refluxed for 6 hours. The reaction mixture was filtered through Celite® reagent and the filtrate was concentrated. The residue was dissolved in ethyl acetate and washed with water and brine. The solution was dried over anhydrous Na$_2$SO$_4$, filtered and concentrated under reduced pressure to provide compound 60.

Yield: 0.98 g (78.2%);
$^1$H-NMR (400 MHz, DMSO-d$_6$): δ 7.20-7.11 (m, 4 H), 6.74-6.71 (m, 1 H), 6.47-6.46 (m, 2 H), 4.33-4.29 (m, 1 H), 4.20-4.15 (m, 4 H), 3.16-3.11 (m, 3 H), 3.07-3.01 (m, 2 H), 2.88-2.81 (m, 3 H) , 2.78-2.71 (m, 1 H) , 1.75-1.67 (m, 4 H) , 1.48-1.37 (m, 2 H) , 1.37-1.34 (m, 1 H) , 1.23-1.17 (m, 1 H) ;

LCMS [M+H]=469.2, RT=3.05 minutes, (Program P1, Column Y).

D. 2-[2-((2,3-Dihydrobenzo[b][1,4]dioxin-6-yl)(indan-2-yl)amino)ethyl]-1-methylpiperidine (compound 61)

To a stirred solution of compound 60 (0.5 g, 1.32 mmol) in DCE (25 mL) were added formaldehyde (35% solution in $H_2O$, 0.17 mL, 1.98 mmol), $Na(OAc)_3BH$ (0.84 g, 3.96 mmol) and AcOH (0.2 mL) successively at 0° C. and the mixture was stirred at rt for 16 hours. The reaction mixture was dissolved in ethyl acetate and basified with 1N NaOH. The organic layer was separated and washed with water and brine. The solution was dried over anhydrous $Na_2SO_4$, filtered and concentrated. The crude material was purified by Combiflash® chromatography eluting with 5-5.2% methanol-DCM to provide compound 61.

Yield: 0.25 g (48.2%);

$^1$H-NMR (400 MHz, DMSO-$d_6$): δ 7.21-7.19 (m, 2 H) , 7.13-7.11 (m, 2 H) , 6.71-6.69 (m, 1 H) , 6.41-6.37 (m, 2 H) , 4.36-4.33 (m, 1 H) , 4.19-4.14 (m, 4 H) , 3.14-3.01 (m, 4 H) , 2.84 (dd, J=16, 8 Hz, 2 H) , 2.67-2.64 (m, 1 H) , 1.97 (s, 3 H) , 1.91-1.86 (m, 1 H) , 1.78 (s, 1 H) , 1.58-1.55 (m, 1 H) , 1.50-1.33 (m, 5 H) , 1.20-1.11 (m, 2 H);

LCMS [M+H]=393.2, RT=3.02 minutes, (Program P1, Column Y)

E. 1,1-Dimethyl-2-[2-β2,3-dihydrobenzo[b][1,4]dioxin-6-yl)(indan-2-yl)amino)ethyl]piperidinium iodide To a stirred solution of compound 61 (0.25 g, 0.64 mmol) in DCE (3 mL) was added methyl iodide (0.15 mL, 2.55 mmol) and the mixture was stirred at rt for 40 hours in a sealed tube. The reaction mixture was concentrated and the crude material was purified by Combiflash® chromatography eluting with 6-7% methanol-DCM to provide a solid. The solid material was triturated with ether and filtered through a sintered funnel and dried under high vacuum to get the desired compound.

Yield: 0.185 g (54.39%);

$^1$H-NMR (400 MHz, DMSO-$d_6$): δ 7.20-7.19 (m, 2 H) , 7.14-7.12 (m, 2 H) , 6.75-6.73 (m, 1 H) , 6.50-6.49 (m, 2 H) , 4.34-4.30 (m, 1 H) , 4.19-4.17 (m, 4 H) , 3.43-3.40 (m, 1 H) , 3.15-3.05 (m, 6 H) , 3.03-2.8 (m, 8 H) , 1.96-1.94 (m, 1 H) , 1.85-1.76 (m, 2 H) , 1.69-1.65 (m, 2 H) , 1.54-1.51 (m, 1 H) , 1.39-1.34 (m, 2 H) ;

LCMS [M$^+$]=407, RT=2.90 minutes, (Program P1, Column Y);

HPLC: 99.78% (RT=3.01 minutes, $λ_{220nm}$, Mobile Phase A. 10 mM ammonium acetate in water, B. Acetonitrile; Column: Gemini® NX-C18 (4.6×50 mm) 3µ).

Example 43

General Procedure M—Preparation of (R)-1,1-dimethyl-2-[2-((indan-2-yl)(2-methylphenyl)amino)ethyl]piperidinium bromide

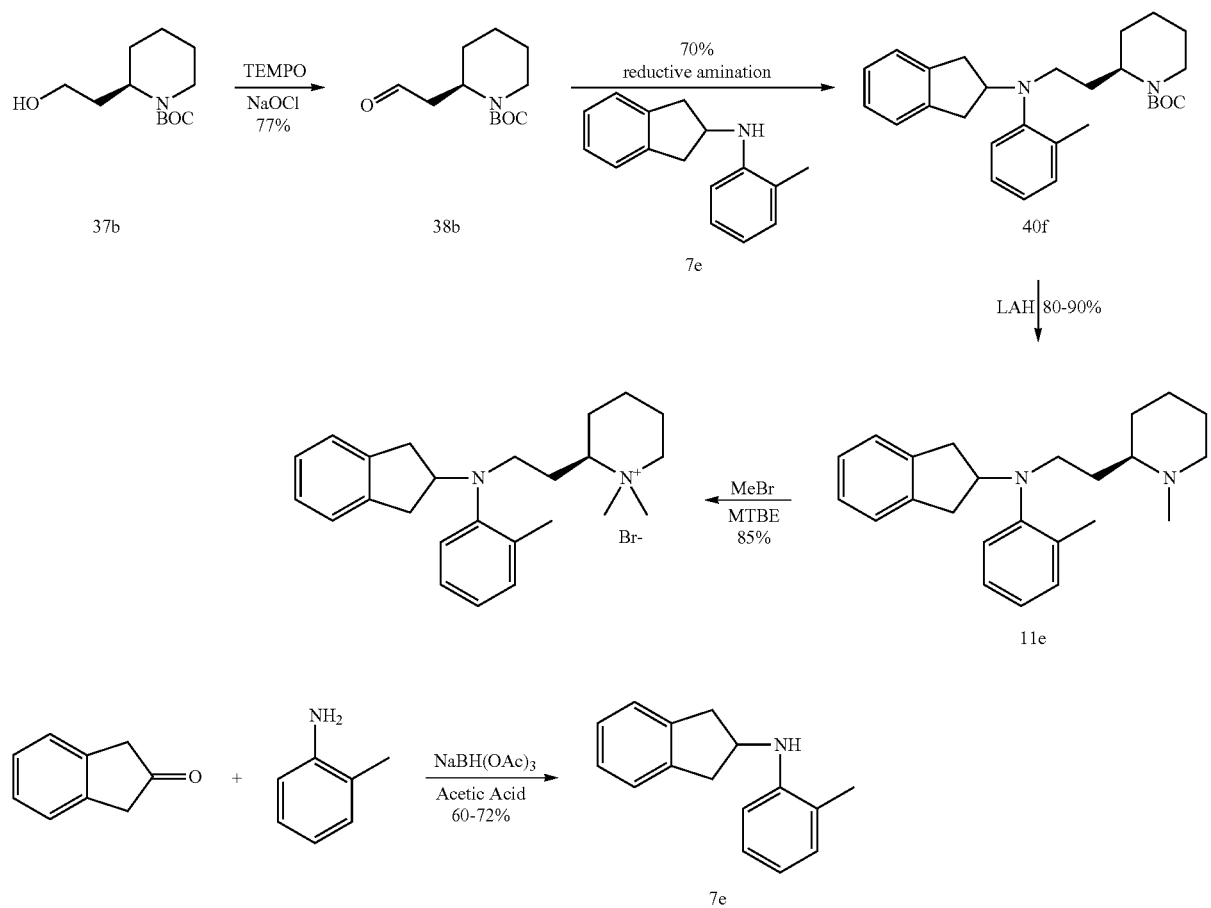

Alcohol 37b was synthesized as previously described (*Tetrahedron* 2007, 63, 3000-3005).

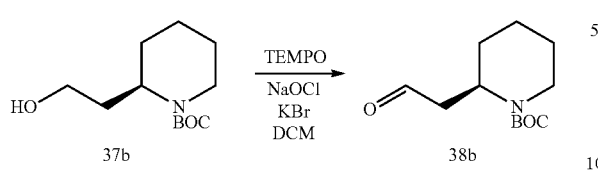

To a 250 mL round bottom flask was charged 2-(2-hydroxyethyl)piperidine-1-carboxylic acid tert-butyl ester 37b (5.0 g, 21.80 mmol), dichloromethane (7.50 mL), a solution of KBr (0.52 g, 4.36 mmol) in 2.0 mL of water and TEMPO (0.1 g, 0.64 mmol). The mixture was cooled to about −5° C. A solution of NaOCl (31.1 mL, 5.25%, 24.1 mmol) was added slowly over 20 minutes while maintaining the temperature at 0° C. The mixture was further stirred at 0° C. for 20 minutes. The organic layer was separated, and the aqueous layer was extracted with dichloromethane. The combined dichloromethane extract was washed with water (50 mL), followed by brine. After drying over MgSO$_4$, the mixture was filtered and concentrated. The crude was purified with silica gel column chromatography to give product 38b (4.1 g, 83%) as colorless oil.

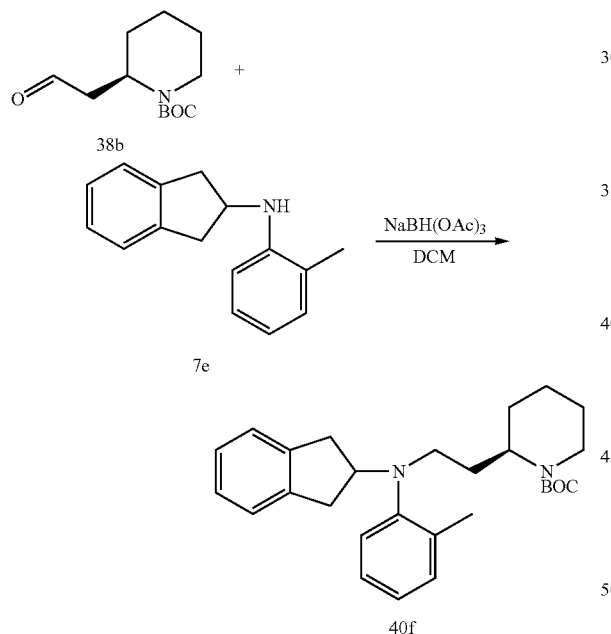

To a clean and dry 250 mL round bottom flask was charged sodium triacetoxyborohydride (5.59 g, 26.40 mmol), 4 Å molecular sieves (10.0 g), amine 7e (7.37 g, 33.00 mmol) and dichloromethane (20.0 mL). The mixture was stirred and cooled to about 0° C., and a solution of aldehyde 38b (5.0 g, 22.00 mmol) in 40 mL of dichloromethane was added. The mixture was then stirred further at 0° C. for about 1 hour and at ambient temperature for an additional 40 minutes. The reaction mixture was quenched with aqueous saturated NaHCO$_3$ (100 mL). After separation of organic layer, the mixture was extracted with dichloromethane. After drying over MgSO$_4$, the organic layer was concentrated. The crude product was purified by silica gel column chromatography to give product 40f (7.2 g, 75.3%) as colorless oil.

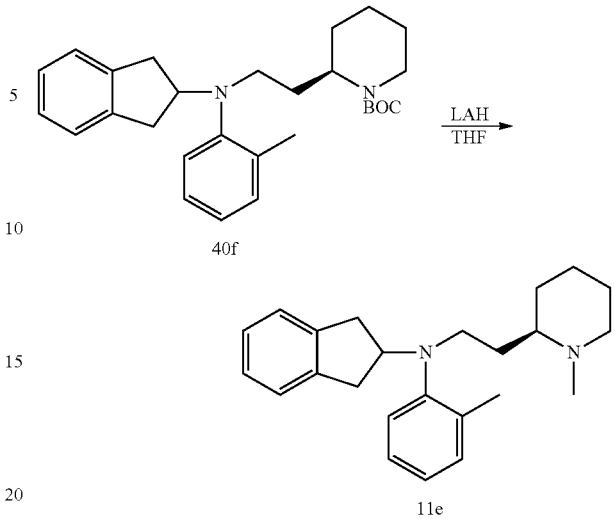

To a clean and dry 250 mL round bottom flask was charged lithium aluminum hydride (1.53 g, 40.27 mmol) and THF (30.0 mL). The mixture was heated to reflux. A solution of carbamate 40f (7.0 g, 16.11 mmol) in THF (40.0 mL) was added dropwise over 5 minutes. After refluxing for 15 h, the reaction mixture was cooled to 0° C., and water (1.55 mL) was added slowly and carefully, followed by THF (100 mL) and 15% NaOH (1.55 mL). After stirring the mixture at room temperature for 1.0 h, MgSO$_4$ was added, and the mixture was stirred further for 15 minutes. The mixture was filtered and concentrated to obtain the crude product, which was purified by silica gel column chromatography to afford product 11e (4.7 g, 84%) as pale yellow oil. Optical purity by chiral HPLC: 99.3% ee.

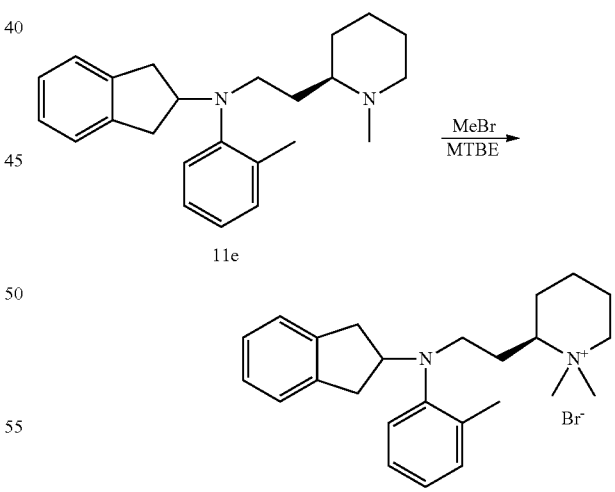

To a clean and dry 250 mL round bottom flask was charged diamine 11e (4.70 g, 13.49 mmol) and 1.07 M bromomethane in MTBE (126.0 mL, 134.8 mmol). After stirring at room temperature for 20 h, the reaction mixture was filtered. The solid cake was washed with MTBE to give the product (4.40 g, 73%) as white powder. Optical purity by chiral HPLC: 99.3% ee.

Example 44

General Procedure N—Preparation of (S)-1,1-dimethyl-2-[2-((indan-2-yl)(2-methylphenyl)amino)ethyl]piperidinium chloride

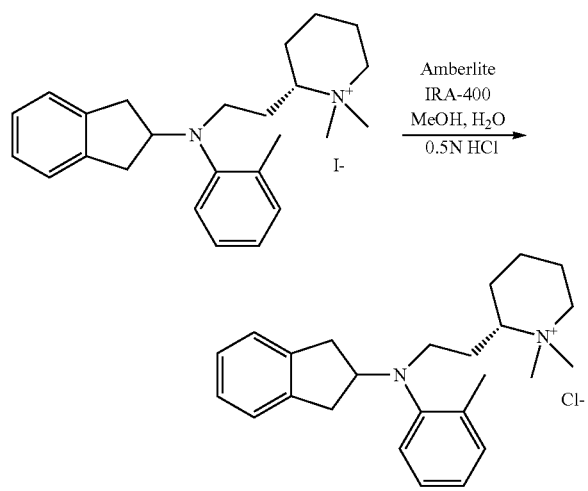

The compound of example 35 (0.185 g, 0.50 mmol) was dissolved in methanol:water (1:9, 20 mL) and was treated with Amberlite IRA-400 chloride form resin for 2 hours. The solution was filtered and washed with methanol. The filtrate was concentrated and the residue was treated with 0.5 N HCl (10 mL) for 30 minutes. The reaction mixture was concentrated and the residue was azeotroped with toluene, twice. The crude material was purified by Combiflash® chromatography (twice), eluting with 15% methanol-DCM to provide a sticky compound which showed a pH between 4 and 5. Then the compound was lyophilized over 16 hours. After lyophilization, the solid material was purified by Combiflash® chromatography again eluting with 15% methanol-DCM to provide a colourless sticky compound which showed a pH of 6. The sticky compound was lyophilized over 16 hours to provide the desired compound as a white solid.

Yield: 0.075 g (49.84%);

$^1$H-NMR (400 MHz, DMSO-$d_6$): δ 7.30 (d, J=8 Hz, 1 H), 7.25-7.15 (m, 4 H), 7.13-7.09 (m, 2 H), 7.04 (t, J=7 Hz, 1 H), 4.04-4.0 (m, 1 H), 3.43 (d, J=12 Hz, 1 H); 3.32-3.26 (m, 1 H), 3.23-3.11 (m, 2 H), 3.01-2.81 (m, 8 H), 2.79 (s, 3 H), 2.31 (s, 3 H), 1.96-1.93 (m, 1 H), 1.79-1.65 (m, 4 H), 1.54-1.49 (m, 1 H), 1.40-1.38 (m, 1 H), 1.28-1.26 (m, 1 H);

LCMS: [M$^+$]=363.2, RT=3.14 minutes, (Program P1, Column Y);

UPLC: 98.07% (RT=5.66 minutes, $\lambda_{200nm}$, Mobile Phase: A 0.05% TFA in water, B Acetonitrile; Column: Zorbax® SB-C18 (50×4.6 mm) 1.8μ).

Examples 45-52

Additional compounds listed in Table 2 were prepared in a similar manner, using the methods described for Examples 36 to 44 and in Schemes 1 to 27. Yields and $^1$H-NMR, LCMS, and HPLC characterization data for Examples 45-52 are provided immediately following Table 2.

TABLE 2

| Ex | Structure | Name | LC program, column | Synthetic Route |
|---|---|---|---|---|
| 1 | 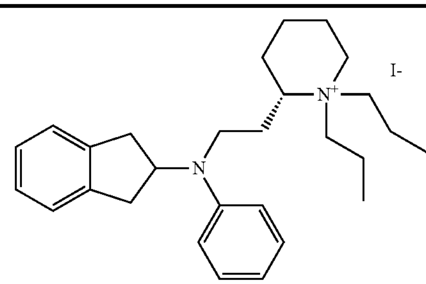 | (S)-1,1-dipropyl-2-[2-((indan-2-yl)(phenyl)amino)ethyl]piperidinium iodide | P1, Y | A1 or M |
| 2 | 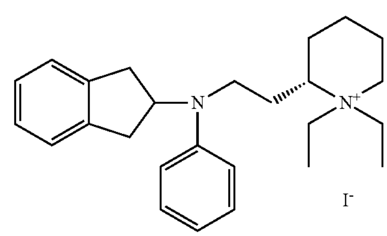 [SMILES: CC[N+]1(CC)CCCC[C@H]1CCN(c1ccccc1)C1Cc2ccccc2C1 ; [I-]] | (S)-1,1-diethyl-2-[2-((indan-2-yl)(phenyl)amino)ethyl]piperidinium iodide | P1, Y | A2 or M |
| 3 | 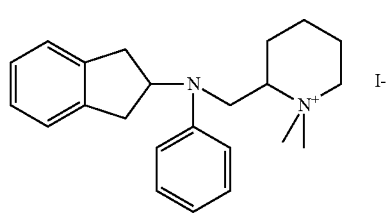 [SMILES: C[N+]1(C)CCCCC1CN(c1ccccc1)C1Cc2ccccc2C1 ; [I-]] | 1-1,dimethyl-2-[((indan-2-yl)(phenyl)amino)methyl]piperidinium iodide | P1, Y | B1 |

TABLE 2-continued

| Ex | Structure | Name | LC program, column | Synthetic Route |
|---|---|---|---|---|
| 4 | 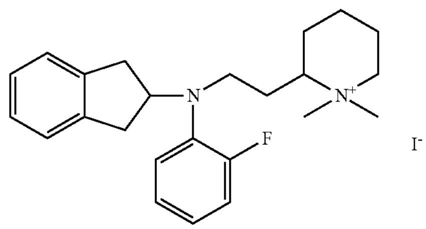 [SMILES: C[N+]1(C)CCCCC1CCN(c1ccccc1F)C1Cc2ccccc2C1 ; [I-]] | 1,1-dimethyl-2-[2-((2-fluorophenyl)(indan-2-yl)amino)ethyl]piperidinium iodide | R1, X | B2 |
| 5 | 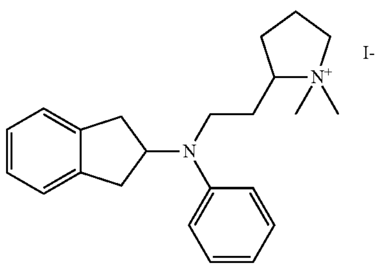 [SMILES: C[N+]1(C)CCCC1CCN(c1ccccc1)C1Cc2ccccc2C1 ; [I-]] | 1,1-dimethyl-2-[2-((indan-2-yl)(phenyl)amino)ethyl]pyrrolidinium iodide | P1, Z | C |
| 7 | 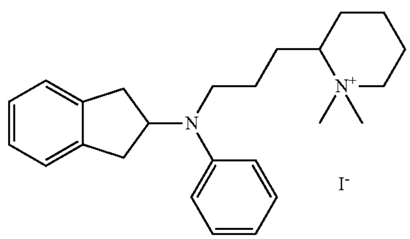 [SMILES: C[N+]1(C)CCCCC1CCCN(c1ccccc1)C1Cc2ccccc2C1 ; [I-]] | 1,1-dimethyl-2-[3-((indan-2-yl)(phenyl)amino)propyl]piperidinium iodide | P1, Y | D |
| 8 | 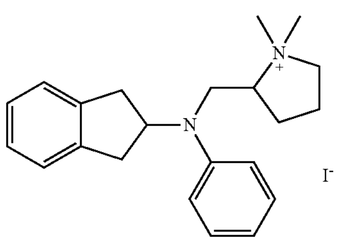 | 1,1-dimethyl-2-[((indan-2-yl)(phenyl)amino)methyl]pyrrolidinium iodide | P1, Y | E |
| 9 | 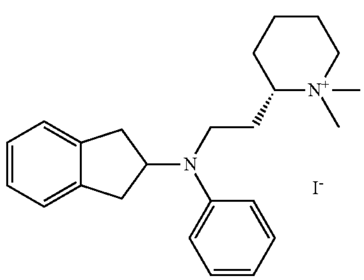 [SMILES: C[N+]1(C)CCCC[C@H]1CCN(c1ccccc1)C1Cc2ccccc2C1 ; [I-]] | (S)-1,1-dimethyl-2-[2-((indan-2-yl)(phenyl)amino)ethyl]piperidinium iodide | P1, X | A2 or M |
| 10 | 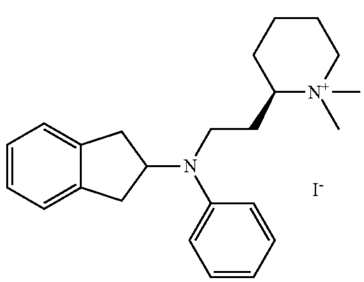 [SMILES: C[N+]1(C)CCCC[C@@H]1CCN(c1ccccc1)C1Cc2ccccc2C1 ; [I-]] | (R)-1,1-dimethyl-2-[2-((indan-2-yl)(phenyl)amino)ethyl]piperidinium iodide | P2, Y | A2 or M |

TABLE 2-continued

| Ex | Structure | Name | LC program, column | Synthetic Route |
|---|---|---|---|---|
| 11 | 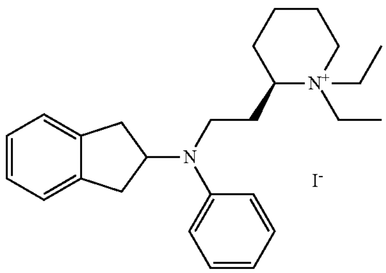 [SMILES: CC[N+]1(CC)CCCC[C@@H]1CCN(c1ccccc1)C1Cc2ccccc2C1 ; [I-]] | (R)-1,1-diethyl-2-[2-((indan-2-yl)(phenyl)amino)ethyl]piperidinium iodide | P1, Y | A2 or M |
| 12 | 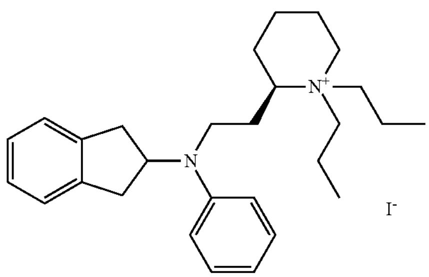 [SMILES: CCC[N+]1(CCC)CCCC[C@@H]1CCN(c1ccccc1)C1Cc2ccccc2C1 ; [I-]] | (R)-1,1-dipropyl-2-[2-((indan-2-yl)(phenyl)amino)ethyl]piperidinium iodide | P1, Y | A2 or M |
| 13 | 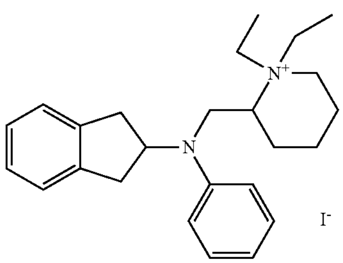 [SMILES: CC[N+]1(CC)CCCCC1CN(c1ccccc1)C1Cc2ccccc2C1 ; [I-]] | 1,1-diethyl-2-[((indan-2-yl)(phenyl)amino)methyl]piperidinium iodide | P1, Y | B1 |
| 14 | 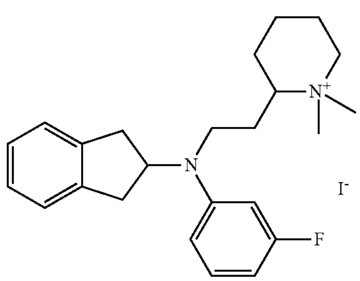 [SMILES: C[N+]1(C)CCCCC1CCN(c1cccc(F)c1)C1Cc2ccccc2C1 ; [I-]] | 1,1-dimethyl-2-[2-((3-fluorophenyl)(indan-2-yl)amino)ethyl]piperidinium iodide | R1, X | B2 |
| 15 | 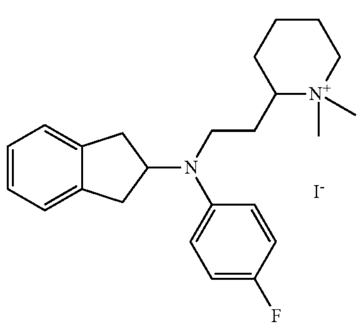 [SMILES: C[N+]1(C)CCCCC1CCN(c1ccc(F)cc1)C1Cc2ccccc2C1 ; [I-]] | 1,1-dimethyl-2-[2-((4-fluorophenyl)(indan-2-yl)amino)ethyl]piperidinium iodide | R1, X | B2 |

TABLE 2-continued

| Ex | Structure | Name | LC program, column | Synthetic Route |
|---|---|---|---|---|
| 16 | 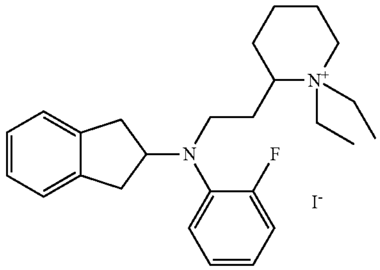 [SMILES: CC[N+]1(CC)CCCCC1CCN(c1ccccc1F)C1Cc2ccccc2C1 ; [I-]] | 1,1-diethyl-2-[2-((2-fluorophenyl)(indan-2-yl)amino)ethyl] piperidinium iodide | P1, Y | B2 |
| 17 | 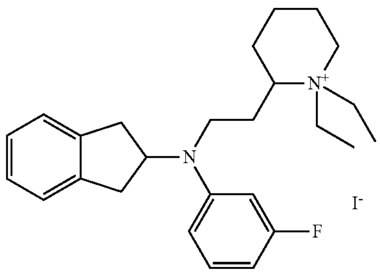 [SMILES: CC[N+]1(CC)CCCCC1CCN(c1cccc(F)c1)C1Cc2ccccc2C1 ; [I-]] | 1,1-diethyl-2-[2-((3-fluorophenyl)(indan-2-yl)amino)ethyl] piperidinium iodide | P1, Y | B2 |
| 18 | 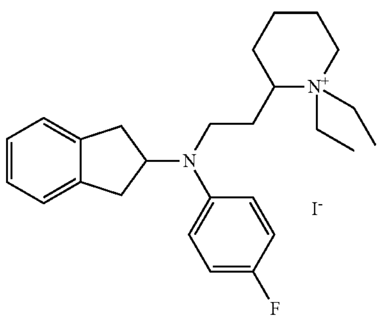 [SMILES: CC[N+]1(CC)CCCCC1CCN(c1ccc(F)cc1)C1Cc2ccccc2C1 ; [I-]] | 1,1-diethyl-2-[2-((4-fluorophenyl)(indan-2-yl)amino)ethyl] piperidinium iodide | P1, Y | B2 |
| 19 | 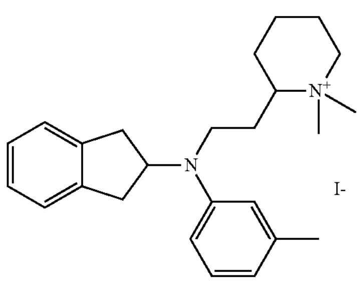 [SMILES: Cc1cccc(N(CCC2CCCC[N+]2(C)C)C2Cc3ccccc3C2)c1 ; [I-]] | 1,1-dimethyl-2-[2-((indan-2-yl)(3-methylphenyl)amino)ethyl]piperidinium iodide | P1, Y | B2 |
| 20 | 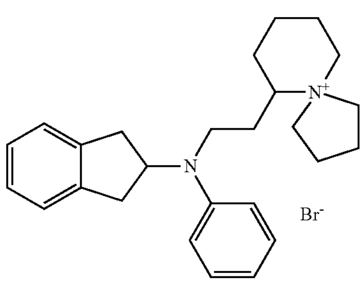 [SMILES: c1ccc(N(CCC2CCCC[N+]23CCCC3)C2Cc3ccccc3C2)cc1 ; [Br-]] | 6-[2-((indan-2-yl)(phenyl)amino)ethyl]-5-azoniasprio[4.5]decane bromide | P1, Y | B2 |

TABLE 2-continued

| Ex | Structure | Name | LC program, column | Synthetic Route |
|---|---|---|---|---|
| 21 | 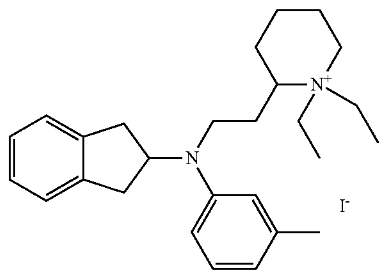 [SMILES: CC[N+]1(CC)CCCCC1CCN(c1cccc(C)c1)C1Cc2ccccc2C1 ; [I-]] | 1,1-diethyl-2-[2-((indan-2-yl)(3-methylphenyl)amino)ethyl]piperidinium iodide | P1, Y | B2 |
| 22 | 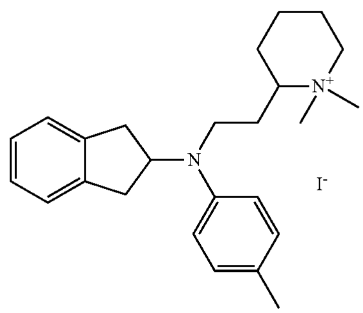 [SMILES: Cc1ccc(N(CCC2CCCC[N+]2(C)C)C2Cc3ccccc3C2)cc1 ; [I-]] | 1,1-dimethyl-2-[2-((indan-2-yl)(4-methylphenyl)amino)ethyl]piperidinium iodide | P1, Y | B2 |
| 23 | 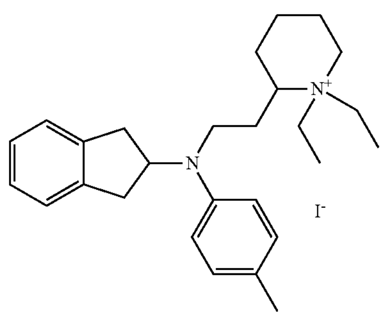 [SMILES: CC[N+]1(CC)CCCCC1CCN(c1ccc(C)cc1)C1Cc2ccccc2C1 ; [I-]] | 1,1-diethyl-2-[2-((indan-2-yl)(4-methylphenyl)amino)ethyl]piperidinium iodide | P1, Y | B2 |
| 24 | 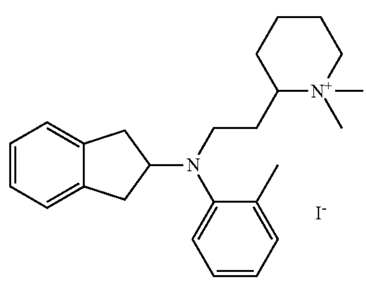 [SMILES: Cc1ccccc1N(CCC1CCCC[N+]1(C)C)C1Cc2ccccc2C1 ; [I-]] | 1,1-dimethyl-2-[2-((indan-2-yl)(2-methylphenyl)amino)ethyl]piperidinium iodide | P1, Z | B2 |
| 25 | 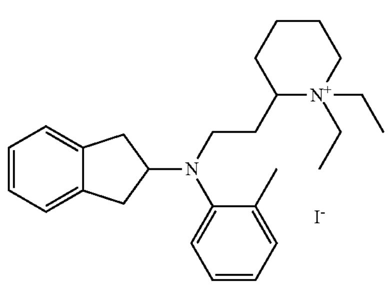 [SMILES: CC[N+]1(CC)CCCCC1CCN(c1ccccc1C)C1Cc2ccccc2C1 ; [I-]] | 1,1-diethyl-2-[2-((indan-2-yl)(2-methylphenyl)amino)ethyl]piperidinium iodide | P1, Y | B2 |

TABLE 2-continued

| Ex | Structure | Name | LC program, column | Synthetic Route |
|---|---|---|---|---|
| 26 | 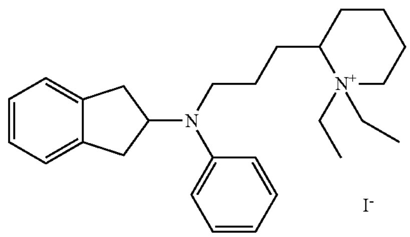 [SMILES: CC[N+]1(CC)CCCCC1CCCN(c1ccccc1)C1Cc2ccccc2C1 ; [I-]] | 1,1-diethyl-2-[3-((indan-2-yl)(phenyl)amino)propyl]piperidinium iodide | P1, Y | D |
| 27 | 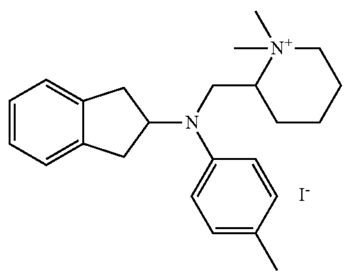 [SMILES: Cc1ccc(N(CC2CCCC[N+]2(C)C)C2Cc3ccccc3C2)cc1 ; [I-]] | 1,1-dimethyl-2-[((indan-2-yl)(4-methylphenyl)amino)methyl]piperidinium iodide | P1, X | B1 |
| 28 | 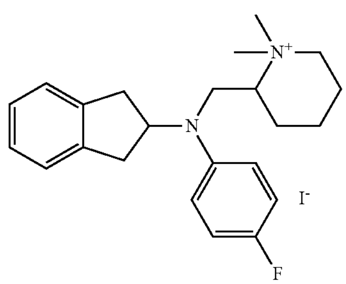 [SMILES: C[N+]1(C)CCCCC1CN(c1ccc(F)cc1)C1Cc2ccccc2C1 ; [I-]] | 1,1-dimethyl-2-[((4-fluorophenyl)(indan-2-yl) amino)methyl] piperidinium iodide | P1, Y | B1 |
| 29 | 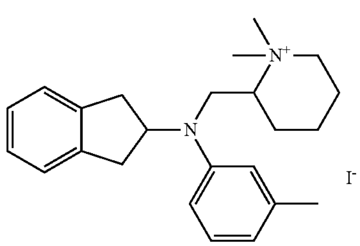 [SMILES: Cc1cccc(N(CC2CCCC[N+]2(C)C)C2Cc3ccccc3C2)c1 ; [I-]] | 1,1-dimethyl-2-[((indan-2-yl)(3-methylphenyl)amino)methyl]piperidinium iodide | P1, Y | B1 |
| 30 | 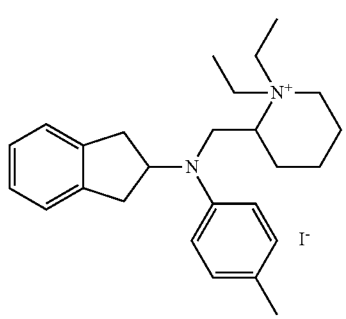 [SMILES: CC[N+]1(CC)CCCCC1CN(c1ccc(C)cc1)C1Cc2ccccc2C1 ; [I-]] | 1,1-diethyl-2-[((indan-2-yl)(4-methylphenyl)amino)methyl]piperidinium iodide | P1, Y | B1 |

TABLE 2-continued

| Ex | Structure | Name | LC program, column | Synthetic Route |
|---|---|---|---|---|
| 31 | 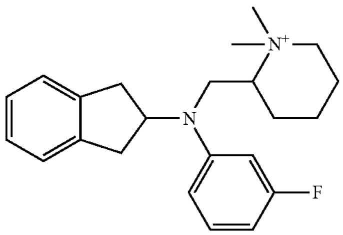 | 1,1-dimethyl-2-[((3-fluorophenyl)(indan-2-yl) amino)methyl] piperidinium iodide | P1, Y | B2 |
| 32 | 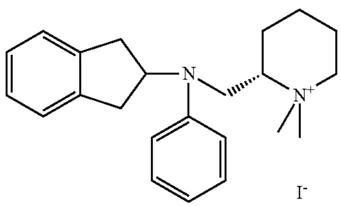 [SMILES: C[N+]1(C)CCCC[C@H]1CN(c1ccccc1)C1Cc2ccccc2C1 ; [I-]] | (S)-1,1-dimethyl-2-[((indan-2-yl)(phenyl)amino) methyl]piperidinium iodide | | B1 |
| 33 | 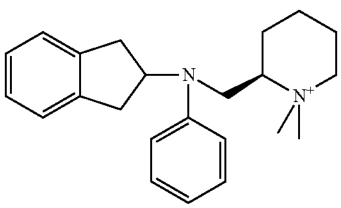 | (R)-1,1-dimethyl-2-[((indan-2-yl)(phenyl)amino) methyl]piperidinium iodide | | B1 |
| 34 | 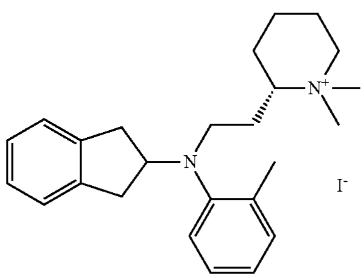 [SMILES: Cc1ccccc1N(CC[C@@H]1CCCC[N+]1(C)C)C1Cc2ccccc2C1 ; [I-]] | (S)-1,1-dimethyl-2-[2-((indan-2-yl)(2-methylphenyl)amino) ethyl]piperidinium iodide | | A2 or M |
| 35 | 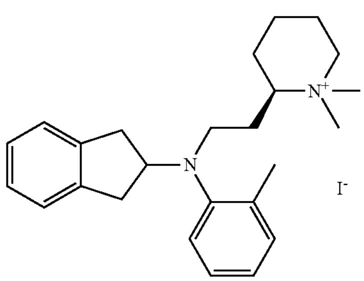 [SMILES: Cc1ccccc1N(CC[C@H]1CCCC[N+]1(C)C)C1Cc2ccccc2C1 ; [I-]] | (R)-1,1-dimethyl-2-[2-((indan-2-yl)(2-methylphenyl)amino) ethyl]piperidinium iodide | | A2 or M |
| 36 | 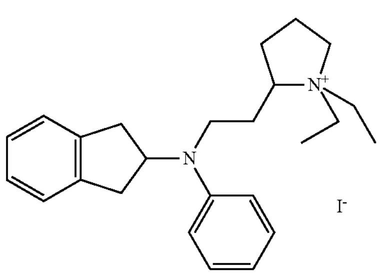 [SMILES: CC[N+]1(CC)CCCC1CCN(c1ccccc1)C1Cc2ccccc2C1 ; [I-]] | 1,1-diethyl-2-[2-((indan-2-yl)(phenyl)amino)ethyl] pyrrolidinium iodide | P1, Y | F |

TABLE 2-continued

| Ex | Structure | Name | LC program, column | Synthetic Route |
|---|---|---|---|---|
| 37 | 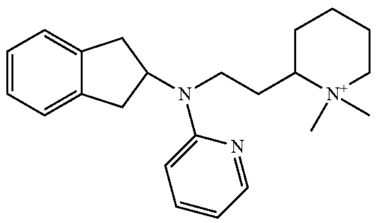 | 1,1-dimethyl-2-[2-((indan-2-yl)(pyridine-2-yl)amino)ethyl]piperidinium iodide | R1, Z | G |
| 38 | 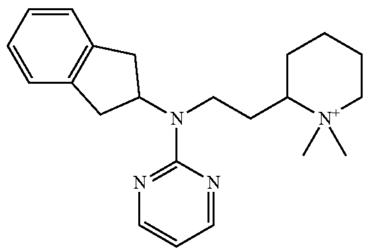 | 1,1-dimethyl-2-[2-((indan-2-yl)(pyrimidine-2-yl)amino)ethyl]piperidinium iodide | P1, Y | H |
| 39 | 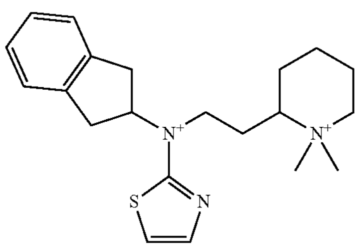 | 1,1-dimethyl-2-[2-((indan-2-yl)(thiazol-2-yl)amino)ethyl]piperidinium iodide | R1, Z | I |
| 40 | 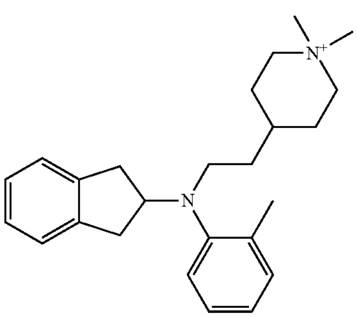 | 1,1-dimethyl-4-[2-((indan-2-yl)(2-methylphenyl)amino)ethyl]piperidinium bromide | P1, Y | J |
| 41 | 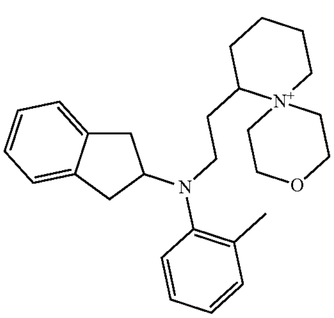 | 7-[2-((indan-2-yl)(2-methylpheny)amino)ethyl]-3-oxa-6-azaspiro[5.5]undecan-6-ium chloride | P1, Y | K |

TABLE 2-continued

| Ex | Structure | Name | LC program, column | Synthetic Route |
|---|---|---|---|---|
| 42 | 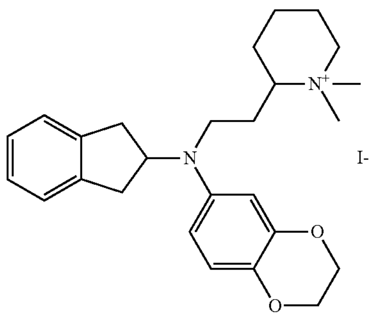 [SMILES: C[N+]1(C)CCCCC1CCN(c1ccc2c(c1)OCCO2)C1Cc2ccccc2C1 ; [I-]] | 1,1-dimethyl-2-[2-((2,3-dihydrobenzo[b][1,4]dioxin-6-yl)(indan-2-yl)amino)ethyl]piperidinium iodide | P1, Y | L |
| 43 | 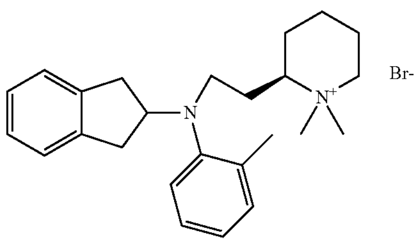 [SMILES: Cc1ccccc1N(CC[C@H]1CCCC[N+]1(C)C)C1Cc2ccccc2C1 ; [Br-]] | (R)-1,1-dimethyl-2-[2-((indan-2-yl)(2-methylphenyl)amino)ethyl]piperidinium bromide | P1, X | M |
| 44 | 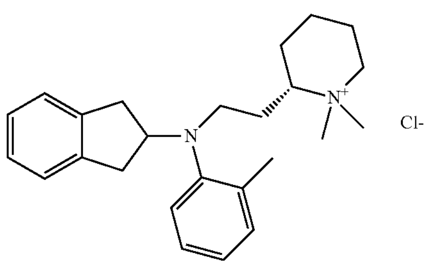 [SMILES: Cc1ccccc1N(CC[C@@H]1CCCC[N+]1(C)C)C1Cc2ccccc2C1 ; [Cl-]] | (S)-1,1-dimethyl-2-[2-((indan-2-yl)(2-methylphenyl)amino)ethyl]piperidinium chloride | P1, Y | N |
| 45 | 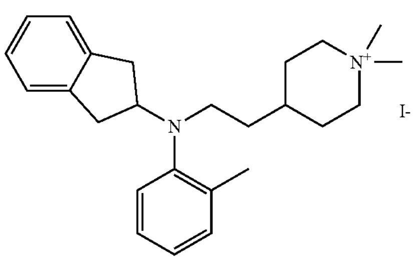 [SMILES: Cc1ccccc1N(CCC1CC[N+](C)(C)CC1)C1Cc2ccccc2C1 ; [I-]] | 1,1-dimethyl-4-[2-((indan-2-yl)(2-methylphenyl)amino)ethyl]piperidinium iodide | P1, Y | B1 |
| 46 | 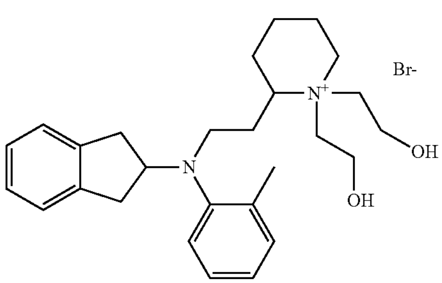 [SMILES: Cc1ccccc1N(CCC1CCCC[N+]1(CCO)CCO)C1Cc2ccccc2C1 ; [Br-]] | 1,1-bis(2-hydroxyethyl)-2-[2-((indan-2-yl)(2-methylphenyl)amino)ethyl]piperidinium bromide | P1, Y | B2 |

TABLE 2-continued

| Ex | Structure | Name | LC program, column | Synthetic Route |
|---|---|---|---|---|
| 47 | 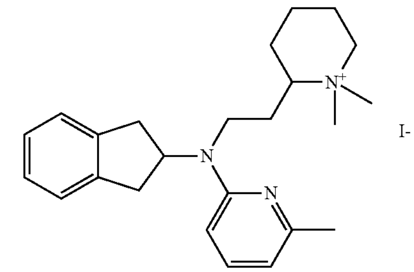 [SMILES: Cc1cccc(N(CCC2CCCC[N+]2(C)C)C2Cc3ccccc3C2)n1 ; [I-]] | 1,1-dimethyl-2-[2-((indan-2-yl)(6-methylpyridine-2-yl)amino)ethyl] piperidinium iodide | P1, Y | F |
| 48 | 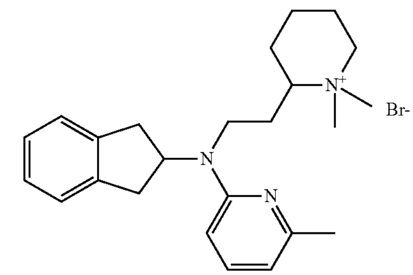 [SMILES: Cc1cccc(N(CCC2CCCC[N+]2(C)C)C2Cc3ccccc3C2)n1 ; [Br-]] | 1,1-dimethyl-2-[2-((indan-2-yl)(6-methylpyridine-2-yl)amino)ethyl] piperidinium bromide | P1, V | J |
| 49 | 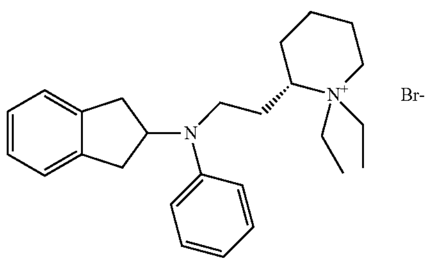 [SMILES: CC[N+]1(CC)CCCC[C@H]1CCN(c1ccccc1)C1Cc2ccccc2C1 ; [Br-]] | (S)-1,1-diethyl-2-[2-((indan-2-yl)(phenyl)amino) ethyl]piperidinium bromide | P1, Y | A2 or M |
| 50 | 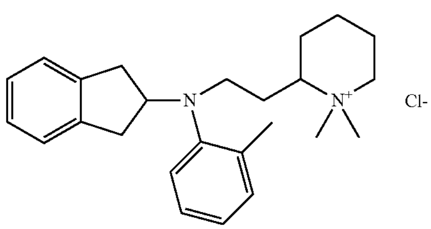 [SMILES: Cc1ccccc1N(CCC1CCCC[N+]1(C)C)C1Cc2ccccc2C1 ; [Cl-]] | 1,1-dimethyl-2-[2-((indan-2-yl)(2-methylphenyl)amino) ethyl]piperidinium chloride | P1, W | N |
| 51 | 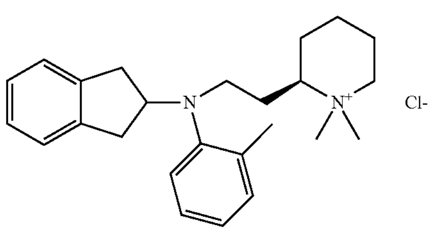 [SMILES: Cc1ccccc1N(CC[C@H]1CCCC[N+]1(C)C)C1Cc2ccccc2C1 ; [Cl-]] | (R)-1,1-dimethyl-2-[2-((indan-2-yl)(2-methylphenyl)amino) ethyl]piperidinium chloride | P1, V | N |
| 52 | 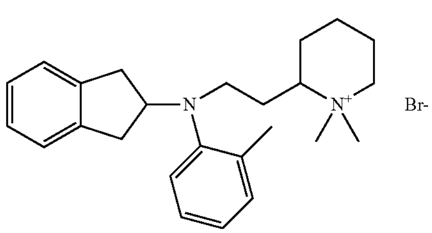 [SMILES: Cc1ccccc1N(CCC1CCCC[N+]1(C)C)C1Cc2ccccc2C1 ; [Br-]] | 1,1-dimethyl-2-[2-((indan-2-yl)(2-methylphenyl)amino) ethyl]piperidinium bromide | P1, X | M |

Example 9

(S)-1,1-Dimethyl-2-[2-((indan-2-yl)(phenyl)amino)ethyl]piperidinium iodide

Yield: 0.25 g (66.48%);
$^1$H-NMR (400 MHz, DMSO-d$_6$): δ 7.25-7.16 (m, 6H), 6.87 (d, J=8 Hz, 2H), 6.72 (t, J=7 Hz, 1H), 4.67-4.64 (m, 1H), 3.44-3.41 (m, 1H), 3.27-3.15 (m, 6H), 3.02-2.92 (m, 5H), 2.82 (s, 3H), 2.02-1.98 (m, 1H), 1.85-1.77 (m, 2H), 1.69-1.65 (m, 2H), 1.55-1.52 (m, 1H), 1.42-1.33 (m, 2H);
LCMS: m/z=349.6 [M$^+$], RT=3.18 minutes;
HPLC: 98.41%, RT=2.73 minutes, λ$_{200nm}$, Mobile Phase (i) 0.05% TFA in water (ii) acetonitrile; Column: Zorbax® SB-C18 (4.6×50 mm) 1.8μ.

Example 10

(R)-1,1-Dimethyl-2-[2-((indan-2-yl)(phenyl)amino)ethyl]piperidinium iodide

Yield: 0.1 g (33.35%);
$^1$H-NMR (400 MHz, DMSO-d$_6$): δ 7.25-7.16 (m, 6H), 6.87 (d, J=8 Hz, 2H), 6.72 (t, J=7 Hz, 1H), 4.67-4.64 (m, 1H), 3.45-3.42 (m, 1H), 3.28-3.15 (m, 6H), 3.02-2.93 (m, 5H), 2.82 (s, 3H), 2.02-1.99 (m, 1H), 1.85-1.77 (m, 2H), 1.69-1.66 (m, 2H), 1.55-1.52 (m, 1H), 1.42-1.36 (m, 2H);
LCMS: m/z=349.2 [M$^+$], RT=8.98 minutes;
HPLC: 96.78%, RT=2.73 minutes, λ$_{200nm}$, Mobile Phase (i) 0.05% TFA in water, (ii) acetonitrile; Column: Zorbax® SB-C18 (4.6×50 mm) 1.8μ.

Example 11

(R)-1,1-Diethyl-2-[2-((indan-2-yl)(phenyl)amino)ethyl]piperidinium iodide

Yield: 0.23 g (72.29%);
$^1$H-NMR (400 MHz, DMSO-d$_6$): δ 7.26-7.16 (m, 6H), 6.87 (d, J=8 Hz, 2H), 6.72 (t, J=7 Hz, 1H), 4.68-4.63 (m, 1H), 3.50-3.47 (m, 1H), 3.39-3.16 (m, 9H), 3.02-2.92 (m, 3H), 1.89-1.85 (m, 2H), 1.66-1.47 (m, 6H), 1.10 (t, J=7 Hz, 6H);
LCMS: m/z=377.0 [M$^+$], RT=3.35 minutes;
UPLC: 96.63%, RT=3.66 minutes, λ$_{200nm}$, Mobile Phase (i) 0.05% TFA in water, (ii) acetonitrile; Column: Zorbax® SB-C18 (4.6×50 mm) 1.8μ.

Example 12

(R)-1,1-Dipropyl-2-[2-((indan-2-yl)(phenyl)amino)ethyl]piperidinium iodide

Yield: 0.12 g (32.69%);
$^1$H-NMR (400 MHz, DMSO-d$_6$): δ 7.25-7.16 (m, 6H), 6.87 (d, J=8 Hz, 2H), 6.73 (t, J=7 Hz, 1H), 4.68-4.64 (m, 1H), 3.41-3.37 (m, 3H), 3.27-3.13 (m, 8H), 3.01-2.85 (m, 3H), 1.95-1.82 (m, 2H), 1.70-1.50 (m, 9H), 0.87 (t, J=7 Hz, 3H), 0.80 (t, J=7 Hz, 3H);
LCMS: m/z=405.0 [M$^+$], RT=3.54 minutes;
UPLC: 97.82%, RT=4.00 minutes, λ$_{200nm}$, Mobile Phase (i) 0.05% TFA in water, (ii) acetonitrile; Column: Zorbax® SB-C18 (4.6×50 mm) 1.8μ.

Example 13

1,1-Diethyl-2-[((indan-2-yl)(phenyl)amino)methyl]piperidinium iodide

Yield: 0.06 g (21.15%);
$^1$H-NMR (400 MHz, DMSO-d$_6$): δ 7.33 (t, J=8 Hz, 2H), 7.18-7.11 (m, 6H), 7.05 (t, J=7 Hz, 1H), 4.25 (t, J=8 Hz, 1H), 3.69-3.64 (m, 2H), 3.51-3.47 (m, 1H), 3.43-3.39 (m, 1H), 3.22-3.16 (m, 4H), 3.09-3.03 (m, 2H), 2.96-2.78 (m, 3H), 2.10-2.07 (m, 1H), 1.94-1.82 (m, 1H), 1.71-1.62 (m, 3H), 1.51-1.39 (m, 1H), 1.16 (t, J=7 Hz, 3H), 0.99 (t, J=7 Hz, 3H);
LCMS: m/z=363.1 [M$^+$], RT=3.37 minutes;
HPLC: 95.74%, RT=11.27 minutes, λ$_{200nm}$, Mobile Phase (i) acetonitrile, (ii) 0.05% TFA in water; Column: Atlantis® dC18 (150×4.6 mm) 5n.

Example 14

1,1-Dimethyl-2-[2-β3-fluorophenyl)(indan-2-yl)amino)ethyl]piperidinium iodide

Yield: 63 mg (44.9%);
$^1$H-NMR (400 MHz, DMSO-d$_6$): δ 7.27-7.17 (m, 5 H), 1.63 (t, J=8 Hz, 2 H), 6.46 (t, J=8 Hz, 1 H), 4.73-4.66 (m, 1 H), 3.45-3.39 (m, 2 H), 3.26-3.17 (m, 6 H), 3.03-2.93 (m, 5 H), 2.81 (s, 3 H), 2.00-1.98 (m, 1 H), 1.80 (t, J=15 Hz, 2 H), 1.67 (d, J=13 Hz, 2 H), 1.54-1.51 (m, 1 H), 1.45-1.34 (m, 2 H);
LCMS: m/z=367.2 [M$^+$], RT=2.66 minutes;
UPLC: 97.81%, RT=3.97 minutes, λ$_{200nm}$, Mobile phase: (i) 0.05% TFA in water, (ii) acetonitrile; Column: Zorbax® SB C18 (50×4.6 mm) 1.8 n.

Example 15

1,1-Dimethyl-2-[2-((4-fluorophenyl)(indan-2-yl)amino)ethyl]piperidinium iodide

Yield: 0.065 g (46%);
$^1$H-NMR (400 MHz, DMSO-d$_6$): δ 7.24-7.22 (m, 2 H), 7.16-7.14 (m, 2 H), 7.07 (t, J=9 Hz, 2 H), 6.97-6.93 (m, 2 H), 4.51-4.47 (m, 1 H), 3.42 (d, J=13 Hz, 1 H), 3.32-3.26 (m, 2 H), 3.17-3.09 (m, 4 H), 2.96-2.87 (m, 5 H), 2.80 (s, 3 H), 1.97 (brs, 1 H), 1.81 (t, J=16 Hz, 2 H), 1.67 (d, J=12 Hz, 2 H), 1.55-1.51 (m, 1 H), 1.39-1.37 (m, 2 H);
LCMS: m/z=367.2 [M$^+$], RT=2.59 minutes;
HPLC: 98.57%, RT=4.01 minutes, λ$_{204nm}$, Mobile phase: (i) 10 mM NH$_4$OAc in water, (ii) acetonitrile; Column: Xbridge™ C18 (50×4.6 mm) 5μ.

Example 16

1,1-Diethyl-2-[2-((2-fluorophenyl)(indan-2-yl)amino)ethyl]piperidinium iodide

Yield: 119 mg (38.53%);
$^1$H-NMR (400 MHz, DMSO-d$_6$): δ 7.30 (t, J=16 Hz, 1 H), 7.19-7.09 (m, 7H), 4.25-4.21 (m, 1 H), 3.54-3.49 (m, 1 H), 3.30 (s, 1 H), 3.28-3.19 (m, 4 H), 3.11-2.97 (m, 4 H), 2.89-2.84 (m, 2 H), 1.87-1.84 (m, 2 H), 1.65 (brs, 4 H), 1.49-1.47 (brs, 2 H), 1.09-1.02 (m, 6 H);
LCMS: m/z=395.4 [M$^+$], RT=3.25 minutes;
UPLC: 98.74%, RT=3.77 minutes, λ$_{200nm}$, Mobile phase: (i) 10 mM NH$_4$OAc in Water, (ii) acetonitrile; Column. Xbridge™ C18 (50×4.6 mm) 3μ.

Example 17

1,1-Diethyl-2-[2-((3-fluor-phenyl)(indan-2-yl)amino)ethyl)piperidinium iodide

Yield: 0.060 g (35.32%);
$^1$H-NMR (400 MHz, DMSO-d$_6$): δ 7.27-7.17 (m, 5 H), 6.65-6.59 (m, 2 H), 6.47 (t, J=9 Hz, 1 H), 4.71-4.68 (m, 1 H), 3.48-3.46 (m, 1 H), 3.40-3.34 (m, 2 H), 3.30-3.19 (m, 5 H), 3.03-2.93 (m, 4 H), 1.85 (m, 2 H), 1.66-1.44 (m, 7 H), 1.11 (t, J=6 Hz, 6 H);

LCMS: m/z=395.4 [M$^+$], RT=3.25 minutes;

HPLC: 97.91%, RT=4.28 minutes, $\lambda_{200nm}$, Mobile phase: (i) 10 mM NH$_4$OAc in water, (ii) acetonitrile; Column: Xbridge™ C18 (50×4.6 mm) 5μ.

Example 18

1,1-Diethyl-2-[2-β4-fluorophenyl)(indan-2-yl)amino)ethyl]piperidinium iodide

Yield: 0.101 g (32%);

$^1$H-NMR (400 MHz, DMSO-d$_6$): δ 7.23 (brs, 2 H), 7.17-7.14 (m, 2 H), 7.07 (t, J=9 Hz, 2 H), 6.95-6.92 (m, 2 H), 4.51 (m, 1 H), 3.55-3.45 (m, 1 H), 3.31 (s, 1 H), 3.29-3.23 (m, 2 H), 3.19-3.11 (m, 5 H), 3.01-2.91 (m, 4 H), 1.85 (brs, 2 H), 1.66-1.62 (m, 4 H), 1.46 (brs, 2 H), 1.11-1.06 (m, 6 H);

LCMS: m/z=395.4 [M$^+$], RT=3.21 minutes;

HPLC: 99.51%, RT=3.71 minutes, $\lambda_{200nm}$, Mobile phase: (i) 10 mM NH$_4$OAc in water, (ii) acetonitrile; Column: Xbridge™ C18 (50×4.6 mm) 3μ.

Example 19

1,1-Dimethyl-2-[2-((indan-2-yl)(3-methylphenyl)amino)ethyl]piperidinium iodide

Yield: 0.053 g (40.47%);

$^1$H-NMR (400 MHz, DMSO-d$_6$): δ 7.24 (brs, 2 H), 7.16 (t, J=3 Hz, 2 H), 7.09 (t, J=8 Hz, 1 H), 6.69-6.66 (m, 2 H), 6.55 (d, J=7 Hz, 1 H), 4.65-4.61 (m, 1 H), 3.43 (d, J=12 Hz, 1 H), 3.28-3.22 (m, 2 H), 3.19-3.13 (dd, J=7, 16 Hz, 3 H), 3.00-2.91 (m, 5 H), 2.81 (s, 3 H), 2.25 (s, 3 H), 2.00 (brs, 1 H), 1.81 (t, J=14 Hz, 2 H), 1.67 (d, J=13 Hz, 2 H), 1.54-1.51 (m, 2 H), 1.39-1.36 (m, 2 H);

LCMS: m/z=363.4 [M$^+$], RT=1.21 minutes;

HPLC: 95.71%, RT=3.79 minutes, $\lambda_{200nm}$, Mobile phase: (i) 10 mM NH$_4$OAc in water, (ii) acetonitrile; Column: Xbridge™ C18 (50×4.6 mm) 3μ.

Example 20

6-[2-((Indan-2-yl)(phenyl)amino)ethyl]-5-azoniaspiro[4.5]decane bromide

Yield: 0.020 g (11.72%);

$^1$H-NMR (400 MHz, DMSO-d$_6$): δ 7.25-7.16 (m, 6 H), 6.88 (d, J=8 Hz, 2 H), 6.72 (t, J=7 Hz, 1 H), 4.67-4.64 (m, 1 H), 3.59-3.57 (m, 1 H), 3.50-3.39 (m, 1 H), 3.31 (s, 1 H), 3.26-3.17 (m, 7 H), 3.00-2.96 (m, 2 H), 1.99-1.72 (m, 10 H), 1.49-1.44 (m, 3 H);

LCMS: m/z=375 [M$^+$], RT=3.63 minutes;

UPLC: 99.64%, RT=3.62 minutes, $\lambda_{200nm}$, Mobile phase: (i) 0.05% TFA in water, (ii) acetonitrile; Column: Zorbax® SB C18 (50×4.6 mm) 1.8μ.

Example 21

1,1-Diethyl-2-[2-((indan-2-yl)(3-methylphenyl)amino)ethyl]piperidinium iodide

Yield: 0.194 g (47.38%);

$^1$H-NMR (400 MHz, DMSO-d$_6$): δ 7.25 (brs, 2 H), 7.17 (t, J=3 Hz, 2 H), 7.09 (t, J=8 Hz, 1 H), 6.67 (d, J=8 Hz, 2 H), 6.55 (d, J=7 Hz, 1 H), 4.65-4.62 (m, 1 H), 3.49-3.46 (m, 1 H), 3.36-3.31 (m, 2 H), 3.25-3.15 (m, 6 H), 3.03-2.90 (m, 4 H), 2.24 (s, 3 H), 1.84 (brs, 2 H), 1.66-1.58 (m, 4 H), 1.46 (brs, 2 H), 1.11-1.10 (m, 6 H);

LCMS: m/z=391.2 [M$^+$], RT=3.95 minutes;

HPLC: 97.75%, RT=3.73 minutes, $\lambda_{200nm}$, Mobile phase: (i) 0.05% TFA in Water, (ii) acetonitrile; Column: Zorbax® SB C18 (50×4.6 mm) 1.8μ.

Example 22

1,1-Dimethyl-2-[2-((indan-2-yl)(4-methylphenyl)amino)ethyl]piperidinium iodide

Yield: 0.202 g (73.56%);

$^1$H-NMR (400 MHz, DMSO-d$_6$): δ 7.23-7.22 (m, 2 H), 7.16-7.14 (m, 2 H), 7.04 (d, J=8 Hz, 2 H), 6.83 (d, J=8 Hz, 2 H), 4.54-4.50 (m, 1 H), 3.42 (d, J=13 Hz, 1 H), 3.29-3.23 (m, 3 H), 3.16-3.09 (m, 3 H), 2.96-2.88 (m, 5 H), 2.80 (s, 3 H), 2.21 (s, 3 H), 1.98 (brs, 1 H), 1.84-1.73 (m, 2 H), 1.67 (d, J=12 Hz, 2 H), 1.53-1.47 (m, 1 H), 1.39-1.36 (m, 2 H);

LCMS: m/z=363.2 [M$^+$], RT=3.33 minutes;

UPLC: 99.25%, RT=3.38 minutes, $\lambda_{200nm}$, Mobile phase: (i) 0.05% TFA in water, (ii) acetonitrile; Column: Zorbax® SB C18 (50×4.6 mm) 1.8μ.

Example 23

1,1-Diethyl-2-[2-((indan-2-yl)(4-methylphenyl)amino)ethyl]piperidinium iodide

Yield: 0.318 mg (51.26%);

$^1$H-NMR (400 MHz, DMSO-d$_6$): δ 7.24-7.22 (m, 2 H), 7.17-7.15 (m, 2 H), 7.04 (d, J=8 Hz, 2 H), 6.81 (d, J=8 Hz, 2 H), 4.54-4.52 (m, 1 H), 3.52-3.48 (m, 1 H), 3.30-3.23 (m, 3 H), 3.21-3.11 (m, 6 H), 3.00-2.90 (m, 3 H), 2.20 (s, 3 H), 1.84 (brs, 2 H), 1.65-1.59 (m, 4 H), 1.45 (brs, 2 H), 1.11-1.07 (m, 6 H);

LCMS: m/z=391.2 [M$^+$], RT=3.28 minutes;

HPLC: 98.10%, RT=3.95 minutes, $\lambda_{200nm}$, Mobile phase: (i) 10 mM NH$_4$OAc in water, (ii) MeOH; Column: Xbridge™ C18 (50×4.6 mm) 5μ.

Example 24

1,1-Dimethyl-2-[2-((indan-2-yl)(2-methylphenyl)amino)ethyl]piperidinium iodide

Yield: 0.092 g (31.35%);

$^1$H-NMR (400 MHz, DMSO-d$_6$): δ 7.30 (d, J=8 Hz, 1 H), 7.25-7.17 (m, 4 H), 7.12-7.10 (m, 2 H), 7.05 (t, J=7 Hz, 1 H), 4.04-4.01 (m, 1 H), 3.41 (d, J=13 Hz, 1 H), 3.32-3.22 (m, 2 H), 3.19-3.10 (m, 2 H), 3.02-2.96 (m, 2 H), 2.93-2.84 (m, 2 H), 2.79 (s, 6 H), 2.31 (s, 3 H), 2.05-1.93 (m, 1 H), 1.77 (d, J=14 Hz, 2 H), 1.67 (d, J=10 Hz, 2 H), 1.53-1.50 (m, 1 H), 1.43-1.37 (m, 1 H), 1.29-1.23 (m, 1 H);

LCMS: m/z=363.1 [M$^+$], RT=2.85 minutes;

HPLC: 98.66%, RT=4.20 minutes, $\lambda_{210nm}$, Mobile phase: (i) 10 mM NH$_4$OAc in water, (ii) acetonitrile; Column: Xbridge™ C18 (50×4.6 mm) 5μ.

Example 25

1,1-Diethyl-2-[2-((indan-2-yl)(2-methylphenyl)amino)ethyl]piperidinium iodide

Yield: 0.140 g (30.15%);

$^1$H-NMR (400 MHz, DMSO-d$_6$): δ 7.31 (d, J=8 Hz, 1 H), 7.25-7.23 (m, 1 H), 7.20-7.17 (m, 3 H), 7.12-7.10 (m, 2 H), 7.05 (t, J=7 Hz, 1 H), 4.02-3.98 (m, 1 H), 3.50-3.47 (m, 1 H), 3.25-3.17 (m, 6 H), 3.02-2.93 (m, 3 H), 2.87 (d, J=8 Hz, 2 H), 2.84-2.80 (m, 1 H), 2.30 (s, 3 H), 1.84-1.79 (m, 2 H), 1.69-1.62 (m, 4 H), 1.49-1.43 (m, 2 H), 1.04 (t, J=6 Hz, 3 H), 0.89 (t, J=7 Hz, 3 H);

LCMS: m/z=391.2 [M$^+$], RT=3.49 minutes;
HPLC: 99.51%, RT=8.11 minutes, $\lambda_{210nm}$, Mobile phase: (i) 10 mM NH$_4$OAc in water, (ii) acetonitrile; Column: XTerra® C18 (250×4.6 mm) 5μ.

Example 26

1,1-Diethyl-2-[3-((indan-2-yl)(phenyl)amino)propyl]piperidinium iodide

Yield: 58 mg (33%);
$^1$H-NMR (400 MHz, DMSO-d$_6$): δ 7.24-7.15 (m, 6 H), 6.85 (d, J=8 Hz, 2 H), 6.69 (t, J=7 Hz, 1 H), 4.63 (t, J=7 Hz, 1 H), 3.59-3.52 (m, 1 H), 3.48-3.42 (m, 1 H), 3.36-3.34 (m, 1 H), 3.19-3.13 (m, 6 H), 3.04-2.93 (m, 4 H), 1.76-1.62 (m, 6 H), 1.46-1.35 (m, 4 H), 1.16 (t, J=7 Hz, 6 H);
LCMS: m/z=391.2 [M+], RT=3.29 minutes;
UPLC: 99.47%, RT=3.27 minutes, $\lambda_{200nm}$, Mobile phase: (i) 0.05% TFA in Water (ii) Acetonitrile; Column: Zorbax® SB C18 (50×4.6 mm) 1.8μ.

Example 27

1,1-Dimethyl-2-[((indan-2-yl)(4-methylphenyl)amino)methyl]piperidinium iodide

Yield: 193 mg (32%);
$^1$H NMR (400 MHz, DMSO-d$_6$): δ 7.18 (t, J=4 Hz, 2 H), 7.14-7.10 (m, 4 H), 7.02 (d, J=3 Hz, 2 H), 7.01 (d, J=8 Hz, 2 H), 4.33-4.29 (m, 1 H), 3.77 (d, J=12 Hz, 1 H), 3.38 (d, J=7 Hz, 2 H), 3.20 (s, 1 H), 3.16 (s, 3 H), 2.99-2.92 (m, 8 H), 2.24 (s, 3 H), 1.97 (d, J=13 Hz, 1 H), 1.72-1.63 (m, 4 H), 1.39-1.23 (m, 1 H);
LCMS: m/z=349 [M+], RT=1.40 minutes;
UPLC: 99.42%, RT=4.40 minutes, $\lambda_{200nm}$, Mobile phase: (i) 0.05% TFA in Water, (ii) Acetonitrile; Column: Zorbax® SB C18 (50×4.6 mm) 1.8μ.

Example 28

1,1-Dimethyl-2-[((4-fluorophenyl)(indan-2-yl)amino)methyl]piperidinium iodide

Yield: 164 mg (30%);
$^1$H-NMR (400 MHz, DMSO-d$_6$): δ 7.19-7.11 (m, 8 H), 4.29-4.25 (m, 1 H), 3.77 (d, J=11 Hz, 1 H), 3.39-3.35 (m, 2 H), 3.25-3.15 (m, 5 H), 3.01-2.87 (m, 7 H), 1.98 (d, J=14 Hz, 1 H), 1.78-1.64 (m, 4 H), 1.33-1.30 (m, 1 H);
LCMS: m/z=353.2 [M+], RT=3.17 minutes;
UPLC: 99.87%, RT=3.19 minutes, $\lambda_{200nm}$, Mobile phase: (i) 0.05% Acetic acid in Water, (ii) Acetonitrile; Column: Gemini® NX C18 (50×4.6 mm) 3μ.

Example 29

1,1-Dimethyl-2-[((indan-2-yl)(3-methylphenyl)amino)methyl]piperidinium iodide

Yield: 193 mg (42%);
$^1$H-NMR (400 MHz, DMSO-d$_6$): δ 7.23-7.13 (m, 5 H), 6.86 (t, J=8 Hz, 2 H), 6.72 (d, J=7 Hz, 1 H), 4.46 (t, J=8 Hz, 1 H), 3.82 (d, J=11 Hz, 1 H), 3.42-3.37 (m, 2 H), 3.25 (s, 1 H), 3.19 (s, 3 H), 3.03 (t, J=9 Hz, 2 H), 2.98-2.95 (m, 5 H), 2.26 (s, 3 H), 1.95 (d, J=13 Hz, 1 H), 1.76-1.65 (m, 4 H), 1.35-1.31 (m, 1 H);
LCMS: m/z=348.8 [M+], RT=3.34 minutes, (Mobile phase: ammonium acetate in water/acetonitrile; Column: X-Bridge);
UPLC: 99.85%, RT=3.19 minutes, $\lambda_{200nm}$, Mobile phase: (i) 0.05% Acetic acid in Water, (ii) Acetonitrile; Column: Gemini® NX C18 (50×4.6 mm) 3μ.

Example 30

1,1-Diethyl-2-[((indan-2-yl)(4-methylphenyl)amino)methyl]piperidinium iodide

Yield: 90 mg (29%);
$^1$H-NMR (400 MHz, DMSO-d$_6$): δ 7.17-7.10 (m, 8 H), 4.14-4.08 (m, 1 H), 3.66-3.60 (m, 2 H), 3.52-3.47 (m, 1 H), 3.39-3.34 (m, 1 H), 3.25-3.15 (m, 5 H), 3.07-3.01 (m, 1 H), 2.91-2.82 (m, 3 H), 2.27 (s, 3 H), 2.12 (d, J=14 Hz, 1 H), 1.89-1.86 (m, 1 H), 1.66 (brs, 3 H), 1.43 (brs, 1 H), 1.16 (t, J=8 Hz, 3 H), 0.95 (t, J=7 Hz, 3 H);
LCMS: m/z=377 [M+], RT=3.40 minutes;
HPLC: 95.06%, RT=6.08 minutes, $\lambda_{210nm}$, Mobile phase: (i) 10 mM NH$_4$OAc in Water, (ii) Acetonitrile; Column: XBridge® C18 (50×4.6 mm) 5μ.

Example 31

1,1-Dimethyl-2-[((3-fluorophenyl)(indan-2-yl)amino)methyl]piperidinium iodide

Yield: 75 mg (25%);
$^1$H-NMR (400 MHz, DMSO-d$_6$): δ 7.28-7.16 (m, 5 H), 6.79 (t, J=4 Hz, 2 H), 6.64-6.60 (q, J=6 Hz, 1 H), 4.58 (q, J=9 Hz, 1 H), 3.86 (d, J=11 Hz, 1 H), 3.47-3.41 (m, 4 H), 3.21 (s, 3 H), 3.13-3.02 (m, 4 H), 3.00 (s, 3 H), 1.88-1.70 (m, 5 H), 1.35-1.32 (m, 1 H);
LCMS: m/z=353 [M+], RT=3.09 minutes;
UPLC: 99.58%, RT=3.15 minutes, $\lambda_{200nm}$, Mobile phase: (i) 0.05% Acetic acid in Water, (ii) Acetonitrile; Column: Gemini® NX C18 (50×4.6 mm) 3μ.

Example 32

(S)-1,1-Dimethyl-2-[((indan-2-yl)(phenyl)amino)methyl]piperidinium iodide

Yield: 1 g (69.2%);
$^1$H-NMR (DMSO-d$_6$): δ 7.27 (t, J=8 Hz, 2 H), 7.22-7.20 (m, 2 H), 7.16-7.14 (m, 2 H), 7.05 (d, J=8 Hz, 2 H), 6.90 (t, J=7 Hz, 1 H), 4.52-4.44 (m, 1 H), 3.85 (d, J=12 Hz, 1 H), 3.43-3.36 (m, 4 H), 3.21 (s, 3 H), 3.06 (d, J=8 Hz, 2 H), 3.01-2.99 (m, 5 H), 1.96-1.92 (m, 1 H), 1.76-1.69 (m, 4 H), 1.34-1.31 (m, 1 H);
LCMS: m/z=335.4 [M$^+$], RT=2.97 minutes;
UPLC: 98.93% (RT=3.13 minutes; $\lambda_{200nm}$, Mobile Phase A. 0.05% HCOOH in water, B. Acetonitrile; Column: Gemini NX C18 (50×4.6 mm) 3μ);
Specific rotation: [−9.3°] at ≈25° C. (0.60% solution in MeOH);

Chiral HPLC: 100% ee (RT=5.47 minutes; $\lambda_{254nm}$, Mobile Phase. Hexane:EtOH:DEA:TFA=60:40:0.1:0.1; Column. Chiralpak®-IC (4.6×250 mm) 5μ).

Example 33

(R)-1,1-Dimethyl-2-[((indan-2-yl)(phenyl)amino) methyl]piperidinium iodide

Yield: 0.62 g (78%);
$^1$H-NMR (DMSO-$d_6$): δ 7.27 (t, J=8 Hz, 2 H) , 7.22-7.20 (m, 2 H) , 7.16-7.14 (m, 2 H) , 7.05 (d, J=8 Hz, 2 H) , 6.90 (t, J=7 Hz, 1 H) , 4.52-4.44 (m, 1 H) , 3.84 (d, J=12 Hz, 1 H) , 3.43-3.35 (m, 4 H) , 3.19 (s, 3 H) , 3.06 (d, J=8 Hz, 2 H) , 3.01-2.99 (m, 5 H) , 1.96-1.92 (m, 1 H) , 1.76-1.69 (m, 4 H) , 1.34-1.31 (m, 1 H) ;
LCMS: m/z=335.0 [M$^+$], RT=3.07 minutes;
UPLC: 99.83% (RT=3.13 minutes; $\lambda_{200nm}$, Mobile Phase A. 0.05% HCOOH in water, B. Acetonitrile; Column: Gemini NX C18 (50×4.6 mm) 3μ);
Specific rotation: [+9.3°] at ≈25° C. (0.60% solution in MeOH);
Chiral HPLC: 99.3% ee (RT=5.97 minutes; $\lambda_{254nm}$, Mobile Phase. Hexane:EtOH:DEA:TFA=60:40:0.1:0.1; Column: Chiralpak®-IC (4.6×250 mm) 5μ).

Example 34

(S)-1,1-Dimethyl-2-[2-((indan-2-yl)(2-methylphenyl)amino)ethyl]piperidinium iodide Yield: 0.193 g (39.9%);
$^1$H-NMR (DMSO-$d_6$): δ 7.31 (d, J=8 Hz, 1 H) , 7.25-7.17 (m, 4 H) , 7.13-7.10 (m, 2 H) , 7.05 (t, J=7 Hz, 1 H) , 4.05-4.00 (m, 1 H) , 3.43-3.40 (m, 1 H) , 3.26-3.12 (m, 3 H) , 3.02-2.93 (m, 2 H) , 2.90-2.82 (m, 5 H) , 2.79 (s, 3 H) , 2.31 (s, 3 H) , 1.99-1.95 (m, 1 H) , 1.79-1.66 (m, 4 H) , 1.53-1.50 (m, 1 H) , 1.40-1.37 (m, 1 H) , 1.29-1.23 (m, 1 H) ;
LCMS: m/z=363.0 [M$^+$], RT=3.23 minutes;
HPLC: 99.11% (RT=4.28 minutes; $\lambda_{212nm}$, Mobile Phase A. 10 mM NH$_4$OAc in water, B. Acetonitrile; Column: Xbridge-C18 (50×4.6 mm) 5μ);
Specific rotation: [+13.5°] at ≈25° C. (0.599% solution in MeOH);
Chiral HPLC: 100% ee (RT=8.66 minutes; $\lambda_{212nm}$, Mobile Phase. Hexane:EtOH:DEA:TFA=70:30:0.1:0.1; Column. Chiralpak®-IC (4.6×250 mm) 5μ).

Example 35

(R)-1,1-Dimethyl-2-[2-((indan-2-yl)(2-methylphenyl)amino) ethyl]piperidinium iodide Yield: 0.4 g (41.9%);
$^1$H-NMR (DMSO-$d_6$): δ 7.31 (d, J=8 Hz, 1 H) , 7.25-7.17 (m, 4 H) , 7.13-7.10 (m, 2 H) , 7.05 (t, J=7 Hz, 1 H) , 4.05-4.00 (m, 1 H) , 3.43-3.40 (m, 1 H) , 3.26-3.12 (m, 3 H) , 3.02-2.96 (m, 2 H) , 2.91-2.84 (m, 5 H) , 2.79 (s, 3 H) , 2.31 (s, 3 H) , 1.99-1.95 (m, 1 H) , 1.79-1.66 (m, 4 H) , 1.53-1.50 (m, 1 H) , 1.40-1.37 (m, 1 H) , 1.29-1.24 (m, 1 H) ;
LCMS: m/z=362.8 [M$^+$], RT=3.20 minutes;
UPLC: 98.82% (RT=4.86 minutes; $\lambda_{200nm}$, Mobile Phase A. 0.05% TFA in water, B. Acetonitrile; Column: Zorbax SB C18 (50×4.6 mm) 1.8μ);
Specific rotation: [−14.5°] at ≈25° C. (0.60% solution in MeOH); Chiral HPLC: 98.5% ee (RT=12.79 minutes; 2212 nm, Mobile Phase. Hexane:EtOH:DEA:TFA=70:30:0.1:0.1; Column: Chiralpak®-IC (4.6×250 mm) 5μ).

Example 45

1,1-Dimethyl-4-[2-((indan-2-yl)(2-methylphenyl) amino)ethyl]piperidinium iodide

Yield: 0.081 g (13.9%);
$^1$H-NMR (DMSO-$d_6$): δ 7.29-7.27 (m, 1 H) , 7.23-7.19 (m, 2 H) , 7.16-7.14 (m, 2 H) , 7.10-7.08 (m, 2 H) , 7.04-7.01 (m, 1 H) , 3.98-3.94 (m, 1 H) , 3.36-3.31 (m, 2 H) , 3.23-3.17 (m, 2 H) , 3.05 (s, 3 H) , 3.01-2.90 (m, 7 H) , 2.82-2.76 (m, 2 H) , 2.28 (s, 3 H), 1.69-1.66 (m, 2 H) , 1.50-1.45 (m, 3 H) , 1.26 (brs, 2 H) ;
LCMS [M$^+$]=363, RT=3.38 minutes, (Program P1, Column Y);
UPLC: 99.47% (RT=5.02 minutes, $\lambda_{220nm}$, Mobile Phase A. 0.05% TFA, B. Acetonitrile; Column: Zorbax® XDB-C18 (4.6×50 mm) 1.8μ).

Example 46

1,1-Bis(2-hydroxyethyl)-2-[2-((indan-2-yl)(2-methylphenyl)amino)ethyl]piperidinium bromide Yield: 0.033 g (10%);
$^1$H-NMR (DMSO-$d_6$): δ 7.30-7.28 (m, 1 H) , 7.24-7.09 (m, 6 H) , 7.04 (t, J=7 Hz, 1 H) , 5.35-5.34 (m, 1 H) , 5.27-5.24 (m, 1 H) , 4.04-4.02 (m, 1 H) , 3.73-3.55 (m, 6 H), 3.50 (s, 3 H) , 3.41-3.32 (m, 1 H) , 3.07-2.95 (m, 5 H) , 2.88-2.77 (m, 2 H) , 2.29 (s, 3 H) , 1.95 (brs, 1 H) , 1.86-1.83 (m, 2 H) , 1.64-1.61 (m, 3 H) , 1.46-1.36 (m, 2 H) ;
LCMS [M$^+$]=423, RT=3.19 minutes, (Program P1, Column Y);
UPLC: 99.71% (RT=4.89 minutes, $\lambda_{220nm}$, Mobile Phase: A 0.05% TFA in water, B Acetonitrile; Column: Zorbax® SB-C18 (50×4.6 mm) 1.8μ).

Example 47

1,1-Dimethyl-2-[2-((indan-2-yl)(6-methylpyridine-2-yl)amino)ethyl]piperidinium iodide Yield: 0.15 g (36.20%);
$^1$H-NMR (DMSO-$d_6$): δ 7.40 (t, J=8 Hz, 1 H) , 7.26-7.25 (m, 2 H) , 7.18-7.16 (m, 2 H) , 6.54 (d, J=8 Hz, 1 H) , 6.48 (d, J=7 Hz, 1 H) , 5.12-5.05 (m, 1 H) , 3.46-3.41 (m, 3 H) , 3.28-3.22 (m, 2 H) , 3.19-3.13 (m, 2 H) , 3.05 (s, 3 H) , 3.02-2.98 (m, 2 H), 2.86 (s, 3 H) , 2.29 (s, 3 H) , 2.17-2.13 (m, 1 H) , 1.97-1.93 (m, 1 H) , 1.83-1.77 (m, 1 H) , 1.70-1.67 (m, 2 H) , 1.61-1.55 (m, 1 H) , 1.51-1.37 (m, 2 H) ;
LCMS [M$^+$]=364.2, RT=3.19 minutes, (Program P1, Column Y);
UPLC: 99.39% (RT=4.04 minutes, $\lambda_{220nm}$, Mobile Phase A. 0.05% TFA in water, B. Acetonitrile; Column: Zorbax® XDB-C18 (4.6×50 mm) 1.8μ).

Example 48

1,1-Dimethyl-2-[2-((indan-2-yl)(6-methylpyridine-2-yl)amino)ethyl]piperidinium bromide Yield: 0.057 g (18.8%);
$^1$H-NMR (DMSO-$d_6$): δ 7.40 (t, J=8 Hz, 1 H) , 7.26-7.25 (m, 2 H) , 7.19-7.16 (m, 2 H) , 6.54 (d, J=8 Hz, 1 H) , 6.48 (d, J=7 Hz, 1 H) , 5.10-5.06 (m, 1 H) , 3.46-3.42 (m, 3 H) , 3.26-3.22 (m, 2 H), 3.19-3.13 (m, 2 H), 3.05-2.98 (m, 5 H), 2.86 (s, 3 H), 2.29 (s, 3 H), 2.17-2.13 (m, 1 H), 1.97-1.93 (m, 1 H), 1.83-1.77 (m, 1 H), 1.70-1.57 (m, 3 H), 1.47-1.37 (m, 2 H);

LCMS: [M$^+$]=364.2, RT=3.04 minutes, (Program P1, Column V);

UPLC: 99.87% (RT=4.02 minutes, $\lambda_{200nm}$, Mobile Phase A. 0.05% TFA in water, B. Acetonitrile; Column: Zorbax® SB-C18 (4.6×50 mm) 1.8µ).

Example 49

(S)-1,1-Diethyl-2-[2-((indan-2-yl)(phenyl)amino)ethyl]piperidinium bromide

Yield: 2.9 g (25%);
$^1$H-NMR (DMSO-d$_6$): δ 7.25-7.16 (m, 6 H), 6.87 (d, J=8 Hz, 2 H), 6.72 (t, J=7 Hz, 1 H), 4.67-4.63 (m, 1 H), 3.52-3.47 (m, 1 H), 3.40-3.34 (m, 1 H), 3.28-3.16 (m, 8 H), 3.04-2.92 (m, 3 H), 1.88-1.86 (m, 2 H), 1.67-1.47 (m, 6 H), 1.10 (t, J=6 Hz, 6 H);

LCMS [M$^+$]=377.0, RT=3.11 minutes, (Program P1, Column Y);

UPLC: 99.77% (RT=5.08 minutes, $\lambda_{200nm}$, Mobile Phase A. 0.05% TFA in water, B. Acetonitrile; Column: Zorbax® SB-C18 (50×4.6 mm) 1.8µ);

Chiral HPLC: 100% ee (RT=6.47 minutes, $\lambda_{257nm}$, Mobile Phase. MeOH:DEA:TFA=100:0.1:0.1, Column: Chiralpak®-IA (4.6×250 mm) 5µ);

Specific optical rotation: [−10.8°] at ≅25° C. (0.39% solution in CHCl$_3$)

Example 50

1,1-Dimethyl-2-[2-((indan-2-yl)(2-methylphenyl)amino)ethyl]piperidinium chloride Yield: 0.14 g (43%);
$^1$H-NMR (DMSO-d$_6$): δ 7.31 (d, J=8 Hz, 1 H), 7.25-7.17 (m, 4 H), 7.12-7.11 (m, 2 H), 7.05 (t, J=7 Hz, 1 H), 4.05-4.01 (m, 1 H), 3.43 (d, J=12 Hz, 1 H), 3.28-3.12 (m, 4 H), 3.00-2.96 (m, 2 H), 2.92-2.80 (m, 8 H), 2.31 (s, 3 H), 1.99-1.96 (m, 1 H), 1.79-1.65 (m, 4 H), 1.57-1.47 (m, 1 H), 1.41-1.36 (m, 1 H), 1.28-1.26 (m, 1 H);

LCMS: [M$^+$]=363.2, RT=2.85 minutes, (Program P1, Column W);

UPLC: 99.29% (RT=5.80 minutes, $\lambda_{200nm}$, Mobile Phase: A 0.05% TFA in water, B Acetonitrile; Column: Zorbax® SB-C18 (50×4.6 mm) 1.8µ).

Example 51

(R)-1,1-Dimethyl-2-[2-((indan-2-yl)(2-methylphenyl)amino)ethyl]piperidinium chloride Yield: 0.033 g (20%);
$^1$H-NMR (DMSO-d$_6$): δ 7.31 (d, J=8 Hz, 1 H), 7.25-7.17 (m, 4 H), 7.13-7.10 (m, 2 H), 7.05 (t, J=7 Hz, 1 H), 4.05-4.01 (m, 1 H), 3.43 (d, J=12 Hz, 1 H), 3.26-3.10 (m, 3 H), 3.02-2.96 (m, 2 H), 2.93-2.80 (m, 9 H), 2.31 (s, 3 H), 1.99-1.95 (m, 1 H), 1.79-1.65 (m, 4 H), 1.55-1.47 (m, 1 H), 1.40-1.36 (m, 1 H), 1.29-1.26 (m, 1 H);

LCMS [M$^+$]=363, RT=3.53 minutes, (Program P1, Column V);

UPLC: 98.46% (RT=4.94 minutes, $\lambda_{200nm}$, Mobile Phase: A 0.05% HCOOH in water, B Acetonitrile; Column: Gemini® NX C18 (50×4.6 mm) 3µ).

Example 52

1,1-Dimethyl-2-[2-((indan-2-yl)(2-methylphenyl)amino)ethyl]piperidinium bromide

Yield: 0.215 g (42%);
$^1$H-NMR (DMSO-d$_6$): δ 7.31 (d, J=8 Hz, 1 H), 7.25-7.17 (m, 4 H), 7.12-7.10 (m, 2 H), 7.05 (t, J=7 Hz, 1 H), 4.05-4.01 (m, 1 H), 3.42 (d, J=12 Hz, 1 H), 3.26-3.12 (m, 3 H), 3.02-2.96 (m, 2 H), 2.91-2.79 (m, 9 H), 2.31 (s, 3 H), 1.99-1.95 (m, 1H), 1.79-1.65 (m, 4 H), 1.57-1.47 (m, 1 H), 1.43-1.36 (m, 1 H), 1.29-1.26 (m, 1 H);

LCMS: [M$^+$]=363.4, RT=1.83 minutes, (Program P1, Column V);

UPLC: 99.74% (RT=5.80 minutes, $\lambda_{200nm}$, Mobile Phase A. 0.05% TFA in water, B. Acetonitrile; Column: Zorbax® SB-C18 (50×4.6 mm) 1.8µ).

Example 53 hTRVI1-Expressing Cells and In vitro Assays

In vitro assays were developed for assessing the inhibition of sodium channel response with compounds following stimulation by heat (47° C.) in cells expressing hTRPV1.

A. Generation of Cells Expressing hTRPV1

The following cells were developed as a preliminary screen to help select the compound which would progress to further assessment in an in vivo assay.

(i) Plasmid for Delivering hTRPV1 to Cells

In order to prepare the cell line, the open reading frame encoding hTRPV1 was amplified by PCR from a cDNA library based on the human neuroblastoma cell line IMR322 [NCBI dbEST ID: 18353]using the following primers:

(a) TRPV1_KpnIF (Forward Primer)
[SEQ ID NO: 2]
5'-ATAAACGGTACCGCCGCCACCATGAAGAAATGGAGCAGCAC-3'

(b) TRPV1_PmeIR (Reverse Primer)
[SEQ ID NO: 3]
5'-ATCGGTTTAAACTCACTTCTCTCCGGAAGCGGC-3'

The forward primer contains a KpnI site [GGTACC (underlined in (a) above] and a Kozak sequence [GCCGCCACC (double-underlined in (a)]. The reverse primer contains a PmeI site [GTTTAAAC, underlined in (b)].

The open reading frame of hTRPV1 (corresponding to NCBI NM$_{13}$ 080706.3) is: SEQ ID NO:4:

ATGAAGAAATGGAGCAGCACAGACTTGGGGCAGCTGCGGACCCACTCCAAAAGGACACC

TGCCCAGACCCCCTGGATGGAGACCCTAACTCCAGGCCACCTCCAGCCAAGCCCCAGCTC

TCCACGGCCAAGAGCCGCACCCGGCTCTTTGGGAAGGGTGACTCGGAGGAGGCTTTCCCG

GTGGATTGCCCTCACGAGGAAGGTGAGCTGGACTCCTGCCCGACCATCACAGTCAGCCCT

```
GTTATCACCATCCAGAGGCCAGGAGACGGCCCCACCGGTGCCAGGCTGCTGTCCCAGGAC

TCTGTCGCCGCCAGCACCGAGAAGACCCTCAGGCTCTATGATCGCAGGAGTATCTTTGAA

GCCGTTGCTCAGAATAACTGCCAGGATCTGGAGAGCCTGCTGCTCTTCCTGCAGAAGAGC

AAGAAGCACCTCACAGACAACGAGTTCAAAGACCCTGAGACAGGGAAGACCTGTCTGCTG

AAAGCCATGCTCAACCTGCACGACGGACAGAACACCACCATCCCCCTGCTCCTGGAGATC

GCGCGGCAAACGGACAGCCTGAAGGAGCTTGTCAACGCCAGCTACACGGACAGCTACTAC

AAGGGCCAGACAGCACTGCACATCGCCATCGAGAGACGCAACATGGCCCTGGTGACCCTC

CTGGTGGAGAACGGAGCAGACGTCCAGGCTGCGGCCCATGGGGACTTCTTTAAGAAAACC

AAAGGGCGGCCTGGATTCTACTTCGGTGAACTGCCCCTGTCCCTGGCCGCGTGCACCAAC

CAGCTGGGCATCGTGAAGTTCCTGCTGCAGAACTCCTGGCAGACGGCCGACATCAGCGCC

AGGGACTCGGTGGGCAACACGGTGCTGCACGCCCTGGTGGAGGTGGCCGACAACACGGCC

GACAACACGAAGTTTGTGACGAGCATGTACAATGAGATTCTGATCCTGGGGGCCAAACTG

CACCCGACGCTGAAGCTGGAGGAGCTCACCAACAAGAAGGGAATGACGCCGCTGGCTCTG

GCAGCTGGGACCGGGAAGATCGGGGTCTTGGCCTATATTCTCCAGCGGGAGATCCAGGAG

CCCGAGTGCAGGCACCTGTCCAGGAAGTTCACCGAGTGGGCCTACGGGCCCGTGCACTCC

TCGCTGTACGACCTGTCCTGCATCGACACCTGCGAGAAGAACTCGGTGCTGGAGGTGATC

GCCTACAGCAGCAGCGAGACCCCTAATCGCCACGACATGCTCTTGGTGGAGCCGCTGAAC

CGACTCCTGCAGGACAAGTGGGACAGATTCGTCAAGCGCATCTTCTACTTCAACTTCCTG

GTCTACTGCCTGTACATGATCATCTTCACCATGGCTGCCTACTACAGGCCCGTGGATGGC

TTGCCTCCCTTTAAGATGGAAAAAACTGGAGACTATTTCCGAGTTACTGGAGAGATCCTG

TCTGTGTTAGGAGGAGTCTACTTCTTTTTCCGAGGGATTCAGTATTTCCTGCAGAGGCGG

CCGTCGATGAAGACCCTGTTTGTGGACAGCTACAGTGAGATGCTTTTCTTTCTGCAGTCA

CTGTTCATGCTGGCCACCGTGGTGCTGTACTTCAGCCACCTCAAGGAGTATGTGGCTTCC

ATGGTATTCTCCCTGGCCTTGGGCTGGACCAACATGCTCTACTACACCCGCGGTTTCCAG

CAGATGGGCATCTATGCCGTCATGATAGAGAAGATGATCCTGAGAGACCTGTGCCGTTTC

ATGTTTGTCTACATCGTCTTCTTGTTCGGGTTTTCCACAGCGGTGGTGACGCTGATTGAA

GACGGGAAGAATGACTCCCTGCCGTCTGAGTCCACGTCGCACAGGTGGCGGGGGCCTGCC

TGCAGGCCCCCGATAGCTCCTACAACAGCCTGTACTCCACCTGCCTGGAGCTGTTCAAG

TTCACCATCGGCATGGGCGACCTGGAGTTCACTGAGAACTATGACTTCAAGGCTGTCTTC

ATCATCCTGCTGCTGGCCTATGTAATTCTCACCTACATCCTCCTGCTCAACATGCTCATC

GCCCTCATGGGTGAGACTGTCAACAAGATCGCACAGGAGAGCAAGAACATCTGGAAGCTG

CAGAGAGCCATCACCATCCTGGACACGGAGAAGAGCTTCCTTAAGTGCATGAGGAAGGCC

TTCCGCTCAGGCAAGCTGCTGCAGGTGGGGTACACACCTGATGGCAAGGACGACTACCGG

TGGTGCTTCAGGGTGGACGAGGTGAACTGGACCACCTGGAACACCAACGTGGGCATCATC

AACGAAGACCCGGGCAACTGTGAGGGCGTCAAGCGCACCCTGAGCTTCTCCCTGCGGTCA

AGCAGAGTTTCAGGCAGACACTGGAAGAACTTTGCCCTGGTCCCCCTTTTAAGAGAGGCA

AGTGCTCGAGATAGGCAGTCTGCTCAGCCCGAGGAAGTTTATCTGCGACAGTTTTCAGGG

TCTCTGAAGCCAGAGGACGCTGAGGTCTTCAAGAGTCCTGCCGCTTCCGGAGAGAAGTGA
```

ATG: Start codon of the gene (starting of ORF)
TGA: Stop codon of the gene (ending of ORF)
GGG→GGA: wobble done in reverse primer (Glycine to Glycine)

ATG→ATC: Reported single nucleotide polymorphism (SNP) in Genecard, Met--->Ile, SNP ID: rs222747.

A hybrid expression vector was created from two commercially-available vectors, as follows. Vector pTK-Hygro (Clonetech Catalog No. 631750) was digested with HindIIII and AvaI to release the hygromycin cassette containing the TK promoter, the hygromycin gene and HSV-TK polyA signal. This hygromycin cassette was cloned into pcDNA4myc-HisB (Invitrogen Catalog No. V863-20) using the AvrII site. The hTRPV1 coding sequence was inserted into the resulting pcDNA Hygro vector at Kpnl (5') and Pmel (3') sites and was thus flanked upstream by the cytomegalovirus promoter and downstream by the bovine growth hormone poly adenylation signal. Correct insertion of the entire ORF into the recombinant expression vector DNA (henceforth mentioned as DNA) was confirmed by sequence analysis. The complete plasmid backbone contains a pUC point of origin (ori), an ampicillin resistance gene, the pCMV promoter, a multiple cloning site containing KpnI and PmeI sites, an *E. coli* EM-7 promoter, and a hygromycin resistance gene in addition to the hTRPV1ORF.

(ii) Development of Recombinant N1E115 Expressing hTRPV1

The following materials were used for the process:
Lipofectamine 2000 (Invitrogen, Catalog No. 11668-019), Poly-ethyleneimine (Aldrich, Catalog No. J40872), Hygromycin-B (Invitrogen, Catalog No. 10687-010). Ultra pure kit prepared super-coiled DNA while the transfection carried out in antibiotic free, serum free DMEM.

For cell passage, N1E115 cells [American Type Culture Collection, Manassas, Va. (US), Accession number CRL2263]were cultured in Growth medium containing 1×DMEM (Sigma)+10% FBS (Gibco)+1% Penicillin-Streptomycin (Gibco) in 175 cm² flasks (Nunc). On the day of plating, spent media from the flasks was aspirated and the flasks were tapped from the sides with palms to dislodge the cells from the bottom of the flasks. Ten mL Growth media was added to suspend the cells and 1 mL of the suspended cells was inoculated in a fresh T-175 flask containing 35 mL Growth media.

Cell plating protocol for transfection was as follows: 0.2× $10^6$ cells in 2 mL growth medium was added to each well of a 6 well plates with lids inside the laminar air-flow. The plates were incubated at 37° C. and 5% $CO_2$ in a $CO_2$ incubator (Thermo) for 24 hours.

On the day of Lipofectamine mediated transfection, DNA and Lipofectamine were diluted in the laminar hood in the following way: 4 µg of DNA was diluted in 250 µL of DMEM. Next, 10 µg Lipofectamine was diluted in 250 µL of DMEM. The solutions were allowed to stand at room temperature (RT) for 7 minutes, after which they were mixed and allowed to stand at rt for another 20 minutes. Once the transfection mix was prepared, plated cells were washed with 500 µL DMEM. After washing, 500 µL of Lipofectamine-DNA mix was added to the wells. In control wells, Lipofectamine-DMEM was added and the plate was incubated at 37° C. and 5% $CO_2$ for 4.5 hours. After incubation, the media from transfected cells was carefully decanted without disturbing the cells. Cells were then washed once with 1 mL of DMEM. Growth media (DMEM+10% FBS) was added to the cells after washing and the cells were incubated at 37° C. and 5% $CO_2$ for 24 hours.

Twenty-four hours post incubations, the transfected cells were examined visually for viability and adherence. Spent media was removed from the wells and 1.2 mL fresh growth media containing 300 µg/mL hygromycin was added per well. The cells were dislodged by pipetting up and down. Cells from each well were split 1:4 and transferred to fresh 6 well plate (300 µL cells/well). Transfected cells and control cells were observed every day, spent media was changed every other day initially. By the end of second week transfected stable colonies would appear which were then expanded and tested functionally in a calcium assay and a sodium assay performed as follows.

(iii) Cell Passages and Clonal Isolation of Cells

The cell passage protocol described above was followed for passaging cells as before. And the clonal isolation by limiting dilution method was performed as described below.

Preparation of Feeder cells: Healthy looking N1E115 (wild type cells) were harvested. $1 \times 10^6$ cells/mL of N1E115 cells were treated with mitomycin C at a concentration of 10 µg/L×$10^6$ cells for 20 minutes at 37° C. in $CO_2$ incubator. After 20 minutes, cells were washed with DMEM 5-6 times. Cells were then transferred to a 75 cm² flask containing 15 mL of growth media and incubated at 37° C. for 4 hours in a $CO_2$ incubator. After incubation the feeder cells are washed with DMEM and cells became ready for plating.

Preparation of stable cells: Healthy looking cells of hTRPV1-N1E115 were pelleted down and resuspended in growth media in a concentration that if plated in a 96 well plate the distribution will be 0.3 cells/well/100 µL media. Selective antibiotic hygromycin b (300 µg/mL) was added to it.

Feeder cells were plated in 96 well plates at a concentration of 1000 cells/100 µL/well. Cells were not plated in the wells at the edges. Two hundred µL of sterile phosphate buffered saline (PBS) was added instead. To the feeder cell layer, 100 µL of the stable cell suspension containing 0.3 cells/well/100 µL was added. Plates were incubated at 37° C. and 5% $CO_2$. Plates were left undisturbed in $CO_2$ incubator for 10 days. From the $10^{th}$ day onwards, all the cell plates were observed very carefully for single colony (assumed to be generated from one single cell). Each and every well was checked carefully. The wells with only single colony were marked.

To the marked wells media change was given, spent media was discarded and fresh growth media containing 300 µg/mL hygromycin B was added. Marked wells with single colonies were expanded from 96 well plate to 48 well plate followed by 6 well plate. Finally the cells were transferred to 25 cm² flasks (5 mL growth media +300 µg/mL hygromycin B). From the cultured flasks cells were counted and plated for functional screening in Sodium and Calcium assay platforms. Final clonal candidate for the study was selected based on the assay data which confirmed a robust expression of hTRPV1 using a capsaicin-evoked calcium response in the calcium assay and no loss of the constitutive sodium channel activity as judged by a robust veratridine response in the membrane potential assay.

(iv) Calcium Assay to Assess hTRPV1-Expressing Cell Function

For the calcium assay, cells were plated at 5000 per 50 µL of DMEM+10% FBS+300 µg/mL Hygromycin per well in a 384 clear-bottom poly-D-lysine coated plate and incubated at 37° C. and 5% $CO_2$ for 48 hours. On the day of the assay, media were discarded gently and washed with modified Tyrodes buffer (20 µL/well)] which was then discarded gently.

Composition of Modified Tyrodes Buffer for
Calcium Channel Assay

| Salt | Concentration (mM) |
|---|---|
| NaCl | 145 |
| KCl | 2.5 |
| $CaCl_2\ 2\ H_2O$ | 5.4 |
| $MgCl_2\ 6\ H_2O$ | 1.2 |
| HEPES | 10 |
| Glucose | 10 (180 mg/100 mL) |
| Probenecid | 2.943 |

Volume was made up to 500 mL with Milli-Q® water reagent.

pH was adjusted to 7.4 with KOH.

Pluronic acid was added to FLIPR® Calcium 4 dye (Molecular Devices) at a concentration of 0.025% (250 μL of 1% stock for 10 mL of the dye). Next, 20 μL of FLIPR® Calcium 4 dye (Molecular Devices) prepared in modified Tyrodes buffer (Probenecid (42 mg in 60 μL 5N NaOH) was added to 50 mL modified Tyrodes buffer before pH adjustment) per well was added and the plate was incubated at 25° C. for 30 minutes before Capsaicin addition (capsaicin stock was 20 mM in DMSO, working stock 1 mM (in buffer) and final concentration in assay plate was 10 μM and was utilized for calcium assay following manufacturer's instructions.) Twenty μL of 2×(20 μM) Capsaicin was added to the cells in the FLIPR®(Molecular Devices, Inc.) and read was taken for 15 minutes.

(v) Membrane potential Assay to Assess Sodium Channel Function in hTRPV1-Expressing Cells Cells were plated at 5000 per 50 μL [DMEM+10% FBS+ 300 μg/mL Hygromycin]per well, in a 384 clear bottom poly-D-lysine coated plate and incubated at 37° C. and 5% $CO_2$ for 48 hours. On the day of the assay, media were discarded gently and 30 μL of the dye (FMP blue dye was prepared in assay buffer) per well was added and dye-loading was allowed to proceed for 20 minutes at room temperature. An 'agonist' drug-addition plate was prepared for the FLIPR® instrument according to manufacturer's instructions; this plate contained both veratidine (Sigma-Aldrich, Catalog No. V5754) and Toxin-II from *Anemonia sulcata* (ATX-II, Sigma-Aldrich Catalog No. T3268). The concentrations of veratridine and ATX-II in the drug-addition plate were 400 μM and 12 μM, respectively in order to achieve final assay concentrations of 100 μM and 3 μM when 10 μL of the combined solution was dispensed into the cell plate using the FLIPR® instrument. The agonist addition was programmed on the FLIPR® instrument to coincide with the initiation of fluorescence signal reading and such reads were taken at regular intervals for 10 minutes duration.

B. In Vitro Assay Developed for Assessing the Inhibition of Sodium Channel Response with Compounds Following Stimulation by Heat (47° C.) in Cells Expressing hTRPV1.

hTRPV1-N1E115 cells were passaged by culturing in Growth medium (containing 1×DMEM (Sigma)+10% FBS (Gibco)+1% Penicillin-Streptomycin (Gibco)+300 μg/mL Hygromycin B (Invitrogen, as the selection marker)) in 175 mL flasks (Nunc). The cells were split 1:10. Spent media from the flasks were aspirated and the flasks were tapped from sidewise with palms to dislodge the cells from the bottom of the flask. Growth media (10 mL) was added to suspend the cells and the suspended cells (1 mL) were inoculated in a fresh T-175 flask containing Growth media (35 mL). For plating the cells for the Assay, 5000 cells in 50 μL Growth medium was added to each well of 384-well, clear bottomed, sterile poly-D-lysine coated plates with lids (Greiner-bio one) inside the laminar air-flow. The plates were incubated at 37° C. and 5% $CO_2$ in a $CO_2$ incubator (Thermo). Forty eight hours later, on the day of the assay the cell seeded plates were observed under microscope to check the health, attachment and confluency of the monolayer prior to the assay.

The spent media from the cell seeded plates were decanted gently and FLIPR® Membrane potential Dye-Blue (available commercially from Molecular Devices Inc., US, as is "FLIPR Membrane potential assay kit blue") was added into each well of the plates. The dye was prepared in assay buffer following manufacturer's instructions. The dye added plate was incubated at 25° for 30 minutes inside a plate incubator (Thermo). Assay Buffer was prepared according to Table 3. The pH was adjusted to 7.4 with KOH (Sigma) and the volume was made up to 500 mL with Milli-Q® water (Millipore). Unless otherwise mentioned, all the dilutions were done in Assay Buffer.

TABLE 3

| Salt | Concentration (mM) |
|---|---|
| NaCl | 150 |
| KCl | 3.25 |
| $CaCl_2\ 2\ H_2O$ | 2 |
| $MgCl_2\ 6\ H_2O$ | 3 |
| HEPES | 10 |
| Glucose | 11 (198 mg/100 mL) |

The compounds were diluted in the Assay Buffer and added to 384 well-polypropylene round bottomed well plates (Costar) to serve as source plates for compound addition. After the dye incubation period was over, the dye loaded plates and the compound source plates were inserted inside the FLIPR® $^{Tetra}$ (Molecular Devices, Inc.) with 384 FLIPR® tip boxes (Molecular Devices, Inc.). The compounds were added to the dye loaded plates by the FLIPR® $^{Tetra}$ ($1^{st}$ addition) system. After compound addition, the plates were immediately transferred to 47° C. plate incubator (Thermo) and incubated for 10 minutes to activate hTRPV1. The plates were then immediately transferred to 25° C. plate incubator (Thermo) and incubated for 30 minutes. The cell-seeded plates which were not to be activated were transferred to 25° C. plate incubator (Thermo) and incubated for 30 minutes. An agonist plate containing Veratridine (Sigma) and ATX-II was prepared, as described above, prior to the $2^{nd}$ addition. Agonist addition was achieved using FLIPR® software and was timed to coincide with fluorescence readings that were taken at regular intervals for a total duration of 12 minutes.

The reference compound, QX-314 had a hTRPV1-N1E115, 47° C. $IC_{50}$ value of 733 mM in the FLIPR® assay. An $IC_{50}$ of ≤100 μM indicates a 10 fold better activity than QX-314.

C. Method for Assessing the Extent of Inhibition of Sodium Channel Response with Compounds in hNav1.5-HEK293 Cells.

The following assay was used to assess the tendency of the test compounds to block the dominant cardiac sodium channel isoform. Nav1.5 sodium channels are known to be permeable to quaternary sodium channel blockers such as QX-314 and, thus, the assay was performed in the absence of a chemical TRPV1 agonist.

The hNav1.5-HEK-293 cells (CreaCell, France, a human embryonic kidney cell line expressing the human Nav1.5 sodium channel) were cultured in Growth medium (containing 1×DMEM (Gibco)+10% FBS (PAA Gold)+2% Glutamine 100 mM (Gibco)+1% penicillin 10,000 U/mL streptomycin 10,000 μg/mL (Invitrogen)+1.2 mg/mL Geneticin G418 (Invitrogen)) in 75 mL cell bind flasks (Corning). The following steps were followed exactly as mentioned. The spent medium was discarded and the cells rinsed once with PBS-1×. Accutase® (1-2 mL; PAA) solution was added. The plate was placed on a 37° C. warming incubator 3-5 minutes. As soon as cells are detached, 37° C. complete medium (9 mL) was added. The cell suspension was drawn into a sterile pipette and cells homogenized gently to dissociate cell aggregates. The cells were counted using a hemocytometer with Blue Trypan and then centrifuged 5 minutes at 400 g. The cells can be amplified or maintained by seeding 2,105 cells/mL in a T75 flask (final volume: 15 mL). 8000 cells in 50 µL Growth medium was added to each well of 384-well, clear bottomed, sterile poly-D-lysine coated plates with lid (Greiner-bio one) inside the laminar air-flow. The plates were incubated at 37° C. and 5% $CO_2$ in a $CO_2$ incubator (Thermo) for 48 hours.

On the day of the assay, cells were washed with Assay buffer, which was prepared using the components and amounts in Table 4. The pH was adjusted to 7.4 with NaOH, volume made up to 500 mL with Milli-Q® water.

TABLE 4

| Salt | Concentration (mM) |
|---|---|
| NaCl | 165 |
| KCl | 4.5 |
| $CaCl_2\, 2H_2O$ | 2 |
| $MgCl_2\, 6H_2O$ | 1 |
| HEPES | 10 |
| Glucose | 10 (180 mg/100 mL) |

Assay Buffer was added to the cells and incubated at rt (25° C.) for 10 minutes. The compounds were diluted in assay buffer. The compounds were added and incubated at rt (25° C.) for 10 minutes. Red FMP Dye (MDC) was added to the cells and the plate was incubated at rt (25° C.) for 30 minutes. Veratridine stock (20 mM; Sigma) was prepared in DMSO; veratridine (final concentration of 30 µM) in assay buffer was added to each well of the cell seeded plates in the FLIPR® system and read taken for 10 minutes. Table 5 provides data illustrating the sodium channel activity of the test compounds in response to the presence or absence of heat stimulation in cells expressing hTRPV1. The compounds were tested for differential activity at 25° C. and 47° C. and at two test concentrations. Compounds showing the most promising profiles were further evaluated for $IC_{50}$ in the 47° C. assay, examples are shown in Table 5.

TABLE 5

| Ex | hTRPV1-N1E Nav 0.1 mM (% inhibition) | | hTRPV1-N1E Nav 1 mM (% inhibition) | | hTRPV1-N1E $IC_{50}$ (µM) |
|---|---|---|---|---|---|
| | 25° C. | 47° C. | 25° C. | 47° C. | 47° C. |
| 1 | 56 (N = 4, DMSO) | 87 (N = 4, DMSO) | NT | NT | NT |
| 2 | 44 (N = 2, 0.5 mM) | 89 (N = 2, 0.5 mM) | 50 (N = 2) | NT | 9 |
| 3 | 16 (N = 2) | 67 (N = 2) | 23 (N = 2) | 60 (N = 2) | 37 |
| 4 | 0 (N = 3) | 94.7 (N = 3) | 0 (N = 3) | 67.0 (N = 3) | B' |
| 5 | 21 (N = 2) | 50 (N = 2) | NT | NT | B' |
| 9 | 16 (N = 2, 0.5 mM) | 77 (N = 2, 0.5 mM) | NT | NT | B' |
| 10 | 24 (N = 2, 0.5 mM) | 91 (N = 2, 0.5 mM) | 6.5 (N = 2) | NT | B' |
| 11 | 0 | 72 | 71 (N = 2) | NT | B' |
| 12 | 49 (N = 4, DMSO) | 87 (N = 4, DMSO) | NT | NT | NT |
| 13 | 67 (N = 2) | 99 (N = 2) | 64 (N = 2) | 92 (N = 2) | B' |
| 14 | 6.3 (N = 3) | 76.7 (N = 3) | 3.8 (N = 3) | 25.3 (N = 3) | B' |
| 15 | 2.8 (N = 3) | 75.2 (N = 3) | 0.7 (N = 3) | 35.0 (N = 3) | B' |
| 16 | 0 (N = 2) | 92.9 (N = 2) | Insoluble | Insoluble | B' |
| 17 | 1 (N = 3) | 86.1 (N = 3) | 6.1 (N = 3) | 28.9 (N = 3) | B' |
| 18 | 0 (N = 3) | 86.9 (N = 3) | 0 (N = 3) | 38.2 (N = 3) | B' |
| 19 | 0 (N = 2) | 87.9 | Insoluble | Insoluble | B' |
| 20 | 11.2 (N = 3) | 94.8 (N = 3) | 0 (N = 3) | 48.9 (N = 3) | B' |
| 21 | 44.7 (N = 3) | 80.2 (N = 3) | 58.2 (N = 3) | 64.3 (N = 3) | B' |
| 22 | 8.7 (N = 2) | 62.7 (N = 2) | 48 (N = 2) | 69.9 (N = 2) | B' |
| 23 | 19.7 (N = 2) | 89.6 (N = 2) | Insoluble | Insoluble | A' |
| 24 | 25.1 (N = 2) | 88.5 (N = 2) | 57.9 (N = 2) | 84.2 (N = 2) | A' |
| 25 | 26.4 (N = 2) | 89.6 (N = 2) | Insoluble | Insoluble | A' |
| 7 | 27.3 (N = 2) | 57.9 (N = 2) | Insoluble | Insoluble | B' |
| 26 | 44.6 (N = 2) | 64.7 (N = 2) | Insoluble | Insoluble | B' |
| 27 | 68.1 (N = 2) | 81.3 (N = 2) | 61.4 (N = 2) | 71.9 (N = 2) | NT |
| 28 | 30.2 (N = 2) | 43.7 (N = 2) | 61.8 (N = 2) | 86.6 (N = 2) | NT |
| 29 | 68.9 (N = 2) | 82.9 (N = 2) | 64.6 (N = 2) | 75.3 (N = 2) | NT |
| 30 | 59.4 (N = 2) | 97.2 (N = 2) | Insoluble | Insoluble | NT |
| 31 | 3.8 (N = 2) | 62.6 (N = 2) | Insoluble | Insoluble | NT |
| 8 | 6.5 (N = 2) | 22.7 (N = 2) | 39.9 (N = 2) | 69.5 (N = 2) | NT |
| 32 | NT | NT | NT | NT | B' |
| 33 | NT | NT | NT | NT | B' |
| 34 | NT | NT | NT | NT | B' |
| 35 | NT | NT | NT | NT | B' |
| 36 | 5.4 (N = 2) | 74.0 (N = 2) | NT | NT | B' |
| 37 | 21.5 (N = 2) | 60.7 (N = 2) | 59.5 (N = 2) | 24.0 (N = 2) | B' |
| 38 | 25.9 (N = 2) | 37.5 (N = 2) | 46.6 (N = 2) | 70.4 (N = 2) | NT |
| 39 | 10.6 (N = 2) | 11.3 (N = 2) | 31.3 (N = 2) | 62.4 (N = 2) | NT |
| 40 | 34.3 (N = 3) | NT | NT | NT | B' |

TABLE 5-continued

| Ex | hTRPV1-N1E Nav 0.1 mM (% inhibition) | | hTRPV1-N1E Nav 1 mM (% inhibition) | | hTRPV1-N1E IC$_{50}$ (µM) |
|---|---|---|---|---|---|
|  | 25° C. | 47° C. | 25° C. | 47° C. | 47° C. |
| 41 | 8.3 (N = 3) | NT | NT | NT | B' |
| 42 | 0 (N = 2) | 64.9 (N = 2) | NT | NT | NT |
| 43 | 93.9 (N = 2) | NT | NT | NT | A' |
| 44 | NT | NT | NT | NT | B' |
| 45 | 23.1 (N = 2) | 83.3 (N = 2) | NT | NT | B' |
| 46 | 31.8 (N = 2) | 94.4 (N = 2) | NT | NT | B' |
| 47 | 30.7 (N = 2) | 79.5 (N = 2) | NT | NT | B' |
| 48 | 29.6 (N = 2) | NT | NT | NT | B' |
| 49 | 22.2 (N = 2) | NT | NT | NT | B' |
| 50 | NT | NT | NT | NT | B' |
| 51 | NT | NT | NT | NT | A' |
| 52 | NT | NT | NT | NT | B' |

A': IC$_{50}$ = 1-<10 µM
B': IC$_{50}$ = 10-100 µM
NT: Not tested

Similarly, Table 6 provides the data illustrating the sodium channel activity of test compounds that showed a prominent inhibition of response at 47° C. together with minimal inhibition at 25° C. were assessed for their ability to block the cardiac sodium channel in a cell expressing Nav1.5. Data for several such compounds are shown in Table 6, the concentrations of these compounds required to block NaV1.5 are shown to be higher than those required to block the sodium channel response in the TRPV1-N1E115 cell line.

TABLE 6

| Ex | HEK Nav 1.5 % inh. @ 0.5 mM | HEK Nav 1.5% inh. @ 1.5 mM | HEK Nav 1.5 IC$_{50}$ (µM) (AVG) |
|---|---|---|---|
| 2 | 89.2 | 98.1 | 247 |
| 3 | 77.6 | 99.1 | 190 |
| 9 | 72.4 | 97.2 | 647 |
| 10 | 76.1 | 97.6 | 667 |
| 11 | 97.9 | 97.8 | 44 |

Example 54

In Vivo Assay of Mechanical Nociception

This assay was performed to monitor the time course of analgesia when compounds were injected either alone, or in combination with lidocaine directly into the vicinity of the sciatic nerve.

Male Sprague Dawley (SD) rats were of 180-220 gram body weight range. Animals were acclimatized for three days with the laboratory technician and the experimental environment. At day 1, all animals were given three sessions of acclimatization with the laboratory (30-45 minutes) and being wrapped in a towel (1 minute per animal). At day 2, the same acclimatization schedule was followed along with pincher touch (application without force) in session 3. At day 3, an acclimatization schedule similar to that of day 2 was followed and the first baseline was recorded. At day 4, the second baseline was recorded before administering the drug/test compound injection. The second baseline was considered for evaluation of treatment effect.

Withdrawal/Vocalization Force threshold (PWF) of the ipsilateral (right hind) paw were recorded for all the animals in morning of the experimentation day. The pincher was applied at the base of last phalange, somewhere at the midway of 5$^{th}$ and 4$^{th}$ metatarsus, with a cut-off of 500 grams. The forceps' arms of the pincher were kept in a fashion that the gauged end faced the dorsum of the paw and flat end faced the plantar surface. Force application with pincher arms was done in a fashion to increase slowly and steadily. Force application speed was optimized with practice to reach the cut off value (500 g) in approximately 6-7 seconds.

For the injection, rats were anesthetized with isoflurane (obtained from Baxter Pharma, US) for a brief period and held in the prone position with the limbs splayed. The greater trochanter and ischial tuberosity were localized by palpation and an imaginary line was drawn between the two and a point was estimated on that line at about one third of the distance caudal to the greater trochanter. Respective test compound/vehicle solution (about 100 µL or 200 µL, separate experiments) was injected with the injection needle advanced from a dorsolateral direction at a 45° angle and the needle tip touching the ischium. A 27 gauge needle connected to a tuberculin syringe was used for the injection. Injection volume was pushed gently. Post injection, the animals were kept in the recovery chamber and only after complete recovery from anesthesia were they returned to the cages. Care was taken that mild anesthesia was given so that the animals remain anesthetized for a very brief time.

Test compounds that were not soluble in normal saline solution were formulated at the required concentration in a modified vehicle (0-15% aqueous solution of the Cremophor® reagent) to provide the solution formulation. All compounds were administered in a simple normal saline formulation if possible. The Cremophor® reagent was used as a last resort. Lidocaine.HCl powder (Sigma, USA) was then dissolved in the same solution to provide a combination solution formulation of test compound and lidocaine. Sonication was used to reduce the particle size in case required. The final formulation was filter sterilized with syringe top filters (0.22 µm) prior to administration.

On day 4, after compound/vehicle injection, the two readouts of PWL were taken at 0.5 and 2 hours post injection followed by readouts at intervals of 1 hour or 2 hours depending upon whether the response remained at cut-off or showed signs of regained sensitivity. Recordings were continued until the gram-force response declined to a level that was not significantly different from pre-drug baseline. Otherwise, recordings were continued up to 14 hours, followed by the next readout on day 5 at 24 hours post injection. When significant anti-nociception effect was still observed at 24 hours, recordings were further continued as on day 4.

GraphPad® Prism 5 statistical software was used for analysis. Under column analysis, one way analysis of variance (ANOVA) was performed for each group followed by Dunnett's test for checking the significance of difference between baseline values and readouts at different time points.

A: Comparison of Compounds with Prior Art QX-314

Using the summary and assay provided above, the formulations of Table 7 were prepared and tested. The results of these assays are provided in FIGS. 1-7 and summarized in Table 7. Specifically, FIGS. 1-7 are plots of paw withdrawal vocalization force (g) vs. time (hours).

TABLE 7

Duration of Analgesia for Mechanical Nociception

| Test Compound | Test Compound Amount (%) | Lidocaine Amount (%) | Total Injection Amount (μL) | Average Time of Analgesia (h) |
|---|---|---|---|---|
| QX-314 | 0.5 | 2 | 200 | 9 |
|  |  | 2 | 100 | 6 |
|  |  | 0 | 200 | 2 |
|  |  | 0 | 100 | 2 |
| Ex. 2 | 0.5 | 2 | 200 | >14 |
|  |  | 2 | 100 | 10 |
|  |  | 0 | 200 | 4 |
|  |  | 0 | 100 | 0 |
| Ex. 3 | 0.5 | 2 | 200 | >15 |
|  |  | 2 | 100 | 12 |
|  |  | 0 | 200 | 9 |
|  |  | 0 | 100 | 4 |
| Ex. 9 | 0.5 | 2 | 100 | 5 |
| Ex. 11 | 0.5 | 2 | 100 | 7 |
| Ex. 24 | 0.5 | 2 | 200 | >168 |
|  | 0.5 | 2 | 100 | 32 |
|  | 0.25 | 1 | 200 | 24 |
|  | 0.5 | 0 | 200 | 12 |
|  | 0.25 | 0 | 200 | 4 |
| Ex. 43 | 0.2 | 2 | 200 | 28 |

These data illustrate that the compounds of Examples 2, 3, 11, 24 and 43 provided analgesic effects for at least 7 hours, which is greater than QX-314. Of significance, the compound of Example 3 provided analgesic effects of significant duration in the absence of lidocaine.

B: Comparison of Compounds of Formula (I)

Using the summary and assay provided above, the formulations of Table 8 were prepared and tested. The results of these assays are provided in FIG. 5 and summarized in Table 8. Specifically, FIG. 5 is a plot of paw withdrawal vocalization force (2) vs. time (hours).

TABLE 8

| Example | Test Compound Amount (%) | Lidocaine Amount (%) | Total Injection Amount (μL) | Average Time of Analgesia (h) |
|---|---|---|---|---|
| 4 | 0.5 | 2 | 100 | 1 |
| 16 | 0.5 | 2 | 100 | 6 |
| 23 | 0.5 | 2 | 100 | 2 |
| 24 | 0.5 | 2 | 100 | 32 |

These data illustrate that the compound of Example 24 at a 100 μL injection volume displayed anti-nociception effect up to 32 hours. Further, the compound of example 16 at a 100 μL injection volume displayed anti-nociception effect up to 6 hours.

C: Effect of Injection Volume and Concentration

Injections were prepared according to the description provided above and included (i) 100 μL of a solution containing 0.5% of the compound of Example 24 and 2% lidocaine and (ii) 200 μL of a solution containing 0.25% of the compound of Example 24 and 1% lidocaine. These injections were administered as described above, thereby permitting analysis of the effect of 100 μL vs. 200 μL volumes of the formulation.

The results of these assays are provided in FIGS. 6 and 7. Specifically, FIGS. 6 and 7 are plots of paw withdrawal vocalization force (g) vs. time (hours). It is noted that at test compound amounts of 0.5%, the overall duration of antinociception was reduced for 100 μL injection volumes. It is also noted that the increase in injection volume from 100 μL to 200 μL did not affect the response distribution until about 12 hours and the lidocaine combination effected, excluding the innate effect, remained unchanged at 20 hours for this test compound.

Example 55

Sciatic Function Assay

The sciatic function test is a simple observational gait analysis that provides a rudimentary assessment of hind-limb motor function according to a predetermined scoring scale based on a visual inspection of the animals foot prints as it ambulates on a flat surface (the basic principles of this test are provided in Lowdon (Journal of Neuroscience Methods 24(3), 1988, 279-281)). Following the injection of a test substance(s), the animal's hind paws are inked and it is then placed on a flat paper surface and permitted to ambulate freely. The footprint pattern left by the inked footpads on the paper is inspected and assigned a 'foot print score' based on a subjective assessment. The scoring system rates impairment severity according to the following scheme: A footprint score of 0 indicates that no weight was borne on the injected paw, the paw was dragged or twisted with the plantar surface facing up. A footprint score of 1-3 reflected that the weight bearing was primarily on the knees, that the ankle and toes were used sparingly, the toes were curled, and or the plantar surface of the paw is uplifted in a concave fashion. A footprint score of 4-6 reflects that the weight bearing is primarily on the knees and angle, with very little weight bearing on the toes. A footprint score of 6-10 reflects that the weight bearing is distributed over the knee, ankle, and toes and that there is an occasional sparing of the knee joints. A footprint score of 11 indicates that the weight distribution is normal and there is perfect placement of the plantar surface of the paw.

The data in FIG. 8 show the mean foot print score vs. time for a cohort of rats that were administered, by peri-sciatic injection, doses of 0.25% and 0.5% solutions of 1,1-dimethyl-2-[2-((indan-2-yl)(2-methylphenyl)amino) ethyl]piperidinium iodide in the presence and absence of fixed amounts (1 and 2%) of lidocaine. The squares (■) represent results for a 200 μL injection of a combined solution of 1,1-dimethyl-2-[2-((indan-2-yl)(2-methylphenyl)amino) ethyl]piperidinium iodide (0.5%) and lidocaine (2%). The circles (●) represent results for a 200 μL injection of a combined solution of 1,1-dimethyl-2-[2-((indan-2-yl)(2-methylphenyl)amino)ethyl]piperidinium iodide (0.25%) and lidocaine (1%). The upright triangles (▲) represent results for a 200 μL injection of a 1,1-dimethyl-2-[2-((indan-2-yl)(2-methylphenyl)amino)ethyl]piperidinium iodide-only (0.25%) solution. The inverted triangles (▼) represent results for a 200 μL of an injection of a lidocaine-only (2%) solution.

The data in FIG. 10 show the mean foot print score vs. time for a cohort of rats administered, by unilateral peri-sciatic injection, a dose of 200 μL of 0.2% of the compound of example 43, i.e., ((R)-2-[2-(Indan-2-yl-o-tolyl-amino)-ethyl]-1,1-dimethyl-piperidinium bromide), in combination with 2% lidocaine. The injection produced a marked motor deficit for 2 hours post injection which improved to a moderate impairment (score 5 to 8) over the subsequent 4 hours and thence gradually returned to 'normal' over the remaining 20 or so hours of assessment.

Example 56

Topical Anesthetic Activity

Aliquots (0.25 mL) of test solutions are applied into the conjunctival sac of conscious rabbits (either sex; 2-4 kg) and the eye-lids are kept closed for about 20 seconds. The corneal reflex is checked before application of the test solution and every 5 minutes thereafter. To test the corneal reflex, the cornea is touched six times with a stalked elastic bristle. The duration of anesthesia is calculated as the period from the time-point when the animal does not feel any of the six touches by the bristle to the time point when the animal again reacts to three of the six touches. To verify the reversibility of the topical anesthetic effect, the testing continues until the animal reacts to all six touches of the bristle for at least 15 minutes.

Example 57

Cutaneous Anesthetic Activity

Rats were subjected to several days of acclimatization to the environment and the investigator prior to entering the study. About 24 hours before each experiment, the skin on the back of male rats was shaved using electronic clippers. The anesthetic action of test agents, following subcutaneous injection was determined using a "pin-prick" method as described by Khan (Khan et al., Anesthesiology, January 2002, 96(1): 109-116). Injection volumes were standardized at 100 μL, each injection caused a small wheal to develop— the boundary of which was marked with ink. The cutaneous trunci muscle reflex (CTMR) is a reflex movement of the skin due to twitches of the lateral thoracospinal muscles elicited by noxious stimulation of the dorsal cutaneous area. An 18-guage needle was used as the noxious stimulus; six stimuli were presented to an area of 'normal' skin to determine baseline sensitivity and this was then repeated in the area of the wheal. Local anesthesia was estimated based on the number of stimulus presentations that failed to elicit a response. Data were represented as % maximal possible effect (MPE) where 100% indicates complete lack of response to each of the six needle presentations in the injected area. The extent of local anesthesia was assessed at regular intervals in order to generate efficacy-duration time plots.

Example 58

C. Local (Infiltration) Anesthetic Activity

About 18-24 hours before each experiment, the skin is prepared according to Example 36. The anesthetic action of each agent following intradermal injection is determined using a "pin-prick" method similar to that described in Example 36. Before and at various intervals after treatment, the area of the skin is tested for the presence or absence of a skin twitch in response to six standardized cutaneous probings with a pointed metal "algesimeter" at a predetermined maximum force of 20 grams. The average number of probings not producing a skin twitch response is designated as the "anesthetic score". In this system, six responses to six stimuli represent "no anesthetic activity" and no response to six stimuli represents a "maximal anesthetic activity". In experiments with intradermal injections of agents, the backs of the guinea pigs are divided into four sections using a marking pen, and injections of 0.1 mL of 0.25%, 0.5% and 1.0% solutions of the test compounds in physiological saline, vehicle (physiological saline) and at least one reference compounds are made, one injection into each of the four defined areas.

Example 59

Acute Intravenous Toxicity in Mice

Mice (males) of the NMRI strain, weighing 20 to 22 g are used after a stabilization period of at least ten days at the testing facility and at least one hour in the laboratory. Food but not water is withheld from all animals for 16 hours before the test. The animals are given free access to food starting two hours after the drug administration, that usually takes place around 9.00 AM. All animals are observed daily for 7 days post dosing.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

---

What is claimed is:

1. A compound of formula (I) or (II):

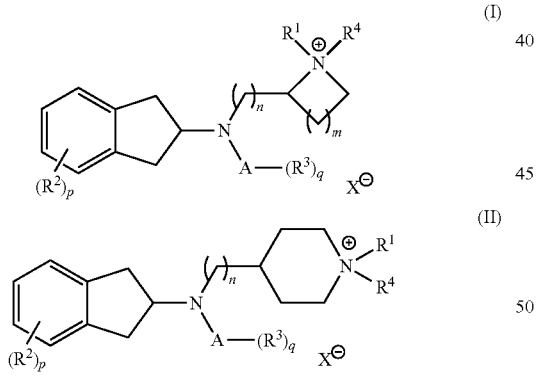

wherein:
A is phenyl or heteroaryl;
$R^1$ and $R^4$ are, independently, $C_1$ to $C_6$ alkyl or $CH_2CH_2OH$; or
$R^1$ and $R^4$ are joined to form a 4- or 6-membered carbocyclic or heterocyclic ring;
$R^2$ is independently selected from the group consisting of hydrogen, halogen, $NO_2$, OH, and $C_1$ to $C_6$ alkoxy;
$R^3$ is independently selected from the group consisting of hydrogen, halogen, CN, $NO_2$, $NH_2$, optionally substituted $C_1$ to $C_6$ alkyl, $C_2$ to $C_6$ alkenyl, $C_2$ to $C_6$ alkynyl, OH, $CF_3$, $OCF_3$, $SCF_3$, optionally substituted $C_1$ to $C_6$ alkoxy, $C_2$ to $C_6$ alkynyloxy, heterocyclyloxy, heteroaryloxy, optionally substituted $C_1$ to $C_6$ alkylthio, heteroarylthio, $C(O)O(C_1$ to $C_6$ alkyl), $C(O)(C_1$ to $C_6$ alkyl), C(O)(aryl), C(O)(heterocycle), $C(O)NH_2$, $C(O)NH(C_1$ to $C_6$ alkyl), C(O)NH(aryl), C(O)NH(heterocycle), C(O)NH(heteroaryl), $C(O)N(C_1$ to $C_6$ alkyl)($C_1$ to $C_6$ alkyl), $C(O)N(aryl)(C_1$ to $C_6$ alkyl), $C(S)NH_2$, optionally substituted aryl, heteroaryl, heterocycle, $NHC(O)(C_1$ to $C_6$ alkyl), NHC(O)(aryl), NHC(O)(heteroaryl), $NHC(O)O(C_1$ to $C_6$ alkyl), $N(C_1$ to $C_6$ alkyl)C(O)($C_1$ to $C_6$ alkyl), $N(C_1$ to $C_6$ alkyl)C(O)O($C_1$ to $C_6$ alkyl), $NHC(O)NH_2$, $NHC(O)NH(C_1$ to $C_6$ alkyl), NHC(O)NH(heteroaryl), $NHSO_2(C_1$ to $C_6$ alkyl), $SO_2(C_1$ to $C_6$ alkyl), $SO_2NH_2$, $SO_2NH(C_1$ to $C_6$ alkyl), $SO_2NH(C_2$ to $C_6$ alkynyl), $SO_2N(C_1$ to $C_6$ alkyl)($C_1$ to $C_6$ alkyl), $SO_2NH$(heteroaryl), $NH(C_1$ to $C_6$ alkyl), $N(C_1$ to $C_6$ alkyl)($C_1$ to $C_6$ alkyl), $N(C_1$ to $C_6$ alkyl)($C_2$ to $C_6$ alkenyl), and $N(C_1$ to $C_6$ alkyl)(heterocycle); or
q is 2 and two $R^3$ groups are joined to form an optionally substituted 6-membered aryl, optionally substituted 5- or 6-membered carbocyclic ring, or optionally substituted 5- or 6-membered heterocycle or heteroaryl containing 1 to 3 oxygen, nitrogen, or sulfur atoms and 4 or 5 carbon atoms;
m is 1 to 5;
n is 1 to 3;
p is 0 to 2;
q is 0 to 4; and
$X^-$ is a halogen ion, trifluoroacetate, sulfate, phosphate, acetate, fumarate, maleate, citrate, pyruvate, succinate, oxalate, bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate, edisylate, isethionate, D-mandelate, L-mandelate, propionate, tartarate, phthalate, hydrochlorate, hydrobromate, nitrate, methanesulfonate, ethanesulfonate, napthalenesulfonate, benzenesulfonate, toluenesulfonate, mesitylenesulfonate, camphorsulfonate or trifluoromethanesulfonate.

2. The compound according to claim 1, wherein two hydrogen atoms attached to a carbon atom are replaced with a double bond to an oxygen atom to form a carbonyl.

3. The compound according to claim 1, which contains at least 1 chiral center.

4. The compound according to claim 1, which is a mixture of enantiomers.

5. The compound according to claim 1, which is an R-enantiomer.

6. The compound according to claim 1, which is an S-enantiomer.

7. The compound according to claim 1, wherein p is 0.

8. The compound according to claim 1, wherein q is 0.

9. The compound according to claim 1, wherein n is 1.

10. The compound according to claim 1, wherein n is 2.

11. The compound according to claim 1, wherein n is 3.

12. The compound according to claim 1, wherein m is 3.

13. The compound according to claim 1, wherein m is 2.

14. The compound according to claim 1 which has the structure:

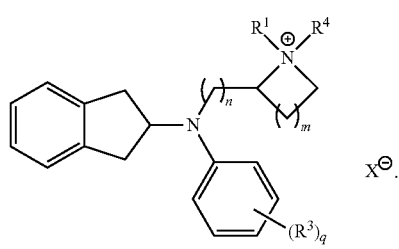

15. The compound according to claim 1 which has the structure:

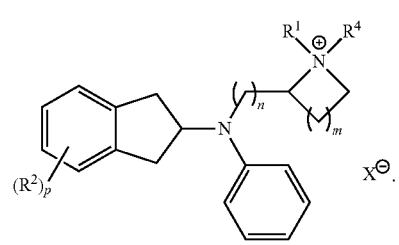

16. The compound according to claim 1 which has the structure:

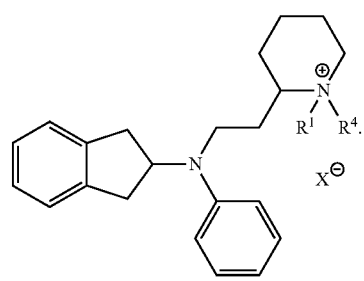

17. The compound according to claim 16 which has the structure:

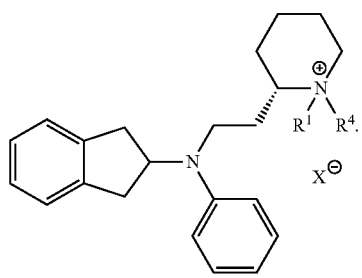

18. The compound according to claim 1 which is:

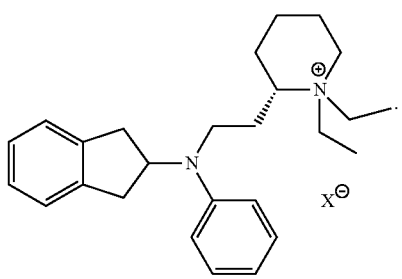

19. The compound according to claim 1 which is:

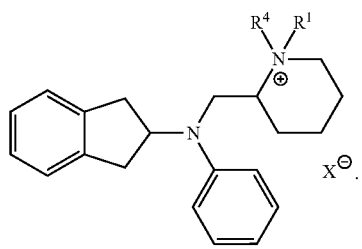

20. The compound according to claim 19 which is:

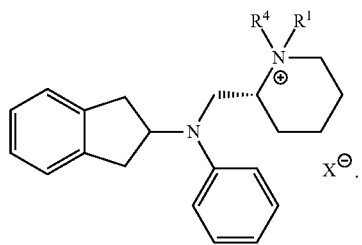

21. The compound according to claim 1 which is:

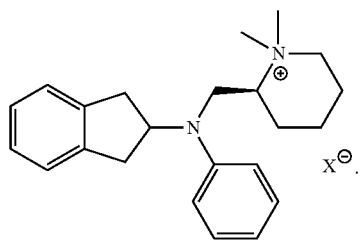

22. The compound according to claim 1 which is: a racemic mixture of

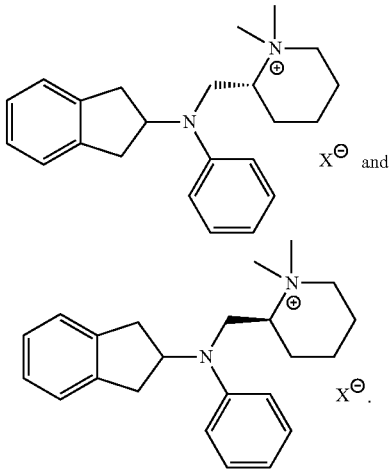

23. The compound according to claim 1 which is selected from the group consisting of
- (S)-1,1-dimethyl-2-[2-((indan-2-yl)(phenyl)amino)ethyl] piperidinium iodide,
- (R)-1,1-dimethyl-2-[2-((indan-2-yl)(phenyl)amino)ethyl] piperidinium iodide,
- (S)-1,1-diethyl-2-[2-((indan-2-yl)(phenyl)amino)ethyl] piperidinium iodide,
- (R)-1,1-diethyl-2-[2-((indan-2-yl)(phenyl)amino)ethyl] piperidinium iodide,
- (S)-1,1-dipropyl-2-[2-((indan-2-yl)(phenyl)amino)ethyl] piperidinium iodide,
- (R)-1,1-dipropyl-2-[2-((indan-2-yl)(phenyl)amino)ethyl] piperidinium iodide,
- (S)-1,1-dimethyl-2-[((indan-2-yl)(phenyl)amino)methyl] piperidinium iodide,
- (R)-1,1-dimethyl-2-[((indan-2-yl)(phenyl)amino)methyl] piperidinium iodide,
- (S)-1,1-dimethyl-2-[2-((indan-2-yl)(2-methylphenyl) amino)ethyl]piperidinium iodide,
- (R)-1,1-dimethyl-2-[2-((indan-2-yl)(2-methylphenyl) amino)ethyl]piperidinium iodide,
- 1,1-dimethyl-2-[((indan-2-yl)(phenyl)amino)methyl]piperidinium iodide,
- 1,1-dimethyl-2-[2-((indan-2-yl)(phenyl)amino)ethyl]pyrrolidinium iodide,
- 1,1-diethyl-2-[((indan-2-yl)(phenyl)amino)methyl]piperidinium iodide,
- 1,1-dimethyl-2-[2-((2-fluorophenyl)(indan-2-yl)amino) ethyl]piperidinium iodide,
- 1,1-dimethyl-2-[2-((3-fluorophenyl)(indan-2-yl)amino) ethyl]piperidinium iodide,
- 1,1-dimethyl-2-[2-((4-fluorophenyl)(indan-2-yl)amino) ethyl]piperidinium iodide,
- 1,1-diethyl-2-[2-((2-fluorophenyl)(indan-2-yl)amino) ethyl]piperidinium iodide,
- 1,1-diethyl-2-[2-((3-fluorophenyl)(indan-2-yl)amino) ethyl]piperidinium iodide,
- 1,1-diethyl-2-[2-((4-fluorophenyl)(indan-2-yl)amino) ethyl]piperidinium iodide,
- 1,1-dimethyl-2-[2-((indan-2-yl)(3-methylphenyl)amino) ethyl]piperidinium iodide,
- 1,1-diethyl-2-[2-((indan-2-yl)(3-methylphenyl)amino) ethyl]piperidinium iodide,
- 1,1-dimethyl-2-[2-((indan-2-yl)(4-methylphenyl)amino) ethyl]piperidinium iodide,
- 1,1-diethyl-2-[2-((indan-2-yl)(4-methylphenyl)amino) ethyl]piperidinium iodide,
- 1,1-dimethyl-2-[2-((indan-2-yl)(2-methylphenyl)amino) ethyl]piperidinium iodide,
- 1,1-diethyl-2-[2-((indan-2-yl)(2-methylphenyl)amino) ethyl]piperidinium iodide,
- 6-[2-((indan-2-yl)(phenyl)amino)ethyl]-5-azoniaspiro [4.5]decane bromide,
- 1,1-dimethyl-2-[3-((indan-2-yl)(phenyl)amino)propyl]piperidinium iodide,
- 1,1-diethyl-2-[3-((indan-2-yl)(phenyl)amino)propyl]piperidinium iodide,
- 1,1-dimethyl-2-[((indan-2-yl)(4-methylphenyl)amino) methyl]piperidinium iodide,
- 1,1-dimethyl-2-[((4-fluorophenyl)(indan-2-yl)amino)methyl]piperidinium iodide,
- 1,1-dimethyl-2-[((indan-2-yl)(3-methylphenyl)amino) methyl]piperidinium iodide,
- 1,1-diethyl-2-[((indan-2-yl)(4-methylphenyl)amino)methyl]piperidinium iodide,
- 1,1-dimethyl-2-[(3-fluorophenyl)(indan-2-yl)amino)methyl]piperidinium iodide,
- 1,1-dimethyl-2-[((indan-2-yl)(phenyl)amino)methyl]pyrrolidinium iodide,
- 1,1-diethyl-2-[2-((indan-2-yl)(phenyl)amino)ethyl]pyrrolidinium iodide,
- 1,1-dimethyl-2-[2-((indan-2-yl)(pyridine-2-yl)amino) ethyl]piperidinium iodide.
- 1,1-dimethyl-2-[2-((indan-2-yl)(pyrimidine-2-yl)amino) ethyl]piperidinium iodide,
- 1,1-dimethyl-2-[2-((indan-2-yl)(thiazol-2-yl)amino) ethyl]piperidinium iodide,
- 1,1-dimethyl-4-[2-((indan-2-yl)(2-methylphenyl)amino) ethyl]piperidinium bromide,
- 7-[2-((indan-2-yl)(2-methylphenyl)amino)ethyl]-3-oxa-6-azaspiro[5.5]undecan-6-ium chloride,
- 1,1-dimethyl-2-[2-((2,3-dihydrobenzo[b][1,4]dioxin-6-yl)(indan-2-yl)amino)ethyl]piperidinium iodide,
- (R)-1,1-dimethyl-2-[2-((indan-2-yl)(2-methylphenyl) amino)ethyl]piperidinium bromide,
- (S)-1,1-dimethyl-2-[2-((indan-2-yl)(2-methylphenyl) amino)ethyl]piperidinium chloride,
- 1,1-dimethyl-4-[2-((indan-2-yl)(2-methylphenyl)amino) ethyl]piperidinium iodide,
- 1,1-bis(2-hydroxyethyl)-2-[2-((indan-2-yl)(2-methylphenyl)amino) ethyl]piperidinium bromide,
- 1,1-dimethyl-2-[2-((indan-2-yl)(6-methylpyridine-2-yl) amino)ethyl]piperidinium iodide,
- 1,1-dimethyl-2-[2-((indan-2-yl)(6-methylpyridine-2-yl) amino)ethyl]piperidinium bromide,
- (S)-1,1-diethyl-2-[2-((indan-2-yl)(phenyl)amino)ethyl] piperidinium bromide,
- 1,1-dimethyl-2-[2-((indan-2-yl)(2-methylphenyl)amino) ethyl]piperidinium chloride,
- (R)-1,1-dimethyl-2-[2-((indan-2-yl)(2-methylphenyl) amino)ethyl]piperidinium chloride, and
- 1,1-dimethyl-2-[2-((indan-2-yl)(2-methylphenyl)amino) ethyl]piperidinium bromide.

24. A composition comprising said compound of formula (I) or formula (II) of claim 1, or a combination thereof, and a carrier.

25. A method for treating pain or itch in a patient, said method comprising administering to said patient said compound of formula (I) or formula (II) of claim 1, or a combination thereof.

26. A method for preparing said compound (I) of claim 1, wherein A is phenyl, said method comprising:

(i) converting

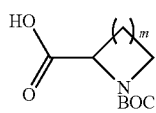

1a to

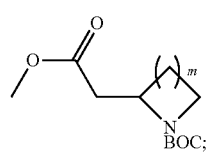

2a (ii) converting said compound 2a to

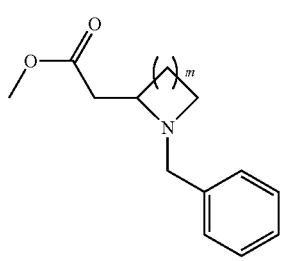

4a (iii) reducing said compound 4a to

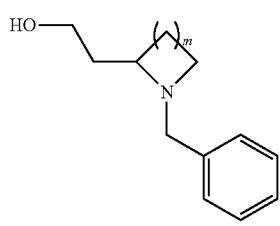

5a (iv) chlorinating said compound 5a to form

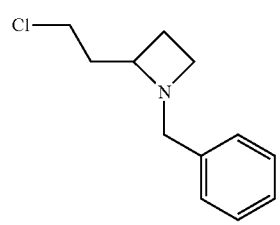

6a (v) coupling said compound 6a with

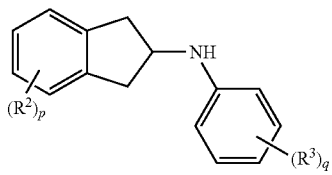

7a to form

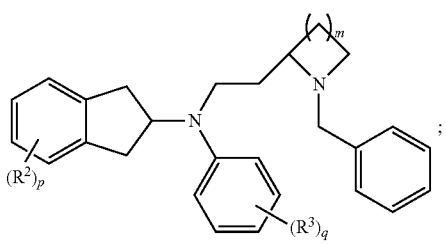

8a (vi) removing the benzyl group of compound 8a via hydrogenation to form

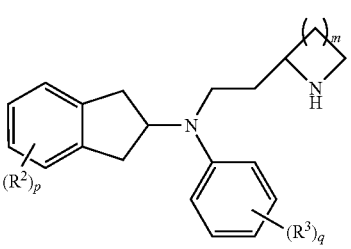

9a (vii) $R^1$ substituting compound 9a to form

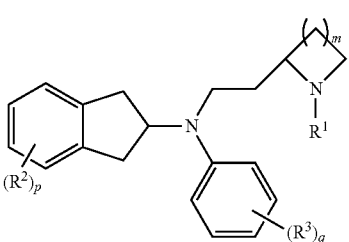

11a and (viii) $R^4$ substituting compound 11a.

27. The method according to claim 26, wherein said compound 1a is

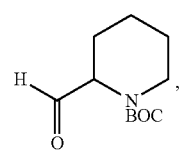

compound 2a is

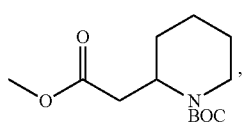

compound 4a is

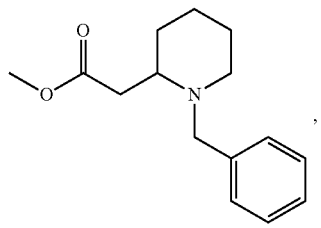 [SMILES: COC(=O)CC1CCCCN1Cc1ccccc1]

compound 5a is

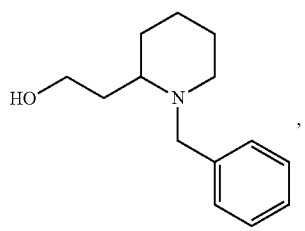 [SMILES: OCCC1CCCCN1Cc1ccccc1]

compound 6a is

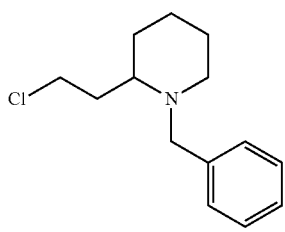

compound 8a is

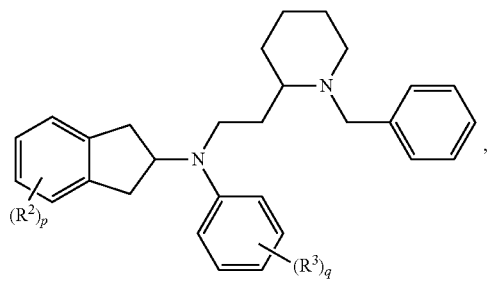

compound 9a is

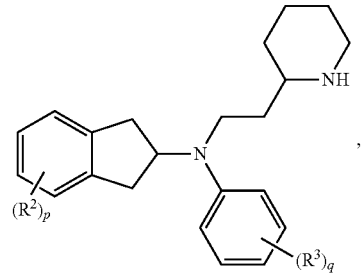

and compound 11a is

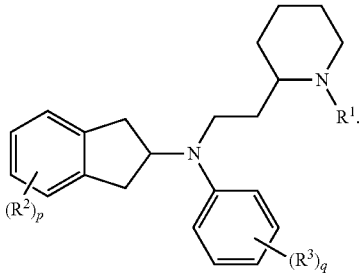

28. A method for preparing said compound of claim 1, wherein A is phenyl, said method comprising:

(vii) $R^1$ and $R^4$ substituting compound 9c:

9c

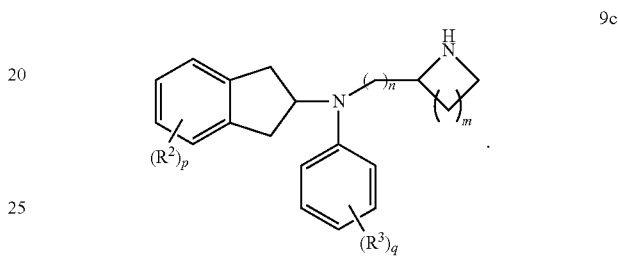

29. The method according to claim 28, wherein said compound 9c is

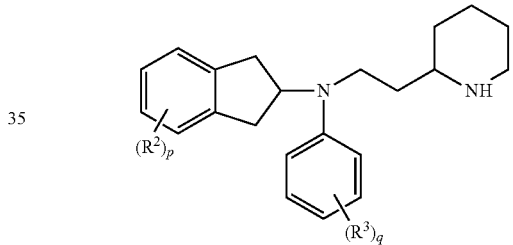

30. A method for preparing said compound of claim 1, wherein A is phenyl, said method comprising:

(i) protecting the nitrogen atom of

12a

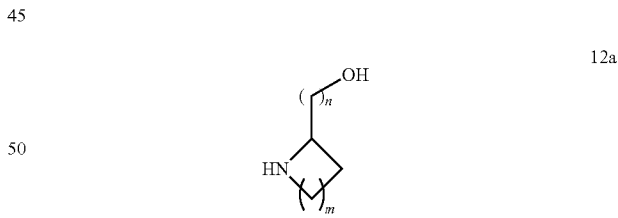

to form

13a

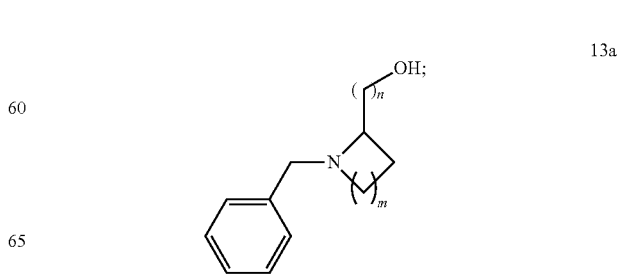

(ii) chlorinating said compound 13a to form

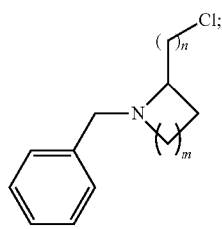

(iii) coupling said compound 14a with

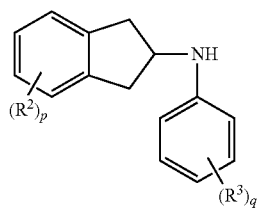

to form

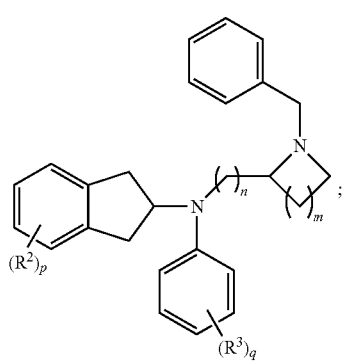

(iv) deprotecting compound 15a to form

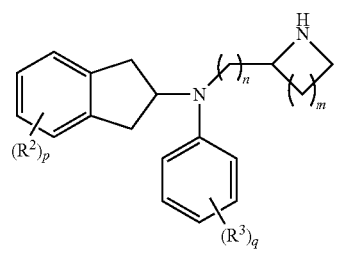

(v) R¹ substituting said compound 16a to form

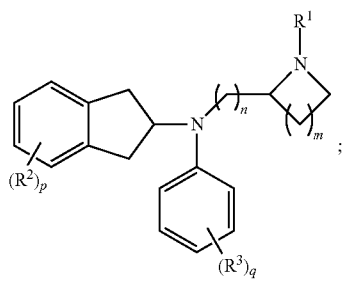

and
(vi) R⁴ substituting compound 17a.

31. The method according to claim 30, wherein said compound 12a is piperidine-2-methanol, compound 13a is

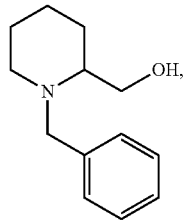 [SMILES: OCC1CCCCN1Cc1ccccc1]

compound 14a is

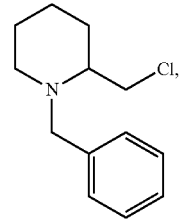 [SMILES: ClCC1CCCCN1Cc1ccccc1]

compound 15a is

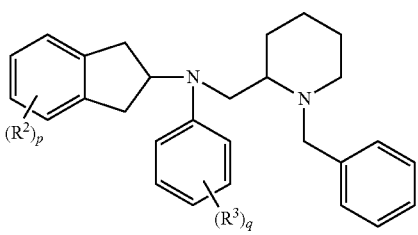

compound 16a is

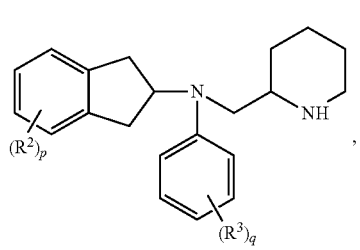

and compound 17a is

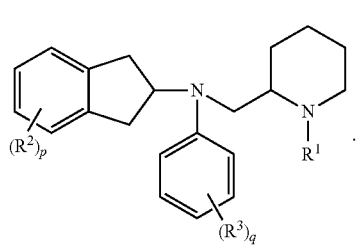

32. A method for preparing said compound of claim 1, wherein A is phenyl, R³ is 2-F, m is 2, and q is 1, said method comprising:

(vi) $R^1$ and $R^4$ substituting compound 9d:

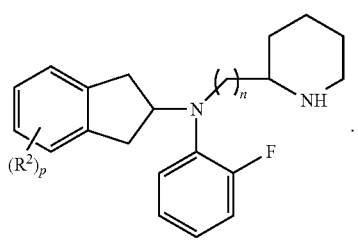
9d

33. The method according to claim 32, wherein compound 9d has the following structure:

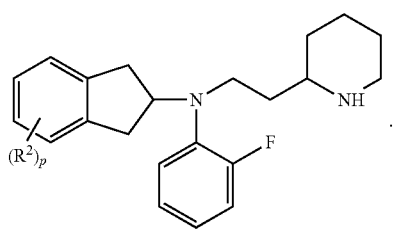

34. A method for preparing said compound of claim 1, wherein A is phenyl, said method comprising:
(i) coupling

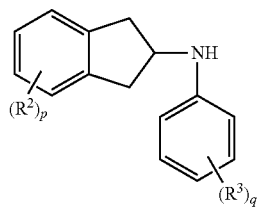
7a and

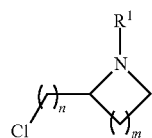
18a to form

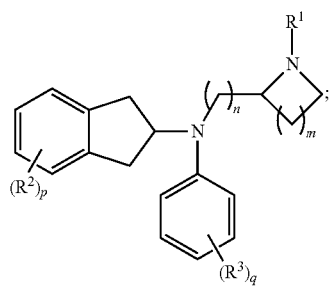
17a and
(ii) $R^4$ substituting compound 17a.

35. The method according to claim 34, wherein said compound 18a is

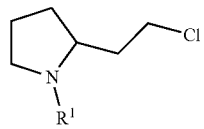
5 and compound 17a is

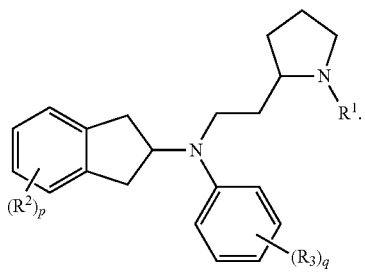

36. A method for preparing said compound of claim 1, wherein m is 3, said method comprising:
(i) reducing

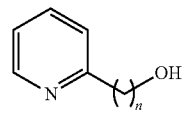
20a using an acid to form

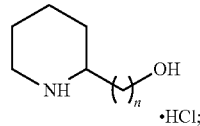
21a (ii) protecting compound 21a with a benzyl group to provide

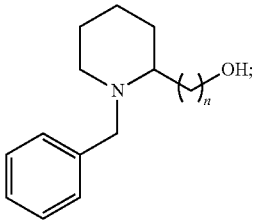
22a (iii) oxidizing compound 22a to provide

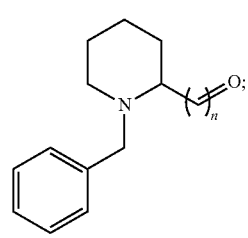
23a (iv) coupling compound 23a with

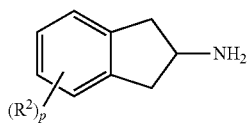

to provide

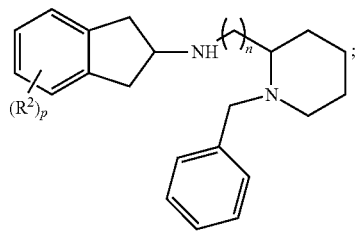

(v) substituting the nitrogen atom of said compound 24a with a R³-substituted phenyl group to form

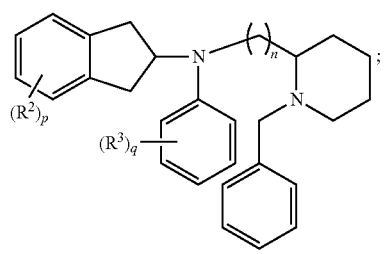

(vi) deprotecting said compound 25a to provide

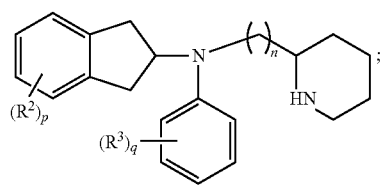

and (v) R¹ and R⁴ substituting said compound 26a.

37. The method according to claim 36, wherein said compound 20a is

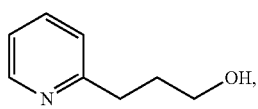

compound 21a is

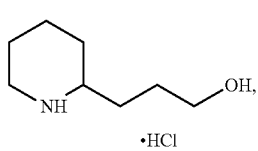

·HCl compound 22a is

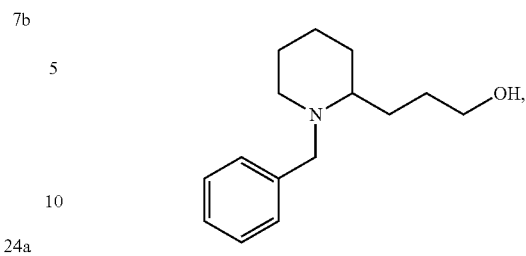

compound 23a is

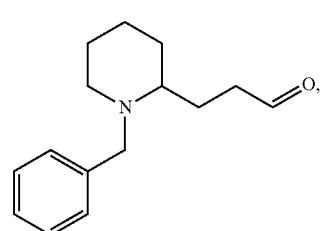

compound 24a is

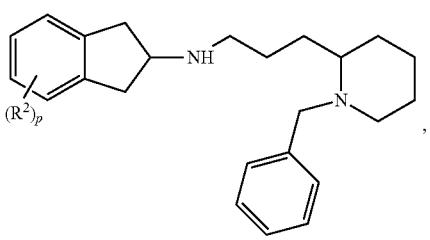

compound 25a is

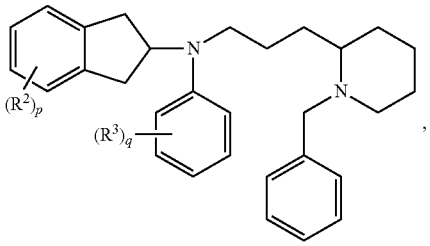

and compound 26a is

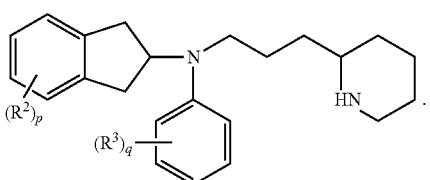

38. A method for preparing said compound of claim 1, wherein A is phenyl, said method comprising:

(i) converting

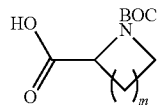

to

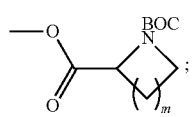

(ii) converting said compound 2a to

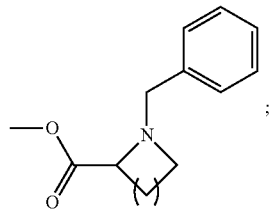

(iii) reducing said compound 4a to

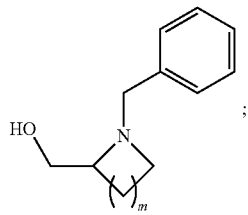

(iv) oxidizing compound 5a to provide

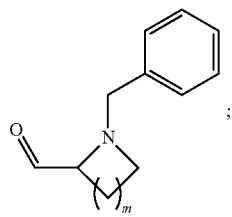

(v) coupling said compound 23a with

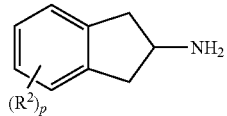

to provide

(v) substituting the nitrogen atom of compound 24c with an $R^3$-substituted phenyl group to provide

and (vi) deprotecting compound 8c to form

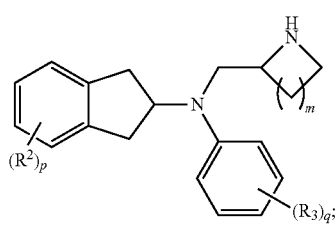

and (vii) $R^1$ and $R^4$ substituting the nitrogen ring.

39. The method according to claim 38, wherein said compound 1a is

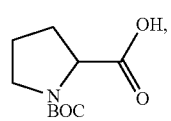

compound 2c is

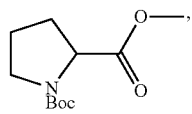 [SMILES: COC(=O)C1CCCN1C(=O)OC(C)(C)C]

compound 4c is
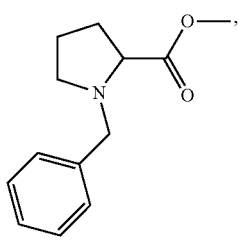 [SMILES: COC(=O)C1CCCN1Cc1ccccc1]
compound 5c is
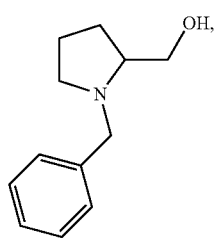 [SMILES: OCC1CCCN1Cc1ccccc1]
compound 31 is
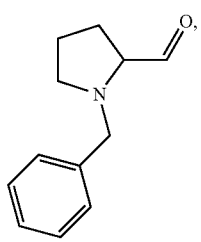 [SMILES: O=CC1CCCN1Cc1ccccc1]
compound 24c is
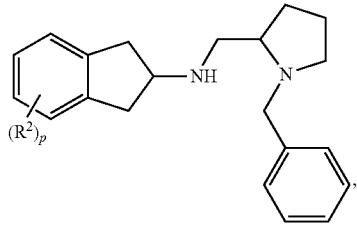
compound 8c is
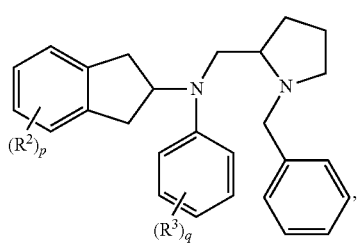
and compound 9f is
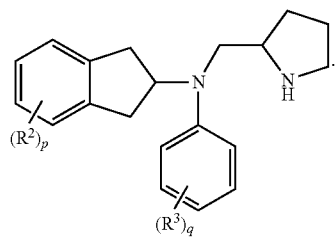
40. A method for preparing said compound of claim 1, said method comprising:
(i) converting
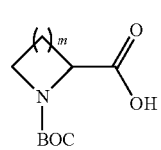   1a
to
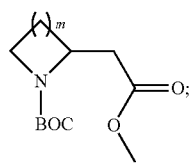   2b
(ii) reducing compound 2b to
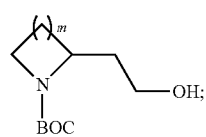   37a
(iii) oxidizing compound 37a to
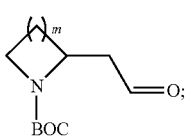   38a
(iv) coupling compound 38a with
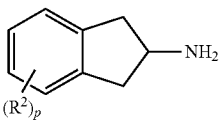   7b to compound 39a is

[Structure 39a: indane-NH-CH2-CH2-azetidine-BOC with (R²)ₚ]

(v) coupling compound 39a with an A-(R³)_q group to form

[Structure 40a]

(vi) deprotecting compound 40a to form

[Structure 41a]

and
(vii) R¹ and R⁴ substituting compound 41a.
41. The method according to claim 40, wherein:
compound 1a is

[Structure: BOC-pyrrolidine-COOH]

compound 2b is

[Structure: BOC-pyrrolidine-CH2-C(O)-OMe]

compound 37a is

[Structure: BOC-pyrrolidine-CH2-CH2-OH]

compound 38a is

[Structure: BOC-pyrrolidine-CH2-CHO]

compound 39a is

[Structure 39a with pyrrolidine]

compound 40a is

[Structure 40a with pyrrolidine]

and compound 41a is

[Structure 41a with pyrrolidine-NH]

42. A method for preparing said compound of claim 1, said method comprising:
(i) BOC protecting

[Structure 12b: azetidine-NH with CH2CH2OH]

to form

[Structure 37a: BOC-azetidine-CH2CH2OH]

(ii) oxidizing compound 37a to form

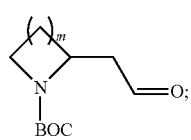
38a (iii) coupling compound 38a with

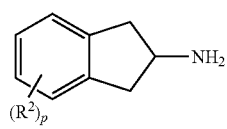

to form

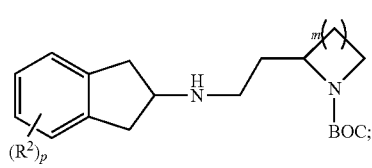
39a (iv) substituting compound 39a with A-(R³)_q to form

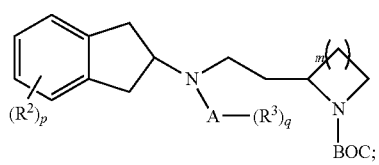
40a (v) deprotecting compound 40a to form

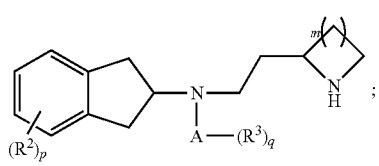
41a and
(vi) R¹ and R⁴ substituting compound 41a.

43. The method according to claim 42, wherein:
compound 12b is

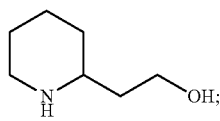

compound 37a is

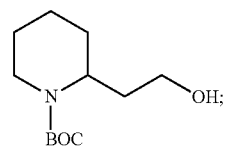 [SMILES: CC(C)(C)OC(=O)N1CCCCC1CCO]

compound 38a is

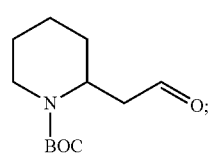 [SMILES: CC(C)(C)OC(=O)N1CCCCC1CC=O]

compound 39a is

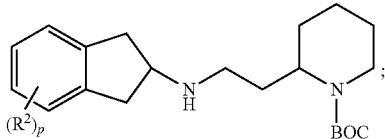

compound 40a is

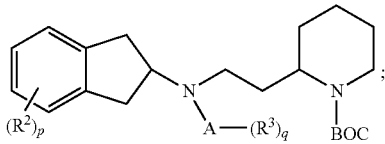

and compound 41a is

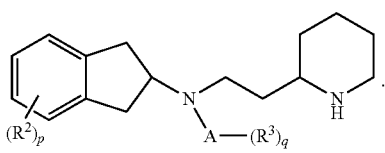

44. A method for preparing said compound of claim 1, wherein n is 2, said method comprising:

(i) substituting

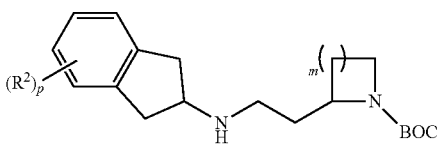
39a with A-(R³)q to form

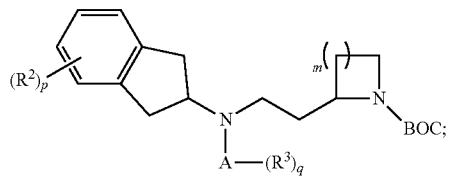
40a (ii) deprotecting compound 40a to form

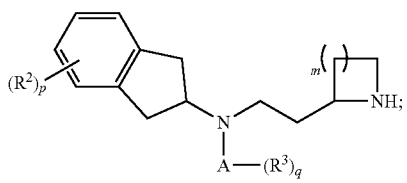
41a and (iii) R¹ and R⁴ substituting compound 41a.

45. The method according to claim 44, wherein:
compound 39a is

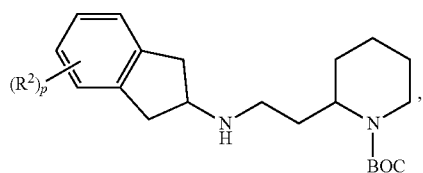

compound 40a is

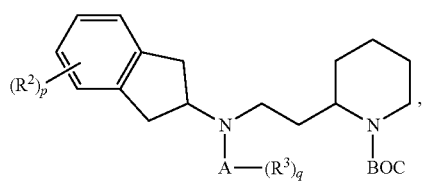

and compound 41a is

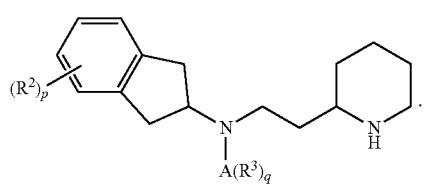
41a

46. A method for preparing said compound of claim 1, said method comprising:

(i) protecting

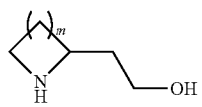
12b to form

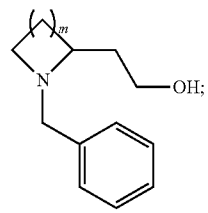
5a (ii) oxidizing compound 5a to form

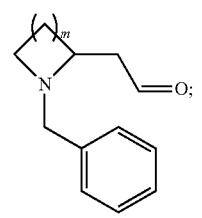
23c (iii) coupling compound 23a with

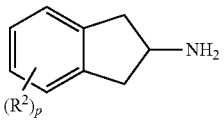
7b to form

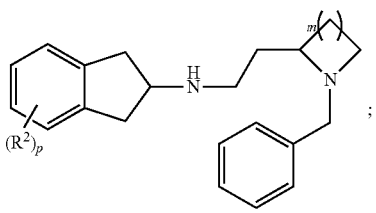
24f (iv) substituting compound 24f with A-(R³)q to form

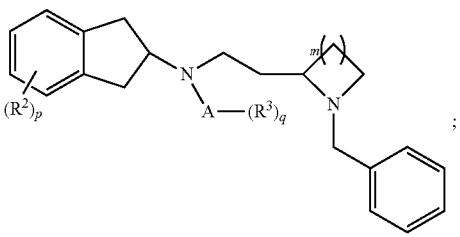
8e (v) deprotecting compound 8e to form

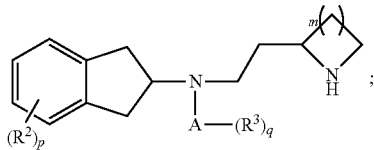

(vi) R¹ substituting compound 41a to form

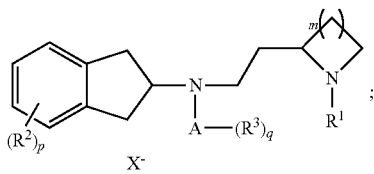

and (vii) R⁴ substituting compound 61c.

47. The method according to claim 46, wherein:

compound 12b is

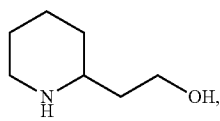

compound 5a is

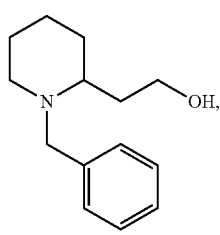 [SMILES: OCCC1CCCCN1Cc1ccccc1]

compound 23c is

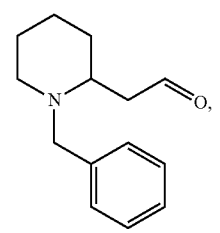 [SMILES: O=CCC1CCCCN1Cc1ccccc1]

compound 24f is

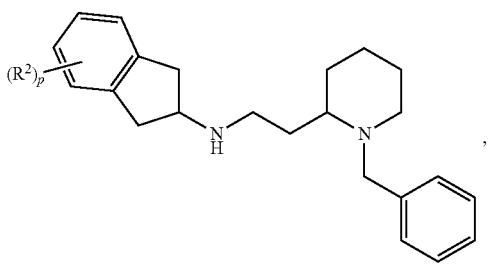

compound 8e is

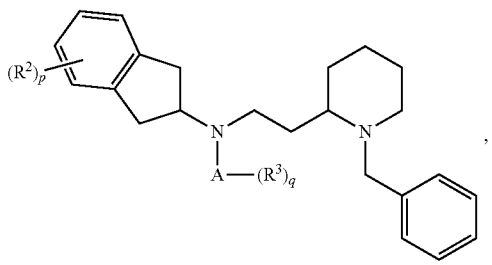

compound 41a is

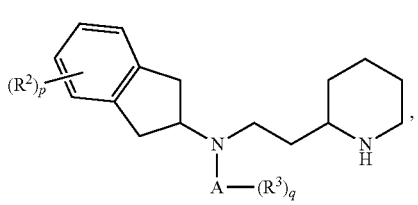

and compound 61c is

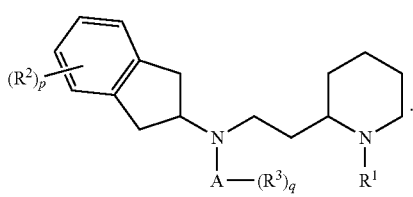

48. A method for preparing said compound of claim 1, said method comprising reacting

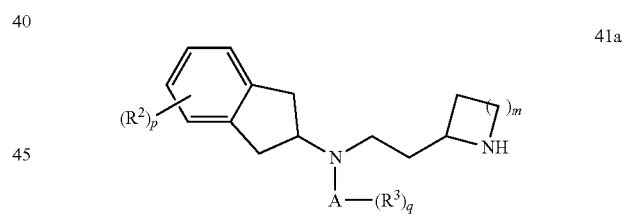

with X″—(CH₂)$_r$—Y—(CH₂)$_s$—X″, wherein:
r is 1 to 4;
s is 1 to 4;
Y is CH₂, O, or S; and
X″ is a leaving group.

49. The method according to claim 48, wherein compound 41a is

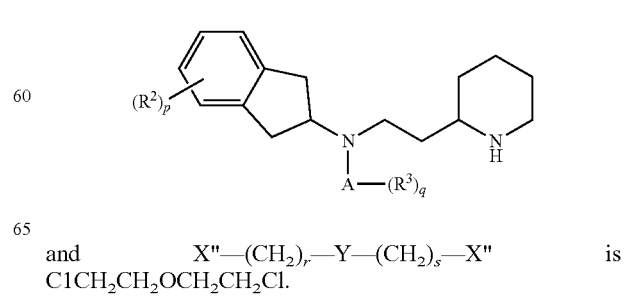

and    X″—(CH₂)$_r$—Y—(CH₂)$_s$—X″    is ClCH₂CH₂OCH₂CH₂Cl.

50. A method for preparing said compound of claim 1, said method comprising:

(i) reacting

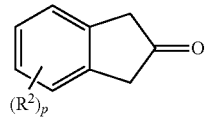

with H$_2$N-A-(R$^3$)$_q$ to form

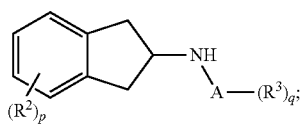

(ii) coupling compound 7c with

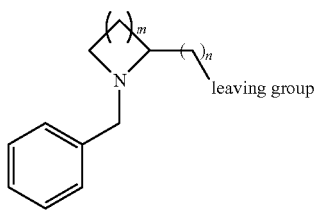

to form

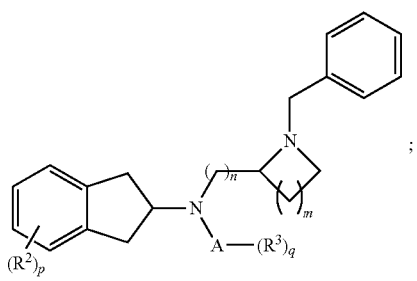

(iii) deprotecting compound 8f to form

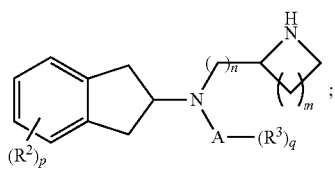

(iv) R$^1$ substituting compound 9h to form

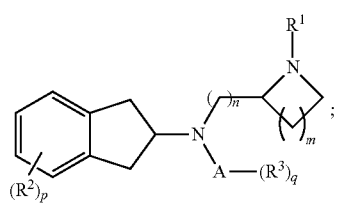

and (v) R$^4$ substituting compound 61a.

51. The method according to claim 50, wherein H$_2$N-A-(R$^3$)$_q$ is

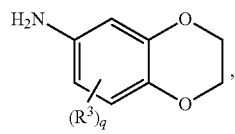

compound 7c is

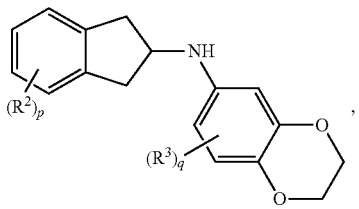

compound 58a is

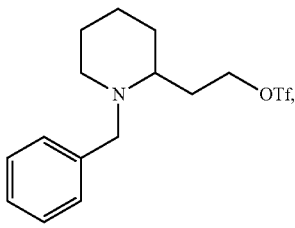 [SMILES: O=S(=O)(OCCC1CCCCN1Cc1ccccc1)C(F)(F)F]

compound 8f is

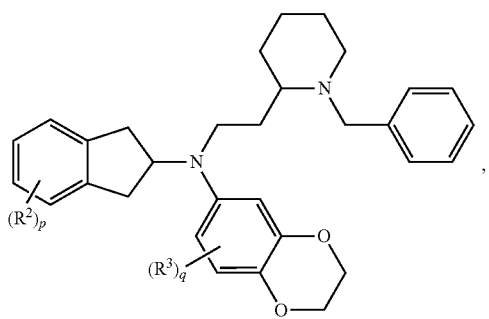

compound 9h is

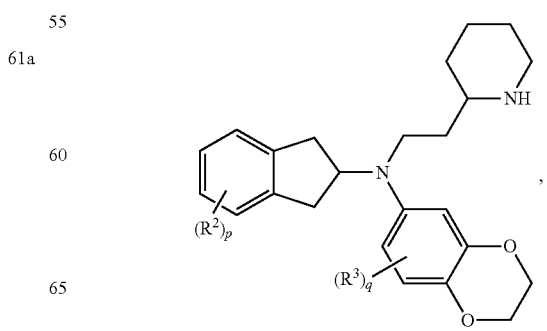

and compound 61a is

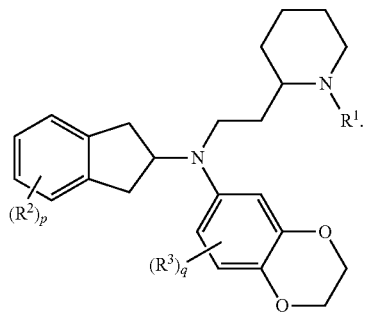

52. A method for preparing said compound of claim 1, wherein $R^4$ is $CH_3$, said method comprising:

(i) oxidizing

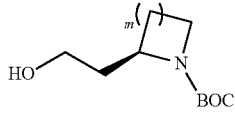

to form

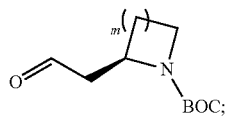

(ii) coupling compound 38a with

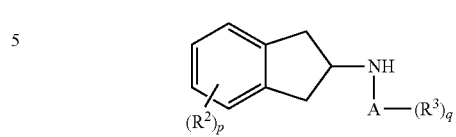

to form

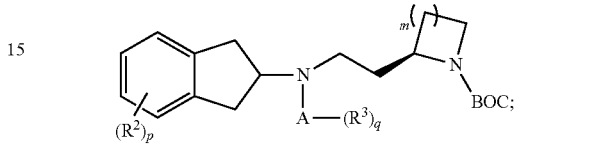

(iii) reducing compound 40a to form

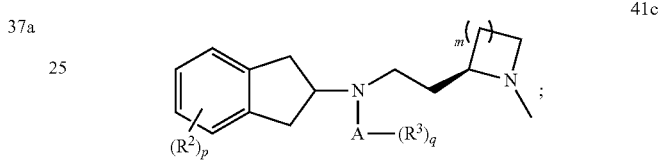

and (iv) $R^1$ substituting compound 41c.

53. The method according to claim 52, wherein compound 40a is prepared by adding compound 38a to a solution comprising compound 7c and a mild reducing agent.

54. The method according to claim 53, wherein said mild reducing agent is $Na(OAc)_3BH$.

55. The method according to claim 52, wherein the % ee of compound 40a is at least about 97% ee.

* * * * *

SEQUENCE LISTING

```
<160> NUMBER OF SEQ ID NOS: 4

<210> SEQ ID NO 1
<211> LENGTH: 839
<212> TYPE: PRT
<213> ORGANISM: Unknown
<220> FEATURE:
<223> OTHER INFORMATION: human TRPV1

<400> SEQUENCE: 1

Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
            20                  25                  30
```

```
Pro Pro Pro Ala Lys Pro Gln Leu Ser Thr Ala Lys Ser Arg Thr Arg
         35                  40                  45

Leu Phe Gly Lys Gly Asp Ser Glu Glu Ala Phe Pro Val Asp Cys Pro
 50                  55                  60

His Glu Glu Gly Glu Leu Asp Ser Cys Pro Thr Ile Thr Val Ser Pro
 65                  70                  75                  80

Val Ile Thr Ile Gln Arg Pro Gly Asp Gly Pro Thr Gly Ala Arg Leu
                 85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
                115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
                195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
            355                 360                 365

Lys Phe Thr Glu Trp Ala Tyr Gly Pro Val His Ser Ser Leu Tyr Asp
        370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
                420                 425                 430

Arg Ile Phe Tyr Phe Asn Phe Leu Val Tyr Cys Leu Tyr Met Ile Ile
            435                 440                 445
```

```
Phe Thr Met Ala Ala Tyr Tyr Arg Pro Val Asp Gly Leu Pro Pro Phe
    450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                485                 490                 495

Leu Gln Arg Arg Pro Ser Met Lys Thr Leu Phe Val Asp Ser Tyr Ser
                500                 505                 510

Glu Met Leu Phe Phe Leu Gln Ser Leu Phe Met Leu Ala Thr Val Val
            515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
                580                 585                 590

Thr Ala Val Val Thr Leu Ile Glu Asp Gly Lys Asn Asp Ser Leu Pro
            595                 600                 605

Ser Glu Ser Thr Ser His Arg Trp Arg Gly Pro Ala Cys Arg Pro Pro
    610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
                660                 665                 670

Ile Leu Leu Leu Asn Met Leu Ile Ala Leu Met Gly Glu Thr Val Asn
        675                 680                 685

Lys Ile Ala Gln Glu Ser Lys Asn Ile Trp Lys Leu Gln Arg Ala Ile
    690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
                725                 730                 735

Asp Asp Tyr Arg Trp Cys Phe Arg Val Asp Glu Val Asn Trp Thr Thr
                740                 745                 750

Trp Asn Thr Asn Val Gly Ile Ile Asn Glu Asp Pro Gly Asn Cys Glu
            755                 760                 765

Gly Val Lys Arg Thr Leu Ser Phe Ser Leu Arg Ser Ser Arg Val Ser
    770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
            835
```

```
<210> SEQ ID NO 2
<211> LENGTH: 41
<212> TYPE: DNA
<213> ORGANISM: Unknown
<220> FEATURE:
<223> OTHER INFORMATION: forward primer based on homo sapiens

<400> SEQUENCE: 2
ataaacggta ccgccgccac catgaagaaa tggagcagca c                             41

<210> SEQ ID NO 3
<211> LENGTH: 33
<212> TYPE: DNA
<213> ORGANISM: Unknown
<220> FEATURE:
<223> OTHER INFORMATION: reverse primer based on homo sapiens

<400> SEQUENCE: 3
atcggtttaa actcacttct ctccggaagc ggc                                     33

<210> SEQ ID NO 4
<211> LENGTH: 2520
<212> TYPE: DNA
<213> ORGANISM: Unknown
<220> FEATURE:
<223> OTHER INFORMATION: human TRPV1

<400> SEQUENCE: 4
atgaagaaat ggagcagcac agacttgggg gcagctgcgg acccactcca aaaggacacc       60
tgcccagacc ccctggatgg agaccctaac tccaggccac ctccagccaa gcccagctc       120
tccacggcca agagccgcac ccggctcttt ggaagggtg actcggagga ggctttccg       180
gtggattgcc ctcacgagga aggtgagctg actcctgcc cgaccatcac agtcagccct       240
gttatcacca tccagaggcc aggagacggc cccaccggtg ccaggctgct gtcccaggac       300
tctgtcgccg ccagcaccga aagaccctc aggctctatg atcgcaggag tatctttgaa       360
gccgttgctc agaataactg ccaggatctg agagcctgc tgctcttcct gcagaagagc       420
aagaagcacc tcacagacaa cgagttcaaa gaccctgaga cagggaagac ctgtctgctg       480
aaagccatgc tcaacctgca cgacggacag aacaccacca ccccctgct cctggagatc       540
gcgcggcaaa cggacagcct gaaggagctt gtcaacgcca gctacacgga cagctactac       600
aagggccaga cagcactgca catcgccatc gagagacgca catggcct ggtgacctc       660
ctggtggaga acggagcaga cgtccaggct gcggcccatg gggacttctt taagaaaacc       720
aaagggcggc ctggattcta cttcggtgaa ctgcccctgt ccctggccgc gtgcaccaac       780
cagctgggca tcgtgaagtt cctgctgcag aactcctggc agacggccga catcagcgcc       840
agggactcgg tgggcaacac ggtgctgcac gccctggtgg aggtggccga caacacggcc       900
gacaacacga gtttgtgac gagcatgtac aatgagattc tgatcctggg ggccaaactg       960
cacccgacgc tgaagctgga ggagctcacc aacaagaagg gaatgacgcc gctggctctg      1020
gcagctggga ccgggaagat cggggtcttg gcctatattc tccagcggga gatccaggag      1080
cccgagtgca ggcaccctgt caggaagttc accgagtggg cctacggcc gtgcactcc       1140
tcgctgtacg acctgtcctg catcgacacc tgcgagaaga actcggtgct ggaggtgatc      1200
gcctacagca gcagcgagac ccctaatcgc cacgacatgc tcttggtgga gccgctgaac      1260
cgactcctgc aggacaagtg ggacagattc gtcaagcgca tcttctactt caacttcctg      1320
gtctactgcc tgtacatgat catcttcacc atggctgcct actacaggcc cgtggatggc      1380
```

-continued

```
ttgcctccct ttaagatgga aaaaactgga gactatttcc gagttactgg agagatcctg  1440
tctgtgttag gaggagtcta cttcttttc cgagggattc agtatttcct gcagaggcgg   1500
ccgtcgatga agaccctgtt tgtggacagc tacagtgaga tgcttttctt tctgcagtca  1560
ctgttcatgc tggccaccgt ggtgctgtac ttcagccacc tcaaggagta tgtggcttcc  1620
atggtattct ccctggcctt gggctggacc aacatgctct actacacccg cggtttccag  1680
cagatgggca tctatgccgt catgatagag aagatgatcc tgagagacct gtgccgtttc  1740
atgtttgtct acatcgtctt cttgttcggg ttttccacag cggtggtgac gctgattgaa  1800
gacgggaaga atgactccct gccgtctgag tccacgtcgc acaggtggcg ggggcctgcc  1860
tgcaggcccc ccgatagctc ctacaacagc ctgtactcca cctgcctgga gctgttcaag  1920
ttcaccatcg gcatgggcga cctggagttc actgagaact atgacttcaa ggctgtcttc  1980
atcatcctgc tgctggccta tgtaattctc acctacatcc tcctgctcaa catgctcatc  2040
gccctcatgg gtgagactgt caacaagatc gcacaggaga gcaagaacat ctggaagctg  2100
cagagagcca tcaccatcct ggacacggag aagagcttcc ttaagtgcat gaggaaggcc  2160
ttccgctcag gcaagctgct gcaggtgggg tacacacctg atggcaagga cgactaccgg  2220
tggtgcttca gggtggacga ggtgaactgg accacctgga acaccaacgt gggcatcatc  2280
aacgaagacc cgggcaactg tgagggcgtc aagcgcaccc tgagcttctc cctgcggtca  2340
agcagagttt caggcagaca ctggaagaac tttgccctgg tccccctttt aagagaggca  2400
agtgctcgag ataggcagtc tgctcagccc gaggaagttt atctgcgaca gttttcaggg  2460
tctctgaagc cagaggacgc tgaggtcttc aagagtcctg ccgcttccgg agagaagtga  2520
```